(12) United States Patent
Sawler et al.

(10) Patent No.: US 11,312,988 B2
(45) Date of Patent: Apr. 26, 2022

(54) METHODS AND COMPOSITIONS FOR CANNABIS CHARACTERIZATION

(71) Applicant: Anandia Laboratories Inc., Vancouver (CA)

(72) Inventors: Jason Sawler, Vancouver (CA); Sean Myles, Wolfville (CA)

(73) Assignee: ANANDIA LABORATORIES INC., Vancouver (CA)

( * ) Notice: Subject to any disclaimer, the term of this patent is extended or adjusted under 35 U.S.C. 154(b) by 313 days.

(21) Appl. No.: 15/735,825

(22) PCT Filed: Jun. 13, 2016

(86) PCT No.: PCT/CA2016/050678
§ 371 (c)(1),
(2) Date: Dec. 12, 2017

(87) PCT Pub. No.: WO2016/197258
PCT Pub. Date: Dec. 15, 2016

(65) Prior Publication Data
US 2018/0171394 A1    Jun. 21, 2018

Related U.S. Application Data

(60) Provisional application No. 62/175,006, filed on Jun. 12, 2015.

(51) Int. Cl.
*C12Q 1/6827* (2018.01)
*G16B 20/00* (2019.01)
(Continued)

(52) U.S. Cl.
CPC .......... *C12Q 1/6827* (2013.01); *C07H 21/04* (2013.01); *C12Q 1/6895* (2013.01); *C40B 30/04* (2013.01);
(Continued)

(58) Field of Classification Search
CPC .......... C12N 15/8261; C12N 2840/007; C12N 2840/65; C12N 5/04; C12N 9/63; A24B 15/303; G01N 33/5097; G01N 33/948; G16B 20/00; G16B 30/00; G16B 40/00; G16B 20/20; G16B 25/00; G16B 10/00; G16B 40/20; G16B 20/40; G16B 30/10;
(Continued)

(56) References Cited

U.S. PATENT DOCUMENTS 9,095,554 B2 *  8/2015  Lewis ................... A01H 6/28
10,653,085 B1 *  5/2020  Stanley ................. A01H 5/02
(Continued)

FOREIGN PATENT DOCUMENTS

WO    2013/173635 A1    11/2013

OTHER PUBLICATIONS

Sequence alignments of elected sequences v McKernan, compiled May 20, 2021. (Year: 2021).*
(Continued)

*Primary Examiner* — Mary K Zeman
(74) *Attorney, Agent, or Firm* — Bereskin & Parr LLP; Carmela De Luca

(57) ABSTRACT

Provided are methods for determining if a *cannabis* sample comprises hemp or marijuana, or *Cannabis sativa* and/or *Cannabis indica* as well as primers and kits for use in the methods.

14 Claims, 12 Drawing Sheets

Specification includes a Sequence Listing.

(51) Int. Cl.
*C40B 40/06* (2006.01)
*G16B 20/20* (2019.01)
*C07H 21/04* (2006.01)
*C12Q 1/6895* (2018.01)
*C40B 30/04* (2006.01)

(52) U.S. Cl.
CPC .............. *C40B 40/06* (2013.01); *G16B 20/00* (2019.02); *G16B 20/20* (2019.02); *C12Q 2535/125* (2013.01); *C12Q 2600/13* (2013.01); *C12Q 2600/156* (2013.01)

(58) Field of Classification Search
CPC .......... G16B 30/20; G16B 20/10; G16B 5/00; G16B 50/00; G16B 50/30; G16B 35/00; G16B 5/20; G16B 50/10; G16H 50/30; G16H 15/00; G16H 20/10; G16H 10/40; G16H 10/60; G16H 50/70; G16H 70/40; C40B 30/04; C40B 40/06; C12Q 2600/156; C12Q 2600/106; C12Q 1/6895; C12Q 1/6883; C12Q 1/6827; C12Q 2600/158; C12Q 2600/172; C12Q 1/68; C12Q 1/686; C12Q 2600/13; C12Q 2600/136; A01H 6/28; A01H 1/00; A01H 1/04; A01H 4/00; A01H 4/005; A01H 1/101; A01H 5/12; A01H 5/04; A01H 5/10; A01H 5/02; A01G 22/00; G06F 19/00; G06F 3/0484; G06F 40/169; G06F 17/11; G06F 17/18; Y02A 40/146; C12Y 121/03007; C12Y 121/03008; A61P 25/00; A61P 25/04; G06T 11/206; G06N 7/005; G06N 20/00; G06N 20/20; G06N 5/003; G06N 5/02; G06N 5/022; G06N 5/04; G06N 7/00; A61K 31/00

See application file for complete search history.

(56) References Cited

U.S. PATENT DOCUMENTS

| | | | |
|---|---|---|---|
| 10,888,059 B1* | 1/2021 | Reel | A01H 5/02 |
| 10,888,060 B1* | 1/2021 | Reel | A01H 5/12 |
| 2006/0035236 A1* | 2/2006 | Keim | C12Q 1/6895 435/6.13 |
| 2009/0094717 A1* | 4/2009 | Troukhan | C12Q 1/6895 800/290 |
| 2011/0191912 A1 | 8/2011 | Alexandrov et al. | |
| 2014/0057251 A1* | 2/2014 | McKernan | C07K 16/40 435/6.11 |
| 2016/0132635 A1* | 5/2016 | Buntjer | G16B 20/20 506/2 |
| 2016/0177404 A1* | 6/2016 | McKernan | C12N 9/88 435/6.12 |
| 2018/0171394 A1* | 6/2018 | Sawler | G16B 20/00 |
| 2018/0258439 A1* | 9/2018 | Boudko | A61K 36/185 |
| 2018/0295804 A1* | 10/2018 | Muck | A01H 5/02 |
| 2019/0185946 A1* | 6/2019 | McKernan | C12Y 121/03007 |
| 2019/0297821 A1* | 10/2019 | Crawford | C12Q 1/6827 |
| 2020/0015440 A1* | 1/2020 | Crawford | A01H 5/02 |
| 2020/0015441 A1* | 1/2020 | Crawford | A01H 5/02 |
| 2020/0253921 A1* | 8/2020 | May | G16B 20/00 |
| 2020/0270623 A1* | 8/2020 | Pauli | C12Q 1/6895 |
| 2020/0288659 A1* | 9/2020 | Crawford | A01H 5/04 |
| 2020/0405685 A1* | 12/2020 | Lewis | A61K 36/185 |
| 2021/0045311 A1* | 2/2021 | Lewis | A01H 1/101 |
| 2021/0112743 A1* | 4/2021 | Llosa Llacer | A01H 5/12 |
| 2021/0144947 A1* | 5/2021 | Fletcher | A01H 5/12 |

OTHER PUBLICATIONS

Sequence alignments of elected sequences v van Bakel, compiled May 20, 2021. (Year: 2021).*
Van Bakel 2011 Genome Biology 12: R102 1-18. cited previously. (Year: 2011).*
Sawler, J. et al. The Genetic Structure of Marijuana and Hemp. PLOS ONE, Aug. 26, 2015. vol. 10, No. 8, p. e0133292.
Rotherham D. et al. Differentiation of drug and non-drug Cannabis using a single nucleotide polymorphism (SNP) assay. Forensic Science International, Apr. 15, 2011. vol. 207, No. 1-3, pp. 193-197.
Piluzza G. et al. Differentiation between fiber and drug types of hemp (*Cannabis sativa* L.) from a collection of wild and domesticated accessions. Getetic Resources and Crop Evolution, Aug. 1, 2013. vol. 60, pp. 2331-2342.
Gilmore, Simon et al. Short tandem repeat (STR) DNA markers are hypervariable and informative in *Cannabis sativa*: implications for forensic investigations. Forensic Science International, Jan. 9, 2003. vol. 131, No. 1, pp. 65-74.
Van Bakel et al. The draft genome and transcriptome of *Cannabis sativa*. Genome Biology, Oct. 20, 2011. vol. 12, No. 10, pp. R102.
Bryc, Katarzyna et al. Genome-wide patterns of population structure and admixture in West Africans and African Americans. PNAS, Jan. 12, 2010. vol. 107, No. 2, pp. 786-791.
Hazekamp A. et al. Cannabis—from cultivar to chemovar. Drug Testing and Analysis. Nov. 18, 2011. vol. 4, pp. 660-667.
Hilling, Karl W. et al. A Chemotaxonomic Analysis of Cannabinoid Variation in Cannabis (*Cannabaceae*). American Journal of Botany. 2004, vol. 91, No. 6, pp. 966-975.
KASP genotyping chemistry user guide and manual. LGC. Jul. 2013.
McVean Gil. A Genealogical Interpretation of Prinicpal Components Analysis. PLOS Genetics. Oct. 2009, vol. 5, Issue 10, pp. 1-10.
Patterson Nick et al. Population Structure and Eigenanalysis. PLOS Genetics, Dec. 2006, vol. 2, Issue 12, pp. 2074-2093.
Sawler, Jason et al. Genomics Assisted Ancestry Deconvolution in Grape. PLOS ONE, Nov. 2013, vol. 8, Issue 11, pp. 1-8.
PLEX Gold Assay for SNP Genotyping. SEQUENOM, Genomics Fine Mapping. Protocol Guide, 2008, p. 37.
Weir, B.S. et al. Estimating F-Statistics for the Analysis of Population Structure. Evolution, Nov. 1984. vol. 38, No. 6, pp. 1358-1370.
Willing, Eva-Maria et al. Estimates of Genetic Differentiation Measured by FST Do Not Necessarily Require Large Sample Sizes When Using Many SNP Markers. PLOS ONE, Aug. 2012. vol. 7, Issue 8, pp. 1-7.
McClure Kendra A., et al. Genomics: A Potential Panacea for the Perennial Problem. American Journal of Botany, 101(10): 1780-1790, 2014.
Myles, Sean. Improving fruit and wine: what does genomics have to offer? Trends in Genetics, Apr. 2013, vol. 29, No. 4.

* cited by examiner a

SEQUENCE LISTING

```
<160> NUMBER OF SEQ ID NOS: 600

<210> SEQ ID NO 1
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 1
cagatcctaa atatgctgat attattcttt tagagaatta tgcagcattt cagaataggt    60
acatatttca ttctttatt ttttctcctg tatctttcat n                        101

<210> SEQ ID NO 2
<211> LENGTH: 100
<212> TYPE: DNA
<213> ORGANISM: Cannabis sativa

<400> SEQUENCE: 2
ataaggagtt attattattt gttttgggtg cattgctgag tagaagcagt ttcatgcagc    60
ttgtatgacc tagccaatgt tgtgcctacc ctagccaagt                         100

<210> SEQ ID NO 3
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 3
caataagact ttcgatcgct cttggtgctg cacgaggcaa gatttctata tttgatattg    60
gcttgtccca tttgacaatt ttccattaaa atggctgatg n                       101

<210> SEQ ID NO 4
<211> LENGTH: 100
<212> TYPE: DNA
<213> ORGANISM: Cannabis sativa

<400> SEQUENCE: 4
aatggggtat tgaggtttga agaattcttt catatgaatc tgcaggatta acttatcttc    60
acacatatgc cggctgcgtt atacataggg atgtgaaatc                         100

<210> SEQ ID NO 5
<211> LENGTH: 101
<212> TYPE: DNA
<213> ORGANISM: Cannabis sativa
```

```
<220> FEATURE:
<221> NAME/KEY: misc_feature
<222> LOCATION: (101)..(101)
<223> OTHER INFORMATION: n is a or c

<400> SEQUENCE: 5
tcctcgattg ttgaaggaat tgtggggagg cctgctttgc gctgctgctg ggcccatgat      60 agttttgct gtagtttcac attttctggt tcaactgtga n                          101

<210> SEQ ID NO 6
<211> LENGTH: 100
<212> TYPE: DNA
<213> ORGANISM: Cannabis sativa

<400> SEQUENCE: 6
agcaaactgc aagttcttga cagtgtactg aggcaacaca aagtgcaatt gtcaattatg      60
atctggaaga gaaaggttcg cagcaaaaga cgcaactaga                           100

<210> SEQ ID NO 7
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 7
ctgaagccag dacaatgcag ccagccagta gtgagtatca tcatcagtat gttgttgctg      60
tcaatggcat gatggacccg agtccacgga agagttcaag n                         101

<210> SEQ ID NO 8
<211> LENGTH: 100
<212> TYPE: DNA
<213> ORGANISM: Cannabis sativa

<400> SEQUENCE: 8
gggcaaagtt tgacgagcca gtctagccaa ttcggaaata actcagatta tagtccaagt      60
ttttgtagag gctctcctac agcagcatat gcaatggaga                           100

<210> SEQ ID NO 9
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 9
ccatcatgaa attcccttac cctggtgcct taactgctct gcagtatttc actagtgctt      60
ttggggtctt catttgtgga tggcttaagt tcattgagca n                         101

<210> SEQ ID NO 10
<211> LENGTH: 100
<212> TYPE: DNA
<213> ORGANISM: Cannabis sativa

<400> SEQUENCE: 10
gaccgacttg agctcctcac aatgtggcgc tttctacctg ctgctgttat attctatctt      60
tcccttttca ccaatagtga gttgctcctt catgccaatg                           100
```

<210> SEQ ID NO 11
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 11
cccatggaaa caaaagttcc ctgatatcaa acagtgaaaa actttagcac aacacagcag     60
catagatatc gataaggaaa cagattaatt gaaaagaaaa n                        101

<210> SEQ ID NO 12
<211> LENGTH: 100
<212> TYPE: DNA
<213> ORGANISM: Cannabis sativa

<400> SEQUENCE: 12
acaagtactg acctcaggag ttccaagaac ccagtcacgg atgtgatcac aagcagagct     60
ggcagcagat aaagcacttg atagcttacg agctttgata                          100

<210> SEQ ID NO 13
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 13
aaccattcat cttcttatca ctgctgccat ttcttgtttg aatgtcataa attttggatt     60
ggcaggattc ttgaatagca tgaacgatct catcacacga n                        101

<210> SEQ ID NO 14
<211> LENGTH: 100
<212> TYPE: DNA
<213> ORGANISM: Cannabis sativa

<400> SEQUENCE: 14
gtataggcca cacaaaccaa aagattagcc ttgttgtttt tggcagtagc tttcatgact     60
ttctcagcag caactctcac aggctcattc aacagtttca                          100

<210> SEQ ID NO 15
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 15
aatggttcct caatcttcaa atcatcagaa gctccttgtt agctcgactc ttccttccac     60
gaagcagctc catcaaatgc cttctcattc agataatagc n                        101

<210> SEQ ID NO 16
<211> LENGTH: 100
<212> TYPE: DNA
<213> ORGANISM: Cannabis sativa

<400> SEQUENCE: 16

```
cccaaggcca agttccacct gtttcatcag gccatgcatt atcaacttcc caacaagttc    60
cagtggcagt tatgggtccc aatcaccagc agctgcagtc                         100
```

<210> SEQ ID NO 17
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 17

```
cgtaccgttc attgtcttta gctaacgacg ccaatgaagc agcagcatcc gatcgttctt    60
ccaatgaccc cgtgtaaaga attgctatct gttcccatat n                      101
```

<210> SEQ ID NO 18
<211> LENGTH: 100
<212> TYPE: DNA
<213> ORGANISM: Cannabis sativa

<400> SEQUENCE: 18

```
aggcatagga ttggctcatt ggcagcaatt gggggtaagc cgaggtactc gtcgtctcga    60
tcgcaggcag aggcagaaac ccgaaggagc aagagacat                         100
```

<210> SEQ ID NO 19
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 19

```
gctccgctgc tgaagatgtt tccaaacctg cacaccaagg agtctctcgt atccctgat    60 gagcttggtc cttttcaggt aaaactatct tgctcatcat n                      101
```

<210> SEQ ID NO 20
<211> LENGTH: 100
<212> TYPE: DNA
<213> ORGANISM: Cannabis sativa

<400> SEQUENCE: 20

```
tgctgctgag tttcttttc attagttgaa ttaatgtatc tacaaactat ttgttactgc    60
taaaagctta ttgtctttaa cttattatca catctatact                        100
```

<210> SEQ ID NO 21
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 21

```
tctctataat caacaaatgg gccatcatga aattccctta ccctggtgcc ttaactgctc    60
tgcagtattt cactagtgct tttggggtct tcatttgtgg n                      101
```

<210> SEQ ID NO 22

```
<211> LENGTH: 100
<212> TYPE: DNA
<213> ORGANISM: Cannabis sativa

<400> SEQUENCE: 22
tggcttaagt tcattgagca tgaccgactt gagctcctca caatgtggcg ctttctacct    60
gctgctgtta tattctatct ttcccttttc accaatagtg                         100

<210> SEQ ID NO 23
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 23
cgcgaaataa cattctcacc ttctcctctc tcgccaccgc tgctgccgct gtcgcatacg    60
tttttctctc ctccgatgat gatcgtgatc ataaggccgc n                       101

<210> SEQ ID NO 24
<211> LENGTH: 100
<212> TYPE: DNA
<213> ORGANISM: Cannabis sativa

<400> SEQUENCE: 24
atcgaacacg gaattcgcaa atacggtgat tcgatcaata acgttttcgt tcacattaag    60
caaaccggtg ttgctgcttc ggttctctgg caatcgctta                         100

<210> SEQ ID NO 25
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 25
aataaaacat gagcttcttg atattctcac taagtttggg tagtggcata gtctttggag    60
aagcagctcg agaaagtgag gaaatagtac ttttggagtc n                       101

<210> SEQ ID NO 26
<211> LENGTH: 100
<212> TYPE: DNA
<213> ORGANISM: Cannabis sativa

<400> SEQUENCE: 26
gatcgctcca ggtaaagcct gcctctgtat gcagccaagt gagcataata aactggggga    60
accaaagaaa ctggtttagt acaccttacg tatgtataac                         100

<210> SEQ ID NO 27
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 27
cactaagttt gggtagtggc atagtctttg gagaagcagc tcgagaaagt gaggaaatag    60
```

```
tactttggga gtccgatcgc tccaggtaaa gcctgcctct n                    101
```

<210> SEQ ID NO 28
<211> LENGTH: 100
<212> TYPE: DNA
<213> ORGANISM: Cannabis sativa

<400> SEQUENCE: 28

```
tatgcagcca agtgagcata ataaactggg ggaaccaaag aaactggttt agtacacctt    60
acgtatgtat aacaaagatt gtacaccagt ttctgtagtt                         100
```

<210> SEQ ID NO 29
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 29

```
taccattttc ttgcccacag gttattttgc tgctatcctt gcgtggttgt ggcccactct    60
ggccaaatcg gttatcctca tcaacagtgc tggaaatgtc n                      101
```

<210> SEQ ID NO 30
<211> LENGTH: 100
<212> TYPE: DNA
<213> ORGANISM: Cannabis sativa

<400> SEQUENCE: 30

```
ttccaggata ttcctttgtg ccatttagta aagtgagtct aaaagcaatg cttatcttta    60
aatatggtat ctggtgcagc tgctgacaac tgaaagctgt                        100
```

<210> SEQ ID NO 31
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 31

```
tcaagagttg gttagaaatt tataacatac cagaagcagc agaaaatgct gtaccgcttc    60
ttttctcagc atcatgatgg tcttttgtag tttttccagg n                      101
```

<210> SEQ ID NO 32
<211> LENGTH: 100
<212> TYPE: DNA
<213> ORGANISM: Cannabis sativa

<400> SEQUENCE: 32

```
gttgatgaag ttttcggct cacatcttta cctggctgag agccagttgc agcatctgtt     60
cctccttcac gttttgtcg agcttgttca gccataagct                         100
```

<210> SEQ ID NO 33
<211> LENGTH: 101
<212> TYPE: DNA
<213> ORGANISM: Cannabis sativa
<220> FEATURE:
<221> NAME/KEY: misc_feature
<222> LOCATION: (101)..(101)

<223> OTHER INFORMATION: n is g or a

<400> SEQUENCE: 33
ctagcagctt caaaatgggt ttctttcttt ggaacagctg ggatatgtcc tccgaggcca      60
atctgtcaaa cagaacttga agtgaagcag agagcaaagc n                         101

<210> SEQ ID NO 34
<211> LENGTH: 100
<212> TYPE: DNA
<213> ORGANISM: Cannabis sativa

<400> SEQUENCE: 34
ccaccaacca attcagcagc catattgatc aatgacaaaa gtaacaagtt ctttgttgaa      60
tctgtgtagg ggttacggat gagaatgaag aaagaaagaa                           100

<210> SEQ ID NO 35
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 35
cccaaagagt ttggttattt cctagtgtta cgactgttgg aaaggccctg tctattgtgg      60
tggctgccac agttatgagc catggtgcag tgtttgaaat n                         101

<210> SEQ ID NO 36
<211> LENGTH: 100
<212> TYPE: DNA
<213> ORGANISM: Cannabis sativa

<400> SEQUENCE: 36
gtttgtgaag tgggaccact atttcctgca gatgaaacaa ccgtgatccc ctttgatgct      60
gcatggaagg acccaattgc aattgtgtca cgcagatcaa                           100

<210> SEQ ID NO 37
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 37
ttgatctact gttgcagaac atgtatgctc agttgctgcc tcttgctttg cctgccccac      60
ctatgccggg aatgggagga ccaggaatgg gaggctatgc n                         101

<210> SEQ ID NO 38
<211> LENGTH: 100
<212> TYPE: DNA
<213> ORGANISM: Cannabis sativa

<400> SEQUENCE: 38
ccacctccta tgggggaat gggaatgcct ccaatgccac cctatggcat gccacccatg       60
gggagcagct attgagatgt atcaggacta cgagttgtga                           100

<210> SEQ ID NO 39
<211> LENGTH: 101

```
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 39
ctgacaatat agcaatgctt cattaaatct cattattaca aatacactca taagctcatc    60
aatatagata atagatatag taagatacaa gctgcaatac n                       101

<210> SEQ ID NO 40
<211> LENGTH: 100
<212> TYPE: DNA
<213> ORGANISM: Cannabis sativa

<400> SEQUENCE: 40
caaaattcaa accacaagat cactctaaca agtcacaaca aacacataaa agcatcaact    60
ctagcagcac caccaccacc aaaccaaggc atcatcccga                         100

<210> SEQ ID NO 41
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 41
gactaagcct caactgggtt tggaagaatt ttgaccatga atctgaaccg tcggctgctc    60
tcaaaaagta atgtaactga gaacgatgga accggcaccg n                       101

<210> SEQ ID NO 42
<211> LENGTH: 100
<212> TYPE: DNA
<213> ORGANISM: Cannabis sativa

<400> SEQUENCE: 42
ttagggaacc cagtgacctc gaattcttca gactctgttt tccggtgagg gagttcgttc    60
cagatagaaa tgaaggctgc agagccgtaa gcgccagaag                        100

<210> SEQ ID NO 43
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 43
acaagaagaa tagaaaggct gctcttacta ttttctatgc cttggccttg gctgaagctc    60
tgttgtttct aatggagaaa gcttattggg aatggaaggt n                       101

<210> SEQ ID NO 44
<211> LENGTH: 100
<212> TYPE: DNA
<213> ORGANISM: Cannabis sativa

<400> SEQUENCE: 44
acttactgca agctgcttga tgaggtgaac aaagagagtg aattgggagg agcttctggt    60
```
atggtttcaa tcagaaggtt cttctatgat gcctattcga                          100

<210> SEQ ID NO 45
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 45
ccaattccgc cactgctcca ctgctgcttg ctagattctt ctcagatgag cgctcaatct    60
cttttgacaa agatccacca agctcaggct tatcatcacc n                       101

<210> SEQ ID NO 46
<211> LENGTH: 100
<212> TYPE: DNA
<213> ORGANISM: Cannabis sativa

<400> SEQUENCE: 46
gtttcagcat cattaccatt taatttatcc tctggtactg ggctgctgtc tggaccccat    60
tctgatgagt ctttaacatc tgcttcaact tcatgcgagg                         100

<210> SEQ ID NO 47
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 47
gtactgggct gctgtctgga ccccattctg atgagtcttt aacatctgct tcaacttcat    60
gcgaggtaga tgtagatacc acagattctg acatagtttc n                       101

<210> SEQ ID NO 48
<211> LENGTH: 100
<212> TYPE: DNA
<213> ORGANISM: Cannabis sativa

<400> SEQUENCE: 48
gtttctaaac tagctgcagt agcatccatt tgatccacag tttccaagga agatccagat    60
ctatttataa ttccaccagt gaggggtgca tccacatcat                         100

<210> SEQ ID NO 49
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 49
tccattgcaa aaactaccac catggctctg atcagcagca gcaaaagagc taggcttcac    60
ttcctccaca agatcaaaact ctttcttctc ttgcttggtt n                      101

<210> SEQ ID NO 50
<211> LENGTH: 100
<212> TYPE: DNA
<213> ORGANISM: Cannabis sativa

<400> SEQUENCE: 50
gatcagaaga tttatgagtt gcttcttcag aaagttggta accttgttcc gagtgttgac        60
ttgaggtatt tgctgcaaat ggagacttct ctcgctggct                              100

<210> SEQ ID NO 51
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 51
aagcagcatg gcggcgatac agtaagaaaa agcttgaaga gtctcttagg gaagaggaga        60
ataggttgca ggatgcgttg gccaaggccg gggcgagctc n                            101

<210> SEQ ID NO 52
<211> LENGTH: 100
<212> TYPE: DNA
<213> ORGANISM: Cannabis sativa

<400> SEQUENCE: 52
cctagtttag gtgccaccat ttatgcttca cgctttgctg caaacgcact gcgtgccata        60
aggcgtaata gtacacgtaa aacaaggatg cccgaaagaa                              100

<210> SEQ ID NO 53
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 53
aggaggcaac ggactcttca acttagcagc agcggaaggc gagggtttag gaatcggagg        60
caaggagttt ggatcggcat agggcggagc attctccttg n                            101

<210> SEQ ID NO 54
<211> LENGTH: 100
<212> TYPE: DNA
<213> ORGANISM: Cannabis sativa

<400> SEQUENCE: 54
aagatttctg cttccgcgga tgtcggatct tggcggtggt gctgctaggg tttggagatg        60
gcggaggttc cgtctctctc aagatgttat ttcttggctg                              100

<210> SEQ ID NO 55
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 55
accattatgc ggtgtgtgca aattcgaatt gctctcccca tctgagtagt ctgatatcaa        60
gtgatctgat ggacttcttg tgctgctatc tgaacccacc n                            101

<210> SEQ ID NO 56
<211> LENGTH: 100
<212> TYPE: DNA
<213> ORGANISM: Cannabis sativa

<400> SEQUENCE: 56
cttcttcatc ttcagaactc tcatcatcat ccttgaaaat tgaccctggt gttaatcttt    60
tgttttgttt tgagctgttc aagatttctc cattgtactt                         100

<210> SEQ ID NO 57
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 57
acttcggctc taggcagccc tgcgcttcgc attcctagcc tcaaacaacg aagccgagta    60
tgaagcccta attgcaggac taaagttatc aaaggccgta n                       101

<210> SEQ ID NO 58
<211> LENGTH: 100
<212> TYPE: DNA
<213> ORGANISM: Cannabis sativa

<400> SEQUENCE: 58
gggctgcaag agtagaagtc ttcagcgatt cacagttagt ggtcaatcaa gtgtcggggg    60
aataccaaac gcgtggagaa aaaatagccg cttacgtagc                         100

<210> SEQ ID NO 59
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 59
tgtgttcaac gctttccggg tcacgcccca gacgcccaat tgccgtggca gcattctcct    60
gaccttccat tcggccttct tttgccaatt tcagaagtgg n                       101

<210> SEQ ID NO 60
<211> LENGTH: 100
<212> TYPE: DNA
<213> ORGANISM: Cannabis sativa

<400> SEQUENCE: 60
gccaccccac cttcctcaat aataagctta ccgtaccgtt cattgtcttt agctaacgac    60
gccaatgaag cagcagcatc cgatcgttct tccaatgacc                         100

<210> SEQ ID NO 61
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 61

```
gagaagagaa attatcatat gccaccatga gcaaaaccgc agcctccttt gcgaggatag     60
aattttctac cgagagagtt ttgtcggtcg ctttctccat n                        101
```

<210> SEQ ID NO 62
<211> LENGTH: 100
<212> TYPE: DNA
<213> ORGANISM: Cannabis sativa

<400> SEQUENCE: 62

```
gcaaacagtg cttgtttctc ccattcgttt cgaacattta gcatggtatt atcactagca     60
gcttttttgg aaaaactaag gaaatacttc aagatggcga                          100
```

<210> SEQ ID NO 63
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 63

```
acttggcaat gttagcagcc tggtccagag aactagagag caagggatgg aagcatatat     60
ggtccacaat accaagccgg ggatgactgc cactgtgcaa n                        101
```

<210> SEQ ID NO 64
<211> LENGTH: 100
<212> TYPE: DNA
<213> ORGANISM: Cannabis sativa

<400> SEQUENCE: 64

```
tcaaggtcaa tggactccag agcagcctta accatggcta ggactgaggt tctcaagggg     60
catggatccg aagatggttg tggatccaac ttggaaacaa                          100
```

<210> SEQ ID NO 65
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 65

```
gtaaatgcag tccttgtgat tgttgttgtt gtaaatgccc gtcgtgtttc agttgctcgt     60
taccaaaatg gcgttgccct cgttgttcat gttcgtgtcc n                        101
```

<210> SEQ ID NO 66
<211> LENGTH: 100
<212> TYPE: DNA
<213> ORGANISM: Cannabis sativa

<400> SEQUENCE: 66

```
cgaccaaatt gctgtaaaaa gaagtcatgc aacagaagtt gttgctgcct attccctact     60
tcttgttgtt catgccctga ttgcccctct tgcagatgca                          100
```

<210> SEQ ID NO 67
<211> LENGTH: 101
<212> TYPE: DNA
<213> ORGANISM: Cannabis sativa
<220> FEATURE:

<221> NAME/KEY: misc_feature
<222> LOCATION: (101)..(101)
<223> OTHER INFORMATION: n is t or a

<400> SEQUENCE: 67
attgctctag gggcagcccg aggcttagct tatctacatg aagactccaa tccacgagtg    60
attcatcgag atttcaagtc cagcaacatc ctgttagagc n                       101

<210> SEQ ID NO 68
<211> LENGTH: 100
<212> TYPE: DNA
<213> ORGANISM: Cannabis sativa

<400> SEQUENCE: 68
tgactttaca cctaaggtct cagactttgg attggccaga gcagcattag acggtaacag    60
acatatctca acacatgtta tgggcacttt tgggtaagga                         100

<210> SEQ ID NO 69
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 69
aaaaagttgc agcggcaaca aaggtctgt gttgggattg agaggctttg agagaagaga    60
ccctcgaggg agaaacccac gaagactgag gagctaggtt n                       101

<210> SEQ ID NO 70
<211> LENGTH: 100
<212> TYPE: DNA
<213> ORGANISM: Cannabis sativa

<400> SEQUENCE: 70
ggtgggttgt tggagccaat tgagtatatt tcaacggagg aagtgtcgga atcggagtcg    60
aaaaaggcga tggctgcgaa ccggtccaag gccgtgactg                         100

<210> SEQ ID NO 71
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 71
agataaaagt cgctcattct gaacctcttc ctctaacgaa gctgctttta agagcaaggt    60
gttgacctca ttttcaacta ctctcaatcg agactctgcc n                       101

<210> SEQ ID NO 72
<211> LENGTH: 100
<212> TYPE: DNA
<213> ORGANISM: Cannabis sativa

<400> SEQUENCE: 72
attctctctt agcttgtgat gcttttactt cttcctctgc agctttcttt gattcagtag    60
caagaaccat ctttatttgc agctcctgca aatccattgc                         100

<210> SEQ ID NO 73
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 73
aagcaaatta acaacctgct tatcaaccaa acccggatga gtagtgacta cataagggtt    60
attatcatgg ggcagccacg ggtcatttag aatgctaacc n    101

<210> SEQ ID NO 74
<211> LENGTH: 100
<212> TYPE: DNA
<213> ORGANISM: Cannabis sativa

<400> SEQUENCE: 74
aggctccact agcaattgat cttcttgcac ccttcctcac taagtcttga gcagcccata    60
tactccgcca aataaaacta ggattatttc ctaactcagc    100

<210> SEQ ID NO 75
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 75
caacctgctt atcaaccaaa cccggatgag tagtgactac ataagggtta ttatcatggg    60
gcagccacgg gtcatttaga atgctaaccg aggctccact n    101

<210> SEQ ID NO 76
<211> LENGTH: 100
<212> TYPE: DNA
<213> ORGANISM: Cannabis sativa

<400> SEQUENCE: 76
gcaattgatc ttcttgcacc cttcctcact aagtcttgag cagcccatat actccgccaa    60
ataaaactag gattatttcc taactcagca tcaagaaagg    100

<210> SEQ ID NO 77
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 77
tgccggattt agtgtgtaat aaagacgaat cgagcagctt tgggttcaag aatttgatgg    60
agactttctg ggttgacgtt caagaagctg aagagagacc n    101

<210> SEQ ID NO 78
<211> LENGTH: 100
<212> TYPE: DNA
<213> ORGANISM: Cannabis sativa

<400> SEQUENCE: 78

```
ttgaggctta aactcatcac tgagcctgct gagactgctt cgtcgtctca gcttcaaaat    60
atggccatta gagttgaatt gaggaatggc tgcgtcggat                         100

<210> SEQ ID NO 79
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 79
gcacttccat ttacttggcc tcaggcaaaa tataccagga agagaaacat ctagctccgc    60
tgctgaagat gtttccaaac ctgcacacca aggagtctct n                      101

<210> SEQ ID NO 80
<211> LENGTH: 100
<212> TYPE: DNA
<213> ORGANISM: Cannabis sativa

<400> SEQUENCE: 80
gtatcccctg atgagcttgg tccttttcag gtaaaactat cttgctcatc atctgctgct    60
gagtttcttt ttcattagtt gaattaatgt atctacaaac                        100

<210> SEQ ID NO 81
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is  t or c

<400> SEQUENCE: 81
catctagctc cgctgctgaa gatgtttcca aacctgcaca ccaaggagtc tctcgtatcc    60
cctgatgagc ttggtccttt tcaggtaaaa ctatcttgct n                      101

<210> SEQ ID NO 82
<211> LENGTH: 100
<212> TYPE: DNA
<213> ORGANISM: Cannabis sativa

<400> SEQUENCE: 82
atcatctgct gctgagtttc tttttcatta gttgaattaa tgtatctaca aactatttgt    60
tactgctaaa agcttattgt ctttaactta ttatcacatc                        100

<210> SEQ ID NO 83
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 83
ctagttttaa ggatgcacag tggctcctca tccagaaagc tgaagaggaa aagcttcttc    60
aagtgactat taagctgcca gaggagaaac taaataagtt n                      101

<210> SEQ ID NO 84
<211> LENGTH: 100
```

-continued

<212> TYPE: DNA
<213> ORGANISM: Cannabis sativa

<400> SEQUENCE: 84
ataaatgact tcaatgagta ctatcttagt gatggtgtta gtaagtctgc tcaactgtgg    60
aatgagcagc gaaagttgat attgcaggat gctcttttta                          100

<210> SEQ ID NO 85
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 85
tgcagcccat tgttgagatg aatgagatgt tacatgcttg aagttatgtt gatgtctcat    60
ttctctttcc ttagctatca tagtcaaagc atcaccaatg n                        101

<210> SEQ ID NO 86
<211> LENGTH: 100
<212> TYPE: DNA
<213> ORGANISM: Cannabis sativa

<400> SEQUENCE: 86
aagcagcaac ttctgtgata tccagtgggt ttactaaaat agcgccagca ccgagtgaat    60
ttactgcacc tgcacactaa atttaaatgg aataaacaag                          100

<210> SEQ ID NO 87
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 87
tgttaacagc atcagcagca gcagcagtat tatccctatt tcgtaaggaa caaggacgcc    60
acatatatgt tacaggagcg atcggcttag aaactggtgc n                        101

<210> SEQ ID NO 88
<211> LENGTH: 100
<212> TYPE: DNA
<213> ORGANISM: Cannabis sativa

<400> SEQUENCE: 88
ccaatatggt ggagctgcaa catggggatt agtcagacat agccaattcc ttaatccacc    60
tcaatgaaaa agaaaaggac agtaactaac cattgcatta                          100

<210> SEQ ID NO 89
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 89
acgacgccta ctaccaataa cccaaatagg gcagcaagga tgatgatgat gaccacacaa    60
tcctgctccc caacactctc cagaccaccc aacacatcca n               101

<210> SEQ ID NO 90
<211> LENGTH: 100
<212> TYPE: DNA
<213> ORGANISM: Cannabis sativa

<400> SEQUENCE: 90
tactactact actactacta ctactactgc tgccttcttc aggggtagca ccatggtgga    60
taagctaatc aaggccagaa gatcatcatc aacaacacct                         100

<210> SEQ ID NO 91
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 91
cccaaatagg gcagcaagga tgatgatgat gaccacacaa tcctgctccc caacactctc    60
cagaccaccc aacacatcca atactactac tactactact n                       101

<210> SEQ ID NO 92
<211> LENGTH: 100
<212> TYPE: DNA
<213> ORGANISM: Cannabis sativa

<400> SEQUENCE: 92
ctactactgc tgccttcttc aggggtagca ccatggtgga taagctaatc aaggccagaa    60
gatcatcatc aacaacacct acctacatat tataacacaa                         100

<210> SEQ ID NO 93
<211> LENGTH: 101
<212> TYPE: DNA
<213> ORGANISM: Cannabis sativan
<220> FEATURE:
<221> NAME/KEY: misc_feature
<222> LOCATION: (101)..(101)
<223> OTHER INFORMATION: n is c or a

<400> SEQUENCE: 93
atgatgattt aaaatgcatt aacttcacat cccaatattt ctcaccaacc catagactca    60
taactttagc ctttccctct aaatattgga ttgcaaattt n                       101

<210> SEQ ID NO 94
<211> LENGTH: 100
<212> TYPE: DNA
<213> ORGANISM: Cannabis sativa

<400> SEQUENCE: 94
ctcggaaaag gctgcaaaaa tgataatcat aactagcata aaatattgat cttaattcat    60
aactaaacca tatatttata gaatcaaaac ttttcaaaca                         100

<210> SEQ ID NO 95
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 95
caaaaccatc gccggagaga gagaggttgt tttcagcatc tcgctcagcc ttgttgaagg    60
cattggaggc gatgaggatg gaggcgtcgc agccttcgac n                       101

<210> SEQ ID NO 96
<211> LENGTH: 100
<212> TYPE: DNA
<213> ORGANISM: Cannabis sativa

<400> SEQUENCE: 96
aggcaatcat ggaagaggag gcggagagtg gcggcagctg tggttgggac caccgattgc    60
ttttcctgta caatctgccg tacgatgtcg gggaatttcg                         100

<210> SEQ ID NO 97
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 97
tcgccttaca ggctttactt gcacagtcaa agaccggtct cagctctttg catcgtgggc    60
agatttcgat gtctatcgtt ggctggtctt tgtagtaatg n                       101

<210> SEQ ID NO 98
<211> LENGTH: 100
<212> TYPE: DNA
<213> ORGANISM: Cannabis sativa

<400> SEQUENCE: 98
ctgattgttg agaagttttt gtactcgtga aatagaagga gaggccgctg tggcttttgc    60
tgctctttcg ggttatgttg aagacacgaa gagagtgttt                         100

<210> SEQ ID NO 99
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 99
ttgggtggtg gctatggctg caggcactaa gagcaagccc acaaaccaag ctgttgaaag    60
aagcatgcag cccgtataat gccacagact ttgctgattt n                       101

<210> SEQ ID NO 100
<211> LENGTH: 100
<212> TYPE: DNA
<213> ORGANISM: Cannabis sativa

<400> SEQUENCE: 100
ttctccaatc tgaacgccac tctctccgat ctcggggctc agattcgaga gggagataag    60
tggtttgcaa cggcgcagca ggcacgggga tcagaccctg                         100

<210> SEQ ID NO 101
<211> LENGTH: 101
<212> TYPE: DNA

<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 101
gaaaacgaat gctgcaaatc gatcggtgag cctgttatgc aactcttcct tgtttatttg    60
atgatctttt tagtctcttt tcatacatta ttgtaattgt n                       101

<210> SEQ ID NO 102
<211> LENGTH: 100
<212> TYPE: DNA
<213> ORGANISM: Cannabis sativa

<400> SEQUENCE: 102
ataacaaatc ttggagctgc attgtgatga tgatgatgat gatgatgatg attgatagtc    60
atggtgttat gtttttcaca ataataaaaa aaagaaagtc                         100

<210> SEQ ID NO 103
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 103
aaagcctgct gcgcttcccg ggctcttgag gagattcttc acttacaatt tgcttagcta    60
attcttgtaa gagatcatgc atccatattt tgtcaccaac n                       101

<210> SEQ ID NO 104
<211> LENGTH: 100
<212> TYPE: DNA
<213> ORGANISM: Cannabis sativa

<400> SEQUENCE: 104
atagttacca tagatttttc tgtcaatact tttaaatcga tacccggata gcattcgcag    60
cattctaaaa tctttttcac ccgaatttcg ctctctccct                         100

<210> SEQ ID NO 105
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 105
gattataccc agaaaccaaa gcagccttag gacattccag atttcgttta caacaatcca    60
tagccgaagt acccaaaagc tcatcttccc ttctctcaaa n                       101

<210> SEQ ID NO 106
<211> LENGTH: 100
<212> TYPE: DNA
<213> ORGANISM: Cannabis sativa

<400> SEQUENCE: 106
cttaaccaag cagccagaac aattttggtg tgaacatcaa cagcatgctg ccttgctgac    60
cggagactcc gccggaaaaa tttgggatcc gagagtccct                         100

<210> SEQ ID NO 107
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 107
gattcgagtc ataacttggc acaactaaac tacagtcctg acagtcggat ccacaatctg    60
tgaaaaaagc agcaatatct cgcccagata taaaaaaccg n                      101

<210> SEQ ID NO 108
<211> LENGTH: 100
<212> TYPE: DNA
<213> ORGANISM: Cannabis sativa

<400> SEQUENCE: 108
gagtaaacac ttttcctctg ttcatcagac tgactctcct gcagcattaa attactcaat    60
tctggatgat gcaaaatcaa cttgaaacag actaagttat                        100

<210> SEQ ID NO 109
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 109
agtccagtta caacaatgtt tgagcctcaa aatagtatag agaaaaggga caatagtagc    60
aatgcaaatt ctggctctgc agccttaaca aaaacagtaa n                      101

<210> SEQ ID NO 110
<211> LENGTH: 100
<212> TYPE: DNA
<213> ORGANISM: Cannabis sativa

<400> SEQUENCE: 110
agcaccagaa aagaagctta ccctctttgc tcttaggctt gctgttcttg aaaaagcagc    60
aactggcctt ggaacacttg gttttatctg ggcaacagtt                        100

<210> SEQ ID NO 111
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 111
gttttagata ccaaaaataa aagatgtaga tgaccggagg aaacaagcag ctgggtctgc    60
caattcaaaa cagtctcagt tgcataatta cttgtcttaa n                      101

<210> SEQ ID NO 112
<211> LENGTH: 100
<212> TYPE: DNA
<213> ORGANISM: Cannabis sativa -continued

<400> SEQUENCE: 112 atctctttt tggctaatgc agctataaag catggggttc tcttctggga caacagttat    60
cagaaagaga cattattgtg gcgtgcatag attacaggtt                        100

<210> SEQ ID NO 113
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 113
ctaactcaat atgtttcatt cttgcatgat aaacagaact tgcagctggt gcactagcac    60
tcatgttgtc acaccatgtt actgatgtgc ataattgtgt n                      101

<210> SEQ ID NO 114
<211> LENGTH: 100
<212> TYPE: DNA
<213> ORGANISM: Cannabis sativa

<400> SEQUENCE: 114
tgttgtagaa agagcagcag cgaacataag ttttaagttc aagtaatttg ttagtcaaat    60
ttcaaagtga cacttccttt attggaaagg aaaaggtaca                        100

<210> SEQ ID NO 115
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 115
cccatggctt ggacgagctc cgacctgtga tcagacatcc tcgttacaag actgagattt    60
gcagaatggt tctggctggc gatccctgcc cttacggcca n                      101

<210> SEQ ID NO 116
<211> LENGTH: 100
<212> TYPE: DNA
<213> ORGANISM: Cannabis sativa

<400> SEQUENCE: 116
aggtgccatt tccgtcactc cctcactgag caggagaagt tgatgctgcc tcattgatca    60
ccatggaagt gaaattatac cctttagcag gcagattaag                        100

<210> SEQ ID NO 117
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 117
gttgtatttg ctgccacgat aaaattgctt ggacatatct aaagtagact ctgacttgct    60
ccctgatttt gtctcccggc caactttgct tgcagaaaca n                      101

```
<210> SEQ ID NO 118
<211> LENGTH: 100
<212> TYPE: DNA
<213> ORGANISM: Cannabis sativa

<400> SEQUENCE: 118
gtggctcaac ctttgctcta tattcagtat tttggttaca gctgcaggaa tggtagtcat    60
atctctcaac tgttcttcca ttgctggagc agtgaaactt                          100

<210> SEQ ID NO 119
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 119
tctttgtctt taatcatatc aaagacttct tgagcagctt ccaattgccc acacttggaa    60
tacatgtcaa caagtgaatt ccaactaaa acattatcta n                         101

<210> SEQ ID NO 120
<211> LENGTH: 100
<212> TYPE: DNA
<213> ORGANISM: Cannabis sativa

<400> SEQUENCE: 120
aagaccaatc ttaattgcaa aagcatggac ttccagccct tgttgagtg atcttagaga     60 tgcacaagct gaagctgcac ttgctatagt aactgcattc                          100

<210> SEQ ID NO 121
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 121
gacataatga gtagacaatg aaggtattaa gatgtgggcc tattcaataa caacggaagc    60
aaaatgagta ccttagcttc aggttcatct aaggtgtcta n                        101

<210> SEQ ID NO 122
<211> LENGTH: 100
<212> TYPE: DNA
<213> ORGANISM: Cannabis sativa

<400> SEQUENCE: 122
actctcacat agtgttgcaa tgatggattc gtagctgcaa gggaatagag ataaaacaaa    60
atttttaaag gagatttaat aataataata ataataataa                          100

<210> SEQ ID NO 123
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 123
```

```
aattacagga acaagggcta aagccagatc acatcacctt tttgggtgtt ttagctgcct        60
gtactcatgg aggtcttgtt gatgaaggaa gaaaatattt n                          101
```

<210> SEQ ID NO 124
<211> LENGTH: 100
<212> TYPE: DNA
<213> ORGANISM: Cannabis sativa

<400> SEQUENCE: 124

```
gaaattatga gaaaggaatt caatgtaatg ccagggctgc agcactatgc ttgctcggta        60
agtctgttag gtcgcgcagg cttgcttgac gaggcattga                            100
```

<210> SEQ ID NO 125
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 125

```
taccccatca ttatattgat tttgatgatg aggtagtgga acagggaaga gtatggcagc        60
ggctgcggca gccttggtgg tgggcttggc atcgccattg n                          101
```

<210> SEQ ID NO 126
<211> LENGTH: 100
<212> TYPE: DNA
<213> ORGANISM: Cannabis sativa

<400> SEQUENCE: 126

```
tatcgaaaag cttggcttta agtgctccta gtaagccctc tgaggctgca gagctagtag        60
gagcacacac ttgctcgaaa caaaagggct ccaagttatt                            100
```

<210> SEQ ID NO 127
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 127

```
ggtggcctta atgcctggtt cgggaacagg ctgcagcaat gacagccata gccacttgct        60
caacgctttt aggccgatta ttaatgagtc tccggtgact n                          101
```

<210> SEQ ID NO 128
<211> LENGTH: 100
<212> TYPE: DNA
<213> ORGANISM: Cannabis sativa

<400> SEQUENCE: 128

```
ctgcatccca ccaacatccc ggtggttgtg gagatgatac tagcagtact actagtcatc        60
ggtgactgca gctactatat atatatatat atatatatat                            100
```

<210> SEQ ID NO 129
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 129 ccatttctcgc cttacaggct ttacttgcac agtcaaagac cggtctcagc tctttgcatc    60
gtgggcagat ttcgatgtct atcgttggct ggtctttgta n                       101

<210> SEQ ID NO 130
<211> LENGTH: 100
<212> TYPE: DNA
<213> ORGANISM: Cannabis sativa

<400> SEQUENCE: 130
taatgtctga ttgttgagaa gtttttgtac tcgtgaaata gaaggagagg ccgctgtggc    60
ttttgctgct ctttcgggtt atgttgaaga cacgaagaga                          100

<210> SEQ ID NO 131
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 131
tgtaggctgg agtttctgaa catgcaaaag cattagggcc aaaagggtca gatgcccaca    60
aagcagctgt aataggtgac acaattgggg atccccttaa n                       101

<210> SEQ ID NO 132
<211> LENGTH: 100
<212> TYPE: DNA
<213> ORGANISM: Cannabis sativa

<400> SEQUENCE: 132
gacacttctg gtccttcact taatattctc atcaaactta tggcagttga gtctttggtc    60
tttgctccat tctttgctgc tcatgggggc ttaatcttca                          100

<210> SEQ ID NO 133
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 133
tcctccgtta cttggatcaa ttcggtaaga caaaagtcca cactaatctc tgtcccttt     60 tcgggcaccc gaatccccca ggtccatgcc cctgcccgct n                       101

<210> SEQ ID NO 134
<211> LENGTH: 100
<212> TYPE: DNA
<213> ORGANISM: Cannabis sativa

<400> SEQUENCE: 134
aggcaggcat ggggcagcct agatgccctg atagggcgtc ttagggcagc ttttgaggag    60
catgggggaa aacccgaggc gaacccttcc ggggctcggg                          100

<210> SEQ ID NO 135

<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 135
gggttcaagc tccatcaaga ctttggctgc tcgtcttccc agcttttcgt tcttatgtac    60
cctgcaactt ctcaaaaacg agctccacat catcgtgtct n                      101

<210> SEQ ID NO 136
<211> LENGTH: 100
<212> TYPE: DNA
<213> ORGANISM: Cannabis sativa

<400> SEQUENCE: 136 cgtttcccctt tgccttaatt agcagcttct cggcttcatc tagtaagcct gcacggccta    60
agagatcaac catacatgaa taatgttgtc gatcagggca                        100

<210> SEQ ID NO 137
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 137
gagaaaattc tatagctcac aggctttagg gggtcaccaa aatgctcaca agagagaaag    60
aggagcagcc aagaggtacc actctcatag aatgatgatg n                      101

<210> SEQ ID NO 138
<211> LENGTH: 100
<212> TYPE: DNA
<213> ORGANISM: Cannabis sativa

<400> SEQUENCE: 138
acacaatggg cttgggcttt aacccttttca cccaactcac tacacctcga tctcttggag    60
tccaggccca ctctctcgtt cacaagccca atagcagaga                        100

<210> SEQ ID NO 139
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 139
ccactctcat agaatgatga tgaacacaat gggcttgggc tttaaccctt tcacccaact    60
cactacacct cgatctcttg gagtccaggc ccactctctc n                      101

<210> SEQ ID NO 140
<211> LENGTH: 100
<212> TYPE: DNA
<213> ORGANISM: Cannabis sativa

<400> SEQUENCE: 140
ttcacaagcc caatagcaga gaagtagcgt cctctgctgc tatggttgca agatttagtg    60

```
atgctgaaac tggatttggg tctgggtctg ggcctgggcc                    100
```

<210> SEQ ID NO 141
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 141

```
agcttgtctc ccccacggca gccactagcc agctgccact tgtccgcctc tcgttcaatc    60
cgagctccag cagcctccca tgtgcgccaa gtgtcgtctc n                       101
```

<210> SEQ ID NO 142
<211> LENGTH: 100
<212> TYPE: DNA
<213> ORGANISM: Cannabis sativa

<400> SEQUENCE: 142

```
tccttccatc cgccattttc aaattatttt gatgctgcca agtgtcccaa tgcatgaaaa    60
agtactcaaa atgtcaattt caaaaataca ttacaatttt                        100
```

<210> SEQ ID NO 143
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 143

```
ctcactttc gaggagatgc ttacctatcg aaatgatcat cgatgcaaaa gtaatggctt     60
ctacacttac gacgccttca taactgctgc tagaattttt n                      101
```

<210> SEQ ID NO 144
<211> LENGTH: 100
<212> TYPE: DNA
<213> ORGANISM: Cannabis sativa

<400> SEQUENCE: 144

```
cgggctttga tactactggc tctcttgaaa ctcgtacaag agaactagct gcgttctttg    60
gccaaacttc tcaggaaacc acaggaatac atactggttc                        100
```

<210> SEQ ID NO 145
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 145

```
gaggagatgc ttacctatcg aaatgatcat cgatgcaaaa gtaatggctt ctacacttac    60
gacgccttca taactgctgc tagaattttt ccgggctttg n                      101
```

<210> SEQ ID NO 146
<211> LENGTH: 100
<212> TYPE: DNA

<213> ORGANISM: Cannabis sativa

<400> SEQUENCE: 146
tactactggc tctcttgaaa ctcgtacaag agaactagct gcgttctttg gccaaacttc    60
tcaggaaacc acaggaatac atactggttc atttatacat    100

<210> SEQ ID NO 147
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 147
tgcttaccta tcgaaatgat catcgatgca aaagtaatgg cttctacact tacgacgcct    60
tcataactgc tgctagaatt tttccgggct ttgatactac n    101

<210> SEQ ID NO 148
<211> LENGTH: 100
<212> TYPE: DNA
<213> ORGANISM: Cannabis sativa

<400> SEQUENCE: 148
ggctctcttg aaactcgtac aagagaacta gctgcgttct ttggccaaac ttctcaggaa    60
accacaggaa tacatactgg ttcatttata catgaaatgt    100

<210> SEQ ID NO 149
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 149
cgagctcaag catttcattc tctcgattct cgacgacccg attgtcagtc gagttttttgg    60 ggaagccgga tttaggagct gcgatatcaa gctagcgatt n    101

<210> SEQ ID NO 150
<211> LENGTH: 100
<212> TYPE: DNA
<213> ORGANISM: Cannabis sativa

<400> SEQUENCE: 150
ttcatccacc gacaccggcg aggcaagcct cctcattcat tagggccgc tgcccaccca    60 tgttcctctg taatcttact gattcggatc cgggtcttcg    100

<210> SEQ ID NO 151
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 151
caacgctctt cttggccatg gagacaactc ccctgaccgg agtcccacca ccattggcgg    60
agccgaaaga gcggagcgtg gaggcgacgg cgtgggagaa n    101

<210> SEQ ID NO 152
<211> LENGTH: 100
<212> TYPE: DNA
<213> ORGANISM: Cannabis sativa

<400> SEQUENCE: 152
agagggtcgg ctgctgtgaa gccgaggcga gggagtgtgg tggggcggag acggagggaa    60
gagggtgaga gttgaaggag agaagaacga gtgcgggaag                         100

<210> SEQ ID NO 153
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 153
cctttgggga agcggccgaa ccatggctcg gtttccctgg tccatttcct ttttcgggtg    60
gggaaacagt gtcagcagca tggtttgttg tttcgttgct n                       101

<210> SEQ ID NO 154
<211> LENGTH: 100
<212> TYPE: DNA
<213> ORGANISM: Cannabis sativa

<400> SEQUENCE: 154
ggtgcctgtt gaggagggggt tgatgagtta ccagagcccg atggagggag gaaaactcca    60
gtgccaggaa caggcaagcg aggtggagga tgcctcggtg                         100

<210> SEQ ID NO 155
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 155
cattgaccgc catggatccc catcagctgc ttttggcagt atccccttc ggctccgcga     60 accaaatcct ctctcctcct ccgtcatctg acgatggaag n                       101

<210> SEQ ID NO 156
<211> LENGTH: 100
<212> TYPE: DNA
<213> ORGANISM: Cannabis sativa

<400> SEQUENCE: 156
ggcggtttcg atgattacgg agcgtggtat gggaatatcc agtacttgat taacatttcg    60
gcgattgggg cattcttctg cgtcttcata ttcgtcttct                         100

<210> SEQ ID NO 157
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 157
aagaaggaag aggttgccat ccgggcatgg cgagaagcgc attagccggg ttgattgaag    60
ccggatcaat actcgtcgct actagcagcg tcaccatctc n    101

<210> SEQ ID NO 158
<211> LENGTH: 100
<212> TYPE: DNA
<213> ORGANISM: Cannabis sativa

<400> SEQUENCE: 158
ctatctctct ttagttcact gtcgagtgga atttagtaga agaaaaagtt ggccgacgta    60
caaagagaaa agaagagaag agagtggagt cttattacat    100

<210> SEQ ID NO 159
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 159
gaagagctat ctttagaaag taatgacaaa atctcttcag caagtgaatt taggttcaca    60
gcagcagaaa gcccaaaaag aacctgataa ttaaatgatt n    101

<210> SEQ ID NO 160
<211> LENGTH: 100
<212> TYPE: DNA
<213> ORGANISM: Cannabis sativa

<400> SEQUENCE: 160
aaaagcataa aaatcaaca cattccaata cattttgcaa caattcaatc aaaacaaaca    60
ccaaaagaaa atttgttgtt gcagcaaaag acacaatgaa    100

<210> SEQ ID NO 161
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 161
gtcttacatt ttatattctt tttcagatat ggtatgcagc ttcaaaagct agagctgaga    60
aagctggttg ggaatttgca aaagagaatg ggattgaatt n    101

<210> SEQ ID NO 162
<211> LENGTH: 100
<212> TYPE: DNA
<213> ORGANISM: Cannabis sativa

<400> SEQUENCE: 162
atcaccattc atccaggagt aacacttggc cctctcttgc agcccattat gaatgacagt    60
gtcagtctca ttatgaatct aacaaatggt acacatcatg    100

<210> SEQ ID NO 163
<211> LENGTH: 101
<212> TYPE: DNA
<213> ORGANISM: Cannabis sativa

```
<220> FEATURE:
<221> NAME/KEY: misc_feature
<222> LOCATION: (101)..(101)
<223> OTHER INFORMATION: n is t or a

<400> SEQUENCE: 163
aatggatcct tttgcggcct ctgcaagtga ataactttc ccagctttct tcttttttgtt      60 gttattatta ttactttggt tcccgttttg catagctttc n                          101

<210> SEQ ID NO 164
<211> LENGTH: 100
<212> TYPE: DNA
<213> ORGANISM: Cannabis sativa

<400> SEQUENCE: 164
tgtcactgga ctcagctgaa gctcgattac cctgctgaga ggaagctgca ttcttttag       60 cttctgtctg attactgggg gctgtaacaa cttttggtgt                            100

<210> SEQ ID NO 165
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 165
tgctgcttct taagagtttt ttaaccccaa tcgccccgcc cctgctcgac aattagaaaa      60
ccacacaaac aaccctgcaa ctccatttca cagctccatg n                          101

<210> SEQ ID NO 166
<211> LENGTH: 100
<212> TYPE: DNA
<213> ORGANISM: Cannabis sativa

<400> SEQUENCE: 166
aacagctgat catcaacatt gcaaatcaag caaaggctgc aacgtctaaa aggccattgt      60
gcctaagcag tgcctcaggt gaaggttcgc ggcctcggaa                            100

<210> SEQ ID NO 167
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 167
ttaatttgaa ttagttatga tttttttgaag tttcggaaaa atcagaatcg tgcaacaggg     60
ccacgcgcga ggacagcacg cattcagaaa agctgctcga n                          101

<210> SEQ ID NO 168
<211> LENGTH: 100
<212> TYPE: DNA
<213> ORGANISM: Cannabis sativa

<400> SEQUENCE: 168
gagcgcctgt ctgaaccgct catccgcgcg tggaaatgct gcaaactcct ccctgcgccg      60
aggtttctcg gccaagcact cccttgcgc acgcggaaat                             100
```

<210> SEQ ID NO 169
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 169
ggctcatgcc actgttgctg ccacttaaac tatcatcatc gctagaatct tcaagttcgc     60
ttggtggata accatggtca tctgaagtat tccatgaata n                        101

<210> SEQ ID NO 170
<211> LENGTH: 100
<212> TYPE: DNA
<213> ORGANISM: Cannabis sativa

<400> SEQUENCE: 170
cgactagtga ataactggt atctagtgca ctctccgacg agggaacaaa tgcagcctgc      60
acaaataatg agtcgagtta atgtatagga agcgcaacca                          100

<210> SEQ ID NO 171
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 171
cttcaaaact agtaataata attattgggt ggtggctatg gctgcaggca ctaagagcaa     60
gcccacaaac caagctgttg aaagaagcat gcagcccgta n                        101

<210> SEQ ID NO 172
<211> LENGTH: 100
<212> TYPE: DNA
<213> ORGANISM: Cannabis sativa

<400> SEQUENCE: 172
aatgccacag actttgctga tttcttctcc aatctgaacg ccactctctc cgatctcggg     60
gctcagattc gagagggaga taagtggttt gcaacggcgc                          100

<210> SEQ ID NO 173
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 173
gcatgtatcc agacccaaag ctggcgaaaa caagacccta aatctgtagt ctctggtttc     60
acagatccta gactgttaac agcatcagca gcagcagcag n                        101

<210> SEQ ID NO 174
<211> LENGTH: 100
<212> TYPE: DNA
<213> ORGANISM: Cannabis sativa

<400> SEQUENCE: 174

```
attatcccta tttcgtaagg aacaaggacg ccacatatat gttacaggag cgatcggctt    60
agaaactggt gcaccaatat ggtggagctg caacatgggg                         100

<210> SEQ ID NO 175
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 175
tctgtagtct ctggtttcac agatcctaga ctgttaacag catcagcagc agcagcagta    60
ttatccctat ttcgtaagga acaaggacgc cacatatatg n                      101

<210> SEQ ID NO 176
<211> LENGTH: 100
<212> TYPE: DNA
<213> ORGANISM: Cannabis sativa

<400> SEQUENCE: 176
tacaggagcg atcggcttag aaactggtgc accaatatgg tggagctgca acatggggat    60
tagtcagaca tagccaattc cttaatccac ctcaatgaaa                         100

<210> SEQ ID NO 177
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 177
tttttgatgt taagaattgt acgttgagac atgagaacta gcagcgagtg tttctcacct    60
gcatcatagt ttttgagaaa gtcaggagac aaattatggt n                      101

<210> SEQ ID NO 178
<211> LENGTH: 100
<212> TYPE: DNA
<213> ORGANISM: Cannabis sativa

<400> SEQUENCE: 178
tgcttcttgc tgccagtttc tcaaagaggc tcataatgtt atgataagct tttgcaaaca    60
tagagaaaaa taggatgaaa cagagagttg tattaataat                         100

<210> SEQ ID NO 179
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 179
tgagttttgc aggcgcagct cggcctgatg caccagagaa cataaggtcc attctcatca    60
atcagtgcac ctcagtagat gatcaagact gtcaatttct n                      101

<210> SEQ ID NO 180
```

```
<211> LENGTH: 100
<212> TYPE: DNA
<213> ORGANISM: Cannabis sativa

<400> SEQUENCE: 180
gactgcaatt caggtggctg cagccaaccc gagtctgtta tcgagctttt catggagtct      60
gaattctgtt tgcagccacc aggagatagc ccaactagaa                          100

<210> SEQ ID NO 181
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 181
gaacttgatc aatcccataa ctcagtcctc cattgtcatg gagccagcgg ctcttctccc      60
taccctgcaa atcaaaagag tcttggctgc cataaaaccc n                        101

<210> SEQ ID NO 182
<211> LENGTH: 100
<212> TYPE: DNA
<213> ORGANISM: Cannabis sativa

<400> SEQUENCE: 182
gacatgttct tccgctgaat gaggcaccca taactcttgc aagtataagg atcccaaatg      60
atgctgctgt ccggcgggat tgaccagagg ctgtctggaa                          100

<210> SEQ ID NO 183
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 183
tgcctaattt gttgtttatt tgtcattggt ggcagcatga tgctgcatgc cgtgtgattg      60
caagactaaa gaaagaaaga gatgaagcaa gatcactact n                        101

<210> SEQ ID NO 184
<211> LENGTH: 100
<212> TYPE: DNA
<213> ORGANISM: Cannabis sativa

<400> SEQUENCE: 184
gctcaggctg agagacacat ccccgcatca acacccatta cagtaaatgc gtctgcagtt      60
agcaatggaa gaacaggtcc tttttgtttt atatatgctg                          100

<210> SEQ ID NO 185
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 185
ggccgttctt ggggacgacc tctccgtccg attcgccaaa ctcagagcct ccttgtctca      60
```

```
gtcgcctgct gcttccattt ccggcactgg tggcgttcgt n                101
```

<210> SEQ ID NO 186
<211> LENGTH: 100
<212> TYPE: DNA
<213> ORGANISM: Cannabis sativa

<400> SEQUENCE: 186

```
ccaatacaaa attggagagc cttggtgatg aagatgaaga ggaggatgaa gatgatgagg    60
ttgagaagtt gattaggtgg gccaaggacg ctgctcgcct                        100
```

<210> SEQ ID NO 187
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 187

```
tacatacata catacacaaa taaataatta taaatagtaa tacctccact agagcagcct    60
ctttcctggg aagtgaccca attatggcgg gagacacacc n                      101
```

<210> SEQ ID NO 188
<211> LENGTH: 100
<212> TYPE: DNA
<213> ORGANISM: Cannabis sativa

<400> SEQUENCE: 188

```
gcgtctctgg cacctgcaac cattgcagct tcggtccacc ccaacttaag ctgcaccaac    60
tcatcccaaa cgctacaatt aaaaattcac ccccaatttt                        100
```

<210> SEQ ID NO 189
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 189

```
ttttaggtgt tttgaaacag tctcagaatc agcatacgaa ttttgtcttg ctgaacactg    60
atgctgcttg ggcaagaaat gtagagaaaa gatccgtttg n                      101
```

<210> SEQ ID NO 190
<211> LENGTH: 100
<212> TYPE: DNA
<213> ORGANISM: Cannabis sativa

<400> SEQUENCE: 190

```
agtaatggaa agttggtttc tatcgatgtc ttcgagtttg tttctgctgc taagaattac    60
tggtcttcag aagttctctc tgttggtttt atggttctac                        100
```

<210> SEQ ID NO 191
<211> LENGTH: 101
<212> TYPE: DNA
<213> ORGANISM: Cannabis sativa
<220> FEATURE:
<221> NAME/KEY: misc_feature
<222> LOCATION: (101)..(101)

<223> OTHER INFORMATION: n is t or c

<400> SEQUENCE: 191
tattcccttc ttgggtgcaa atgtgacatt agaatcttta ccaattgtgt tagcatgctg    60
ccctttctct atgggttacg aatcgcttct gagatatctt n    101

<210> SEQ ID NO 192
<211> LENGTH: 100
<212> TYPE: DNA
<213> ORGANISM: Cannabis sativa

<400> SEQUENCE: 192
taccacctgt gtgctgcaaa ttcttaaacc tgtcattcct ctttctattg atgactgtag    60
tcattaaaaa aaattattaa cttaaactaa agttaggttg    100

<210> SEQ ID NO 193
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 193
tcactctctt cctaatggga ttgaccatta gttggaatgg ttctgctgca aatggtccca    60
tgtttgctga ggttgtccca gccaagcacc ggaccatgat n    101

<210> SEQ ID NO 194
<211> LENGTH: 100
<212> TYPE: DNA
<213> ORGANISM: Cannabis sativa

<400> SEQUENCE: 194
tatgcctttg atcgagcttt cgagggctcg gtctcttcct tcgcagctcc cttggttgga    60
attctgtcgg agaaaatgtt cgggtatgat tcgaaagggg    100

<210> SEQ ID NO 195
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 195
taatgggatt gaccattagt tggaatggtt ctgctgcaaa tggtcccatg tttgctgagg    60
ttgtcccagc caagcaccgg accatgatct atgcctttga n    101

<210> SEQ ID NO 196
<211> LENGTH: 100
<212> TYPE: DNA
<213> ORGANISM: Cannabis sativa

<400> SEQUENCE: 196
cgagctttcg agggctcggt ctcttccttc gcagctccct tggttggaat tctgtcggag    60
aaaatgttcg ggtatgattc gaaaggggtg gatccattgt    100

<210> SEQ ID NO 197
<211> LENGTH: 101

<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 197
tgaccattag ttggaatggt tctgctgcaa atggtcccat gtttgctgag gttgtcccag      60
ccaagcaccg gaccatgatc tatgcctttg atcgagcttt n                         101

<210> SEQ ID NO 198
<211> LENGTH: 100
<212> TYPE: DNA
<213> ORGANISM: Cannabis sativa

<400> SEQUENCE: 198
gagggctcgg tctcttcctt cgcagctccc ttggttggaa ttctgtcgga gaaaatgttc     60
gggtatgatt cgaaggggt ggatccattg ttggggtcta                           100

<210> SEQ ID NO 199
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 199
cagagaaaga agagaaaggt actaaaattg gcacagacta accgggcctc catggtgttg     60
agtgggcccc cacccacgaa ctgtaacggg gcccattcat n                         101

<210> SEQ ID NO 200
<211> LENGTH: 100
<212> TYPE: DNA
<213> ORGANISM: Cannabis sativa

<400> SEQUENCE: 200
gggacacgtg tcaagcatca ctcggttgag agtggggccc atcacagggt ggactcgagg     60
tgggcctttt gcctgtttca tgctgcgtca ggtaaaacca                          100

<210> SEQ ID NO 201
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 201
tccagtagcc aaggtcatcg gcggtgccct aaacaagctc tccaagatta aggttgtgag     60
gcttttaagt ttgattgct cgtgtgttga cggtgatatc n                          101

<210> SEQ ID NO 202
<211> LENGTH: 100
<212> TYPE: DNA
<213> ORGANISM: Cannabis sativa

<400> SEQUENCE: 202
cgaatgcata aggctgctgt aaagaatgtt tacgagaaca agaggttcat tccactcgat     60
ctccatagga agaagatcag ggagatttgc agaaggctta        100

<210> SEQ ID NO 203
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 203
tcttattcaa ccaaatgcca taaccggcca tagctgcata aaaaatatca gctataaacc        60
tcctgggctt tctgctattc atccaatgta tccagtcctc n        101

<210> SEQ ID NO 204
<211> LENGTH: 100
<212> TYPE: DNA
<213> ORGANISM: Cannabis sativa

<400> SEQUENCE: 204
tgaacactcg gccaaagctt gctgcctagc cccttcccaa tgagatgcat aactggccaa        60
gagtaaggac aagagaaaaa taaatcagaa tggctccaaa        100

<210> SEQ ID NO 205
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 205
atgaccgctg ttccaatgct gccaacttgg tgactgaaac aaagtttact tcatgttact        60
agtgttcctc tgccattggg cagctcgcaa aaggtcggaa n        101

<210> SEQ ID NO 206
<211> LENGTH: 100
<212> TYPE: DNA
<213> ORGANISM: Cannabis sativa

<400> SEQUENCE: 206
aaggaagaca aagagagcga gctacaatct ctggcagcag cagccttgga gaaggactac        60
aaacgaagag cacctgcaac actgtccttg attacgaccg        100

<210> SEQ ID NO 207
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 207
tagtagtggt agtgccactc tcggtggttt agccaaaatc gccctccaag cagcggcttc        60
aagtgccaaa acacccaag cccagatcac tagcctactc n        101

<210> SEQ ID NO 208
<211> LENGTH: 100
<212> TYPE: DNA
<213> ORGANISM: Cannabis sativa

<400> SEQUENCE: 208
aaaccgctac cgataagagt gtcatagcgg ccttgaagga ttgcagtgat aattatgata      60
gcgccaatga ggaactcggt gactcgctca aagctattga                          100

<210> SEQ ID NO 209
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 209
tgtacaaaga tctttgtgag aagacactgc gagcagaccc tagtagtggt agtgccactc      60
tcggtggttt agccaaaatc gccctccaag cagcggcttc n                        101

<210> SEQ ID NO 210
<211> LENGTH: 100
<212> TYPE: DNA
<213> ORGANISM: Cannabis sativa

<400> SEQUENCE: 210
agtgccaaaa acacccaagc ccagatcact agcctactca aaaccgctac cgataagagt      60
gtcatagcgg ccttgaagga ttgcagtgat aattatgata                          100

<210> SEQ ID NO 211
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 211
tccaatttca gtgagagaga gagctgctgt atggaagcta aaaaaaagca gcaatgacaa      60
gaatcaaggt tgaccagctg aggcagaaga acaagacctt n                        101

<210> SEQ ID NO 212
<211> LENGTH: 100
<212> TYPE: DNA
<213> ORGANISM: Cannabis sativa

<400> SEQUENCE: 212
tgaacaagct tagggatctc aaggctgagc tccttttcct tccagtagcc aaggtcatcg      60
gcggtgccct aaacaagctc tccaagatta aggttgtgag                          100

<210> SEQ ID NO 213
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 213
actgctggaa atggtagtgt tcttttcact atttcttaag ttgcctccca gagaggtagt      60
ttcatcaatg tgcaagctgc tgtcttcatc catggtggtc n                        101

<210> SEQ ID NO 214
<211> LENGTH: 100
<212> TYPE: DNA
<213> ORGANISM: Cannabis sativa

<400> SEQUENCE: 214
tccctaaatc taacaaacca acttttgcac agttttctgc tgacaaagta gcatcttttt        60
ggacactatt atcatgcaat gcagcgacct caatactaca                             100

<210> SEQ ID NO 215
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 215
ctgtaatagc tgctgctgct gctgaagctg ttactcttgc aaaagcagct gtgagggttg        60
caaaggatgc tgctctgcta gtgaaaactt ctgaaaaaca n                           101

<210> SEQ ID NO 216
<211> LENGTH: 100
<212> TYPE: DNA
<213> ORGANISM: Cannabis sativa

<400> SEQUENCE: 216
caaagtactt ctgtagttac tttagaagct agttattcgg attttaaggg tgttcataat        60
atgaaaacta cacaagctgc tgtattagga gattctgtgg                             100

<210> SEQ ID NO 217
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 217
ttcttggttg gtgtatattg cagcactttc acccttgaag attaggctag ggggcacttt        60
acaagacaaa gtcatatacc agaacgagag tgaaaaaact n                           101

<210> SEQ ID NO 218
<211> LENGTH: 100
<212> TYPE: DNA
<213> ORGANISM: Cannabis sativa

<400> SEQUENCE: 218
aagcagccca atcttgtact cactttgatt ttgttaaaaa tggctctgaa ttatttagct        60
tctctcatgg ttgcttatct atgtctcggt gggatcaact                             100

<210> SEQ ID NO 219
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 219

```
catatacatg ctgactgggc agcatgtgta ggacacaaga aggtccaaaa caggttttg      60 tgttttcctt gggagatctt tagtgtcctg gaaaagtaag n                         101

<210> SEQ ID NO 220
<211> LENGTH: 100
<212> TYPE: DNA
<213> ORGANISM: Cannabis sativa

<400> SEQUENCE: 220
aacaacacgc aataccgagg tcctcagctg aagctgattg tagggctatg tgaaacacta     60
gtgaattggt atggctgcta tcattactaa aggaactgaa                          100

<210> SEQ ID NO 221
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 221
gaggtagact ttgtattttg aagcttttgg atattagagc tatcagggtt ttaatggctt     60
cccaggtgaa taacgatggc gttgagaaat tgttagctgc n                        101

<210> SEQ ID NO 222
<211> LENGTH: 100
<212> TYPE: DNA
<213> ORGANISM: Cannabis sativa

<400> SEQUENCE: 222
agcaagtcat tgagggttag cttagagaaa tcaaagtccc tagggttagc tctacagaag     60
acaggaccta gattggaaga gattaaccaa cgattacctg                          100

<210> SEQ ID NO 223
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 223
acactttcat taaatatatg tccggtatgt acagaacgca acattcatgg cataattaac     60
acgtcagcca ataacattc aatcataatc aattgcagca n                         101

<210> SEQ ID NO 224
<211> LENGTH: 100
<212> TYPE: DNA
<213> ORGANISM: Cannabis sativa

<400> SEQUENCE: 224
tgcatcttta gacaaattac acattgaagt tgatacttct agctgagcta ggctaggccg     60
actcgcagct aatatttaat caaataaaaa gtacctaaaa                          100

<210> SEQ ID NO 225
<211> LENGTH: 101
<212> TYPE: DNA
<213> ORGANISM: Cannabis sativa
<220> FEATURE:
```

```
<221> NAME/KEY: misc_feature
<222> LOCATION: (101)..(101)
<223> OTHER INFORMATION: n is g or t

<400> SEQUENCE: 225
aggtgagata tgagaagggt cgaatggtaa aatatacaat gtgcaattta ttggctaaga      60
gaaatagtaa aaagagcaca tgtatttgct gctgaaactc n                        101

<210> SEQ ID NO 226
<211> LENGTH: 100
<212> TYPE: DNA
<213> ORGANISM: Cannabis sativa

<400> SEQUENCE: 226
gattgaagga ggagcggaca agtgtcgctc atgtgatggc tggaggagag gagctgctgg     60
agagagaggg gacaggcggg tcccacgcag ctggcgctgg                          100

<210> SEQ ID NO 227
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 227
gttgatactt gactaatttc atatggtgct gtggaaatgt aacaggtgga tgttgtggat     60
acagttggtt gcggggatag ttttgtagct gctattgcat n                        101

<210> SEQ ID NO 228
<211> LENGTH: 100
<212> TYPE: DNA
<213> ORGANISM: Cannabis sativa

<400> SEQUENCE: 228
tggttttata aacagtttgc cgatggctag tacgctgtca attgcaaacg cagttggtgc     60
tgcaactgct atgggttgtg gtgctggtag gaatgtggca                          100

<210> SEQ ID NO 229
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 229
tataggtgtg ttcggctatg gagataagtg gattcttctt gtgcttagtt ggggcagcga     60
gaataacgca cagagctcaa aggatagtgt cgatagcaac n                        101

<210> SEQ ID NO 230
<211> LENGTH: 100
<212> TYPE: DNA
<213> ORGANISM: Cannabis sativa

<400> SEQUENCE: 230
agatggcacg tgcttgtcac atgcgcatca gcagctggtg ggccggaccc atccaaagcc     60
cattttctag aagccaattg caaggatgat cagcagaggt                          100
```

```
<210> SEQ ID NO 231
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 231
ttcttactcc gatgtgctgt gcagatcact ggtcagtcag cattatcatt caagggaagc    60
ccctactgga tggcacctga ggtaaaaatc ttatgaagtt n                       101

<210> SEQ ID NO 232
<211> LENGTH: 100
<212> TYPE: DNA
<213> ORGANISM: Cannabis sativa

<400> SEQUENCE: 232
tttttgctgc ttgtcttgat attctttcat tgtgtatgat cttgattcta tttcatcctt    60
cttcctgcct ttctcccagg taataaagaa ttcaactggc                         100

<210> SEQ ID NO 233
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 233
atttgagatc cttagccgat agaatttgtt ggttaagtct ctgaatctcc tcatcagctt    60
gttttagttc cttatcccaa ttaagagaat cttgctccct n                       101

<210> SEQ ID NO 234
<211> LENGTH: 100
<212> TYPE: DNA
<213> ORGANISM: Cannabis sativa

<400> SEQUENCE: 234
gccatggacg ctccaattct tgttcctct gcttccaaat gtgcagcatg tgcagactcc     60
aacgactcct tcgttgcaat cagctcgata gtgagttcct                         100

<210> SEQ ID NO 235
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 235
ttggttcttc tattgggttt actatacttt ggaacatgaa taggcgaggg tggattgagt    60
attctgtggc tgccttgatt tggtccgtgg ggaatttggg n                       101

<210> SEQ ID NO 236
<211> LENGTH: 100
<212> TYPE: DNA
<213> ORGANISM: Cannabis sativa

<400> SEQUENCE: 236
```

```
atgacactgc ttccaaagca gagagttcca aaggtttggg gagttcccat ggttccatgg      60
ctgccatctc tgtctattgt ggttaatctt tttcttattg                          100

<210> SEQ ID NO 237
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 237
ggaacatgaa taggcgaggg tggattgagt attctgtggc tgccttgatt tggtccgtgg      60
ggaatttggg gatgacactg cttccaaagc agagagttcc n                        101

<210> SEQ ID NO 238
<211> LENGTH: 100
<212> TYPE: DNA
<213> ORGANISM: Cannabis sativa

<400> SEQUENCE: 238
aaggtttggg gagttcccat ggttccatgg ctgccatctc tgtctattgt ggttaatctt      60
tttcttattg ggtctttggg aatggtggcc ttcttcaggt                          100

<210> SEQ ID NO 239
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 239
gtattggacc tcgatctctc aactttcgac cggcttctgg aggtgaacgc ccgaggagtt      60
gcggcgtgcg tgaagcatgc ggcgcgtgcg atggtggagc n                        101

<210> SEQ ID NO 240
<211> LENGTH: 100
<212> TYPE: DNA
<213> ORGANISM: Cannabis sativa

<400> SEQUENCE: 240
gcgcgtgaga ggaagcgttg tttgcacgga gagcgtggct gcctctgtcg gtttgaggac      60
acggacagat tactgcatgt cgaaacacgc ggtgttgggg                          100

<210> SEQ ID NO 241
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 241
gtcaccaaat aaatattgtt ttttaatatt tcagaggagg ttttgcaggg agttgctgct      60
ggcatcgatc ttttcgactc tgagtatgtt tgtcctttct n                        101

<210> SEQ ID NO 242
<211> LENGTH: 100
```

```
<212> TYPE: DNA
<213> ORGANISM: Cannabis sativa

<400> SEQUENCE: 242
ctgcatatca ttttacatttt tcatgtttct ttctgctgct aacttggcca aactccgatg    60
atgtaaatga ctgttttgca ggtatattta ccatcttaca                          100

<210> SEQ ID NO 243
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 243
aaactttggc tgcacctcct gctgaagaga gtgtgcattg cgctgttgct gtagaagcca    60
gtttagttgg caagagactg ctgagaactc gtgttacttc n                       101

<210> SEQ ID NO 244
<211> LENGTH: 100
<212> TYPE: DNA
<213> ORGANISM: Cannabis sativa

<400> SEQUENCE: 244
tgcattgttg gccgatcagt tggttgtttc ttgctgcaaa gcaatgcaag ttgaaatacc    60
ttcctaaccg ccccgagatc cttacatgta gctgtgattt                         100

<210> SEQ ID NO 245
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 245
cacaaacgtt tttatcagct ctccatcttc gctacaagtt tcattagata tttgacagcc    60
agacatggca tctaatatgc atgcattgga tgcagtaatc n                       101

<210> SEQ ID NO 246
<211> LENGTH: 100
<212> TYPE: DNA
<213> ORGANISM: Cannabis sativa

<400> SEQUENCE: 246
gggagtgctg agaatcaatg tttcttagag catcaggcac caactccata gcttcatcac    60
tggaggtagc agcggacact ccattttgat caacaggcaa                         100

<210> SEQ ID NO 247
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 247
ccttagcatc tcctgatttt tatgatgtga gtcttgttga cggtttcaac ttgcccatag    60
```
tcgtcacacc actccacggg caaggaaatt gcagcgtggc n                               101

<210> SEQ ID NO 248
<211> LENGTH: 100
<212> TYPE: DNA
<213> ORGANISM: Cannabis sativa

<400> SEQUENCE: 248
ggatgtgatg gcgacctccg gaccagttgc cctaacgagc tggcggtcaa gagcaatggg         60
aaaacgattg cctgccggag cgcgtgtgac gtgttcgata                              100

<210> SEQ ID NO 249
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 249
caagaacttg ccttgctgct gcatctgctg aactgcagac aacattcatt gctccaatcc         60
tttctgaata aagacccaaa tttttactgt aagactgagc n                            101

<210> SEQ ID NO 250
<211> LENGTH: 100
<212> TYPE: DNA
<213> ORGANISM: Cannabis sativa

<400> SEQUENCE: 250
atcaaaactt ccatgccacg tgcagcaaac agtctcaccg atgatgcatc agcatcaagg         60
cttccactag caaatccctt taagaaaaa taaataata                                100

<210> SEQ ID NO 251
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 251
tatacaacag agacttcact gccaaactta atctctctgt ttaagcagca ccaccagtcc         60
accaccaaac acatttgagc aaacactact agttctcatc n                            101

<210> SEQ ID NO 252
<211> LENGTH: 100
<212> TYPE: DNA
<213> ORGANISM: Cannabis sativa

<400> SEQUENCE: 252
tcatcatcat catacaacca gagaaaaaaa aaaacagtga tgcattttac agagaaagaa         60
aaaagctgca atgatttcta agcagccttt ttttaaacaa                              100

<210> SEQ ID NO 253
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 253
ttatcagctc tccatcttcg ctacaagttt cattagatat ttgacagcca gacatggcat    60
ctaatatgca tgcattggat gcagtaatca gggagtgctg n                       101

<210> SEQ ID NO 254
<211> LENGTH: 100
<212> TYPE: DNA
<213> ORGANISM: Cannabis sativa

<400> SEQUENCE: 254
gaatcaatgt ttcttagagc atcaggcacc aactccatag cttcatcact ggaggtagca    60
gcggacactc cattttgatc aacaggcaaa gagagatcat                         100

<210> SEQ ID NO 255
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 255
atacttcata ttccatttct ctatctccac tctgcctctg gcatgaagta gtccttcagg    60 tggttttgc agcagaaaga tctacggcct gaaaactcgc n                        101

<210> SEQ ID NO 256
<211> LENGTH: 100
<212> TYPE: DNA
<213> ORGANISM: Cannabis sativa

<400> SEQUENCE: 256
gttaaatctt ccaccttccg ctgcaaaaga ggaacattta taaatcaatg tacaatatca    60
gaactagggg tgtgcataaa tcgattaaat ccattaacaa                         100

<210> SEQ ID NO 257
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 257
gctaatggct cttattggtc agtcgttgaa gtggcagcaa caccaaggta tatatacaat    60
cttattgtgc attgacaaga gaaccatatt atcttgcaat n                       101

<210> SEQ ID NO 258
<211> LENGTH: 100
<212> TYPE: DNA
<213> ORGANISM: Cannabis sativa

<400> SEQUENCE: 258
tctttaaagt aacaatttgt ctcccattc cagggttact tcctccaggc acacaatttg    60
acttatttag aggaacagct gctatgaaac aagatgtaga                         100

<210> SEQ ID NO 259
<211> LENGTH: 101
<212> TYPE: DNA

<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 259
aaagggcatt caatccttac ggttcagctg cttacaactt catcaccatg ggaacttaca    60
gaggaggact taacaccttc gccattgttg caatagcttc n                       101

<210> SEQ ID NO 260
<211> LENGTH: 100
<212> TYPE: DNA
<213> ORGANISM: Cannabis sativa

<400> SEQUENCE: 260
aaaccccttc acgtttacgg aagcccaact tacgagtgtc aatggctgca gaattcttct    60
ccctcctccg ttatctcaac tgttgggtac aagatccttc                         100

<210> SEQ ID NO 261
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 261
ctacaaaggt tgcgtttgga ccgagctcct tagccgtggc taggccgaga ttgtgttgga    60
tgtctgctat gactactttg gcaccattgt tgatgaattt n                       101

<210> SEQ ID NO 262
<211> LENGTH: 100
<212> TYPE: DNA
<213> ORGANISM: Cannabis sativa

<400> SEQUENCE: 262
gtggctgttg ctttgcctat tccgcttgct gctcctgtta ttagtgccac cttcccatca    60
agcctgttat tttcaatgag tgaagaaatt gtctgagtag                         100

<210> SEQ ID NO 263
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 263
aattggcaga ggagagttca tatgccaaag gtttagcttc agctgctgct gttgaactga    60
aggcattatc tgaagaagtt gccaaactga tgaaccataa n                       101

<210> SEQ ID NO 264
<211> LENGTH: 100
<212> TYPE: DNA
<213> ORGANISM: Cannabis sativa

<400> SEQUENCE: 264
gagagactag cagctgatct agccgcatcc aagaactccc ccactcagcg caaaagtggc    60
agtatggtca agaatgggcg aagagagagc atgaacaagc                         100

<210> SEQ ID NO 265
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 265
ttcacccaag aaagaaaaat gtgattgtca catatgtttg ctgcatgtgc atggaccatt     60
gggtttaatc ttgcatcatg ctgtttctat attatgatct n                      101

<210> SEQ ID NO 266
<211> LENGTH: 100
<212> TYPE: DNA
<213> ORGANISM: Cannabis sativa

<400> SEQUENCE: 266
ttattgttat gaaatctatg gttgttcagt ctagtgcatt tcaccacaaa aaaaatgtga     60
ttgtcgtata tgcgtgctgc atgcatgggc cattgggttt                         100

<210> SEQ ID NO 267
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 267
caccagcccg cctcatgtca tgaaaggttt gaatagcagc aaagccatca ttgttatgag     60
agcaacaagt gatcatggca ttgtagaaaa cagtatctct n                      101

<210> SEQ ID NO 268
<211> LENGTH: 100
<212> TYPE: DNA
<213> ORGANISM: Cannabis sativa

<400> SEQUENCE: 268
atgctcaatg gagttgcaaa gaatatatcc cttgctaact taagactccc agcagcagag     60
taggcagcaa tcattgtcgt tctcgaaaca atatctggtt                         100

<210> SEQ ID NO 269
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 269
ttcacggaat tttaaatatt tttacgattt ttttgattta aaatgaaata ccttcaaatc     60
ctccgactgg tgtaaatagc tgcaatggtt ggacagagag n                      101

<210> SEQ ID NO 270
<211> LENGTH: 100
<212> TYPE: DNA
<213> ORGANISM: Cannabis sativa

```
<400> SEQUENCE: 270
ggagagagtt agagcaaaga cgatggtatg gaagaagtgg ctaagtgctc tgctgcagta    60
gtacaagtag tatatatatg aagggtata atgggaaatc                         100

<210> SEQ ID NO 271
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 271
gcaatttaaa caacctctcc ttcactgaac tcacagaaga cgatgacaaa gatctctcca    60
tctctgcctc atgatacagt ctccctctat aggcagcaag n                      101

<210> SEQ ID NO 272
<211> LENGTH: 100
<212> TYPE: DNA
<213> ORGANISM: Cannabis sativa

<400> SEQUENCE: 272
tcggcatagt acactggcgg taccaaggag acaggtttgg tgcagcgagc catggtaaaa    60
cacatgctat atatgagctt ctgcaattgg tcagaagtaa                        100

<210> SEQ ID NO 273
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 273
tggtcatgac gttgtactca actgaatgtg cgctgcagtc tttggcccca gcagggcatt    60
tcccaggcgc caatgatatg ttagaggtgc cgaagtcagt n                      101

<210> SEQ ID NO 274
<211> LENGTH: 100
<212> TYPE: DNA
<213> ORGANISM: Cannabis sativa

<400> SEQUENCE: 274
cggtcaaaca tgatgacacg gtcgttgttg agaagctgca tgtgcatggc cgaaatgcca    60
atgcttggtg tcaagaattt ccaccggcca ccggctgcat                        100

<210> SEQ ID NO 275
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 275
tttcgcccaa aaatttgatg ctaccgaaac cgtgtcgtcc aacaacaaag tccttgacac    60
ggcagcagaa tcctggttcg gcccttcct tggcagcaag n                       101
```

```
<210> SEQ ID NO 276
<211> LENGTH: 100
<212> TYPE: DNA
<213> ORGANISM: Cannabis sativa

<400> SEQUENCE: 276
tcttggattc gtggctcggt gtagtaatca gagcgcctga gctttggcat ttgagcctca    60
atatctgcac cgtgctcgta cacaatagca gcctcaccag                         100

<210> SEQ ID NO 277
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 277
gtccaacaac aaagtccttg acacggcagc agaatcctgg ttcggccctt tccttggcag    60
caagttcttg gattcgtggc tcggtgtagt aatcagagcg n                       101

<210> SEQ ID NO 278
<211> LENGTH: 100
<212> TYPE: DNA
<213> ORGANISM: Cannabis sativa

<400> SEQUENCE: 278
ctgagctttg gcatttgagc ctcaatatct gcaccgtgct cgtacacaat agcagcctca    60
ccagctctgt gcccgctaag ggtcttataa gaatccccct                         100

<210> SEQ ID NO 279
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 279
cctgttgttc ccgaaccttg gaagccacta catacactgc cgcctcttct ttcaggtctt    60
gaaatgaatg ttgatgcagc aatcagtatt tctactcgat n                       101

<210> SEQ ID NO 280
<211> LENGTH: 100
<212> TYPE: DNA
<213> ORGANISM: Cannabis sativa

<400> SEQUENCE: 280
gtaagggatg ttcatgggca tgtgactact gcttactcga aggcacattc aaatcacatg    60
agatgaagtt atgacacttt ttcatagcct tctttgggca                         100

<210> SEQ ID NO 281
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 281
```

```
taagagtgag aattttatta tgaagattga ggcgattacc agtgagtaca gaaacgtgtt    60
ctgggagttt aggggcattg gggttttggg ttttttgtgg n                      101
```

<210> SEQ ID NO 282
<211> LENGTH: 100
<212> TYPE: DNA
<213> ORGANISM: Cannabis sativa

<400> SEQUENCE: 282

```
tgagtttgct gttgctgctg ttgttgttgg gagcgtcgaa gagaggagag aggtggttcg    60
atacggaggc ggcgcttcct gcgacggcgc tcagctgcag                         100
```

<210> SEQ ID NO 283
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 283

```
tttttgtatg attaatttat tataatatac agataataac gaatgggaga ttcaagagcg    60
tggagcatag agtgttggca gctgggggag gtgggcctga n                      101
```

<210> SEQ ID NO 284
<211> LENGTH: 100
<212> TYPE: DNA
<213> ORGANISM: Cannabis sativa

<400> SEQUENCE: 284

```
aatgggccta ggactgggcc tagaatatca gcagcttgct ttttttatcc aagcattccc    60
aatattgcga aaccttacgg cccaattaaa gagcttctct                         100
```

<210> SEQ ID NO 285
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 285

```
acctgaagat gcctaattaa aggcattcca ttcttcttcc ttttcagctg ccaatgctcg    60
taaatgactt taattacatc catgggccca actccagcag n                      101
```

<210> SEQ ID NO 286
<211> LENGTH: 100
<212> TYPE: DNA
<213> ORGANISM: Cannabis sativa

<400> SEQUENCE: 286

```
gagctcttct atttcatctg atgtcaacag gtcccgctgt tgagaatatg cagccttctc    60
aaacatgtcc ataattttct caaacatctc ttcagatatc                         100
```

<210> SEQ ID NO 287
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 287
ggttggggct acaatagcta tggtcaggca gccaatgaga aatctaccta tgcttggttt    60
ccatcaccag ttgattggta tggcaaaatt atatcgttca n                       101

<210> SEQ ID NO 288
<211> LENGTH: 100
<212> TYPE: DNA
<213> ORGANISM: Cannabis sativa

<400> SEQUENCE: 288
tagctttatc cttaacactg cttttttcgtt ttctatgttc atggagctcc ctttgcaggt   60
gcgttggcga ggtgcgaaaa ctggcagctg gtggtggcca                         100

<210> SEQ ID NO 289
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 289
cgagctcctt agccgtggct aggccgagat tgtgttggat gtctgctatg actactttgg   60
caccattgtt gatgaatttg gtggctgttg ctttgcctat n                       101

<210> SEQ ID NO 290
<211> LENGTH: 100
<212> TYPE: DNA
<213> ORGANISM: Cannabis sativa

<400> SEQUENCE: 290
ccgcttgctg ctcctgttat tagtgccacc ttcccatcaa gcctgttatt ttcaatgagt   60
gaagaaattg tctgagtaga aagaaggtaa agaaagcaat                         100

<210> SEQ ID NO 291
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 291
ttattcatgt ggaagtagct ctataaaact gtctctaaca tggtatttaa agtgtttgca   60
ttggaaaaat gttcttacca aatgcagctt gagccagttc n                       101

<210> SEQ ID NO 292
<211> LENGTH: 100
<212> TYPE: DNA
<213> ORGANISM: Cannabis sativa

<400> SEQUENCE: 292
acatatctgt tgtacctctt tcctggaaca gcttcatgta gctgaactaa aacccacaga   60
gtataaagct gccaacagta ggctatggtc aaagaaagta                         100

<210> SEQ ID NO 293

```
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 293
ttgacattac taacaattac tgaagccccc attacactaa tttggggcca ataagcttga      60
ctcctcgctt tccaaacgtg ttatattgtt gctgccataa n                         101

<210> SEQ ID NO 294
<211> LENGTH: 100
<212> TYPE: DNA
<213> ORGANISM: Cannabis sativa

<400> SEQUENCE: 294
agaagcaagc acctatttt tgctcttcga actcttcctc ttccttatcc attttataag      60
ctgctaaatc atgaacactt aagtcttcta gttcagccaa                           100

<210> SEQ ID NO 295
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 295
cttgactcct cgctttccaa acgtgttata ttgttgctgc cataacagaa gcaagcacct      60
attttttgct cttcgaactc ttcctcttcc ttatccattt n                         101

<210> SEQ ID NO 296
<211> LENGTH: 100
<212> TYPE: DNA
<213> ORGANISM: Cannabis sativa

<400> SEQUENCE: 296
ataagctgct aaatcatgaa cacttaagtc ttctagttca gccaaatttt gagcacttct      60
atacgtattc tgttgctagg acagaaaaag aaaaggtgtt                           100

<210> SEQ ID NO 297
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 297
cggtggtggc tgtggttggg gtatgcacgt tgtcgtttaa gaaaatagtg ggaacatact      60
tggtgggagt agtgggcctt gccggggtgt tttgcccaga n                         101

<210> SEQ ID NO 298
<211> LENGTH: 100
<212> TYPE: DNA
<213> ORGANISM: Cannabis sativa

<400> SEQUENCE: 298
tgggcttatt tcgaccgtga cttctctcgc tggatccacc cagttaccgc tgatgaaagg      60
```

-continued gcctctcatg ctgcttctca cagatctgga ctaccaaggc                                100

<210> SEQ ID NO 299
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 299
tgcaatcctg tggtgcacta gaaaccgccg ccgcatcagc atctgtctcc ttcccactga          60
aaagctccag ttgcaaacta gacaaagcct cttgcgtaag n                              101

<210> SEQ ID NO 300
<211> LENGTH: 100
<212> TYPE: DNA
<213> ORGANISM: Cannabis sativa

<400> SEQUENCE: 300
ccgtgtggct tctcgttctg ttctcgcaag atttgcagcc ttacagtttg ggagctcaga          60
ttagtagatg gggaacggtc agttgataaa cttgtagagt                                100

<210> SEQ ID NO 301
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 301
aaaatataca atgtgcaatt tattggctaa gagaaatagt aaaaagagca catgtatttg          60
ctgctgaaac tctgattgaa ggaggagcgg acaagtgtcg n                              101

<210> SEQ ID NO 302
<211> LENGTH: 100
<212> TYPE: DNA
<213> ORGANISM: Cannabis sativa

<400> SEQUENCE: 302
tcatgtgatg gctggaggag aggagctgct ggagagagag gggacaggcg ggtcccacgc          60
agctggcgct ggcaggctgg gcaggaggag acaggcgctt                                100

<210> SEQ ID NO 303
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 303
ccagctctgc cggattccaa tccgtaccga cctcgccttg gcggagcctc tctccgtaac          60
cggaaccctc cgctgccgga aacctttcgt catccgatgc n                              101

<210> SEQ ID NO 304
<211> LENGTH: 100
<212> TYPE: DNA

<213> ORGANISM: Cannabis sativa

<400> SEQUENCE: 304
ccggcgagtc atcttcaacg gcagcagatt ctgatttcga tgcgaaagtg ttccgtaaga     60
acttggtccg aagcaagaac tacaatcgga aaggttttgg                          100

<210> SEQ ID NO 305
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 305
gttgctttat ttgaattttt gagcttcatg atctggcaat ggagttaata ctacacagct     60
cactaataaa cgacaaaagt tgttgtcgt tttttgtttc n                         101

<210> SEQ ID NO 306
<211> LENGTH: 100
<212> TYPE: DNA
<213> ORGANISM: Cannabis sativa

<400> SEQUENCE: 306
ggggtctgtt ctgcacacaa taaagaaca ttttaggta tataccaaga taggctgctc      60
tggacatcat ttagcaaggg tcaccatctt ctagcaaaac                          100

<210> SEQ ID NO 307
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 307
acagtaccag tacatcagga aagagcaaga gcaagagcaa gagcaacgac gcctactacc     60
aataacccaa atagggcagc aaggatgatg atgatgacca n                        101

<210> SEQ ID NO 308
<211> LENGTH: 100
<212> TYPE: DNA
<213> ORGANISM: Cannabis sativa

<400> SEQUENCE: 308
acaatcctgc tccccaacac tctccagacc acccaacaca tccaatacta ctactactac     60
tactactact actgctgcct tcttcagggg tagcaccatg                          100

<210> SEQ ID NO 309
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 309
acgccactgt gttgacgtaa tttctacatg tagcagcgta atgacagtat tctattgctg     60
gaacgctatt tgctgaaatg ttatttcttc atttttgtgt n                        101

<210> SEQ ID NO 310
<211> LENGTH: 100
<212> TYPE: DNA
<213> ORGANISM: Cannabis sativa

<400> SEQUENCE: 310
gccgacgcta ctgtgttgac gtgacttcta catgtagcat tgtaatgcca gtattctatt      60
gctgcaatgt tatttcttca tttttatgtc gccaatgcta                           100

<210> SEQ ID NO 311
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 311
gaaacctctg tgccttggaa ttcttgctct taattagcca tattcgatac acacctaggc      60
ccaaaagaac caaatgagaa gtagaaatga ctaaagactc n                         101

<210> SEQ ID NO 312
<211> LENGTH: 100
<212> TYPE: DNA
<213> ORGANISM: Cannabis sativa

<400> SEQUENCE: 312
attgcacaag gtgtgtaaga accaaaagca ctctctacta tctttcccca aaccccataa      60
gctgcaggct tacaatacca acttagtagc tcaaacctca                           100

<210> SEQ ID NO 313
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 313
tggatggcac ctgaggtaaa aatcttatga agttattttt gctgcttgtc ttgatattct      60
ttcattgtgt atgatcttga ttctatttca tccttcttcc n                         101

<210> SEQ ID NO 314
<211> LENGTH: 100
<212> TYPE: DNA
<213> ORGANISM: Cannabis sativa

<400> SEQUENCE: 314
gcctttctcc caggtaataa agaattcaac tggctgcaac cttgctgtgg atatttggag      60
ccttggatgc actgttttgg aaatggctac tacaaaacca                           100

<210> SEQ ID NO 315
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

```
<400> SEQUENCE: 315
tctgccggat tccaatccgt accgacctcg ccttggcgga gcctctctcc gtaaccggaa      60
ccctccgctg ccggaaacct ttcgtcatcc gatgcgccgg n                         101

<210> SEQ ID NO 316
<211> LENGTH: 100
<212> TYPE: DNA
<213> ORGANISM: Cannabis sativa

<400> SEQUENCE: 316
gagtcatctt caacggcagc agattctgat ttcgatgcga aagtgttccg taagaacttg      60
gtccgaagca agaactacaa tcggaaaggt tttggccata                           100

<210> SEQ ID NO 317
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 317
gcttgacaca atcataaatc caatcagagg taattgtatg tatcccccat ttacaagcag      60
cctcatactt tggtccactt gcaaacttgc aaatgagatg n                         101

<210> SEQ ID NO 318
<211> LENGTH: 100
<212> TYPE: DNA
<213> ORGANISM: Cannabis sativa

<400> SEQUENCE: 318
gtgaccttat ttgtcaatct ctctactaat ttggttccaa gaacaaagca taaatttctc      60
aaaagcagcc gatctttctc ttcatattgt gaaacacaaa                           100

<210> SEQ ID NO 319
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 319
ggactcaatc accaatgctg accccaaagc tgcattcatt aactcaaagt aagaaatcta      60
gtcctcttcc aatgcttaat tggccaaccc gagctctcgc n                         101

<210> SEQ ID NO 320
<211> LENGTH: 100
<212> TYPE: DNA
<213> ORGANISM: Cannabis sativa

<400> SEQUENCE: 320
atgccatatt tgttttcgct acaaaatgtg gcattgcgag ctagctgctg ggaaattaga      60
attggatcac aaacacagca aatttatttg aaatccctac                           100

<210> SEQ ID NO 321
<211> LENGTH: 101
<212> TYPE: DNA
<213> ORGANISM: Cannabis sativa
```

```
<220> FEATURE:
<221> NAME/KEY: misc_feature
<222> LOCATION: (101)..(101)
<223> OTHER INFORMATION: n is g or a

<400> SEQUENCE: 321
tatacagata ataacgaatg ggagattcaa gagcgtggag catagagtgt tggcagctgg      60
gggaggtggg cctgagaatg ggcctaggac tgggcctaga n                         101

<210> SEQ ID NO 322
<211> LENGTH: 100
<212> TYPE: DNA
<213> ORGANISM: Cannabis sativa

<400> SEQUENCE: 322
tatcagcagc ttgctttttt tatccaagca ttcccaatat tgcgaaacct tacggcccaa     60
ttaaagagct tctctctcac accaacccac cactctacaa                           100

<210> SEQ ID NO 323
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 323
tttccaacca tccttggatg gcttcccttt cataagtgaa tccatcagca gccacctgag     60
ggtcatgcat tatttcctga aagtaaacca gaacattagg n                         101

<210> SEQ ID NO 324
<211> LENGTH: 100
<212> TYPE: DNA
<213> ORGANISM: Cannabis sativa

<400> SEQUENCE: 324
tgtgagccaa gttaaagaac aagtttgaac cttacaccca aatttcggga aagcttgagc     60
ttgtttagag ttggggtttg attgaaagac atgagaagca                           100

<210> SEQ ID NO 325
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 325
aaagcttcag acagtttaga ggcaagctgt tccagaggcc tcaagcctac agctatcact     60
cttttgtacg tttcaccact ttcctcgaaa aaggcagccc n                         101

<210> SEQ ID NO 326
<211> LENGTH: 100
<212> TYPE: DNA
<213> ORGANISM: Cannabis sativa

<400> SEQUENCE: 326
ccgccataca tcaacattat tctcacaaac catgcagaga tcaaggtatg caagatactg     60
aagaagagac ctcgggctgc tctcttctag tgctgcaagg                           100
```

<210> SEQ ID NO 327
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 327
aaattctaaa ccatgataaa gaaaaaggt tagaggaaaa tcaatcatga aaatctcttt      60
aataacttct gcagcattac tgctattttg tagcaaagta n                       101

<210> SEQ ID NO 328
<211> LENGTH: 100
<212> TYPE: DNA
<213> ORGANISM: Cannabis sativa

<400> SEQUENCE: 328
ggcaattatt accagcttgc agtttgttaa gggaactctt ctgagcaggg caaagctggg      60
caagaagaga acccactgca gccgcatttt gaatcgcagg                          100

<210> SEQ ID NO 329
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 329
ttgacccttt taatgtggca gcccttcgtt gcgcggctga gtttctcgaa atgactgaag      60
aatactgtca tggaaacctc tgtgaacgct ttgatctcta n                       101

<210> SEQ ID NO 330
<211> LENGTH: 100
<212> TYPE: DNA
<213> ORGANISM: Cannabis sativa

<400> SEQUENCE: 330
atgaaccaag ttgtactgca gagttgggat gacacactaa tagtcctcca aaagtgccaa      60
actctgcttc cctggtctga ggagcttctg attgtgagcc                          100

<210> SEQ ID NO 331
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 331
cctaagctaa attctagcta attgtaagcc gaataaaaaa aaaccctaca aactgctgcc      60
ccttaagttt agatcgatga gaggcagatg aatcatgaac n                       101

<210> SEQ ID NO 332
<211> LENGTH: 100
<212> TYPE: DNA
<213> ORGANISM: Cannabis sativa

<400> SEQUENCE: 332
aacagtccat aatcctttg gtttcgtcgc agaatgcaag cagccaaaaa aggaataact    60
agaaatgcta atcaaattta catggaattt cctttcaccc                        100

<210> SEQ ID NO 333
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 333
ccagtgaatg gcgactattg cagcgtacgg tggacattat tattatgtcc tcttccccac    60
cttggaagcc gtcgactgtc ttcaccttta cttggaagcc n                       101

<210> SEQ ID NO 334
<211> LENGTH: 100
<212> TYPE: DNA
<213> ORGANISM: Cannabis sativa

<400> SEQUENCE: 334
tcatttccac tgtacttgtt cccaagttgg tcttgaattg caaccacttg agcagcatat    60
ggagacacaa taccaatact gagctcacat ttcgacttaa                         100

<210> SEQ ID NO 335
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 335
gggccaaagc agcaagatgg tcaggccctg ataaagtgtg caagcaacca gcaaagaaac    60
cagtccatgc actacttagc agttcagtcc gaatcagtgt n                       101

<210> SEQ ID NO 336
<211> LENGTH: 100
<212> TYPE: DNA
<213> ORGANISM: Cannabis sativa

<400> SEQUENCE: 336
cccccaactg ctgcagcagc agcaggggca cctgtcttag ctgcagtttg aaaagttgca    60
aaagctgcag gtgcgaaaat tggttgaatt aagatcataa                         100

<210> SEQ ID NO 337
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 337
atcatggttc ttgagaaggt tggtactttg cttagtgttt gagttgcaaa agttgatggg    60
aatttggaaa ggaagggagt gtgggtcttg ctcttttcta n                       101

<210> SEQ ID NO 338

```
<211> LENGTH: 100
<212> TYPE: DNA
<213> ORGANISM: Cannabis sativa

<400> SEQUENCE: 338
agcgattttc atttgctgct gtgtcataat ataaataaat aagcataaat aggaggaata      60
ataaaaggtt agaaatggga tttttgagct gcttatggtg                           100

<210> SEQ ID NO 339
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 339
gagaaggttg gtactttgct tagtgtttga gttgcaaaag ttgatgggaa tttggaaagg      60
aagggagtgt gggtcttgct cttttctaga gcgattttca n                        101

<210> SEQ ID NO 340
<211> LENGTH: 100
<212> TYPE: DNA
<213> ORGANISM: Cannabis sativa

<400> SEQUENCE: 340
ttgctgctgt gtcataatat aaataaataa gcataaatag gaggaataat aaaaggttag      60
aaatgggatt tttgagctgc ttatggtggt ctagtagtaa                          100

<210> SEQ ID NO 341
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 341
aatgacttct gcacttcagc tccttttgat ctagggtagt gtgcagcaat agagccaggt      60
ttcaaggaaa atcgatccct tggatccgga ataggaaatt n                        101

<210> SEQ ID NO 342
<211> LENGTH: 100
<212> TYPE: DNA
<213> ORGANISM: Cannabis sativa

<400> SEQUENCE: 342
tactggtaat ggacattcaa ctggtgtaag acctctaatt gcagcctcgt atatctagaa      60
taagttttca agttagccca ctaaaataat tagatggaaa                          100

<210> SEQ ID NO 343
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 343
gcttcgtagc aagatgcaat tagcataagc agccagaata atttttctgt agagtattgc      60
```

```
tgccttcagt aatgcagtga ggttgttttc tggtggactt n                  101
```

<210> SEQ ID NO 344
<211> LENGTH: 100
<212> TYPE: DNA
<213> ORGANISM: Cannabis sativa

<400> SEQUENCE: 344

```
gtagaggtct aaagcagacg gaaaagacat tggtgagtat tataaaacat agctaaaacg    60
gggtcgcttt gttgtgtggc tgcaaggcca catggatctc                         100
```

<210> SEQ ID NO 345
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 345

```
ttcatcacca tcaccatcac cacaagtatt tcaaccacgg cgccoctcag attattcagc    60
cgatgaatgt tgctttcggt ggtggcggag cagcaggtac n                       101
```

<210> SEQ ID NO 346
<211> LENGTH: 100
<212> TYPE: DNA
<213> ORGANISM: Cannabis sativa

<400> SEQUENCE: 346

```
gaatcttcga gcgaagatct taatctttac ggatccaccg ccgaggctgc tgctgctgca    60
gcggcggcac cgcctccttt cgggtcaaag aagcggttca                         100
```

<210> SEQ ID NO 347
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 347

```
cagcagtcaa cccagcagga ccagctccta tgacaataat tttctttcca acgtttgtat    60
gacaccgtgg ataaagattc tccttggcat catcattaaa n                       101
```

<210> SEQ ID NO 348
<211> LENGTH: 100
<212> TYPE: DNA
<213> ORGANISM: Cannabis sativa

<400> SEQUENCE: 348

```
gcagcttgaa taggggatga ctctttttct acatccagag tcacaatagg gactttacca    60
acttccaatg tttcacatga tatttctgta cttccaacat                         100
```

<210> SEQ ID NO 349
<211> LENGTH: 101
<212> TYPE: DNA
<213> ORGANISM: Cannabis sativa
<220> FEATURE:
<221> NAME/KEY: misc_feature
<222> LOCATION: (101)..(101)

<223> OTHER INFORMATION: n is c or t

<400> SEQUENCE: 349
agaggtcaac cctcgcattc ttcgcgggga gtatgcacgg ctatgttcgg ccaattctgc     60
tgcagcattg ggaaaataaa gaccccgaca tgaaaatttt n     101

<210> SEQ ID NO 350
<211> LENGTH: 100
<212> TYPE: DNA
<213> ORGANISM: Cannabis sativa

<400> SEQUENCE: 350
ggtaagttac ctaggaagaa gggcaacaaa gtatatgtca actacatgaa gagcagcaag     60
tattgcattt gtgcaaaagg gtatgaagtc aatagtccta     100

<210> SEQ ID NO 351
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 351
gagctaattt ctggaagaaa ccctgttgat tatagtcgac aacaaggaga ggttagtctt     60
gattatgatt tgttaaacct gtagtttgct ttcctgctgc n     101

<210> SEQ ID NO 352
<211> LENGTH: 100
<212> TYPE: DNA
<213> ORGANISM: Cannabis sativa

<400> SEQUENCE: 352
aattataggc tgaaagtgaa tctatatttg caggtgaata tggttgaatg gttaaaaact     60
ttggttggga atcggaaatc tgagcaagta attgatccca     100

<210> SEQ ID NO 353
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 353
gtgaagcaac ctgtgaaagc agaggtgctt ggcttctctt ggctgcttgc atttgaatgt     60
aatactcttt aaactcaacc gggcaattcc taactagttc n     101

<210> SEQ ID NO 354
<211> LENGTH: 100
<212> TYPE: DNA
<213> ORGANISM: Cannabis sativa

<400> SEQUENCE: 354
gtcatgtctt cttcatcgcg ctgcaaatga agagaattat tagacaaact cttagtattt     60
gaacttggtt gagaattgta ctaaaactat aactattcct     100

<210> SEQ ID NO 355
<211> LENGTH: 101

```
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 355
aagcagtcac acaacaagaa cctccacgaa aatcttgttt aagaaagtct gaatctgtgt    60
tcaggtaacc atgcttaact gcctcctcaa tgtggtcatc n                       101

<210> SEQ ID NO 356
<211> LENGTH: 100
<212> TYPE: DNA
<213> ORGANISM: Cannabis sativa

<400> SEQUENCE: 356
ccatccttgc tcactaattc agccaatacg ttcttttcca agttatcagc tgcaaatgct    60
gcagcttttg agcctccatg tccatcaaat acaccaaaga                         100

<210> SEQ ID NO 357
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 357
ccttctcctg caactgcaat caatgagtct ccaaaagaaa caccatctaa accatctgta    60
aaacctccaa caccatctgg tgcagccact aagtcaccta n                       101

<210> SEQ ID NO 358
<211> LENGTH: 100
<212> TYPE: DNA
<213> ORGANISM: Cannabis sativa

<400> SEQUENCE: 358
agaaacacca tcaatcccaa ctctcaaacc ccaaacatct tctactccaa gtcccaaatt    60
taaaacacca tctcgtgcag ccactgaatc tccaaaagta                         100

<210> SEQ ID NO 359
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 359
ccttctgcca tcccattgtc aagtctggct gaggcaggaa atctattgga tggtggagac    60
tgatcgctgg tagcattatt gctgtcttct tgtgtaacta n                       101

<210> SEQ ID NO 360
<211> LENGTH: 100
<212> TYPE: DNA
<213> ORGANISM: Cannabis sativa

<400> SEQUENCE: 360
tgctgctgaa tcatttgttg tttcttgatg taactgtgaa gatgaatgct tattcctacg    60
```

```
gcgtccagca cccacaggta catttctaat tgttccccg                           100
```

<210> SEQ ID NO 361
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 361

```
atttgcaggg aaatgagccg ctggaactgc aacttctgct gcttctggaa taccctgaag    60
agaaaacatc aatagttaaa acaagataaa acaggtgtca n                        101
```

<210> SEQ ID NO 362
<211> LENGTH: 100
<212> TYPE: DNA
<213> ORGANISM: Cannabis sativa

<400> SEQUENCE: 362

```
cagattcagt gaatttaaac atacagagta caaatagtcg actgcgcgtt ctggattgtt    60
atatgctgct cgaagtgcac gagtaacagt ttctctgtcc                          100
```

<210> SEQ ID NO 363
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 363

```
gcagaggtcc aactgttcgt gccgtaacga tagatggcag caactcaagc atggtcagtt    60
ttgtggttga gcagcccact tcatctacca cttcttcaaa n                        101
```

<210> SEQ ID NO 364
<211> LENGTH: 100
<212> TYPE: DNA
<213> ORGANISM: Cannabis sativa

<400> SEQUENCE: 364

```
actctcgtat ctcttcctaa catgagtaag gaacaatggc aaaccattgc tgccatgttt    60
gataacgttc aatattctag caatcgtttg cacaatgagt                          100
```

<210> SEQ ID NO 365
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 365

```
ttgaagtgtg ctcgatagaa gtagatgtgg cccgagcttc gttgattctt tcagtgggaa    60
tttcaacaag gtatgtgtat gcaacttaca agaaaaaccc n                        101
```

<210> SEQ ID NO 366
<211> LENGTH: 100
<212> TYPE: DNA
<213> ORGANISM: Cannabis sativa

<400> SEQUENCE: 366
gtgaccacga atgaagctga agcttgggaa gcagccaaga aagcttcagg aggtttgcat    60
ttccttgcca ttcaagaaga cttggattca gatgactgtg                         100

<210> SEQ ID NO 367
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 367
catattatta ttattattat tattattatt tctatttaac tgctgccctt tattatttct    60
ccatttcgat agcccgaaaa gcgaaaaaga cttgttgccc n                       101

<210> SEQ ID NO 368
<211> LENGTH: 100
<212> TYPE: DNA
<213> ORGANISM: Cannabis sativa

<400> SEQUENCE: 368
gcttgtttga tgatgatctt cctcctcctc ctcctcctcc tgctgcttcg ttggtaatgg    60
cggttgcaga gacatctttg ctctgttttt gatgctccat                         100

<210> SEQ ID NO 369
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 369
ccttccacct ctacgctcct aagtccttct ctactcgctt ccccaacccc ttcaccgctt    60
cacgccgctc cactgcaact ccactatctg caattactac n                       101

<210> SEQ ID NO 370
<211> LENGTH: 100
<212> TYPE: DNA
<213> ORGANISM: Cannabis sativa

<400> SEQUENCE: 370
tcctctgcca caaccgccga ggctccgcag cctaaatcct ctcttcttac tttccagcaa    60
gccattcaac gtctccaggt ttgtttccaa tgtctaattg                         100

<210> SEQ ID NO 371
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 371
tcagagacta agaaacatgc cactataaaa atacgccatc ttgttaatac taagaaatgt    60
cacctcaccg cagcaggcac atcttcttcc aggaagttat n                       101

<210> SEQ ID NO 372
<211> LENGTH: 100
<212> TYPE: DNA
<213> ORGANISM: Cannabis sativa

<400> SEQUENCE: 372
gaaatcccag tcatatttaa agattaactc aaactgttgc tgcaaatctt caagtgtagc    60
agaaatgttc tcctgcaggt ccataaactg ttcagggaat                         100

<210> SEQ ID NO 373
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 373
tatatttata taagaaaaag atgagagaag agaggaagat ttagaaagca gcaaaggacc    60
catatcctcc tccattaagg caactaaacc caactaacta n                       101

<210> SEQ ID NO 374
<211> LENGTH: 100
<212> TYPE: DNA
<213> ORGANISM: Cannabis sativa

<400> SEQUENCE: 374
tctctataca tgtgaaccgt agccattagc cccatttcca ttagcaccat aagggacctt    60
gttctctgtt ttcttcttct tcagtacgta aaaccatgta                         100

<210> SEQ ID NO 375
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 375
gcagcctagc agcactgctt gctccacggc cacggccacc agatggtgat tttgaaccga    60
acttcgtata tctggaagaa ctcttcctag ttaatcttac n                       101

<210> SEQ ID NO 376
<211> LENGTH: 100
<212> TYPE: DNA
<213> ORGANISM: Cannabis sativa

<400> SEQUENCE: 376
ggaagaattt gcagccttgg attctgctcg gtgcctgagt tttcagctgc caactgatag    60
cttttgacca gctcaagctg tcgcgcaatt atttccgagc                         100

<210> SEQ ID NO 377
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 377

```
ggtcattcat taatgtatgg ttagttattg gctgctggca cttgtctgtt atgcatgaaa    60
tacttattgt tatatggtga gttttcaaaa aacatttgca n                       101
```

<210> SEQ ID NO 378
<211> LENGTH: 100
<212> TYPE: DNA
<213> ORGANISM: Cannabis sativa

<400> SEQUENCE: 378

```
gatttttatt caagaactga attcttttat gcaggctgct tacagctaca gttgcctggc    60 cttttcccagc cattatttac attggaatta ttctttcgac                         100
```

<210> SEQ ID NO 379
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 379

```
tgatatagta cagtgcgtcc atggcgtcat cgtaggctgc aggcagacgg tgctccggag    60
ccagacgata ctccacagaa actacaatgg caaagatttc n                        101
```

<210> SEQ ID NO 380
<211> LENGTH: 100
<212> TYPE: DNA
<213> ORGANISM: Cannabis sativa

<400> SEQUENCE: 380

```
gcggctaagt tgaatgtgaa attatgagtc acagttgagg ctgcactgaa taggatgaat    60
ccaccgccat ggaagtagac tataagaggc aatcgtagct                          100
```

<210> SEQ ID NO 381
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 381

```
taaattggtc gtttatatta atgttataaa gaacgcccta gctttagcta gagcagctag    60
agcgtgaacc cggactagtt ttttttact tcttgctcgt n                         101
```

<210> SEQ ID NO 382
<211> LENGTH: 100
<212> TYPE: DNA
<213> ORGANISM: Cannabis sativa

<400> SEQUENCE: 382

```
tcttctatct tctagggttt ggtagttccc ttggacgaaa tcgtggctgc tttactgttt    60
tttgggtttc atggaagatt tttatgagaa tcgaagcaat                          100
```

<210> SEQ ID NO 383
<211> LENGTH: 101
<212> TYPE: DNA
<213> ORGANISM: Cannabis sativa
<220> FEATURE:

```
<221> NAME/KEY: misc_feature
<222> LOCATION: (101)..(101)
<223> OTHER INFORMATION: n is a or t

<400> SEQUENCE: 383
ccagagacca tatctatgcg taatacatgt aaaggctatt tgaagcagca caggcaagtg    60
agttttcggt tggatgccaa gcaagatgga gcaactttgt n                       101

<210> SEQ ID NO 384
<211> LENGTH: 100
<212> TYPE: DNA
<213> ORGANISM: Cannabis sativa

<400> SEQUENCE: 384
gtgaaatcga aaccatttcc gtttgcatca gttccagagg tatccgcacc tttgtggata    60
aacaagtcag ttaagagaca aaatgggatg aaaattaaaa                         100

<210> SEQ ID NO 385
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 385
aaaggctatt tgaagcagca caggcaagtg agttttcggt tggatgccaa gcaagatgga    60
gcaactttgt tgtgaaatcg aaaccatttc cgtttgcatc n                       101

<210> SEQ ID NO 386
<211> LENGTH: 100
<212> TYPE: DNA
<213> ORGANISM: Cannabis sativa

<400> SEQUENCE: 386
gttccagagg tatccgcacc tttgtggata aacaagtcag ttaagagaca aaatgggatg    60
aaaattaaaa gttagctaaa aagtgggcaa gacatacctc                         100

<210> SEQ ID NO 387
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 387
gaaggcgaat gacttggcgt tggaggactg agatagcgcc tacgcagccg tagacaggat    60
ctttcatcct ggcctcggct tcgtaggcca gagaattaac n                       101

<210> SEQ ID NO 388
<211> LENGTH: 100
<212> TYPE: DNA
<213> ORGANISM: Cannabis sativa

<400> SEQUENCE: 388
gcgtcctctc tctggtgagg gaggacctcg ttcaggagct tgctcacatt gctcgcccca    60 aatatttgt ggacgtttgc gaatttctgt ggctcttcag                          100
```

```
<210> SEQ ID NO 389
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 389
gtgatcttcc aacatctgtt gattggagga agaaaggagc agtcactgga gtcaaaaacc       60
aaggcaactg tggtagctgt tgggcattct cagctgtagc n                          101

<210> SEQ ID NO 390
<211> LENGTH: 100
<212> TYPE: DNA
<213> ORGANISM: Cannabis sativa

<400> SEQUENCE: 390
gcagttgaag gtgtcaacca aatcgaaaca aaggagctgg tatctttgtc tgaacaagaa       60
ttggttgatt gcagctcgaa aaaccatggt tgtgaagggg                            100

<210> SEQ ID NO 391
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 391
agccatcaaa gaatgcgaaa tcaacaggga aattgggatc gttgtggagg ctgataaaag       60
gatagatgtt tacagtaaag gaacctccat tgtcgcttaa n                          101

<210> SEQ ID NO 392
<211> LENGTH: 100
<212> TYPE: DNA
<213> ORGANISM: Cannabis sativa

<400> SEQUENCE: 392
aacttaacga tggccaccat gagatctttt atgtctgttc tgaagtcacc gtcggaaggt       60
ttctcactcg agctgccata tacatcagcg tttaaaggga                            100

<210> SEQ ID NO 393
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 393
tagcaaagat cgaagcctca catcaacact cacagatcga agctgcctca catcaaaact       60
cacagatcaa aactgcacaa caacactcgc agatcgaagc n                          101

<210> SEQ ID NO 394
<211> LENGTH: 100
<212> TYPE: DNA
<213> ORGANISM: Cannabis sativa

<400> SEQUENCE: 394
```

```
gcacaacact cgcagatcga agaaaggatg cccacgtctc acaatttcgg ttccaacttt    60
gcagcttttc ctcccagctt cacctcattg ctgacaagtt                         100
```

<210> SEQ ID NO 395
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 395

```
catccgaagt aggatcatgt gcgcggttgc ggcgatgggc cccacttcac tgtccttttc    60
tcacaacact caggacccac atacacataa cataaccccct n                      101
```

<210> SEQ ID NO 396
<211> LENGTH: 100
<212> TYPE: DNA
<213> ORGANISM: Cannabis sativa

<400> SEQUENCE: 396

```
ctccctcttt ctttatactt ctacacagca gcaactactt aacttagcct catcaaaatt    60
cagccaggaa ggaccagatg agatgacctt gcttcttcct                         100
```

<210> SEQ ID NO 397
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 397

```
caatgaagat tcaagaccaa catgtcaatg cccaagaaag tactcttttta ttgatcccaa   60 tgacgaatat ggaagctgca aacccgattt catacaaggc n                       101
```

<210> SEQ ID NO 398
<211> LENGTH: 100
<212> TYPE: DNA
<213> ORGANISM: Cannabis sativa

<400> SEQUENCE: 398

```
gcgctgaaga cgagcttact cccgacatag aagatctcta tgatgttgag gagctgcgca    60
atgtagattg gcccttatca gattatgttg cactgaagcc                         100
```

<210> SEQ ID NO 399
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 399

```
aggttgagac tgcaaggatt tacaatgttg atgatctgaa agaggttgta gctgctaata    60
aagaagatcg tctccgcaaa gcaatggagg ctcaggcaat n                       101
```

<210> SEQ ID NO 400
<211> LENGTH: 100

```
<212> TYPE: DNA
<213> ORGANISM: Cannabis sativa

<400> SEQUENCE: 400
attgctgatg aatcaaaaca atttgaagca tggagggact cactggagac tgttccgacc      60
atcaagaaac tgagagctta tgctgaaaga ataagggctg                            100

<210> SEQ ID NO 401
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 401
aaggaagaag ttggcagcaa gctcaccgtg gtatccactg aggagatcat cctcgagcga      60
cctagggctc tcggtacttt attatcattc cacaatgatt n                          101

<210> SEQ ID NO 402
<211> LENGTH: 100
<212> TYPE: DNA
<213> ORGANISM: Cannabis sativa

<400> SEQUENCE: 402
ttcaactgat tctatttcaa ttcataaatt tttgttttttg aaagttggat tataatatta     60
tataggtagc aaggggaag aagctaagaa ttccggggat                             100

<210> SEQ ID NO 403
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 403
aaggaagaag ttggcagcaa gctcaccgtg gtatccactg aggagatcat cctcgagcga      60
cctagggctc tcggtacttt attatcattc cacaatgatt n                          101

<210> SEQ ID NO 404
<211> LENGTH: 100
<212> TYPE: DNA
<213> ORGANISM: Cannabis sativa

<400> SEQUENCE: 404
ttcaactgat tctatttcaa ttcataaatt tttgttttttg aaagttggat tataatatta     60
tataggtagc aaggggaag aagctaagaa ttccggggat                             100

<210> SEQ ID NO 405
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 405
tcatgttact gctgattatc gtcaccgata attgcttcta acctttctac attgtggttt      60
```

```
ttttgacctg gctgcagaaa gttgaaaaca gagtaagaat n                     101
```

<210> SEQ ID NO 406
<211> LENGTH: 100
<212> TYPE: DNA
<213> ORGANISM: Cannabis sativa

<400> SEQUENCE: 406

```
ctgagtgatt taagagaact tgcttcagca gagaggcctg gatacttcac gctcatttac   60
acaaatattc tcgaacatca acctgactgc ccggtaactt                        100
```

<210> SEQ ID NO 407
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 407

```
ccagcaaaag tggctcgtgc tgatgagagt cgggattgct tttcctgaaa ccagagataa   60
ctctcacccg ggccaaagag gggtgttctg aaacatgcag n                     101
```

<210> SEQ ID NO 408
<211> LENGTH: 100
<212> TYPE: DNA
<213> ORGANISM: Cannabis sativa

<400> SEQUENCE: 408

```
tcagatacac cagtaccatc cacaataacc ctgtggcaga caagttctca agctagtagg   60
aatgaatgtc ctccgcaaat tgaaaccact gttcggatct                        100
```

<210> SEQ ID NO 409
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 409

```
ttgtggtttt tttgacctgg ctgcagaaag ttgaaaacag agtaagaata ctgagtgatt   60
taagagaact tgcttcagca gagaggcctg gatacttcac n                     101
```

<210> SEQ ID NO 410
<211> LENGTH: 100
<212> TYPE: DNA
<213> ORGANISM: Cannabis sativa

<400> SEQUENCE: 410

```
ctcatttaca caaatattct cgaacatcaa cctgactgcc cggtaactta tctgatacta   60
cagaaattgc attttgttct aagcattgct ttcggttttt                        100
```

<210> SEQ ID NO 411
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 411
cgatgtgtgg gttttcagat ctcttttaag gcgtaagaaa attttaataa aggaattgac    60
tatataggca ggcagacaag aagatggtgg cttcactttc n    101

<210> SEQ ID NO 412
<211> LENGTH: 100
<212> TYPE: DNA
<213> ORGANISM: Cannabis sativa

<400> SEQUENCE: 412
taagattaaa aacataaaca aatatgataa cactcatgca gattacaagg aaaatgcaca    60
tggccactgc aggtaacaat gtttgacttt ttgttaatta    100

<210> SEQ ID NO 413
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 413
atgaagcagg ccggagaaaa gacgtttttc ctgttttaaa caatcactaa agttaggagt    60
taggagaact gaaaaacaag tatgagatgt aatcaaatta n    101

<210> SEQ ID NO 414
<211> LENGTH: 100
<212> TYPE: DNA
<213> ORGANISM: Cannabis sativa

<400> SEQUENCE: 414
gaagagttgc gaagagaact cgcttttgc accttaataa tttaacactc agcattattt    60
cttattcgca gagaaagaga gagaggcctc ttcggatgga    100

<210> SEQ ID NO 415
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 415
tgcgacccat agcctgtgaa tcagaagata taatgctgat tgcgcccata tcatgcaaaa    60
tatcttctgc agcaattgtt tctgcccta ttcttgattc n    101

<210> SEQ ID NO 416
<211> LENGTH: 100
<212> TYPE: DNA
<213> ORGANISM: Cannabis sativa

<400> SEQUENCE: 416
gcaaaagcta catcttccgg gatgttcttg tcaaggtgat ggcagaccat ctgtatgtag    60
caagacgaaa gtgagaatat tgaacagcca tagtgcacct    100

<210> SEQ ID NO 417
<211> LENGTH: 101
<212> TYPE: DNA

<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 417

| | |
|---|---|
| attgttggtg catatgagga aggccacctg caggtccata atatccttgc cagtacattg | 60 |
| gcatagcaag cccaccacca tttgcactcg gtgcaggagg n | 101 |

<210> SEQ ID NO 418
<211> LENGTH: 100
<212> TYPE: DNA
<213> ORGANISM: Cannabis sativa

<400> SEQUENCE: 418

| | |
|---|---|
| gaagctcccc atgaccctaa attcccccca ggttgataca aaggcaatga accttgaaaa | 60 |
| gtggacccag gaagtcccag ttgtgctgta tgggaaccaa | 100 |

<210> SEQ ID NO 419
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 419

| | |
|---|---|
| gccacaactc ccaccatctt cctcagccac cctgcagctt catttcttct agaagctgag | 60 |
| gaaaaacata aagacacaa ttaggaaact aaattaaata n | 101 |

<210> SEQ ID NO 420
<211> LENGTH: 100
<212> TYPE: DNA
<213> ORGANISM: Cannabis sativa

<400> SEQUENCE: 420

| | |
|---|---|
| atatgtgaaa aaaaagaac agaaaatttt caaaattgga agattacaag tactggccat | 60 |
| aaacaccaaa caccaaaatt ctcaagagtc agatcctaat | 100 |

<210> SEQ ID NO 421
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 421

| | |
|---|---|
| tagaatggtt ttgctatttg tatatgaatc atgttcactt gagtagaagt ctatactcag | 60 |
| caaaagaatc tgaagcaatc acttatctgc tcccagtttt n | 101 |

<210> SEQ ID NO 422
<211> LENGTH: 100
<212> TYPE: DNA
<213> ORGANISM: Cannabis sativa

<400> SEQUENCE: 422

| | |
|---|---|
| tacgctgatt catgcaaaca aatcttctca agcttcgtag gccaatcttc tccgagaagc | 60 |
| aaagggttca tttccattac aacccggaaa tctatcatgg | 100 |

<210> SEQ ID NO 423
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 423
ccaaaaactt tcatttaac tgttctcatg ttaaaactgt ggaacaagga acgagtagct      60
gcagctgcga aagttttgca ggtaaatttg agtttgataa n                       101

<210> SEQ ID NO 424
<211> LENGTH: 100
<212> TYPE: DNA
<213> ORGANISM: Cannabis sativa

<400> SEQUENCE: 424
agctggtgcc tggaagtcag tactaactga taagctattc ttttctttcc ttccagagtg    60
tctcttctaa agtgatggaa ccttggagaa tcggccggtc                         100

<210> SEQ ID NO 425
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 425
cgccctgagc acccttaatg ggagtggttg gagcagacct cttctgctgc agcgaatgga    60
gttcgtcgat ggtttgggcc ttcaccgttg gcgcactgtc n                       101

<210> SEQ ID NO 426
<211> LENGTH: 100
<212> TYPE: DNA
<213> ORGANISM: Cannabis sativa

<400> SEQUENCE: 426
tcatggcata tttcgctatg tttcttctgc gtctgaattt tcgacagtcc gttccgtgct    60 gtcccttttcc cggtccgaag ctgaactcgc cgttagcgtt                        100

<210> SEQ ID NO 427
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 427
ccaatcaatc tgcagtgacg aacctcagct gagactgaga aaaccaaaca caaatgacag    60
tatgttttca tgtaagctct ccccaaatcc cagccccatt n                       101

<210> SEQ ID NO 428
<211> LENGTH: 100
<212> TYPE: DNA
<213> ORGANISM: Cannabis sativa

<400> SEQUENCE: 428
gcttttgctt atcaccaaca tcaaccactg tcgtcgcaac catcgtttat tcaatgcgca    60
ctgacgaaac aaggccaccg cttcctctcc actctctcag                          100

<210> SEQ ID NO 429
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 429
gtatccactg aggagatcat cctcgagcga cctagggctc tcggtacttt attatcattc    60
cacaatgatt gttcaactga ttctatttca attcataaat n                        101

<210> SEQ ID NO 430
<211> LENGTH: 100
<212> TYPE: DNA
<213> ORGANISM: Cannabis sativa

<400> SEQUENCE: 430 tttgttttg aaagttggat tataatatta tataggtagc aaggggggaag aagctaagaa    60 ttccggggat ccattgagtg cgaaaggcgg tgctgttctc                          100

<210> SEQ ID NO 431
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 431
accaatgaga aaacaaaat tagttacact ttttcggttt taacatctct aaactttaaa     60
ccaataaaca cgttccagca ttataagggt gttcgttcag n                        101

<210> SEQ ID NO 432
<211> LENGTH: 100
<212> TYPE: DNA
<213> ORGANISM: Cannabis sativa

<400> SEQUENCE: 432
tacctgaagt tttataggat caggatttga tccatcaata atgtcaatag ctccattgat    60
ccggaattgc tcccaagagt cagtgaagta ccaacaaatc                          100

<210> SEQ ID NO 433
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 433
aatatcattt gctatcttgt aaagctctaa agctgcaggt agattttgtg cctcctttcc    60
cattccaact gcttgagcac cctgaaataa gaaacagaca n                        101

```
-continued

<210> SEQ ID NO 434
<211> LENGTH: 100
<212> TYPE: DNA
<213> ORGANISM: Cannabis sativa

<400> SEQUENCE: 434
gacacaaaat atagctcaat ataactatac cgaatcaaca tacaacaaac acaatccaac    60
gcacactaca aaaggattca agaattatgt ctccgactaa                         100

<210> SEQ ID NO 435
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 435
ctattagact gtagagcatt gcatgaaagg cttactttat tggtttaaaa agtatagttc    60
gggtagatgg attctgcaga taaagtttca tctttcccat n                      101

<210> SEQ ID NO 436
<211> LENGTH: 100
<212> TYPE: DNA
<213> ORGANISM: Cannabis sativa

<400> SEQUENCE: 436
acattaggca actcctgctg aatggcagtg cttacctgtt ccggaaatgt atgtgttcac    60
acaaaatcag gctcagtatg acctttataa tgtcaattag                        100

<210> SEQ ID NO 437
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 437
gaaaaaacac ccctccagcc tgcaacatca attcagttga cagcttgcag gactcgagca    60
agtttcgtac cagtaactct gcagatcaca gaaaggtatc n                      101

<210> SEQ ID NO 438
<211> LENGTH: 100
<212> TYPE: DNA
<213> ORGANISM: Cannabis sativa

<400> SEQUENCE: 438
gttgagaaac aaacgaaaca tttaaatcca aggaacacgc aagtcacaaa tgccttgaac    60
cgacaccatt cttcccaaga taaaaataac acgatgacat                        100

<210> SEQ ID NO 439
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 439
```

```
cgatcattcg tacctgcagt tgaaagttga acctttttcaa gttcaaatgt tgatgaatta    60
acaatacaag gagacatttg atcttcatcc atgtttgttg n                        101
```

<210> SEQ ID NO 440
<211> LENGTH: 100
<212> TYPE: DNA
<213> ORGANISM: Cannabis sativa

<400> SEQUENCE: 440

```
acatgatgtt acttttttcag taacactacc ccaactactt ccatttaagg ttggtaaccc    60
aatacttcta ccttcatcac atgttgatat ttttcgattc                          100
```

<210> SEQ ID NO 441
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 441

```
tgtaagacca acgtgaacag agctaaggac cataagaagt tgaaggccgt tgaggaacca    60
ggcgaaacac ttgtcgtaat gagtgaacgt cgtcgtttgg n                        101
```

<210> SEQ ID NO 442
<211> LENGTH: 100
<212> TYPE: DNA
<213> ORGANISM: Cannabis sativa

<400> SEQUENCE: 442

```
tccactagga ttttccatag caatgcttgg ctgcagagtg acatgcttat tcggaagtaa    60
ccagcgtgaa acctggttaa aatagatgat aatatgggtt                          100
```

<210> SEQ ID NO 443
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 443

```
cgtaatgctg ttcttgctgt tatgtctgtt tatcgacttc ctggtggtga tcaattgctt    60
gtcgatgcac cggagattat agagaagttt tatcttcgga n                        101
```

<210> SEQ ID NO 444
<211> LENGTH: 100
<212> TYPE: DNA
<213> ORGANISM: Cannabis sativa

<400> SEQUENCE: 444

```
caggataatt ctagtaagca taatgctttt cttatgcttt ttacttgtga tgaagatcgt    60
gctgttaatt acctttttac acatgttgat agaattactg                          100
```

<210> SEQ ID NO 445
<211> LENGTH: 101
<212> TYPE: DNA
<213> ORGANISM: Cannabis sativa
<220> FEATURE:
<221> NAME/KEY: misc_feature

```
<222> LOCATION: (101)..(101)
<223> OTHER INFORMATION: n is g or c

<400> SEQUENCE: 445
cgctagaatt gtcgagaaaa gtttctttag tcggatcttc atctatactt ggaagacctg    60
gattaggccc caaatactgc agcctagatt taagagaact n                       101

<210> SEQ ID NO 446
<211> LENGTH: 100
<212> TYPE: DNA
<213> ORGANISM: Cannabis sativa

<400> SEQUENCE: 446
gaaaaccatg atttctctct ttgctgcatc attcagaaaa gaaaagacaa atatgtggaa    60
aatttagata gttcaaaggg aagttaaaag ctgaactagc                         100

<210> SEQ ID NO 447
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 447
gactcctcaa cctttgatgg agacgaagaa gatgaattgt accaacactt agtttaaaac    60
aaagcttttt actagatttt ctaatcatta ttattttgtg n                       101

<210> SEQ ID NO 448
<211> LENGTH: 100
<212> TYPE: DNA
<213> ORGANISM: Cannabis sativa

<400> SEQUENCE: 448
atccgggcat catttcagtg ccttatttta ttcttggtgt aaagattaaa gattaaaaat    60
caaaaatcaa aaatcaaaat tctttcagaa gatttcaagc                         100

<210> SEQ ID NO 449
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 449
gtatccactg aggagatcat cctcgagcga cctagggctc tcggtacttt attatcattc    60
cacaatgatt gttcaactga ttctatttca attcataaat n                       101

<210> SEQ ID NO 450
<211> LENGTH: 100
<212> TYPE: DNA
<213> ORGANISM: Cannabis sativa

<400> SEQUENCE: 450 tttgttttg aaagttggat tataatatta tataggtagc aaggggggaag aagctaagaa    60 ttccggggat ccattgagtg cgaaaggcgg tgctgttctc                         100

<210> SEQ ID NO 451
```

```
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 451
tggaaacagg aatagatgcc ccaccggaac tttcttctgt attttcacct aaatctctgg      60
gcaaatcctt cacagcttct gccattttct tcataatttt n                        101

<210> SEQ ID NO 452
<211> LENGTH: 100
<212> TYPE: DNA
<213> ORGANISM: Cannabis sativa

<400> SEQUENCE: 452
cgccgcttct tctcttcctt caattgtttc ttcataagaa gcttttccct atattctaac      60
tcatcataat aggccttctt ttgagctttg gaaagctttg                          100

<210> SEQ ID NO 453
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 453
gaaaaaacac ccctccagcc tgcaacatca attcagttga cagcttgcag gactcgagca      60
agtttcgtac cagtaactct gcagatcaca gaaaggtatc n                        101

<210> SEQ ID NO 454
<211> LENGTH: 100
<212> TYPE: DNA
<213> ORGANISM: Cannabis sativa

<400> SEQUENCE: 454
gttgagaaac aaacgaaaca tttaaatcca aggaacacgc aagtcacaaa tgccttgaac      60
cgcaccattc ttcccaagat aaaaataaca cgatgacatc                          100

<210> SEQ ID NO 455
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 455
ggaagtaaag ccaaactagg ccaagagaaa aggcgaagga gatggagcaa tgtagcatcc      60
ataaaagatg gaacaactag cattaaagag ctctgtgaca n                        101

<210> SEQ ID NO 456
<211> LENGTH: 100
<212> TYPE: DNA
<213> ORGANISM: Cannabis sativa

<400> SEQUENCE: 456
cagtgtgcca aggtgtgttc ctgcaggtat tgagcttaag aagttgaaaa tgtccaatac      60
```

-continued accagatagg acaatggacg atctccaaag cttccacgta          100

<210> SEQ ID NO 457
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 457
cacatcataa agagtatcac caatctttag cttgatggca ccacttctgt atacaagcat    60
tttacccacc aagcctgcag gtatctcgtt caatgcacaa n                      101

<210> SEQ ID NO 458
<211> LENGTH: 100
<212> TYPE: DNA
<213> ORGANISM: Cannabis sativa

<400> SEQUENCE: 458
acttcttgac agtgttcgca gccaaaggtg cccgtgtgct ttcgtttact ggctggccat    60
cattggtaac taattgtttc atcagaggca tagttggtgg                        100

<210> SEQ ID NO 459
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 459
tactaaaaat ctggcccgac aatgacgaat tcaaatgagt aattcatccc ggaaaaaaga    60
gcaataaaat aatttcttta acaaaaaaat cctgatcaca n                      101

<210> SEQ ID NO 460
<211> LENGTH: 100
<212> TYPE: DNA
<213> ORGANISM: Cannabis sativa

<400> SEQUENCE: 460
gcagggtagg gtagagagca gcagctgtac tatgtttacc caaatttgaa gccaccaggg    60
gtagggtggg ttggcttgct ccaaaaggaa aaccttgttg                        100

<210> SEQ ID NO 461
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 461
ggtgccatga actaccggga tagttccata tctcatcgca tacaattgat tcaagccaca    60
gggctcaaat ctcgaaggca tcagcagtat atcacagctg n                      101

<210> SEQ ID NO 462
<211> LENGTH: 100
<212> TYPE: DNA

<213> ORGANISM: Cannabis sativa

<400> SEQUENCE: 462
gcaaccagat caagaatcag tcagtcccat gaacatattt cattatgttt aaatagtgaa    60
ataaagagtc acatcccaag ttttgcgtat ctataaaata                         100

<210> SEQ ID NO 463
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 463
ttctactttt cccttcaca cctcccacac ccccaccgag acttcacttt catcatcaag    60
gttctcgcct acaaccgcct cgactcgctg gccgctgcct n                      101

<210> SEQ ID NO 464
<211> LENGTH: 100
<212> TYPE: DNA
<213> ORGANISM: Cannabis sativa

<400> SEQUENCE: 464
cgctcctcgc cgctgcagat tatctctccg atcgggtaca cctccacgtc tatatcgacc    60
acttcgcatt cgtcaatggc tccactgatg tggatcgtat                         100

<210> SEQ ID NO 465
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 465
tgtatgggaa ccaatatcag tcaaaggccc agtaacagct gatggcaagc ttgaagatga    60
ggtaactggg cgagtatagt gagactgcaa catagattca n                      101

<210> SEQ ID NO 466
<211> LENGTH: 100
<212> TYPE: DNA
<213> ORGANISM: Cannabis sativa

<400> SEQUENCE: 466
tttttttaaa gcaagtcaac atttatttac cattttggaa gatgtattat caataagtta    60
aaaaaaacat tcccaatctc ccatacctga atgatagccg                         100

<210> SEQ ID NO 467
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 467
caattgcttg tcgatgcacc ggagattata gagaagtttt atcttcggaa caggataatt    60
ctagtaagca taatgctttt cttatgcttt ttacttgtga n                      101

<210> SEQ ID NO 468
<211> LENGTH: 100
<212> TYPE: DNA
<213> ORGANISM: Cannabis sativa

<400> SEQUENCE: 468
gaagatcgtg ctgttaatta ccttttttaca catgttgata gaattactga ttgggtgaac    60
agcttcagat ggttgtgtta gaattgatta agaaagtttg                          100

<210> SEQ ID NO 469
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 469
ggaaacgaaa ggcaccacgc caaacgtgag cgctccagct gcttgaactg acacagagaa    60
tccacacaag acaacaatgg agccccatag cgagttacct n                        101

<210> SEQ ID NO 470
<211> LENGTH: 100
<212> TYPE: DNA
<213> ORGANISM: Cannabis sativa

<400> SEQUENCE: 470
ggccgagtaa cacgcagagc aacccggcca ctgtctgcac tgcccaggaa ccccaaagtc    60
tccctctcaa tttttctttc tataacttct ttgcattttt                          100

<210> SEQ ID NO 471
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 471
cttcgatttc tgagcttact aagtgagcca tgctgtttga cgtggcttat ctgcagtaaa    60
cggtccactc cactttacaa ggtatttcct taaagtttac n                        101

<210> SEQ ID NO 472
<211> LENGTH: 100
<212> TYPE: DNA
<213> ORGANISM: Cannabis sativa

<400> SEQUENCE: 472
aaccatttga acaaatagg ttcctgatag aaagaagcca tctcacatat cttctgttgc     60
cttggcagat tttcagagca atgtacttca tcgttcaatg                          100

<210> SEQ ID NO 473
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 473 taacgttttcc attctttatg tcttgattttt ttgcacaggt tggattaaag caaggactgg    60
aaatgttgaa tatattcaag agttacacac cgaagacttc n                          101

<210> SEQ ID NO 474
<211> LENGTH: 100
<212> TYPE: DNA
<213> ORGANISM: Cannabis sativa

<400> SEQUENCE: 474
ttgttagacg atttttagctt ctacgaaagc cgagaaaagg tcctcctagc caaaagagcc    60
attaacatca agcctgcagc aacattgaag atggaaacca                            100

<210> SEQ ID NO 475
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 475
acagtactaa tggaatcaac ggaggagatg acggtgtttg attcttcatc aatcggtgac    60
gagggggctt tggagcaaat atttcagtac atgggaaaga n                          101

<210> SEQ ID NO 476
<211> LENGTH: 100
<212> TYPE: DNA
<213> ORGANISM: Cannabis sativa

<400> SEQUENCE: 476
tggtactact tgcaaggaag aagaggcagg tacagaaaac gacaccaatg atgacacaaa    60
cgacaactcg aaaaactgca gatttcttcc aatcaacaac                            100

<210> SEQ ID NO 477
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 477
aaatacttca atataacaaa ttccatagac gagcctatgt gccatactaa aaatctggcc    60
cgacaatgac gaattcaaat gagtaattca tcccggaaaa n                          101

<210> SEQ ID NO 478
<211> LENGTH: 100
<212> TYPE: DNA
<213> ORGANISM: Cannabis sativa

<400> SEQUENCE: 478
agagcaataa ataatttct ttaacaaaaa aatcctgatc acacgcaggg tagggtagag    60
agcagcagct gtactatgtt tacccaaatt tgaagccacc                            100

<210> SEQ ID NO 479
<211> LENGTH: 101
<212> TYPE: DNA
<213> ORGANISM: Cannabis sativa

```
<220> FEATURE:
<221> NAME/KEY: misc_feature
<222> LOCATION: (101)..(101)
<223> OTHER INFORMATION: n is a or g

<400> SEQUENCE: 479
ggagacgaag aagatgaatt gtaccaacac ttagtttaaa acaaagcttt ttactagatt      60
ttctaatcat tattattttg tgaatccggg catcatttca n                         101

<210> SEQ ID NO 480
<211> LENGTH: 100
<212> TYPE: DNA
<213> ORGANISM: Cannabis sativa

<400> SEQUENCE: 480
tgccttattt tattcttggt gtaaagatta aagattaaaa atcaaaaatc aaaaatcaaa      60
attctttcag aagatttcaa gcattgtagt aaatctttat                           100

<210> SEQ ID NO 481
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 481
gatcataatg agtacttgat ctagcttgag cactgttcat ccacaagttg acagaagcta      60
aaaccttttc cttcaaaaat caggctgcag aagtagacaa n                         101

<210> SEQ ID NO 482
<211> LENGTH: 100
<212> TYPE: DNA
<213> ORGANISM: Cannabis sativa

<400> SEQUENCE: 482
tggtagttag attcagagtg agaacaaagg actctttgtt agatggccat agagtagtaa      60
acacagactg gtccaagaga tttacaaacc gtattaatat                           100

<210> SEQ ID NO 483
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 483
accaatgaga aaacaaaat tagttacact ttttcggttt taacatctct aaactttaaa       60
ccaataaaca cgttccagca ttataagggt gttcgttcag n                         101

<210> SEQ ID NO 484
<211> LENGTH: 100
<212> TYPE: DNA
<213> ORGANISM: Cannabis sativa

<400> SEQUENCE: 484
tacctgaagt tttataggat caggatttga tccatcaata atgtcaatag ctccattgat      60
ccggaattgc tcccaagagt cagtgaagta ccaacaaatc                           100
```

<210> SEQ ID NO 485
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 485
aaaaatagtt ttgttatatt atatcttctc atggaaaata gctaatagta ttcatttgaa     60
ttgaaatgtt gaacagacca ttctgggcag gagctgcagg n                        101

<210> SEQ ID NO 486
<211> LENGTH: 100
<212> TYPE: DNA
<213> ORGANISM: Cannabis sativa

<400> SEQUENCE: 486
aatgcagtga tcattgaggc agatgctttc aaagaatcag atgttatcta caaagcccctt   60 agctctagag gccatcatga tatgcttcaa acagctgagc                          100

<210> SEQ ID NO 487
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 487
tatataatat atatatataa gataattaga taacataaca tgtaattaag gattaagcat     60
gaaattatta attttaattt taacataccg gcagccaata n                        101

<210> SEQ ID NO 488
<211> LENGTH: 100
<212> TYPE: DNA
<213> ORGANISM: Cannabis sativa

<400> SEQUENCE: 488
cacaaaatag ttcacccaa agcaaatgtt gatatgacca agcaaggtaa aaaatatgga     60
aatctgttat ttcataatta taaggttaat atgtcattaa                          100

<210> SEQ ID NO 489
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 489
acaattgaaa aagttgtaat tcatttattg agggatggag atcccaacat agagtgagct     60
ccttaccatc tgacccaccc ctttgcagct gcagaacatg n                        101

<210> SEQ ID NO 490
<211> LENGTH: 100
<212> TYPE: DNA
<213> ORGANISM: Cannabis sativa

<400> SEQUENCE: 490

```
gccatctttt tcacttttt gtttattgta ttatagtata ggtacgtcgt agaagaaaaa    60
tgagaagaag agaattaagg aataggtgat attattatat                        100
```

<210> SEQ ID NO 491
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 491

```
gcttgaggag agaagagaga gtaagaaggg gaatggagca acgatcacgt tctgacatca    60 caccettgat ggtacggttg taagcaactc cggagtaacc n                       101
```

<210> SEQ ID NO 492
<211> LENGTH: 100
<212> TYPE: DNA
<213> ORGANISM: Cannabis sativa

<400> SEQUENCE: 492

```
agctccatgg ccatagtagc tagcttgatc cgagtagcct tatcagacgg caaggcctcc    60
aaatatggta tattgagatc aaagaaaccc attcctactc                        100
```

<210> SEQ ID NO 493
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 493

```
ggggagataa ttgtacgaca ttcgatgtta tgtcgtttgg tgcagttgga gatggtgtgg    60
cagacgacac tgcagccttt aaagaggcat ggaaagctgc n                       101
```

<210> SEQ ID NO 494
<211> LENGTH: 100
<212> TYPE: DNA
<213> ORGANISM: Cannabis sativa

<400> SEQUENCE: 494

```
tgtggtgttg aatccggtgt cgttttggcc cctgctgatt attgttttaa attacttcta    60
ctatcttttc tggaccctgc agccccggat taatgttcca                        100
```

<210> SEQ ID NO 495
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 495

```
ccaatcaatc tgcagtgacg aacctcagct gagactgaga aaaccaaaca caaatgacag    60
tatgttttca tgtaagctct ccccaaatcc cagccccatt n                       101
```

<210> SEQ ID NO 496

```
<211> LENGTH: 100
<212> TYPE: DNA
<213> ORGANISM: Cannabis sativa

<400> SEQUENCE: 496
gcttttgctt atcaccaaca tcaaccactg tcgtcgcaac catcgtttat tcaatgcgca      60
ctgacgaaac aaggccaccg cttcctctcc actctctcag                           100

<210> SEQ ID NO 497
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 497
atatttagcc caaatgaaaa attaggaatt tttcctttca cctttgattt tgattttaaa     60
atgttataac attatggccg gctaacttag ctatcgattt n                        101

<210> SEQ ID NO 498
<211> LENGTH: 100
<212> TYPE: DNA
<213> ORGANISM: Cannabis sativa

<400> SEQUENCE: 498
cttttggggt gttattagca aataatttta agctgaattt tctgcagctc ttggctgagg     60
acccatcttt aaagcgattc aagtcacata agcctaatgt                          100

<210> SEQ ID NO 499
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 499
aaacgatctg acgcccttca tcttgatcaa tctcaattaa acaagattta gctgagtccc     60
ctttacagta tttgagcctt agatcaattg agatgtcgta n                        101

<210> SEQ ID NO 500
<211> LENGTH: 100
<212> TYPE: DNA
<213> ORGANISM: Cannabis sativa

<400> SEQUENCE: 500
cctcgcccta ttgagccaat tgcaatctct gcagcttttg gagctggaac tttcagcgcc     60
ataactcacc aacgcctgtt ccttcaccaa tcccagatct                          100

<210> SEQ ID NO 501
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 501
tttcttcacc gtacatgtat aaggaacaac cggtcatagt ttgagaagcc acaaccacag     60
```
atgacgcatc atcacagaat tcaactgcca caggatgacc n        101

<210> SEQ ID NO 502
<211> LENGTH: 100
<212> TYPE: DNA
<213> ORGANISM: Cannabis sativa

<400> SEQUENCE: 502
ccagcgggca agtttattct gaggaatctg cagagataaa tttcataaat ttgaggaata        60
agtacccaaa acgaagaaaa tccataaatg atcattggaa        100

<210> SEQ ID NO 503
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 503
caggaagagg aggcttggtt tgctggttag ctccatcaga agatttggtc ttttcttcac        60
cgtacatgta taaggaacaa ccggtcatag tttgagaagc n        101

<210> SEQ ID NO 504
<211> LENGTH: 100
<212> TYPE: DNA
<213> ORGANISM: Cannabis sativa

<400> SEQUENCE: 504
acaaccacag atgacgcatc atcacagaat tcaactgcca caggatgacc gccagcgggc        60
aagtttattc tgaggaatct gcagagataa atttcataaa        100

<210> SEQ ID NO 505
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 505 taccccctccc ggacttccta tgatgcgtct gcagcgtgtt tttcaggctc ggaatcgtcg        60
acctggaaaa cgaggacgaa gacgaagaag aagtaatggc n        101

<210> SEQ ID NO 506
<211> LENGTH: 100
<212> TYPE: DNA
<213> ORGANISM: Cannabis sativa

<400> SEQUENCE: 506 ttccccttc cggcgtatat atcggaccag ctctccatca gcatctctct cacgcacgct        60
acgtgtagat tgtacttctt gcacttagac cggtagctcc        100

<210> SEQ ID NO 507
<211> LENGTH: 101
<212> TYPE: DNA
<213> ORGANISM: Cannabis sativa
<220> FEATURE:
<221> NAME/KEY: misc_feature
<222> LOCATION: (101)..(101)

<223> OTHER INFORMATION: n is t or c

<400> SEQUENCE: 507
agcctcattt ggctcgattt gaacagcaat caactctctg gcactgtccc cgccgacttg    60
ctaaccaggc tggcctagtg gttcccggta ttgtttctgg n                       101

<210> SEQ ID NO 508
<211> LENGTH: 100
<212> TYPE: DNA
<213> ORGANISM: Cannabis sativa

<400> SEQUENCE: 508
aagcaatttg catttgtgag aaatgagggt ggaacagcct gcaggggagc cggaggacta    60
gttgaattcg agggtgttcg gcctgagaga ctagaaaact                          100

<210> SEQ ID NO 509
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 509 tctactttc cccttcacac ctcccacacc cccaccgaga cttcactttc atcatcaagg     60
ttctcgccta caaccgcctc gactcgctgg cccgctgcct n                       101

<210> SEQ ID NO 510
<211> LENGTH: 100
<212> TYPE: DNA
<213> ORGANISM: Cannabis sativa

<400> SEQUENCE: 510
cgctcctcgc cgctgcagat tatctctccg atcgggtaca cctccacgtc tatatcgacc    60
acttcgcatt cgtcaatggc tcctgatgtg gatcgtatgt                          100

<210> SEQ ID NO 511
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 511
tagagaagag aaactgtaat gcctacctag tttcactcaa gtaagaagag tctgatttta    60
cagttgaaga cgctgctgaa cccttggcac tagcttcctt n                       101

<210> SEQ ID NO 512
<211> LENGTH: 100
<212> TYPE: DNA
<213> ORGANISM: Cannabis sativa

<400> SEQUENCE: 512
ttcaaaccaa acaaagaacc ggaactttcc ttatcctcat catcttcatc aatatcactg    60
tcttcttcac taagcaaagc cccaatgccc aaccttttc                           100

<210> SEQ ID NO 513
<211> LENGTH: 101

```
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 513
tcggcgagca agtatgtgta ggtggatgat tccttctcaa agagctgacg gaagaggagc    60
ttgccaaaga gatgagacga cgtcgtataa gagcaagtcg n                       101

<210> SEQ ID NO 514
<211> LENGTH: 100
<212> TYPE: DNA
<213> ORGANISM: Cannabis sativa

<400> SEQUENCE: 514 tgttttaaa caccctaact tggtcgactt taccggactc gataaaatcc tcgaagaaca    60
attcaacaaa gctggattag atccagtaat ggtgaagact                        100

<210> SEQ ID NO 515
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 515
gccaccaaat gggggcattg aggccaggct ttgggcatac gcgcgggtca aaggctgcag    60
tggagtctat gacgcagata cttgcaaagg agttgaaggg n                       101

<210> SEQ ID NO 516
<211> LENGTH: 100
<212> TYPE: DNA
<213> ORGANISM: Cannabis sativa

<400> SEQUENCE: 516
acgggatcac agccaactgc gtagccccgg ggccgatcgc aacagatatg ttctatatgg    60
gaaagactga ggaacaaatt cagaaagcgg cggaggaaaa                         100

<210> SEQ ID NO 517
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or t

<400> SEQUENCE: 517
atataaaatt caatgccaag tgattcaaaa ccggtttaat cttcaataaa tctttattag    60
taatggcttg cattcttcaa aaagaatcaa cctttacaat n                       101

<210> SEQ ID NO 518
<211> LENGTH: 100
<212> TYPE: DNA
<213> ORGANISM: Cannabis sativa

<400> SEQUENCE: 518
tgtacggtca tatttcttaa aacaaataaa taaataaaat cacacaagcc aattggaaag    60
```
aggctattca actttataca atatagacct ataatgtact                                100

<210> SEQ ID NO 519
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 519
caaagtacca cagagccatt tccaacatgc ccagcgtaat cactagagta atacagttct          60
gcagaggcag aacttctctc caaaatcttg catactgtga n                             101

<210> SEQ ID NO 520
<211> LENGTH: 100
<212> TYPE: DNA
<213> ORGANISM: Cannabis sativa

<400> SEQUENCE: 520
aaccaaaaga gcccaagtaa tacaaaagca aatgacatga gcccataaaa tttcataagt          60
ggtgccattc tgccggtaga tatccatttg ggttttcca                                100

<210> SEQ ID NO 521
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 521
atcagtaacc agattcaccc aaaaagctgc actggtatca tacattcggt attcccaatg          60
ctgcagtcaa gaatatggat ataacctctc caacatttga n                             101

<210> SEQ ID NO 522
<211> LENGTH: 100
<212> TYPE: DNA
<213> ORGANISM: Cannabis sativa

<400> SEQUENCE: 522
gatatcatgt acctgaaaat tgacaatatg aacagaacta tataagttgc tcaacaatga          60
gatatttcat ataagaaagg gtatatatgc agaactaaga                               100

<210> SEQ ID NO 523
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 523
ctcctgtgta caggcagtac ttgaagatga tggaacctca tcttaattaa ttgttccaat          60
cccacaaaaa ctttatggaa aagtttgatt accottccca n                             101

<210> SEQ ID NO 524
<211> LENGTH: 100
<212> TYPE: DNA
<213> ORGANISM: Cannabis sativa

<400> SEQUENCE: 524 accttt ctac caggtaatca aattggatac aacaaagtaa ccaaaactca cagggttctc    60
acttcatgga agaattccaa agacccttta cccggccttt                           100

<210> SEQ ID NO 525
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 525
ccgctagaat tgtcgagaaa agtttcttta gtcggatctt catctatatt ggaagacgct    60
ggattggccc caaatactgc agcctagatt taagagaact n                        101

<210> SEQ ID NO 526
<211> LENGTH: 100
<212> TYPE: DNA
<213> ORGANISM: Cannabis sativa

<400> SEQUENCE: 526
gaaaaccatg atttctctct tgctgcatc attcagaaaa gaaagacaa atatgtggaa       60 aatttagata gttcaaaggg aagttaaaag ctgaactagc                          100

<210> SEQ ID NO 527
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 527
aatttcgatc aggttgcagc caactttaaa caaaatgtct tttgagttct tacatcaatt    60
tgtatgaata ggttcacctg gtcagcagaa gaagaaatct n                        101

<210> SEQ ID NO 528
<211> LENGTH: 100
<212> TYPE: DNA
<213> ORGANISM: Cannabis sativa

<400> SEQUENCE: 528
attccagtaa aaaacttga tatttatttt tcagggccgg gtcaccattt ctctgtcgat     60
ggactacaag ttctagattc ttcatggaac aacctttcaa                          100

<210> SEQ ID NO 529
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 529
gcaacataca tataattaat gtcagccggt gataaaaaca tttctatcaa taaatttcta    60
attaagaaca tcaaacactt tgaccattac aaataataaa n                        101

```
<210> SEQ ID NO 530
<211> LENGTH: 100
<212> TYPE: DNA
<213> ORGANISM: Cannabis sativa

<400> SEQUENCE: 530
tcatttctag ttggagcaac aaagataata ttagatatca tccaaggaga tagacacata      60
tgacattgat atgtgttatt acgtttgaag acccgagcat                           100

<210> SEQ ID NO 531
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 531
cttagggcta atccctccaa cctgcatcaa caaaacaatg ctagatttta agaaatcaca      60
aacacattaa taaatttctt tgtagcatca attgcagttt n                         101

<210> SEQ ID NO 532
<211> LENGTH: 100
<212> TYPE: DNA
<213> ORGANISM: Cannabis sativa

<400> SEQUENCE: 532
ctcactttaa gtccggtctc ctttcaaaca caattgagaa agcctgtcga atagacaagt      60
cttcggtgat ttcttgtctt actttatctg tctgcattat                           100

<210> SEQ ID NO 533
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 533
ataaataaag gctaaaatga gttgaactca acaccacaag agtttgtgga cacactacat      60
caaatgggcc acaacatctt ttacattagg aaaatttaca n                         101

<210> SEQ ID NO 534
<211> LENGTH: 100
<212> TYPE: DNA
<213> ORGANISM: Cannabis sativa

<400> SEQUENCE: 534
ttgatttatg atgttctttg acattctata aagataaatc tatttgtgct catatctatc     60
aaatatcttc caccttaccg gagatattaa tatgtgagta                           100

<210> SEQ ID NO 535
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 535
```
tagatccacc tccaatgagg ggaagaaagc tatacttctt agcaaattct gcccaccggt    60
ttaaaagtct atcctctgtg ccaaccaatg cagcagattt n                       101

<210> SEQ ID NO 536
<211> LENGTH: 100
<212> TYPE: DNA
<213> ORGANISM: Cannabis sativa

<400> SEQUENCE: 536
agaattgtag cctgttacaa aaattaggaa agatattatt gaccaaaaat cacaaatttg    60
aatacatacg tatcgatcat gaaaaaacaa gtttatcatg                         100

<210> SEQ ID NO 537
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 537
atattatttc catccagatg tttccagatc cgggtattat aaaaatgcaa gttaaaatct    60
tgctaatatt agattgagaa aaagatggca ttgaaaagga n                       101

<210> SEQ ID NO 538
<211> LENGTH: 100
<212> TYPE: DNA
<213> ORGANISM: Cannabis sativa

<400> SEQUENCE: 538
aactgggcat atagtaataa ccaactttta tcagtggagc actggtcatc atctcattcc    60
tgcagcagga attctggtta atatcacata caatatctct                         100

<210> SEQ ID NO 539
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 539
gacacatatg acattgatat gtgttattac gtttgaagac ccgagcatag tttattgaaa    60
ttagccagct gatcagaaaa gttagatatg agaaaacaca n                       101

<210> SEQ ID NO 540
<211> LENGTH: 100
<212> TYPE: DNA
<213> ORGANISM: Cannabis sativa

<400> SEQUENCE: 540
cagaagtatt tgagtcacac ttcatcagtt tagtgtaaaa acaagatcct tacagatact    60
gcagcaacag gataataaat ccaacactaa catgctcctc                         100

<210> SEQ ID NO 541
<211> LENGTH: 101
<212> TYPE: DNA
<213> ORGANISM: Cannabis sativa
<220> FEATURE:

```
<221> NAME/KEY: misc_feature
<222> LOCATION: (101)..(101)
<223> OTHER INFORMATION: n is g or a

<400> SEQUENCE: 541
actatgtctt ctaaggcgat tttgtttcgg ttgtttaggc gacgcgacca tggatcttct    60
cgtatgtagt actattagaa tgtttaatct gttttacttg n                       101

<210> SEQ ID NO 542
<211> LENGTH: 100
<212> TYPE: DNA
<213> ORGANISM: Cannabis sativa

<400> SEQUENCE: 542
atgaatcttt tgtaggcctt ggacaccttt aacacagcag ttatatctcc ggtctactat    60
gttatgtgtt acgtcgttca ccatctcgga gctgatcatg                         100

<210> SEQ ID NO 543
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 543
atgtaaggaa ataaacctat gtaatattat ttccatccag atgtttccag atccgggtat    60
tataaaaatg caagttaaaa tcttgctaat attagattga n                       101

<210> SEQ ID NO 544
<211> LENGTH: 100
<212> TYPE: DNA
<213> ORGANISM: Cannabis sativa

<400> SEQUENCE: 544
aaaaagatgg cattgaaaag gaaaactggg catatagtaa taaccaactt ttatcagtgg    60
agcactggtc atcatctcat tcctgcagca ggaattctgg                         100

<210> SEQ ID NO 545
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 545
catgataaac ttgttttttc atgatcgata cgtatgtatt caaatttgtg atttttggtc    60
aataatatct ttcctaattt ttgtaacagg ctacaattct n                       101

<210> SEQ ID NO 546
<211> LENGTH: 100
<212> TYPE: DNA
<213> ORGANISM: Cannabis sativa

<400> SEQUENCE: 546
aaatctgctg cattggttgg cacagaggat agacttttaa accggtgggc agaatttgct    60
aagaagtata gctttcttcc ctcattggag gtggatctac                         100
```

```
<210> SEQ ID NO 547
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 547
aatataaaat tcaatgccaa gtgattcaaa accggtttaa tcttcaataa atctttatta      60
gtaatggctt gcattcttca aaaagaatca acctttacaa n                        101

<210> SEQ ID NO 548
<211> LENGTH: 100
<212> TYPE: DNA
<213> ORGANISM: Cannabis sativa

<400> SEQUENCE: 548
gtgtacggtc atatttctta aaacaaataa ataaataaaa tcacacaagc caattggaaa      60
gaggctattc aactttatac aatatagacc tataatgtac                          100

<210> SEQ ID NO 549
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 549
agcctcattt gctcgatttg aacagcaatc aactctctgg cactgtcccc gccgagcttg      60
ctaaccaggc tggcctagtg gttcccggta ttgtttctgg n                        101

<210> SEQ ID NO 550
<211> LENGTH: 100
<212> TYPE: DNA
<213> ORGANISM: Cannabis sativa

<400> SEQUENCE: 550
aagcaatttg catttgtgag aaatgagggt ggaacagcct gcagggccg gaggactagt       60 tgaattcgag ggtgttcggc ctgagagact agaaaactct                          100

<210> SEQ ID NO 551
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 551
ccagaagtat tccatgttca tttgcactat cgacctacat cattgaaatg aaccaggaac      60
aaaaatatct tgacttaatt aaaacaatat agatatatat n                        101

<210> SEQ ID NO 552
<211> LENGTH: 100
<212> TYPE: DNA
<213> ORGANISM: Cannabis sativa

<400> SEQUENCE: 552
```

```
tatattatat tataaatctc aagagctgca gagattgaaa aaaaaaaagt catacccctaa    60 ttaccgtagc attcttgcaa gaatcattat caattacaac                          100

<210> SEQ ID NO 553
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 553
tgtgaaaacc tttccgtggt atcaatccaa tactttggtt tttgcttgca gtcacccaat    60
tgcagttgag ttaccggggc taatcaagtc atcgcaactt n                       101

<210> SEQ ID NO 554
<211> LENGTH: 100
<212> TYPE: DNA
<213> ORGANISM: Cannabis sativa

<400> SEQUENCE: 554
ttctctcaca caagcattct tggggattgc ataaaaataa tcttcctcct ttggcctgtc    60
tgcaattact ctgcgtcgac ttggttgtcc catccttttc                          100

<210> SEQ ID NO 555
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or g

<400> SEQUENCE: 555
gttacaccat gatggtgaac tctccggaac ttggccattg gacatattgc acacctacaa    60
atcaaacttt ggaataagac aactatcaac aattacatat n                       101

<210> SEQ ID NO 556
<211> LENGTH: 100
<212> TYPE: DNA
<213> ORGANISM: Cannabis sativa

<400> SEQUENCE: 556
taacatttaa tattgtacta attctaatta cacagatacc ttcaaatttc tgtaaactgg    60
ctttgcatac aaatgatcaa taccaagaaa gtaacgatcg                          100

<210> SEQ ID NO 557
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 557
cactacatca aatgggccac aacatctttt acattaggaa aatttacagt tgatttatga    60
tgttctttga cattctataa agataaatct atttgtgctc n                       101

<210> SEQ ID NO 558
<211> LENGTH: 100
```

```
<212> TYPE: DNA
<213> ORGANISM: Cannabis sativa

<400> SEQUENCE: 558
tatctatcaa atatcttcca ccttaccgga gatattaata tgtgagtatg ctcaaataat    60
atgaccagaa aatataacaa aatcaatatt catcgactac                         100

<210> SEQ ID NO 559
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or a

<400> SEQUENCE: 559
ccaattgttt cttcacaata ccacacacct tctccactgt ttctttcttg gcctgcagaa    60
ggatgccata cataattagc tccaaaataa agtaaaaaa n                         101

<210> SEQ ID NO 560
<211> LENGTH: 100
<212> TYPE: DNA
<213> ORGANISM: Cannabis sativa

<400> SEQUENCE: 560
caaatcatta cctttacaca agggttgata gcagaaacat caatgatgct gtgtcataag    60
ggctaaacac aaagtaacgg atgtcaatgg aacaactaca                         100

<210> SEQ ID NO 561
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 561
gccaattgtt tcttcacaat accacacacc ttctccactg tttctttctt ggcctgcaga    60
aggatgccat acataattag ctccaaaata aaagtaaaaa n                        101

<210> SEQ ID NO 562
<211> LENGTH: 100
<212> TYPE: DNA
<213> ORGANISM: Cannabis sativa

<400> SEQUENCE: 562
acaaatcatt acctttacac aagggttgat agcagaaaca tcaatgatgc tgtgtcataa    60
gggctaaaca caaagtaacg gatgtcaatg gaacaactac                         100

<210> SEQ ID NO 563
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 563
cgagacgaga cgcgaccgtg gttttgaaac cacaacaaca acaactaggg ttcatcccta    60
```

```
ccaaaaaccc ctctttacaa ttcctgcaga tttaccgctt n                    101
```

<210> SEQ ID NO 564
<211> LENGTH: 100
<212> TYPE: DNA
<213> ORGANISM: Cannabis sativa

<400> SEQUENCE: 564

```
ttcttttcgc ggaaaccaaa caggaaatac aattgaccat gtcgaagagg aaattcggat    60
tcgaaggctt tggcataaac cgccaaacga cttacaactt                         100
```

<210> SEQ ID NO 565
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 565

```
gattaccta caaaccgcat tcaaaatgga ggaactgagg tcgtcgaggt aaatttcttt    60
atttcttttt agtttgatga atgcctgcag ttcatttgga n                      101
```

<210> SEQ ID NO 566
<211> LENGTH: 100
<212> TYPE: DNA
<213> ORGANISM: Cannabis sativa

<400> SEQUENCE: 566

```
gttagtttag tctgttcaaa ttttccgaat ctgaagtagt atgactttg gtatctcact    60 gaaatgttca ttttggtatc tcagtaaacc aagtaattgc                        100
```

<210> SEQ ID NO 567
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 567

```
ctgagctcca ttatctatat aaactcatga gcacttccgg acgacttctc aacgatatcc    60
acggcttcaa ggtaacaata gtttatcctt tccactggtc n                      101
```

<210> SEQ ID NO 568
<211> LENGTH: 100
<212> TYPE: DNA
<213> ORGANISM: Cannabis sativa

<400> SEQUENCE: 568

```
ataagatacc ttgtttaaaa ccagaaagat aaaatataag ttttcgttgt gatgagtttt    60
tggcattttc taatcactct attggttatg ctgcagagag                        100
```

<210> SEQ ID NO 569
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 569
ctggaaccac tagcgaagaa gcagcgaaag tgacatcatt gcattctaat tgtttgcccc    60
ggatatagaa ttggggcccg atcacccaat tgtatgtaac n                      101

<210> SEQ ID NO 570
<211> LENGTH: 100
<212> TYPE: DNA
<213> ORGANISM: Cannabis sativa

<400> SEQUENCE: 570
acacaactcc tggagacaaa aatgttctga tcaggttaga gatgctcatg tgtcacatat    60
ttatttcggg tagctgggta gccactcctt ttttcacaga                         100

<210> SEQ ID NO 571
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 571
tttctgagga tgttacaaga catcctgagc tccattatct atataaactc atgagcactt    60
ccggacgact tctcaacgat atccacggct tcaaggtaac n                      101

<210> SEQ ID NO 572
<211> LENGTH: 100
<212> TYPE: DNA
<213> ORGANISM: Cannabis sativa

<400> SEQUENCE: 572
atagtttatc ctttccactg gtcgataaga taccttgttt aaaaccagaa agataaaata    60
taagttttcg ttgtgatgag tttttggcat tttctaatca                         100

<210> SEQ ID NO 573
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or c

<400> SEQUENCE: 573 aggggggataa ttgtacgaca ttcgatgtta tgtcgtttgg tgcagttgga gatggtgtgg    60
cagacgacac tgcagccttt aaagaggcat ggaaagctgc n                      101

<210> SEQ ID NO 574
<211> LENGTH: 100
<212> TYPE: DNA
<213> ORGANISM: Cannabis sativa

<400> SEQUENCE: 574
tgtggtgttg aatccggtgt cgttttggcc cctgctgatt attgttttaa aattacttct    60
actatctttt ctggaccctg cagccccgga ttaatgttcc                         100

<210> SEQ ID NO 575
<211> LENGTH: 101
<212> TYPE: DNA

```
<213> ORGANISM: Cannabis sativa
<220> FEATURE:
<221> NAME/KEY: misc_feature
<222> LOCATION: (101)..(101)
<223> OTHER INFORMATION: n is a or t

<400> SEQUENCE: 575
acccgtgatt ctctgaaatc attttatttt ccgtgcctta ttacataagg aaggaagaaa    60
agaactcgta ttttgggttc tttccatctt cgtatgtgtt n                      101

<210> SEQ ID NO 576
<211> LENGTH: 100
<212> TYPE: DNA
<213> ORGANISM: Cannabis sativa

<400> SEQUENCE: 576
gtatttgtat gtttgtgtaa gataaatcat aaatttctaa cgaactcttt aaaccacagt    60
tccatgaccg ccaccacctt catcgaccgc ccggttatat                         100

<210> SEQ ID NO 577
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 577
gagtaggaat gggtttcttt gatctcaata taccatattt ggaggccttg ccgtctgata    60
aggctactcg gatcaagcta gctactatgg ccatggagct n                      101

<210> SEQ ID NO 578
<211> LENGTH: 100
<212> TYPE: DNA
<213> ORGANISM: Cannabis sativa

<400> SEQUENCE: 578
ggttactccg gagttgctta caaccgtacc atcaagggtg tgatgtcaga acgtgatcgt    60
tgctccattc cccttcttac tctctcttct ctcctcaagc                        100

<210> SEQ ID NO 579
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 579
atcataaact tatttggctt aatctgaaaa tagccaacat aaatgatgaa ataacagaag    60
aaaagcaagt aaatttaaga attcagcgat gaaattatct n                      101

<210> SEQ ID NO 580
<211> LENGTH: 100
<212> TYPE: DNA
<213> ORGANISM: Cannabis sativa

<400> SEQUENCE: 580
accatgtaaa cagaggtatc atttgatgga agtgaagagg ctgcaggtaa cactttgaat    60
ttccaatcag gaacgtatag accatataat aaccccgtgt                        100
```

<210> SEQ ID NO 581
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 581
tttctagcat tggagatgac attgatatgg taatgatgtc gacaccatca gcaatagcgt    60
cgtcaaaagc tgccaacata gcttctgaat agcaccctgt n                       101

<210> SEQ ID NO 582
<211> LENGTH: 100
<212> TYPE: DNA
<213> ORGANISM: Cannabis sativa

<400> SEQUENCE: 582
gggctgcaga ctttataagc agcaattctt gcagagggaa ctcctcctct tgcaatgcct    60
tcttttagtc catagaaact gacattttt acattgttcc                          100

<210> SEQ ID NO 583
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 583
tataatctgc tcttcttgtt agtatgtttg cctttatat tccgggtaga tttgtcttat     60
ttaaaaaccc tttctgtgag aagacttta tatgtatagt n                        101

<210> SEQ ID NO 584
<211> LENGTH: 100
<212> TYPE: DNA
<213> ORGANISM: Cannabis sativa

<400> SEQUENCE: 584
aggattgtgt ttgacatttt cttatcttgg tggaaacatt tttaagcaaa cacgtgttgc    60
aggcttgact aatctgattt tcacgtggaa gattgaactt                         100

<210> SEQ ID NO 585
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or g

<400> SEQUENCE: 585
agaatttata cagtagaacc tcactaatat atacgaagaa taacctcaaa aattaaatct    60
tgggcagtta taaataaaaa taatttttaa attgtaaaac n                       101

<210> SEQ ID NO 586
<211> LENGTH: 100
<212> TYPE: DNA
<213> ORGANISM: Cannabis sativa

<400> SEQUENCE: 586
ttgtttataa aattttaatc attaagaaac acagcaaata aacctaacaa gtattgaaaa        60
atgtccatta aaagaaacca tcgttctttc cggtcttgaa                             100

<210> SEQ ID NO 587
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or c

<400> SEQUENCE: 587
gaccataaga cactgcagag ctatggctcg aatcaccacc atttccattt tctgttgagt        60
tcaaatgcaa attagcattc ccctgtact gataactatg n                            101

<210> SEQ ID NO 588
<211> LENGTH: 100
<212> TYPE: DNA
<213> ORGANISM: Cannabis sativa

<400> SEQUENCE: 588 cccccggat cagcaccgtg accatgttct cccgagttcg aatgtgaact attattccct         60
ctgtatcgat tagactatac gaagctgaaa cactgtcatt                             100

<210> SEQ ID NO 589
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or c

<400> SEQUENCE: 589
tctgtttaag gatttctgca gcaatcggga cggttgagtt gactggatta ctgattatgt       60
ggataaaggc atcagggcag ttgtcagcaa cagcctcaat n                           101

<210> SEQ ID NO 590
<211> LENGTH: 100
<212> TYPE: DNA
<213> ORGANISM: Cannabis sativa

<400> SEQUENCE: 590
agtgtcttta ctataccggc attgatgttg aataggtcat cacgagtcat tccaggcttt       60
ctcggaactc cagcaggaat gacaacaaca tttacgcctt                             100

<210> SEQ ID NO 591
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is g or a

<400> SEQUENCE: 591
ccttctgttt aaggatttct gcagcaatcg ggacggttga gttgactgga ttactgatta       60
tgtggataaa ggcatcaggg cagttgtcag caacagcctc n                           101

```
<210> SEQ ID NO 592
<211> LENGTH: 100
<212> TYPE: DNA
<213> ORGANISM: Cannabis sativa

<400> SEQUENCE: 592
atcagtgtct ttactatacc ggcattgatg ttgaataggt catcacgagt cattccaggc    60
tttctcggaa ctccagcagg aatgacaaca acatttacgc                         100

<210> SEQ ID NO 593
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 593
tatttgaatc cactcaagtc cacttcacaa taagtggtta caagctcacg cggccggtgg    60
tgtgaagctc acaatgcaac atttgagcct ttgtagggat n                       101

<210> SEQ ID NO 594
<211> LENGTH: 100
<212> TYPE: DNA
<213> ORGANISM: Cannabis sativa

<400> SEQUENCE: 594
caactcaagt ccatgtagtt ggttgttgat acttgtgatt tacttatata agagtaacga    60
tatgtgcact caaattatgc atcaaaatat tagatacaat                         100

<210> SEQ ID NO 595
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is c or t

<400> SEQUENCE: 595
gaacacacat ctttctccgg caactttagt acattgccgt tcagtgcttg cagaagcttc    60
cttccaatag cagcaagtac acatattcgt gtgatggata n                       101

<210> SEQ ID NO 596
<211> LENGTH: 100
<212> TYPE: DNA
<213> ORGANISM: Cannabis sativa

<400> SEQUENCE: 596
accttcaact tcctaattga caatgcattt ggtaatgatt tttttttct tcaggttacc     60 ttgaaattgt tcacatttat agcagcatga atggttgaaa                         100

<210> SEQ ID NO 597
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is a or g

<400> SEQUENCE: 597
```

```
-continued taatagttct tctattgctg gtaatcgtct gtgctgaagt gtcggtggtc ctcacctaca      60
tgcatctctg cgtagaggat tggcggtggt ggtggaaggc n                         101

<210> SEQ ID NO 598
<211> LENGTH: 100
<212> TYPE: DNA
<213> ORGANISM: Cannabis sativa

<400> SEQUENCE: 598
ttcttcgcat caggttcagt tgcccttat gtattcttgt actctatcaa ttacttggtg      60
tttgacctgc agagtttgag tggacccgtc tccgctgtac                          100

<210> SEQ ID NO 599
<211> LENGTH: 101
<212> TYPE: DNA
<213> ORGANISM: Cannabis sativa
<220> FEATURE:
<221> NAME/KEY: misc_feature
<222> LOCATION: (101)..(101)
<223> OTHER INFORMATION: n is t or a

<400> SEQUENCE: 599
cctatgtgat cgtcgcgaat gtgttatcaa gtgcaggaag gtgggaagaa gtttctgaag      60
tgaggaagat gatgaaaaac cagagggtga agaaggaagt n                         101

<210> SEQ ID NO 600
<211> LENGTH: 100
<212> TYPE: DNA
<213> ORGANISM: Cannabis sativa

<400> SEQUENCE: 600
gggcgtagtt ggattgaagt gcgcggtaag gtccacgagt tcttagccgg cgatcacata      60
cacgaaatga gggacgatat ttataagaaa ctaaccgagt                          100
```

METHODS AND COMPOSITIONS FOR CANNABIS CHARACTERIZATION

CROSS-REFERENCE TO RELATED APPLICATIONS

This application is a national phase entry of PCT/CA2016/050678, filed Jun. 13, 2016, which claims priority from U.S. Provisional patent application Ser. No. 62/175,006 filed Jun. 12, 2015, each of these applications being incorporated herein in their entirety by reference.

INCORPORATION OF SEQUENCE LISTING

A computer readable form of the Sequence Listing "P48554US01_SequenceListing" (161,208 bytes), submitted via EFS-WEB and created on Dec. 12, 2017, is herein incorporated by reference.

FIELD

The present disclosure provides methods, compositions and kits for characterizing *cannabis* samples. The present disclosure also provides method, compositions and kits for distinguishing *Cannabis sativa* from *Cannabis indica*, and marijuana from hemp as well as measuring contribution of *Cannabis sativa* and *Cannabis indica* in marijuana.

BACKGROUND

*Cannabis* is one of humanity's oldest crops, with records of use dating to 6000 years before present. It is used as a source of high-quality bast fibre, nutritious and oil-rich seeds and for the production of cannabinoid compounds including delta-9 tetrahydrocannabinol (THC) and cannabidiol (CBD). The evolutionary history and taxonomy of *Cannabis* remains poorly understood. Hillig (2005) proposed that the genus *Cannabis* consists of three species (*C. sativa, C. indica*, and *C. ruderalis*) [1], whereas an alternative viewpoint is that *Cannabis* is monotypic and that observable subpopulations represent subspecies of *C. sativa: C. sativa* subspecies *sativa, C. sativa* subspecies *indica* and *C. sativa* subspecies *ruderalis* [2]. The putative *ruderalis* type may represent feral populations of the other types or those adapted to northern regions. The classification of *Cannabis* populations is confounded by many cultural factors, and tracing the history of a plant that has seen wide geographic dispersal and artificial selection by humans over thousands of years has proven difficult. Many hemp types have varietal names while marijuana types lack an organized horticultural registration system and are referred to as strains. The draft genome and transcriptome of *C. sativa* were published in 2011 [3]. As both public opinion and legislation in many countries shifts towards recognizing *Cannabis* as a plant of medical and agricultural value [4], the genetic characterization of marijuana and hemp becomes increasingly important for both clinical research and crop improvement efforts.

Differences between *Cannabis sativa* and *Cannabis indica* have been reported.

Although the taxonomy of the genus *Cannabis* remains unclear, many breeders, growers and users (patients) consuming *cannabis* for its psychoactive and/or medicinal properties differentiate *Sativa*-type from *Indica*-type plants.

Hillig & Mahlberg (2004) [20] have reported that mean THC levels and the frequency of the THCA synthase gene ($B_T$ allele) were significantly higher in *C. indica* than *C. sativa*. Plants with relatively high levels of tetrahydrocannabivarin (THCV) and/or cannabidivarin (CBDV) were common only in *C. indica*.

Hazekamp & Fischedick (2011) [10] summarized differences between typical *Sativa* and *Indica* effects upon smoking. As a result of limited understanding and support from the medical community, they indicate that medicinal users of *cannabis* generally adopt the terminology derived from recreational users to describe the therapeutic effects they experience.

They report that the psychoactive effects (the "high") from *Sativa*-type plants are often characterized as uplifting and energetic. The effects are mostly cerebral (head-high), and are also described as spacey or hallucinogenic. *Sativa* is considered as providing pain relief for certain symptoms. In contrast, the high from *Indica*-type plants is most often described as a pleasant body buzz (body-high or body stone). Indicas are primarily enjoyed for relaxation, stress relief, and for an overall sense of calm and serenity and are supposedly effective for overall body pain relief and in the treatment of insomnia.

They reported that the most common way currently used to classify *cannabis* cultivars is through plant morphology (phenotype) with *Indica*-type plants smaller in height with broader leaves, while *Sativa*-type plants taller with long, narrow leaves. *Indica*-type plants typically mature faster than *Sativa*-type plants under similar conditions, and the types tend to have a different smell, perhaps reflecting a different profile of terpenoids.

There remains a need for more accurate classification of *cannabis* for medicinal and other commercial purposes.

SUMMARY

Using 14,031 single-nucleotide polymorphisms (SNPs) genotyped in 81 marijuana and 43 hemp samples, marijuana and hemp are found to be significantly differentiated at a genome-wide level, demonstrating that the distinction between these populations is not limited to genes underlying THC production.

In addition, using additional SNPs including a second set of 9123 SNPs genotyped in 37 reported *Cannabis indica* and 63 reported *Cannabis sativa* samples, ancestry determinations could be made which can be used for example for selecting breeding partners.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

DETAILED DESCRIPTION OF THE DISCLOSURE

Figure 1:
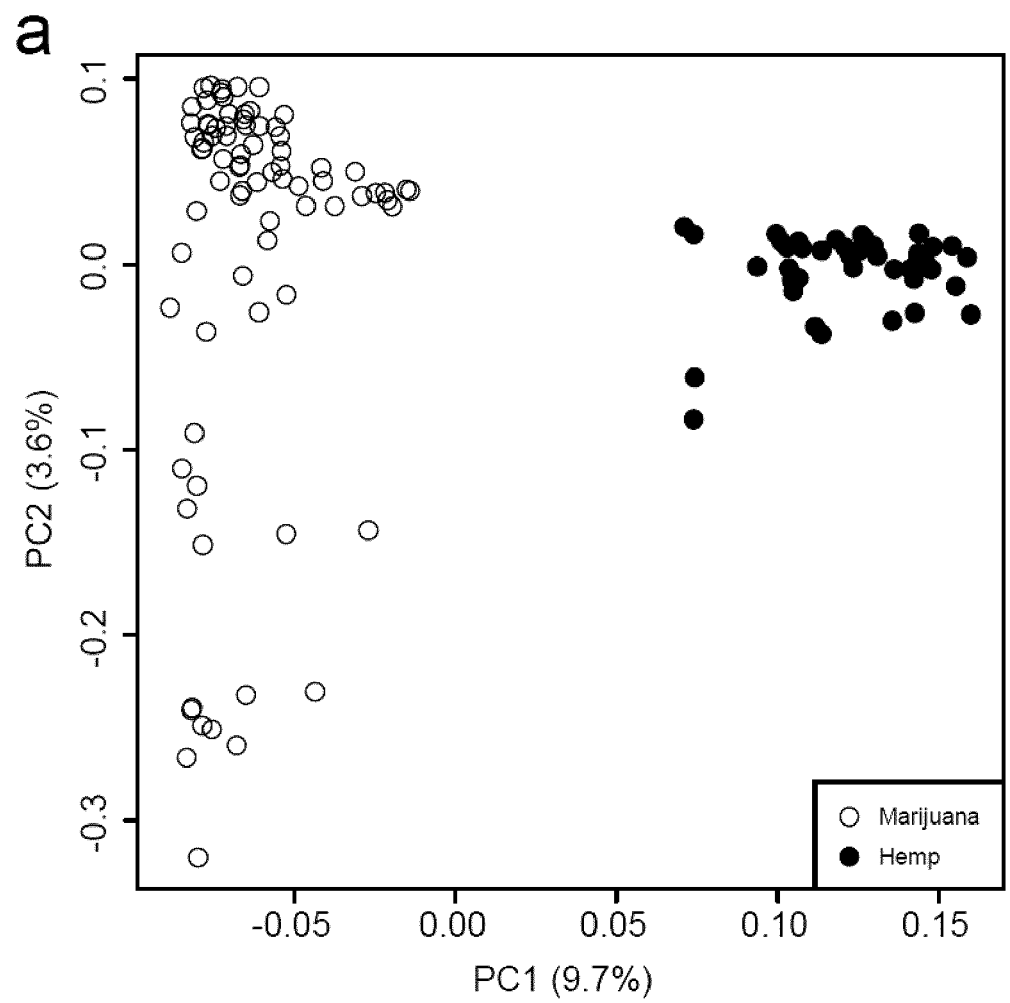
FIG. 1. Genetic structure of marijuana and hemp. (a) Principal Components Analysis (PCA) plot of 42 hemp and 80 marijuana samples using 14,031 SNPs. Hemp samples are closed circles and marijuana samples are open circles. The proportion of the variance explained by each Principal Component (PC) is shown in parentheses along each axis. The two samples labeled with their IDs are discussed in the text. (b) Boxplots showing significantly lower heterozygosity in marijuana than in hemp. (c) Population structure of hemp and marijuana estimated using the fastSTRUCTURE admixture model at K=2. Each sample is represented by a thin vertical line, which is partitioned into two colored segments that represent the sample's estimated membership in each of the two inferred clusters. Hemp and marijuana samples are labeled below the plot.
Figure 1:
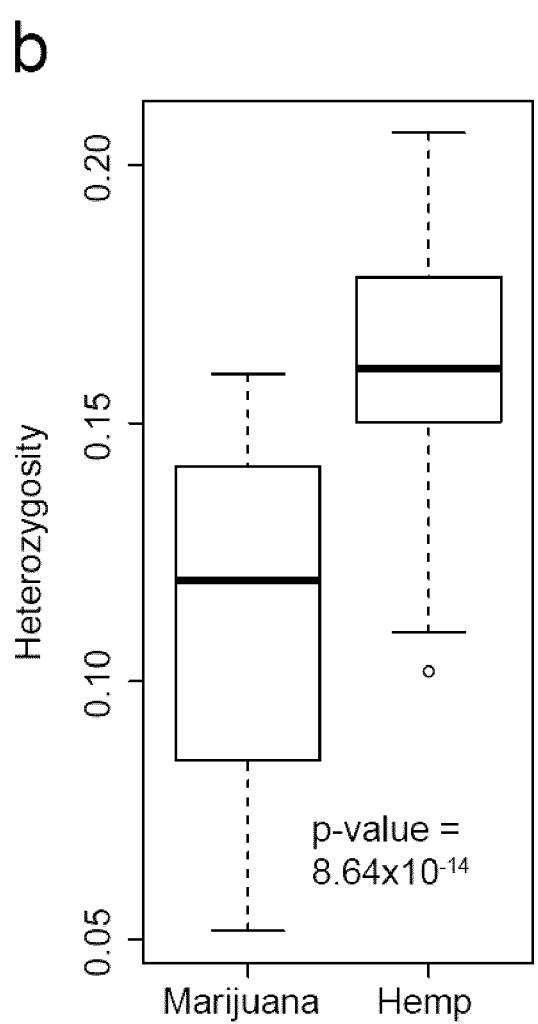
Figure 1:
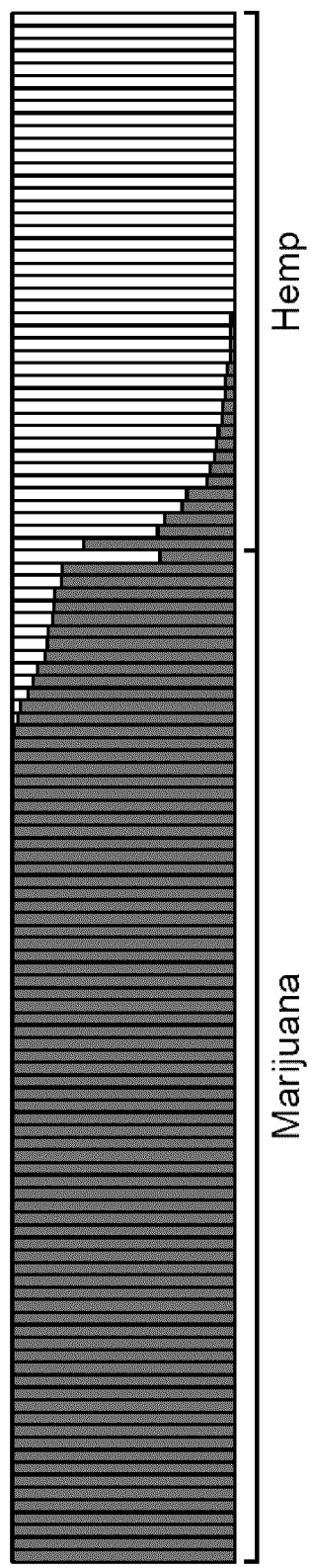

The term "*cannabis* reference" as used herein means a *cannabis* strain, species (e.g. *sativa* or *indica*) (also referred to as subspecies (e.g. *sativa* or *indica*)) or type (marijuana or hemp) with at least some known genotype profile information which is used as a reference comparison to a test sample, optionally wherein the genotype and/or allele frequency of at least 10 SNPs in Table 4, 5 and/or 8 are known, optionally all of the SNPs in any one of Tables 4, 5 and/or 8. The *cannabis* reference can be a *Cannabis sativa* reference, *Cannabis indica* reference, marijuana reference or hemp reference or a reference profile of any of the foregoing.

The term "*Cannabis sativa* reference" and "*Cannabis indica* reference" as used herein mean respectively, a selected *Cannabis sativa* strain or *Cannabis indica* strain which is used as a reference for comparison and/or genotype information of such a strain or genotype information associated with the particular *Cannabis sativa* or *Cannabis indica* reference strain e.g. a reference profile for a particular strain or a reference profile associated with the species. The reference profile comprises at least 10 known SNPs (e.g. genotype and optionally frequency) in Table 4 and/or Table 8, optionally all of the SNPs in Table 4 and/or 8 found in the particular *Cannabis sativa* or *Cannabis indica* strain respectively or a composite of strains of the particular species. The *Cannabis sativa* reference or *Cannabis indica* reference can include in addition to the predominant allele in the species or a particular strain of the species the frequency of the SNP allele in the population.

The term "*cannabis* reference profile" as used herein means genotype information of one (e.g. a particular strain) or plurality of *cannabis* strains and/or species, including *Cannabis sativa* and/or *Cannabis indica* strains or marijuana and/or hemp strains, and includes the genotype of at least 10 SNPs in Table 4, 5 and/or 8, optionally all of the SNPs in Table 4, 5 and/or 8. A *Cannabis sativa* reference profile as used herein means genotype information of a plurality of *cannabis* strains and includes genotype sequence (and optionally including frequency information) associated with *Cannabis sativa* strains and a *Cannabis indica* reference profile as used herein means genotype information of a plurality of *cannabis* strains and includes genotype sequence (and optionally including frequency information) associated with *Cannabis indica* strains.

The term "marijuana" as used herein denotes *cannabis* plants and plant parts that are cultivated and consumed as a drug or medicine. Marijuana often contains high amounts of psychoactive cannabinoids such as tetrahydrocannabinolic acid (THCA) and delta-9 tetrahydrocannabinol (THC) but it may also contain cannabidiolic acid (CBDA) and cannabidiol (CBD). For example, marijuana can be defined as *cannabis* plants and plant parts wherein the leaves and flowering heads of contain more than 0.3% w/w, 0.4% w/w or 0.5% w/w of delta-9-tetrahydrocannabinol (THC) (dry weight). The term "hemp" as used herein denotes *cannabis* plants that are cultivated and used for the production of fibre or seeds rather than as drug or medicine. Often hemp plants often contain high amounts of CBDA and CBD, and low amounts of THCA and THC. For example, hemp can be defined as *cannabis* plants and plant parts wherein the leaves and flowering heads of which do not contain more than 0.3% w/w, 0.4% w/w or 0.5% w/w of delta-9-tetrahydrocannabinol (THC) (dry weight).

The term "polynucleotide", "nucleic acid", "nucleic acid molecule" and/or "oligonucleotide" as used herein refers to a sequence of nucleotide or nucleoside monomers consisting of naturally occurring and/or modified bases, sugars, and intersugar (backbone) linkages, and is intended to include DNA and RNA which can be either double stranded or single stranded, representing the sense or antisense strand.

As used herein, the term "isolated nucleic acid molecule" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

The term "primer" as used herein refers to a nucleic acid molecule, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less, for example 10 nucleotides. The factors involved in determining the appropriate length of primer are readily known to one of ordinary skill in the art.

As used herein, the term "upstream primer" as used herein refers to a primer that can hybridize to a DNA sequence and act as a point of synthesis upstream, or at a 5', of a target polynucleotide sequence e.g. SNP, to produce a polynucleotide complementary to the target polynucleotide anti-sense strand. The term "downstream primer" as used herein refers to a primer that can hybridize to a polynucleotide sequence and act as a point of synthesis downstream, or at a 3' end, of a target polynucleotide sequence, to produce a polynucleotide complementary to the target polynucleotide sense strand.

The term "probe" as used herein refers to a polynucleotide (interchangeably used with nucleic acid) that comprises a sequence of nucleotides that will hybridize specifically to a target nucleic acid sequence. For example the probe comprises at least 18 or more bases or nucleotides that are complementary and hybridize to contiguous bases and/or nucleotides in the target nucleic acid sequence. The length of probe depends on the hybridization conditions and the sequences of the probe and nucleic acid target sequence and can for example be 10-20, 21-70, 71-100 or more bases or nucleotides in length. The probes can optionally be fixed to a solid support such as an array chip or a microarray chip. For example, the PCR product produced with the primers could be used as a probe. The PCR product can be for example be subcloned into a vector and optionally digested and used as a probe.

The term "reverse complement" or "reverse complementary", when referring to a polynucleotide, as used herein refers to a polynucleotide comprising a sequence that is complementary to a DNA in terms of base-pairing and which is reversed so oriented from the 5' to 3' direction.

As used herein, the term "kit" refers to a collection of products that are used to perform a reaction, procedure, or synthesis, such as, for example, a genotyping assay etc., which are typically shipped together, usually within a common packaging, to an end user.

The term "target allele" as used herein means an allele for a SNP listed in Table 4, 5 or 8.

The term "major allele" as used herein is the allele most commonly present in a population. The major allele listed in Tables 4, 5 and 8 is the allele most commonly present in *Cannabis sativa* and *Cannabis indica* strains (Tables 4 and 8) and marijuana and hemp strains (Table 5) respectively.

The term "minor allele" as used herein is the allele least commonly present in a population (e.g. *C. sativa* and *C. indica* or marijuana and hemp). The minor allele listed in Tables 4, 5 and 8 is present in the frequency indicated therein.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U).

The term "hybridize" as used herein refers to the sequence specific non-covalent binding interaction with a complementary nucleic acid.

The term "selectively hybridize" as used herein refers to hybridization under moderately stringent or highly stringent physiological conditions, which can distinguish related nucleotide sequences from unrelated nucleotide sequences. In nucleic acid hybridization reactions, the conditions used to achieve a particular level of stringency are known to vary, depending on the nature of the nucleic acids being hybridized, including, for example, the length, degree of complementarity, nucleotide sequence composition (e.g., relative GC:AT content), and nucleic acid type, i.e., whether the oligonucleotide or the target nucleic acid sequence is DNA or RNA. An additional consideration is whether one of the nucleic acids is immobilized, for example, on a filter, bead, chip, or other solid matrix. Appropriate stringency conditions which promote hybridization are known to those skilled in the art, or can be found in Current Protocols in Molecular Biology, John Wiley & Sons, N.Y. (1989), 6.3.1 6.3.6 and/or Current Protocols in Nucleic Acid Chemistry available at http://onlinelibrary.wiley.com/browse/publications?type=lab protocols.

As used in this application, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

III. Methods and Products

The present disclosure identifies for example a plurality of single nucleotide polymorphisms (SNPs) ancestry informative markers (AIMs) that can be used to characterize *cannabis* samples. *Cannabis* samples can be characterized for example according to their ancestral relatedness and/or whether the sample is likely marijuana or hemp. Accordingly, the present disclosure provides methods, nucleic acids, primers and kits useful for detecting whether a sample is *Cannabis sativa* dominant or *Cannabis indica* dominant, for assessing the relatedness of a test sample to *Cannabis sativa* and/or *Cannabis indica* reference samples as well as methods, nucleic acids, primers and kits for distinguishing marijuana from hemp. Also provided are a computer implemented method, a computer program embodied on a computer readable medium, a system, apparatus and/or processor for carrying out a method or part thereof described herein.

Embodiments of the methods and systems described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the various programmable computers may be a server, network appliance, set-top box, embedded device, computer expansion module, personal computer, laptop, mobile telephone, smartphone or any other computing device capable of being configured to carry out the methods described herein.

The data storage system may comprise a database, such as on a data storage element, in order to provide a database of *Cannabis* reference strains, and/or reference profiles. Furthermore, computer instructions may be stored for configuring the processor to execute any of the steps and algorithms described herein as a computer program.

Each program may be implemented in a high level procedural or object oriented programming or scripting language, or both, to communicate with a computer system. However, alternatively the programs may be implemented in assembly or machine language, if desired. The language may be a compiled or interpreted language. Each such computer program may be stored on a non-transitory computer readable storage medium (e.g. read-only memory, magnetic disk, optical disc). The storage medium so configured causes a computer to operate in a specific and predefined manner to perform the functions described herein.

An aspect of the present method for detecting the presence or absence of each of a set of target alleles in a *cannabis* sample, the method comprising:

I) obtaining a test sample comprising genomic DNA, and
II) either
  i) genotyping the test sample for a set of single nucleotide polymorphisms (SNPs), the set comprising at least 10, 20, 30, 40, 48, 50, 60, 70, 80, 90, 96, 100 or any number between and including 10-200 of the SNPs in Table 4 and/or 8, wherein each SNP comprises a major allele and a minor allele as provided in Table 4 and 8; and
  ii) detecting for each SNP of the set the presence or absence of the major allele and/or the minor allele in the test sample;
  or
  a) genotyping the test sample for a set of SNPs, the set at least 10, 20, 30, 40, 48, 50, 60, 70, 80, 90, 96 or 100 of the comprising the SNPS in Table 5, wherein each SNP comprises a major allele and a minor allele as provided in Table 5; and
  b) detecting for each SNP of the set the presence or absence of the major allele and/or the minor allele in the test sample.

In an embodiment, the SNPS in Table 4 and/or 8 can be used to determine the ancestral contribution of *Cannabis sativa* and/or *Cannabis indica* in a marijuana strain.

The step of obtaining a test sample comprising genomic DNA can be accomplished, for example by taking the *cannabis* sample or an aliquot thereof for example if the *cannabis* sample is isolated genomic DNA, or can comprise preparing an isolated genomic DNA from the *cannabis* sample or a portion thereof.

The *cannabis* sample or the test sample (e.g. comprising at least a portion of the *cannabis* sample) is any *cannabis* sample comprising genomic DNA. The sample can be isolated genomic DNA or a portion of a plant and/or seed comprising genomic DNA and optionally from which genomic DNA can be isolated. For example, the test sample can be a plant sample, a seed sample, a leaf sample, a flower sample, a trichome sample, a pollen sample a sample of dried plant material including leaf, flower, pollen and/or trichomes, or a sample produced through in vitro tissue or cell culture. Genomic DNA can be isolated using a number of techniques such as NaOH extraction, phenol/chloroform extraction, DNA extraction systems such as Qiagen Direct PCR DNA Extraction System (Cedarlane, Burlington ON). In some embodiments, genomic DNA is not purified prior to genotyping. For example, with the Phire Plant Direct PCR Kit the DNA target can be used to detect SNP alleles without prior DNA extraction (Life Technologies, Burlington ON).

In an embodiment, the set of target alleles which are detected are a plurality of SNPs in Tables 4, 5 and/or 8. Tables 4 and 8 each list 100 SNPs, including a major allele and a minor allele and the minor allele frequency in *Cannabis sativa* strains and *Cannabis indica* strains. Table 5 lists 100 SNPs including a major allele and a minor allele and the minor allele frequency in marijuana and hemp. Also described in these Tables is the SNP position in the canSat3 *C. sativa* reference genome assembly which is described in van Bakel et al [3], identified as the SNP name. The genome build assembly is identified by the number 3 for SNPs defined by SEQ ID NOs:1-400 (CanSat3) and the number 5 for SNPs defined by SEQ ID Nos: 401-600 (CanSat5). Tables 6, 7 and 9 also identify the upstream+SNP and downstream sequences associated with each SNP. A person skilled in the art would understand that genomic DNA is double stranded and that the complementary nucleotide on the reverse strand can also be detected based on the complementary base pairing rules.

Genotyping the *cannabis* sample at the loci listed for example in Tables 4, 5 and 8 can be accomplished by various methods and platforms.

In an embodiment, the step of genotyping comprises sequencing genomic DNA for example using a genotyping by sequencing (GBS) method. GBS is typically a multiplexed approach involving tagging randomly sheared DNA from different samples with DNA barcodes and pooling the samples in a sequencing reaction. Target enrichment and/or reduction of genome complexity for example using restriction enzymes.

In another embodiment, the step of genotyping comprises sequencing pooled amplicons, including captured amplicons. In an embodiment, the amplicons are produced using primers flanking the SNPs, for example within 100 nucleotides upstream and/or within 100 nucleotides downstream of the SNP location and amplifying targeted region. The resulting amplification products are then sequenced. Forward primers and reverse primers that amplify for example 25 or more nucleotides surrounding and including the SNP can be used in such genotyping methods.

A variety of sequencing methods can be employed including electrophoresis-based sequencing technology (e.g. chain termination methods, dye-terminator sequencing), by hybridization, mass spectrometry based sequencing, sequence-specific detection of single-stranded DNA using engineered nanopores and sequencing by ligation. For example, amplified fragments can be purified and sequenced directly or after gel electrophoresis and extraction from the gel.

Other PCR based genotyping methods can also be used optionally comprising DNA amplification using forward and reverse primers and/or primer extension.

For example the iPLEX Gold Assay by Sequenom® provides a SNP genotyping assay where PCR primers are designed in a region of approximately 100 base pairs around the SNP of interest and an extension primer is designed adjacent to the SNP. The method involves PCR amplification followed by the addition of Shrimp alkaline phosphatase (SAP) to inactivate remaining nucleotides in the reaction. The primer extension mixture is then added and the mixture is deposited on a chip for data analysis by a TM MALDI-TOF mass spectrometer (Protocol Guide 2008).

In another embodiment, the genotyping method comprises using an allele specific primer. An example is the KASP™ genotyping system is a fluorescent genotyping technology which uses two different allele specific competing forward primers with unique tail sequences and one reverse primer. Each unique tail binds a unique fluorescent labelled oligo generating a signal upon PCR amplification of the unique tail.

In an embodiment, allele specific probes are utilized. For example, an allele specific probe includes the complementary residue for the target allele of interest and under specified conditions preferentially binds the target allele. The probe can comprise a DNA or RNA polynucleotide and the genotyping step can comprise contacting the test sample with a plurality of probes each of the probes specific for a SNP allele of the set of SNPs under conditions suitable for detecting for example the minor SNP alleles.

In an embodiment, the genotyping method comprises using an array. The array can be a fixed or flexible array comprising for example allele specific probes. The array can be a bead array for example as is the Infinium HD Assay by Illumina. In an embodiment, the array comprises primers and/or probes using sequences or parts thereof described in SEQ ID Nos: 1-600. The array format can comprise primers or probes for genotyping for example at least 10, 20, 30, 40, 48, 50, 60, 70, 80, 90, 96 or 100 or more SNPs, for example any number between and including 1 and 300, optionally 10 and 300 or 10 and 200 or 10 and 100. In an embodiment, the array format comprises one or more primers or probes for each SNP. In an embodiment, the array comprises 96 reactions.

Upstream sequence, the SNP as well as downstream sequence for the SNPs in Tables 4, 5 and 8 are provided in Tables 6, 7 and 9.

Figure 7:
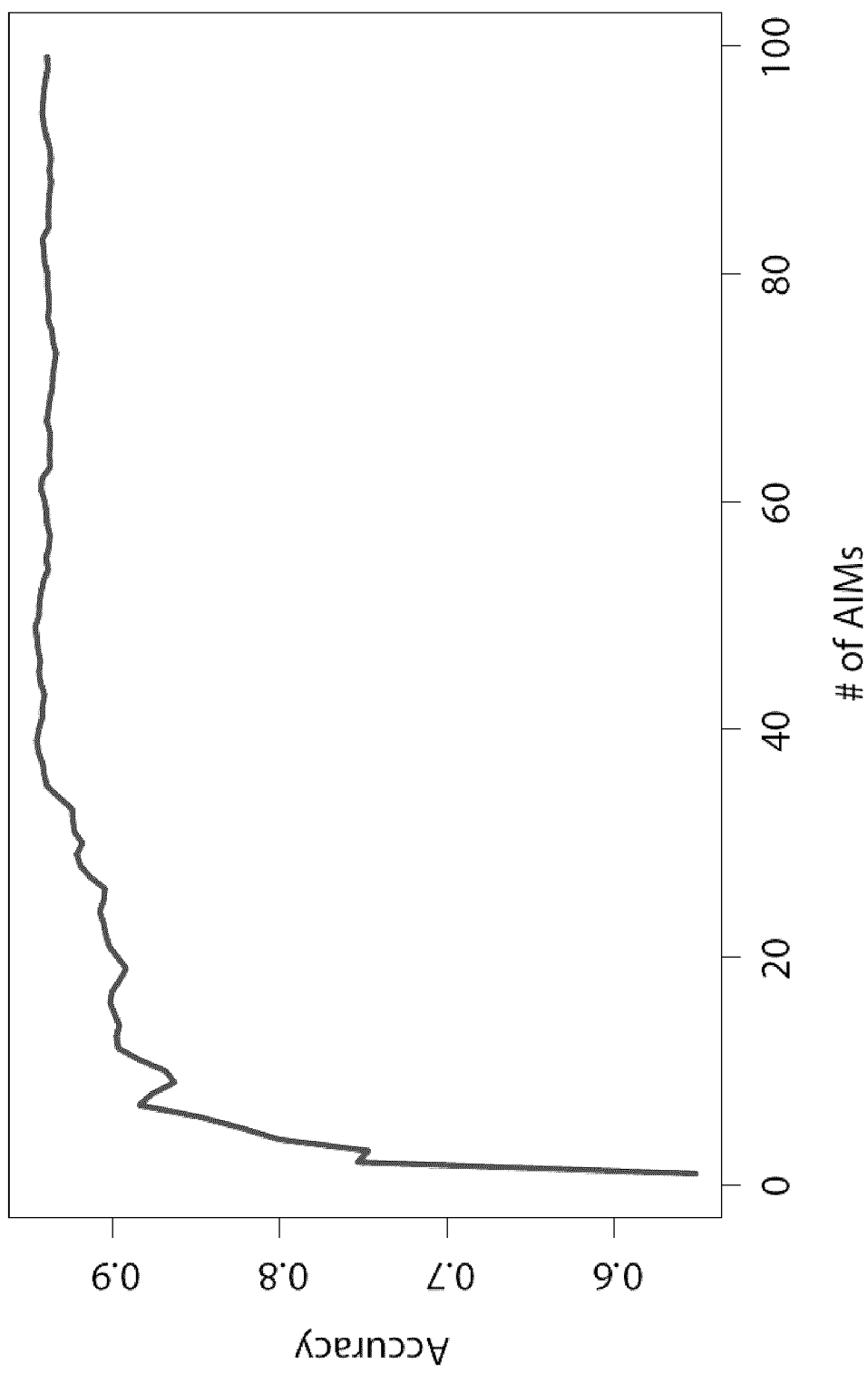
FIG. 7. Example evaluation of panels of ancestry informative markers (AIMS). Accuracy is defined here as the correlation between the positions of non-ancestral samples along PC1 calculated using 9766 SNPs and the positions calculated using a given subset of AIMs.

As demonstrated in FIG. 7, a level of accuracy can be achieved using the 10 SNPs with the highest Fst values. Accordingly in one embodiment, the set of SNPs comprises the first listed 10, 20, 30, 40, 48, 50, 60, 70, 80, 90, 96 or 100 SNPs or any number or combination of SNPs between and including 10 and 300, optionally 10 and 100 in Table 4, 5 or 8, optionally any combination of SNPs in Tables 4 and/or 8. In an embodiment, the set of SNPs comprises a plurality or all of the SNPs in Table 4 and/or 8 with a Fst of greater than 0.712 or 06277. In another embodiment, the set of SNPs comprises a plurality or all of the SNPs in Table 5 with a Fst of greater than 0.679. In an embodiment, the set of SNPs includes at least 2 wherein the allele frequency is 0.

In an embodiment, any number of SNPS listed in Tables 4 and/or 8, or Table 5 is genotyped.

In an embodiment, a plurality of SNPs listed in Tables 4 and/or 8 and 5 are detected. In such methods, both ancestry contribution and marijuana versus hemp assessments can be conducted in one assay.

In an embodiment, the step of detecting the SNP comprises receiving, reviewing and/or extracting from a file, document, reaction, array or database, the genotype for each of the SNPs of the set.

In certain embodiments, the method further comprises displaying and/or providing a document displaying one or more features of the major and/or minor alleles. For example, the one or more features can comprise the position of the SNP, the nucleotide identity of the SNP or the nucleotide identity if a minor allele is detected, the number of reads or reaction, the number of minor alleles, confidence intervals etc. The document can be an electronic document that is provided to a third party. In an embodiment, the one or more features displayed is selected from the allele nucleotide identity and the number of minor alleles in common with *Cannabis sativa, Cannabis indica*, marijuana or hemp.

As demonstrated herein, the SNP allele information can be used to characterize the *cannabis* sample. Accordingly, in an embodiment, the method further comprises determining ancestry contribution of the test sample.

The ancestry contribution is optionally an ancestry contribution estimate or identification of ancestry dominance. For example, the ancestry dominance of the test sample can be *Cannabis sativa* dominant or *Cannabis indica* dominant according to the set of target alleles detected in step II) ii). If the target alleles in combination when compared to a database of *cannabis* reference strains and/or the reference profiles provided in Table 4 and 8 are most similar to alleles more commonly found in *Cannabis sativa*, for example if greater than 50% of the *cannabis* sample's SNPs are alleles more commonly present in *Cannabis sativa*, the *cannabis* sample is identified as *Cannabis sativa* dominant. Conversely, if the target alleles in combination are most similar to alleles more commonly found in *Cannabis indica*, for example if greater than 50% of the *cannabis* sample's SNPs are alleles more commonly present in *Cannabis indica*, the *cannabis* sample is identified as *Cannabis indica* dominant.

An ancestry contribution estimate is calculated in one embodiment, according to a method described in the Examples. Other calculations for determining admixture can also be applied as further described herein.

Other nucleotides may be detected at the SNP positions described or a particular reaction may fail. In an embodiment, if an allele other than an allele reported in Tables 4, 5 and 8 is detected or if the nucleotide at the position is unknown, the allele is not considered in the methods described.

An ancestry contribution estimate can identify a population structure that is associated or is most likely given the nucleotide occurrences of the SNPs in the *cannabis* sample.

In an embodiment, the method further comprises identifying the test sample as marijuana or hemp, according to the set of target alleles detected in step II) b). A *cannabis* sample is identified as hemp for example if the target alleles in combination when compared to a database of *cannabis* reference strains and/or the reference profiles provided in Table 5 are most similar to alleles more commonly found in hemp, the *cannabis* sample is identified as hemp. Conversely, if the target alleles in combination are most similar to alleles more commonly found in marijuana, the *cannabis* sample is identified as marijuana.

An aspect accordingly includes a method of determining ancestry contribution of a *cannabis* sample, optionally to determine if a sample comprises nabis *sativa* and/or *Cannabis indica*, the method comprising:

I) obtaining a test sample comprising genomic DNA,

II) i) genotyping the test sample for a set of single nucleotide polymorphisms (SNPs), the set comprising at least 10, 20, 30, 40, 48, 50, 60, 70, 80, 90, 96 or 100 or more of the SNPs in Table 4 and/or 8, wherein each SNP comprises a major allele and a minor allele as provided in Table 4 and 8; and ii) detecting for each SNP of the set the presence or absence of the major allele and/or the minor allele in the test sample; and III) determining ancestry contribution of the test sample according to the set of target alleles detected in step II) ii and providing an estimate of the ancestry contribution or the identifying the test sample as *Cannabis sativa* dominant or *Cannabis indica* dominant.

As mentioned above, dominance is assigned as *Cannabis sativa* dominant or *Cannabis indica* dominant according to the similarity of the detected alleles. If the set of detected alleles, when compared to a database of *cannabis* reference strains and/or the reference profiles provided in Table 4 and/or 8 are most similar to alleles more commonly found in *Cannabis sativa* as indicated in Table 4 and 8, the *cannabis* sample is assigned as *Cannabis sativa* dominant. Similarly, if the set of detected alleles are most similar to alleles more commonly found in *Cannabis indica* as indicated in Table 4 and 8, the *cannabis* sample is assigned as *Cannabis indica* dominant.

In an embodiment, the method further comprises selecting a breeding partner.

The ancestry estimates can be used for example to identify *Sativa*- or *Indica*-type breeding individuals when classification is unknown or unsure. As an example, the SNPs described herein can be used to breed an offspring with a desired or defined contribution, for example about equal contribution, of *Cannabis indica* and *Cannabis sativa* genetic material. The SNPs in Table 4, 5 and 8 can be used to select for marijuana and hemp, or *Indica*- and *Sativa*-type strains with the desired ancestry contribution for use as parents.

For example, these markers can be used in marker-assisted selection (MAS) to breed *cannabis* plants that contain defined levels of *Indica*-type or *Sativa*-type ancestry.

As another example SNPs as described herein can be used in ancestry selection breeding and used to speed the recovery of the cultivated genetic background (as described in [22]). For example in a cross between a cultivated line and a wild line, the F1 offspring generated from such a cross necessarily derive 50% of its ancestry from each parent. On backcrossing to the cultivated line, each offspring will differ in the proportion of its ancestry from the wild and cultivated sources. Genetic markers distributed across the genome can be used to provide an estimate of the ancestry proportions, and the breeder can then select the offspring with the highest proportion of cultivated ancestry. Such methods can for example be performed with marker assisted selection (which uses trait associated markers), to select a small number of offspring in each generation that carry both the desired trait from the wild and the most cultivate ancestry.

In an embodiment, the method is for assessing if the *cannabis* sample is marijuana. For example, the marijuana can be for medical use.

Also provided is a set of SNPs that can be used to determine if a sample comprises hemp or marijuana. Accordingly another aspect includes a method for determining if a sample likely comprises hemp and/or marijuana, the method comprising:

I) obtaining a test sample comprising genomic DNA,

II) a) genotyping the test sample for a set of single nucleotide polymorphisms (SNPs), the set comprising at least 10, 20, 30, 40, 48, 50, 60, 70, 80, 90, 96 or 100 of the SNPs in Table 5, wherein each SNP comprises a major allele and a minor allele as provided in Table 5; and b) detecting for each SNP of the set the presence or absence of the major allele and/or the minor allele in the test sample; and III) identifying whether the sample likely comprises hemp or marijuana according to the set of target alleles detected in step II) b).

In an embodiment, the method is for differentiating medicinal/drug/pharmaceutical and non-medicinal/non-drug/non-pharmaceutical *cannabis*.

The identifying step comprises for example comparing to a database of reference alleles and/or comparing to the reference profiles in Table 5. The comparing step is further described below.

A further aspect includes a method for measuring genetic relatedness of a *cannabis* sample to a *Cannabis sativa* reference and/or a *Cannabis indica* reference, the method comprising:

I) obtaining a test sample comprising genomic DNA,

II) i) genotyping the test sample for a set of single nucleotide polymorphisms (SNPs), the set comprising at least 10, 20, 30, 40, 48, 50, 60, 70, 80, 90, 96, 100 or any number between 10 and 200 of the SNPs in Table 4 and/or 8, wherein each SNP comprises a major allele and a minor allele as provided in Table 4 and 8; and ii) detecting for each SNP of the set the presence or absence of the major allele and/or the minor allele in the test sample;

III) comparing the test sample SNP to the *Cannabis sativa* reference and/or *Cannabis indica* reference according to the set of target alleles detected in step II) and IV) displaying and/or providing a document displaying the calculated genetic relatedness of the test sample.

In an embodiment, the detecting, identifying and/or comparing step comprises calculating the genetic relatedness of the test sample to the *cannabis* reference, optionally a *Cannabis sativa* reference and/or *Cannabis indica* reference according to the set of target alleles detected in step II). The comparing step in an embodiment is carried out using a computer, for example a computer comprising a database for storing reference profiles for one or more strains or for the particular *Cannabis sativa* reference and/or *Cannabis indica* reference.

In an embodiment, the *Cannabis sativa* reference and/or the *Cannabis indica* reference is a reference profile or plurality of reference profiles stored in a database. The reference profile can for example include the SNP allele identities (e.g. minor allele) in Table 4 and/or 8 and its frequency for the species (e.g. a master reference profile) or the SNP allele identities of a particular strain.

In some embodiments, the reference is a reference sample and the method can comprise genotyping one or more reference samples and the test sample and comparing the detected alleles to identify the number of matches.

A further aspect includes a method for measuring a genetic relatedness of a *Cannabis sativa* sample to a reference marijuana or reference hemp sample, the method comprising:

I) obtaining a test sample comprising genomic DNA,

II) a) genotyping the test sample for a set of single nucleotide polymorphisms (SNPs), the set comprising at least 10, 20, 30, 40, 48, 50, 60, 70, 80, 90, 96 or 100 of the SNPs in Table 5, wherein each SNP comprises a major allele and a minor allele as provided in Table 5; and b) detecting for each SNP of the set the presence or absence of the major allele and/or the minor allele in the test sample;

III) calculating the genetic relatedness of the test sample to the marijuana reference and/or the hemp reference according to the set of target alleles detected in step II) b; and IV) displaying and/or providing a document displaying the calculated genetic relatedness of the test sample.

The method of determining ancestry contribution and/or the comparison for identifying the sample can involve use of a specifically programmed computer using for an example an algorithm to 1) compare the identity of the allele e.g whether the major and/or minor allele is detected, for each of the set of SNPs genotyped in the test sample to one or more *cannabis* references optionally compared to a database comprising a *cannabis* reference profile such as a master *cannabis* profile or a plurality of reference profiles, wherein each *cannabis* reference profile comprises genotype information for the set of SNPs detected; and 2) assign or calculate the ancestry contribution of the *cannabis* sample. Any algorithm for admixture analyses can be used. Computer implemented clustering and assignment protocols can also be used. The comparing step can also comprise comparing the relative frequency differences.

For example as demonstrated herein, the algorithm can direct a principle components analysis or a fastStructure analysis. For example, as demonstrated herein, principal component axes can be established using a plurality of *cannabis* reference strains and/or reference profiles. A *cannabis* sample genotype can be projected onto the two PCs. The ancestry contribution of *Cannabis sativa* for example can then be calculated using the formula:

% *Cannabis sativa*+b/(a+b)', wherein the a and b are the chord distances along the first principal component from the centroids of the *Cannabis sativa* strains and the *Cannabis indica* strains respectively.

In an embodiment, the algorithm is an algorithm described in the Examples.

Both the major allele and the minor allele can be detected in a test sample which can be used in determining the ancestry and/or assessing marijuana and/or hemp relatedness.

Also described herein are isolated nucleic acids, for example as primers or probes to detect the SNPs described herein. Accordingly another aspect includes an isolated nucleic acid comprising at least 9, 12, 15 or at least 18 contiguous nucleotides of any one of SEQ ID Nos 1-600 or the complement thereof.

In an embodiment, the isolated nucleic acid is a probe and comprises at least 12 or at least 18 nucleotides of contiguous sequence including the minor or major allele nucleotide; optionally including upstream sequence and/or downstream sequence contiguous with the minor or major allele.

In an embodiment, the nucleic acid is a primer comprising an isolated nucleic acid described herein.

In an embodiment, the primer is a forward PCR primer that hybridizes with a contiguous set of residues within 1-100 of any one of odd numbered SEQ ID Nos 1-600 or the, complement or reverse complement of residues 1-100 of any one of odd numbered SEQ ID Nos 1-600. In another embodiment, the primer is a reverse PCR primer (downstream primer) that hybridizes with residues 1 to 100 of any one of even numbered SEQ ID Nos 1-600 or the complement or the reverse complement with residues 1 to 100 of any one of even numbered SEQ ID Nos 1-600.

In another embodiment, the primer is an allele specific primer for a major allele and/or a minor allele in Table 4, 5 or 8 and binds to residue 101 of any one of odd numbered SEQ ID Nos 1-600. The odd numbered SEQ ID NOs comprise upstream sequence (for example 10 or more nucleotides) and the SNP allele at position 101 (e.g. 90-101). The even numbered SEQ ID NOs provide downstream sequence as indicated Tables 6, 7 and 9. For example SEQ ID NO:1 provides upstream sequence for SNP scaffold14566:24841 at nucleotides 1-100 and the SNP at nucleotide 101. SEQ ID NO:2 provides downstream sequence for this SNP.

In another embodiment, the primer is a primer extension primer and binds to residue 101 of any one of any one of odd numbered SEQ ID Nos 1-600.

Another aspect includes a plurality of primers for detecting a SNP allele in Table 4, 5 and/or 8, wherein the plurality comprises as least 2 different primers selected from primers described herein.

In an embodiment, the plurality is a plurality of primer pairs.

A further aspect is a probe that is specific for an allele.

In yet another embodiment, the primer or probe further comprises a covalently bound tag, optionally a sequence specific nucleotide tail or label. The primer or probe nucleotide sequence tag can comprise or can be coupled to a fluoresecent, radioactive, metal or other detectable label.

The primer or probe can also comprise a linker.

Yet a further aspect includes an array, optionally a species specific array comprising a plurality of nucleic acid probes attached to a support surface, each isolated nucleic acid probe comprising a sequence of about 9 to about 100 nucleotides, for example about 9 to about 50 nucleotides or about 18 to about 30 nucleotides, wherein the sequence is at least 9, 12, 15 or at least 18 contiguous nucleotides of any one of SEQ ID NOs: 1-600.

The probe can comprise a sequence that is just upstream of the SNP nucleotide, for example nucleotides 83-100 of any odd numbered SEQ ID NO: 1-600. In an embodiment, the array comprises allele specific probes (nucleic acids optionally labeled), for example wherein the probe comprises upstream sequence and the SNP.

In an embodiment, the array further comprises one or more negative control probes and/or one or more positive control probes.

A further aspect includes a kit comprising an isolated nucleic acid, primer, or plurality of primers and/or array described herein.

The kit can comprise various other reagents for amplifying DNA and/or using an array to detect a SNP such as dNTPs, polymerase, reaction buffer, wash buffers and the like. Accordingly in an embodiment, the kit comprises at least one reagent for an amplifying DNA reaction.

In an embodiment, the kit further comprises at least one reagent for a primer extension reaction.

In an embodiment, the set for any of the methods, sets, pluralities, kits, nucleic acids or arrays comprises at least 10, 20, 30, 40 of the SNPS in Table 4, 5 and/or 8.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Despite its cultivation as a source of food, fibre and medicine, and its global status as the most used illicit drug, the genus *Cannabis* has an inconclusive taxonomic organization and evolutionary history. Drug types of *Cannabis* (marijuana), which contain high amounts of the psychoactive cannabinoid delta-9 tetrahydrocannabinol (THC), are used for medicinal purposes and as a recreational drug. Hemp types are grown for the production of seed and fibre, and contain low amounts of THC. Two species or gene pools (*C. sativa* and *C. indica*) are widely used in describing the pedigree or appearance of cultivated *cannabis* plants. Using 14,031 single-nucleotide polymorphisms (SNPs) genotyped in 81 marijuana and 43 hemp samples, marijuana and hemp are found to be significantly differentiated at a genome-wide level, demonstrating that the distinction between these populations is not limited to genes underlying THC production. There is a moderate correlation between the genetic structure of marijuana strains and their reported *C. sativa* and *C. indica* ancestry.

To evaluate the genetic structure of commonly cultivated *Cannabis*, 81 marijuana and 43 hemp samples were genotyped using genotyping-by-sequencing (GBS) [5]. The marijuana samples represent a broad cross section of modern commercial strains and landraces, while the hemp samples include diverse European and Asian accessions and modern varieties. In total, 14,031 SNPs were identified after applying quality and missingness filters. Principal components analysis (PCA) of both marijuana and hemp (FIG. 1a) revealed clear genetic structure separating marijuana and hemp along the first principal component (PC1). This distinction was further supported using the fastSTRUCTURE algorithm [6] assuming K=2 ancestral populations (FIG. 1c). PCA and fastSTRUCTURE produced highly similar results: a sample's position along PC1 was strongly correlated with its group membership according to fastSTRUCTURE at K=2 ($r_2$=0.964; p-value=3.55×$10_{-90}$).

A putative *C. indica* marijuana strain from Pakistan that is genetically more similar to hemp than it is to other marijuana strains was identified (FIG. 1a). Similarly, hemp sample CAN 37/97 clusters more closely with marijuana strains (FIG. 1a). These outliers may be due to sample mix-up or their classification as hemp or marijuana may be incorrect.

These results significantly expand our understanding of the evolution of marijuana and hemp lineages in *Cannabis*. Previous analyses have shown that marijuana and hemp differ in their capacity for cannabinoid biosynthesis, with marijuana possessing the $B_T$ allele coding for tetrahydrocannabinolic acid synthase and hemp typically possessing the $B_D$ allele for cannabidiolic acid synthase [7]. As well, transcriptome analysis of female flowers showed that cannabinoid pathway genes are significantly upregulated in marijuana compared to hemp, as expected from the very high THC levels in the former compared to the latter [3]. The present results indicate that the genetic differences between the two are distributed across the genome and are not restricted to loci involved in cannabinoid production. In addition, levels of heterozygosity are higher in hemp than in marijuana (FIG. 1b, Mann-Whitney U-test, p-value=8.64× $10^{-14}$), which suggests that hemp cultivars are derived from a broader genetic base than that of marijuana strains and/or that breeding among close relatives is more common in marijuana than in hemp.

The difference between marijuana and hemp plants has considerable legal implications in many countries, and to date forensic applications have largely focused on determining whether a plant should be classified as drug or non-drug [8]. EU and Canadian regulations only permit hemp cultivars containing less than 0.3% THC to be grown. While hemp and marijuana appear relatively well separated along PC1 (FIG. 1a), no SNPs with fixed differences were found between these two groups: the highest FST value between hemp and marijuana among all 14,031 SNPs was 0.87 for a SNP with an allele frequency of 0.82 in hemp and 0 in marijuana (Table 1).

Figure 3:
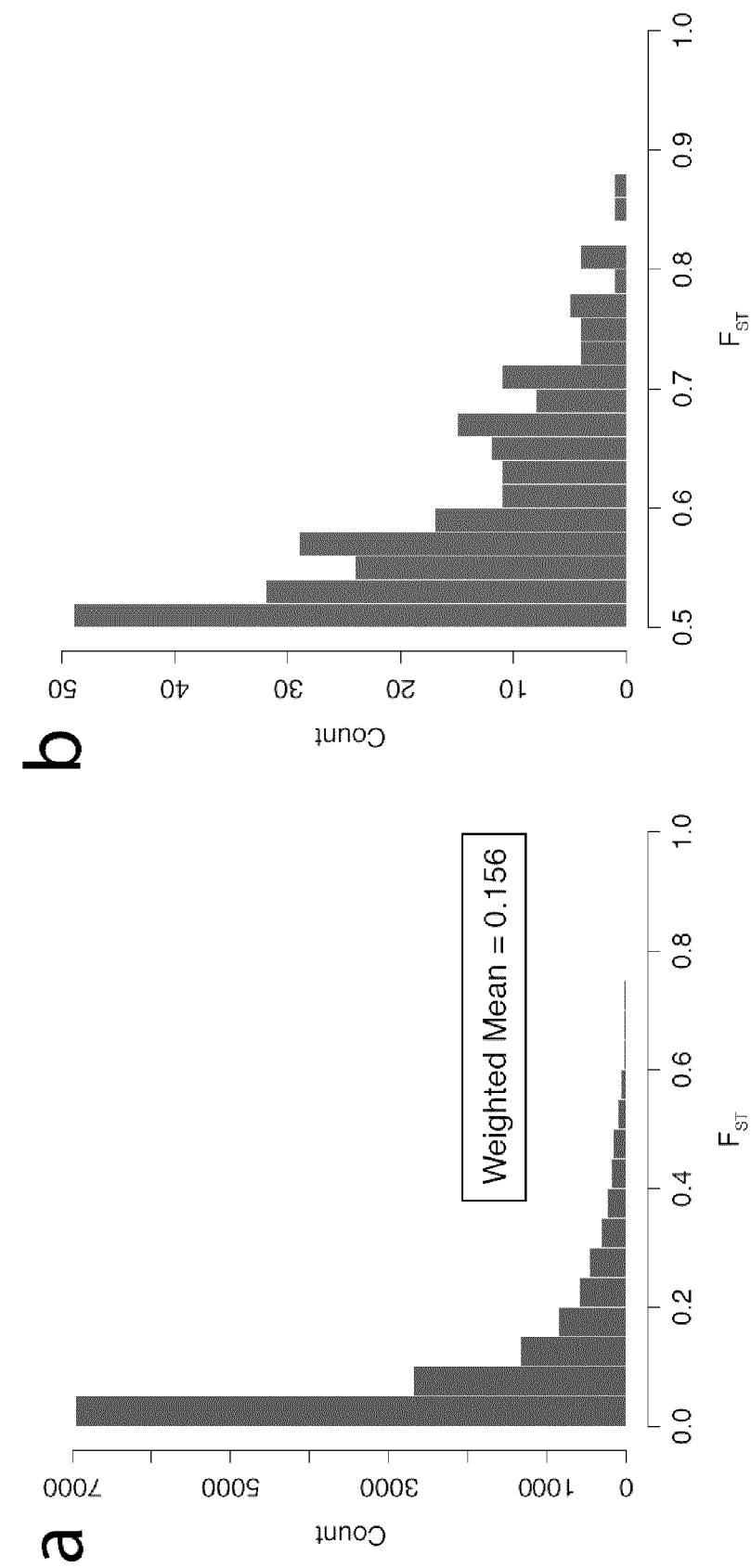
FIG. 3. Distribution of FST between marijuana and hemp samples across 14,031 SNPs. (a) FST distribution for all SNPs genotyped. (b) Distribution of SNPs with FST greater than 0.5. Average FST is weighted by allele frequency and was calculated according to equation 10 in Weir and Cockerham (1984) [19].
Figure 4:
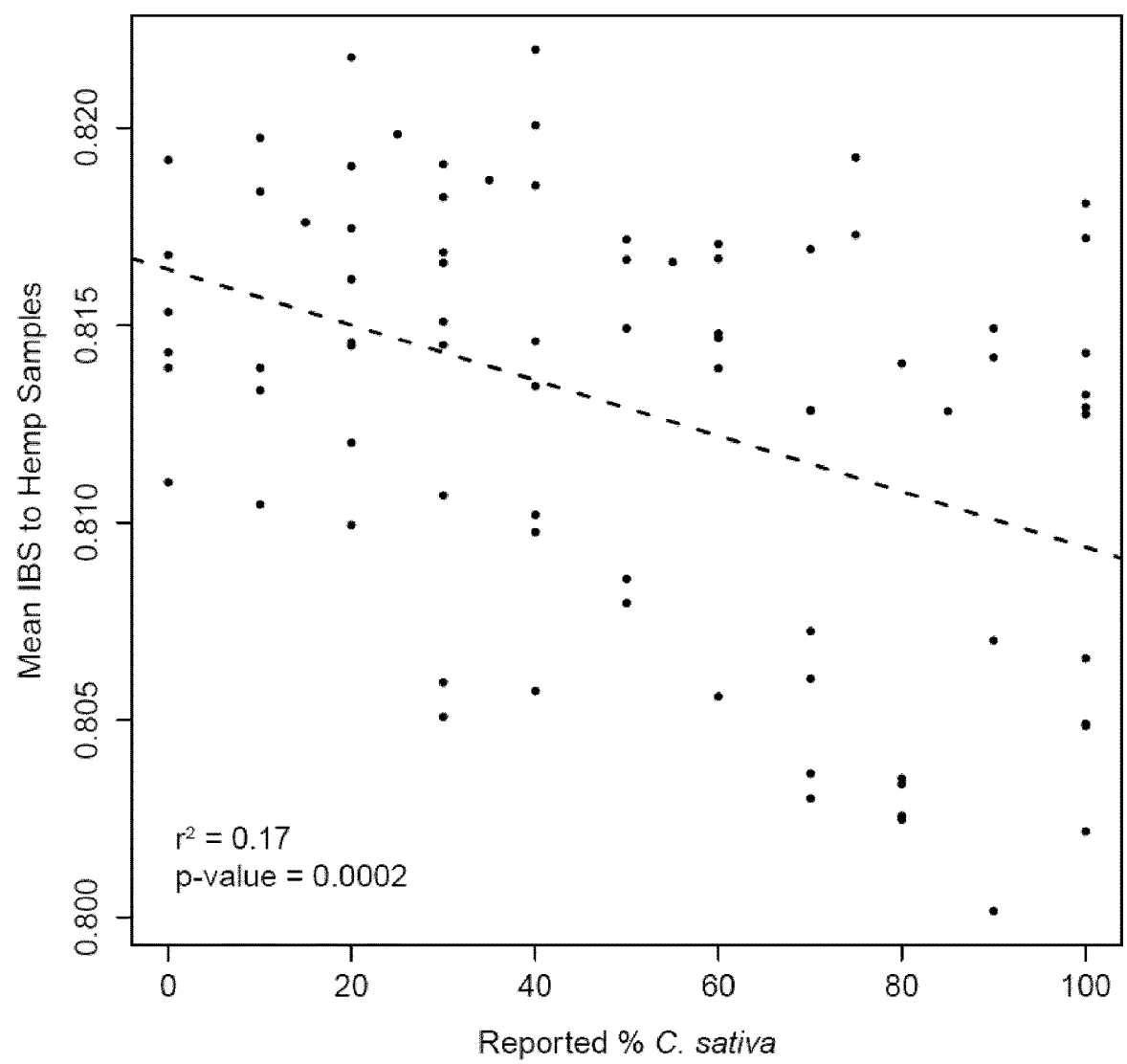
FIG. 4. Mean pairwise Identity by State (IBS) between each marijuana sample and all hemp samples versus reported *C. sativa* ancestry.

The average FST between hemp and marijuana is 0.156 (FIG. 3), which is similar to the degree of genetic differentiation in humans between Europeans and East Asians [9]. Thus, while *cannabis* breeding has resulted in a clear genetic differentiation according to use, hemp and marijuana still largely share a common pool of genetic variation.

Figure 2:
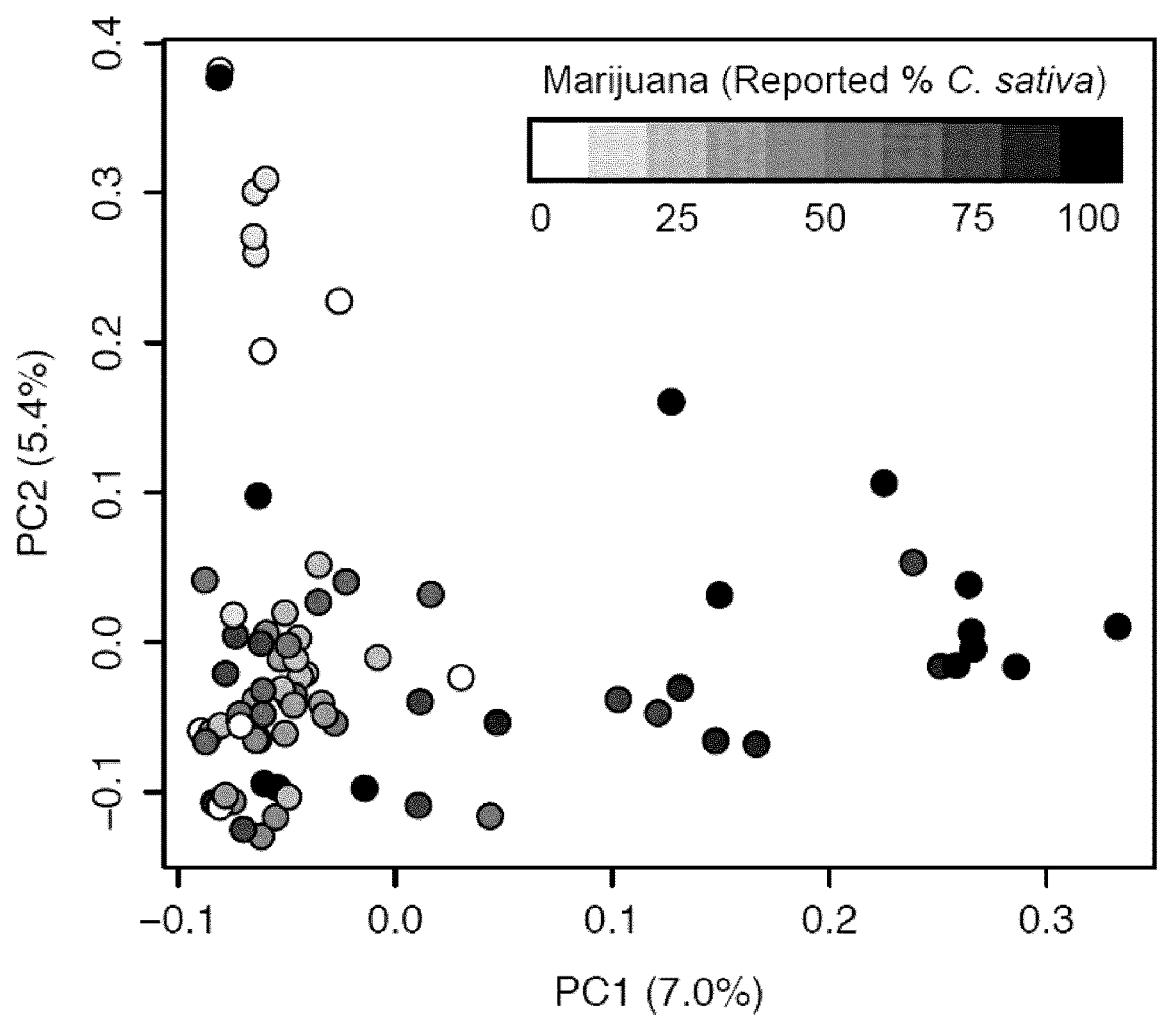
FIG. 2. Genetic structure of marijuana. (a) PCA plot of 81 marijuana samples using 9,776 SNPs. Samples are shaded according to their reported *C. sativa* ancestry. The proportion of the variance explained by each PC is shown in parentheses along each axis. (b) Population structure of marijuana calculated using the fastSTRUCTURE admixture model at K=2. Each sample is represented by a horizontal bar, which is partitioned into two segments that represent the sample's estimated membership in each of the two inferred clusters. Adjacent to each bar is the sample's name and reported % *C. sativa* ancestry. (c) The correlation between the principal axis of genetic structure (PC1) in marijuana and reported *C. sativa* ancestry.
Figure 2:
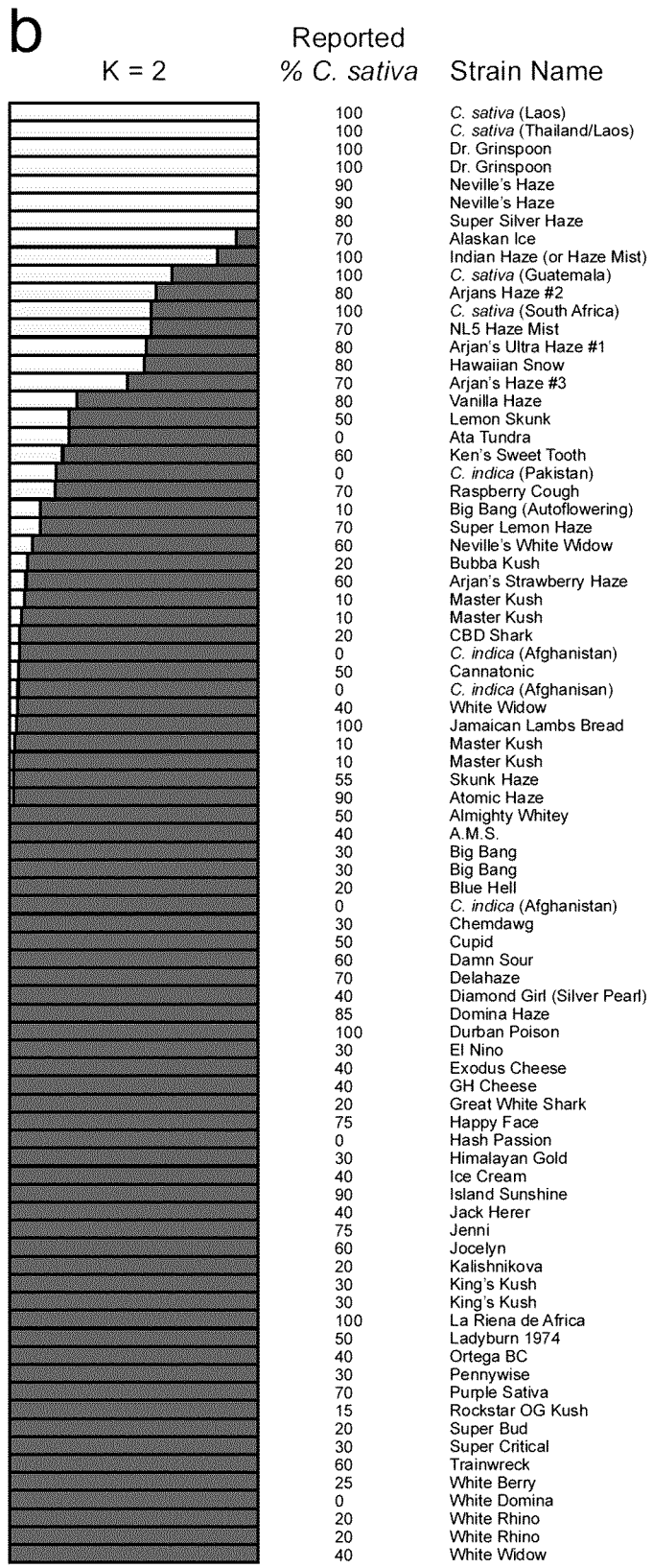
Figure 2:
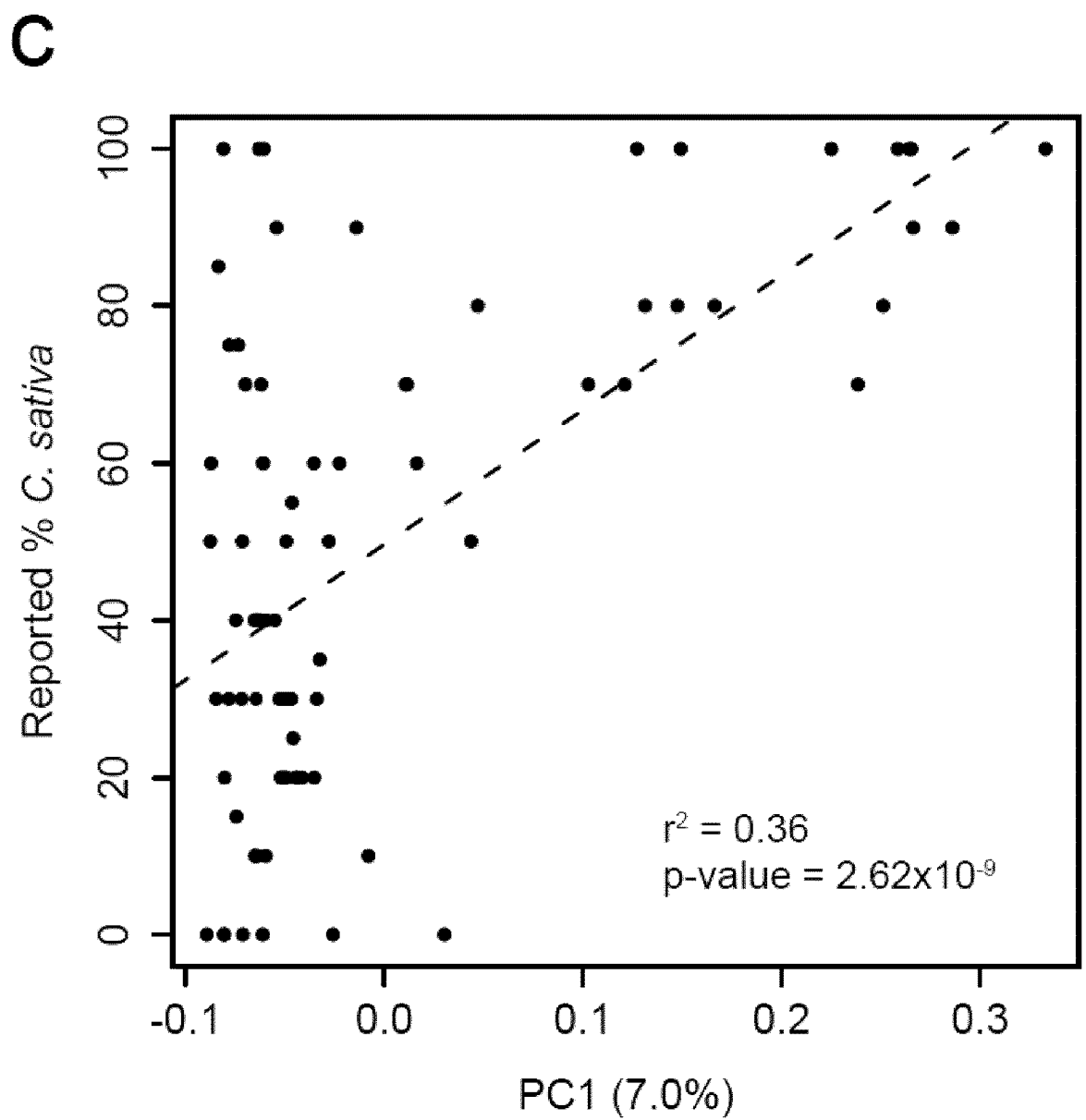

Although the taxonomic separation of the putative taxa *C. sativa* and *C. indica* remains controversial, a vernacular taxonomy that distinguishes between "*Sativa*" and "*Indica*" strains is widespread in the marijuana community. *Sativa*-type plants tall with narrow leaves, are widely believed to produce marijuana with a stimulating, cerebral psychoactive effect while *Indica*-type plants, short with wide leaves, are reported to produce marijuana that is sedative and relaxing. The genetic structure of marijuana is in partial agreement with strain-specific ancestry estimates obtained from various online sources (FIG. 2, Table 2). A moderate correlation between the positions of marijuana strains along the first principal component (PC1) of FIG. 2a and reported estimates of *C. sativa* ancestry (FIG. 2c)($r_2$=0.22; p-value=9× $10^{-6}$) was observed. This relationship is also observed for the second principal component (PC2) of FIG. 1a ($r^2$=0.23; p-value=6.71×$10^{-6}$). This observation suggests that *C. sativa* and *C. indica* may represent distinguishable pools of genetic diversity [1] but that breeding has resulted in considerable admixture between the two. While there appears to be a genetic basis for the reported ancestry of many marijuana strains, in some cases the assignment of ancestry strongly disagrees with our genotype data. For example Jamaican Lambs Bread (100% reported *C. sativa*) was nearly identical (IBS=0.98) to a reported 100% *C. indica* strain from Afghanistan. Sample mix-up cannot be excluded as a potential reason for these discrepancies, but a similar level of misclassification was found in strains obtained from Dutch coffee shops based on chemical composition [10]. The inaccuracy of reported ancestry in marijuana likely stems from the predominantly clandestine nature of *Cannabis* growing and breeding over the past century. Recognizing this, marijuana strains sold for medical use are often referred to as *Sativa* or *Indica* "dominant" to describe their morphological characteristics and therapeutic effects [10]. The results suggest that the reported ancestry of some of the most common marijuana strains only partially captures their true ancestry.

Materials and Methods

Genetic material and genotyping. The marijuana strains genotyped were grown by Health Canada authorized producers and represent germplasm grown and used for breeding in the medical and recreational marijuana industries (Table 2). Hemp strains were obtained from a Health Canada hemp cultivation licensee, and represent modern seed and fibre cultivars grown in Canada as well as diverse European and Asian germplasm (Table 3). DNA was extracted from leaf tissue using standard protocols, and library preparation and sequencing were performed using the GBS protocol published by Sonah et al [15]. SNPs were called using the GBS pipeline developed by Gardner et al. [16], aligning to the canSat3 *C. sativa* reference genome assembly [3]. Quality filtering of genetic markers was performed in PLINK [17] by removing SNPs with (i) greater than 20% missingness by locus (ii) a minor allele frequency less than 1% and (iii) excess heterozygosity (a Hardy-Weinberg equilibrium p-value less than 0.0001). After filtering, 14,031 SNPs remained for analysis.

Collection of reported marijuana ancestry. Reported ancestry proportions (% *C. sativa* and % *C. indica*) were manually obtained from online strain databases, *cannabis* seed retailers, and licensed producers of medical marijuana (Table 2). Ancestry estimates for 26 strains for which no online information was available were assigned.

Analysis of population structure and heterozygosity. Principal components analysis (PCA) was performed using the adegenet v1.4-2 package [18] in R v3.1.1 using default parameters. fastSTRUCTURE [6] was run at K=2 and K=3 using default parameters for hemp and marijuana samples combined (14,031 SNPs) (FIG. 1*a,c*), and marijuana samples alone (10,651 SNPs) (FIG. 2*a,b*). Heterozygosity by individual was calculated in R by dividing the number of heterozygous sites by the number of non-missing genotypes for each sample.

Identity by state (IBS) Analysis. Pairwise proportion IBS between all pairs of samples was calculated using PLINK. One outlier was excluded from this analysis, *C. indica* (Pakistan), because of its significantly higher IBS to hemp than all other marijuana strains (Labeled marijuana sample in FIG. 1*a*).

To determine if the hemp population shared greater allelic similarity to *C. sativa* or *C. indica* marijuana, the mean pairwise IBS was calculated between each marijuana strain and all hemp strains. This analysis was performed at various minor allele frequency thresholds and the result remained unchanged.

Example 2

Selection of *Cannabis* Informative Markers

Nine reported *C. indica* and 9 reported *C. sativa* individuals were selected to form ancestral populations for the selection of genetic markers that are able to differentiate the two groups. Individuals were selected manually on the basis of both their position along the first principal component in FIG. 5 (actual genetic structure observed using 9776 SNPs), as well as their reported *C. sativa* or *C. indica* ancestry.

Selection of Ancestry Informative Markers (AIMs)

The top 100 highest $F_{ST}$ SNPs were extracted and evaluated for their use in estimating genetic structure, which in the present case is being used as a proxy for *C. sativa*/*C. indica* ancestry given the unavailability of true pure *C. sativa* and *C. indica* populations. The same was performed between hemp cultivars and marijuana strains of *Cannabis* (FIG. 1*a*).

Example Evaluation of AIMs for Estimating Population Structure

Figure 5:
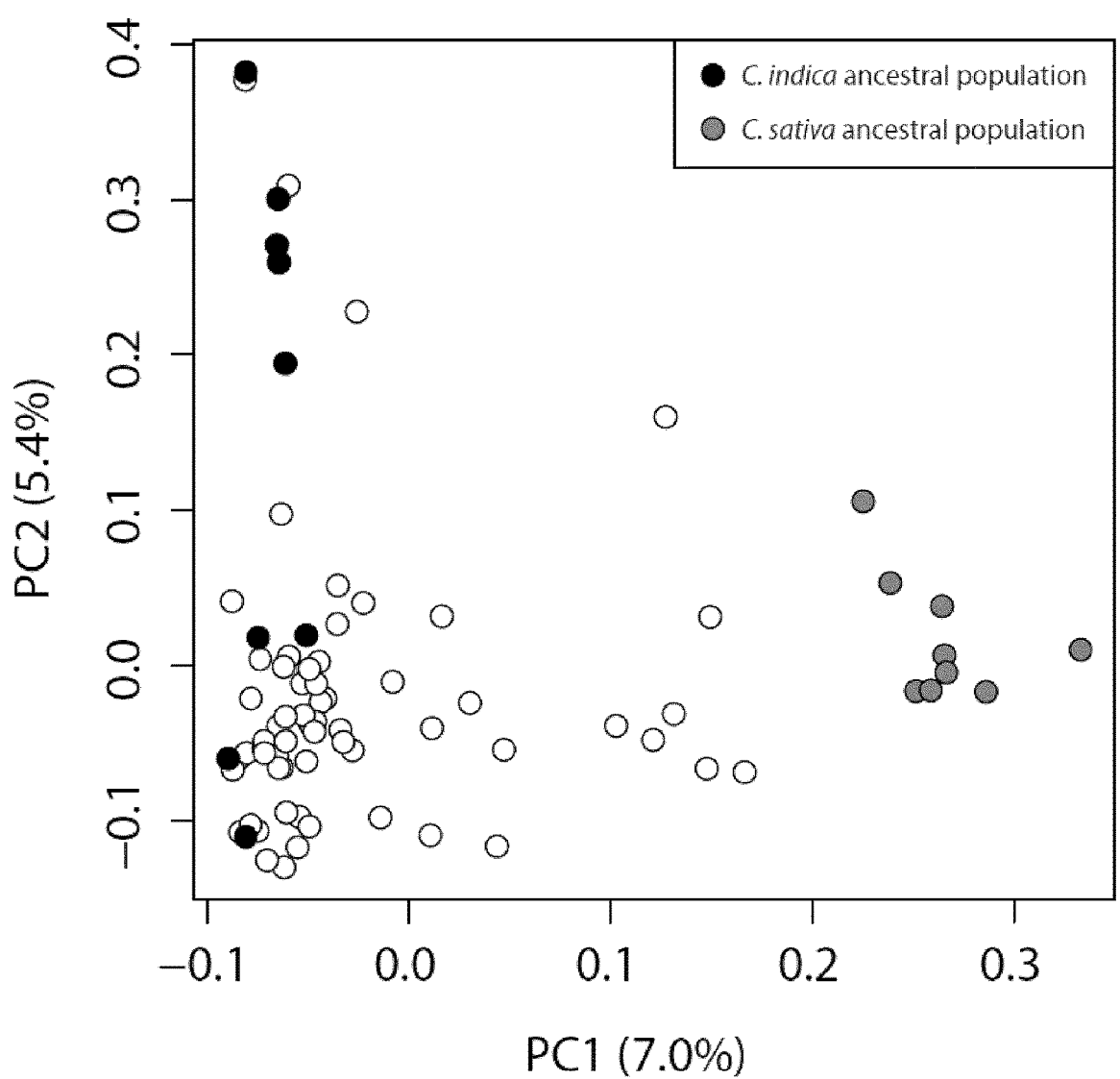
FIG. 5. Example PCA of 81 marijuana strains using 9776 SNPs.

Assuming the first principal component of FIG. 5 is representative of population structure between *C. indica* and *C. sativa* type marijuana strains, a strain's position along the X axis (PC1) represents genetic similarity to each population. In the case of admixed individuals, the position could be representative of genomic contribution from the *C. indica* and *C. sativa* gene pools. For the purposes of this analysis, an individual's position along PC1 using 9776 SNPs (FIG. 5), is considered to be an individual's true ancestry. By projecting samples on to principal components computed using only the ancestral populations, additional samples can be added to the analysis without changing the relative positions of our ancestral strains in PC space and the centroids of the clusters can be used as anchors along PC1 for estimating ancestry. Because not every SNP will contribute equally to an individual's position along PC1, a subset of markers that will capture nearly all the variance accounted for by that component is selected.

Figure 6:
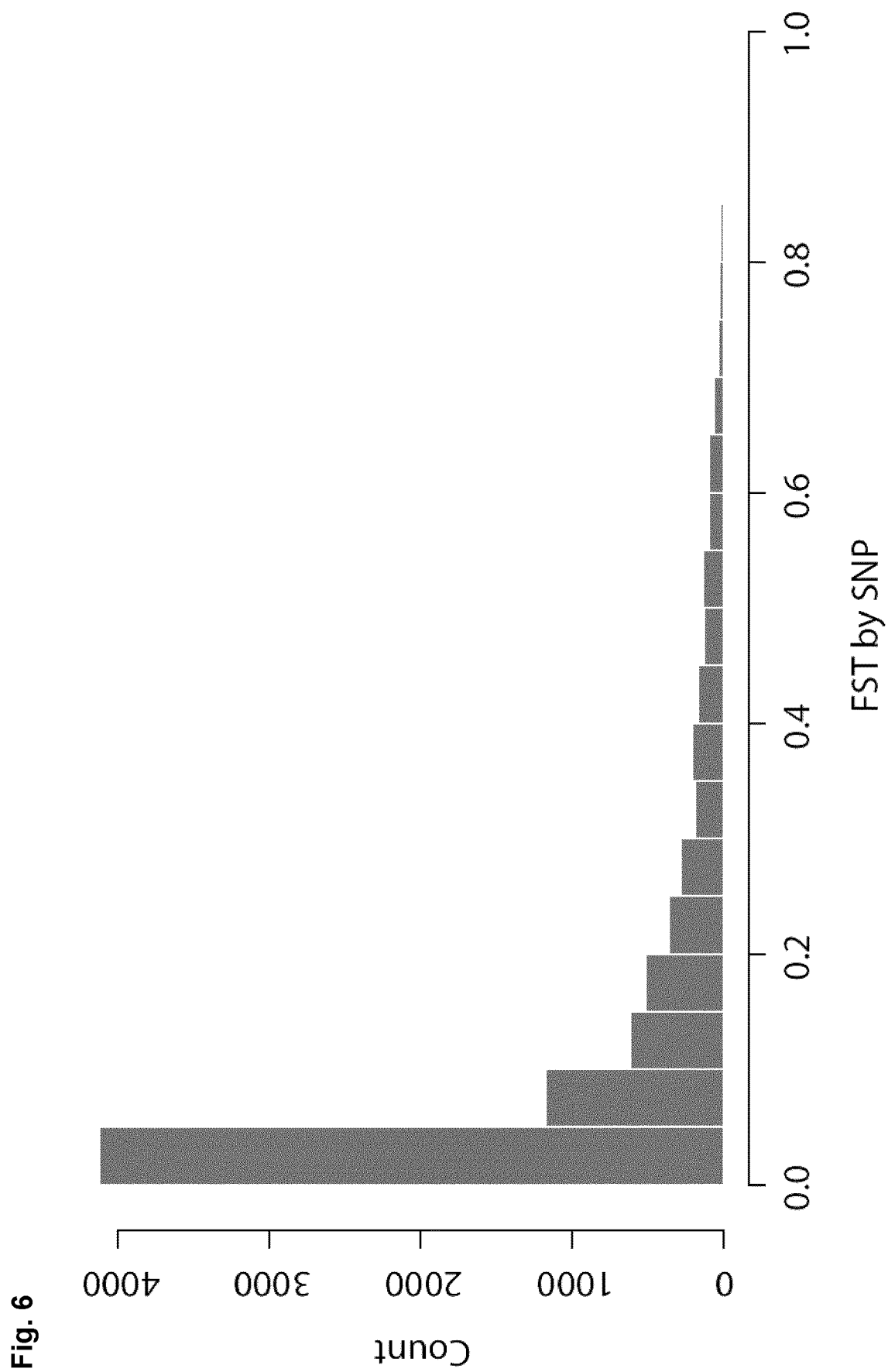
FIG. 6. Example distribution of per-SNP $F_{ST}$ values between 9 presumed *C. indica* and 9 presumed *C. sativa* strains.

First, the 2 highest $F_{ST}$ SNPs are selected, and used to perform PCA using only the ancestral *C. sativa* and *C. indica* populations. The rest of the samples are then projected (n=63) onto those components, and their positions along PC1 stored. To determine the accuracy of this 2 marker panel, the Pearson's product moment correlation coefficient (Y axis, FIG. 6) was calculated between these positions and the positions calculated using the full set of 9766 SNPs. The next highest $F_{ST}$ SNP was added to the panel and this process was repeated for all 100 highest $F_{ST}$ markers. Accuracy is not improved within this dataset for marker panels of more than approximately 40 of the highest $F_{ST}$ SNPs within this population (FIG. 7). Additional ancestry informative SNPs may provide greater accuracy in novel samples and can provide redundancy in the event of failed genotyping reactions.

Example 3

Weighting of SNPs:

To rank SNPs according to their ancestry informativeness, the fixation index ($F_{ST}$) according to Weir and Cockerham (1984) was calculated for each marker. This estimate ranges between 0 and 1, where a SNP with $F_{ST}$=1 has an allele found at 100% frequency in one population, and 0% frequency in another.

Willing, Dreyer, and van Oosterhout (2012) [21] describe the calculation as follows:

"At a single locus k, $F_{ST}^{W\&C}$ is defined as $$\hat{F}_{ST}^{[k]} = \frac{\hat{N}^{[k]}}{\hat{D}^{[k]}}$$

where $$\hat{N}^{[k]} = s^2 - \frac{1}{2n-1}\left[\overline{p}(1-\overline{p}) - \frac{r-1}{r}s^2 - \frac{\overline{h}}{4}\right]$$

$$\hat{D}^{[k]} = \overline{p}(1-\overline{p}) + \frac{s^2}{r}$$

Here, $s^2$ is the observed variance of allele frequencies, n is the number of individuals per population, $\bar{p}$ is the mean allele frequency over all populations, r is the number of sampled populations and $\bar{h}$ is the mean observed heterozygosity."

Example 4

Population Assignment

Population assignment can be performed if the novel sample has been genotyped for ancestry informative markers for which the alleles and allele frequencies are already known in the ancestral populations.

A test sample of a *cannabis* sample to be characterized is obtained. The test sample is genomic DNA and the genomic DNA is subjected to genotyping of at least 10 of the markers in Table 4 or Table 5 depending on whether it is desired that the ancestral contribution be determined or the sample be identified as marijuana or hemp.

An assignment test developed by Paetkau et al (23) and described in Hansen, Kenchington and Nielsen (2001) (24) can be used.

For each *cannabis* sample being assigned, the log-likelihood of it being derived from a specific population is calculated as:

$$\log\left(\prod_{i=1}^{n} p_{ij}^2 \text{ for } i = j, \text{ and } 2p_i p_j \text{ for } i \neq j\right) \quad \text{Equation 1}$$

where n denotes the number of loci, I and j denote the two alleles at the $l$th locus, and $p_i$ and $p_j$ denote the frequency of the ith and jth allele of the $l$th locus in the population being considered.

Calculations are made for each population using the loci and frequencies provided in Table 4 or 5, and the *cannabis* sample is assigned to the population in which it has the highest likelihood of belonging.

Example 5

Ancestry Estimation

Calculation of a novel sample's hybridization index (e.g. ancestry contribution) can be performed if the novel sample has been genotyped for ancestry informative markers for which the alleles and allele frequencies are already known in the ancestral populations.

Ancestry analysis can determine if the *cannabis* sample is a 'pure' descendant of a reference sample or reference profile or if it is the result of interbreeding between individuals from two different populations, i.e. an admixed individual or 'intraspecific hybrid'.

Campton and Utter (1985) developed a "hybrid index" (25). The hybrid index can be regarded as a way of visualizing the relative assignment probabilities in an assignment test involving two parental populations. The hybrid index, $I_H$, requires three samples (or a sample and two reference profiles), i.e. a sample or reference profile of each of the two possible parental populations and a sample of the group of suspected 'hybrids'.

$I_H$ is calculated as:

$$I_H = 1 - \frac{\log(p_x)}{\log(p_x) + \log(p_y)} \quad \text{Equation 2}$$

where $p_x$ denotes the likelihood of the multilocus genotype of an individual in population x and $p_y$ similarly denotes the likelihood in population y, calculated as in equation 1."

Example 6

SNP Discovery

Genetic material and genotyping. The marijuana strains genotyped were grown by Health Canada authorized producers and represent germplasm grown and used for breeding in the medical and recreational marijuana industries (Table 10). DNA was extracted from leaf tissue using standard protocols, and library preparation and sequencing were performed using the GBS protocol published by Poland et al [26] SNPs were called using the GBS pipeline developed by Melo et al. [27], aligning to the canSat5 *C. sativa* reference genome assembly (unpublished). Quality filtering of genetic markers was performed in PLINK [17] by removing SNPs with (i) greater than 20% missingness by locus (ii) a minor allele frequency less than 1% and (iii) excess heterozygosity (a Hardy-Weinberg equilibrium p-value less than 0.0001). After filtering, 9,123 SNPs remained for analysis.

Figure 8:
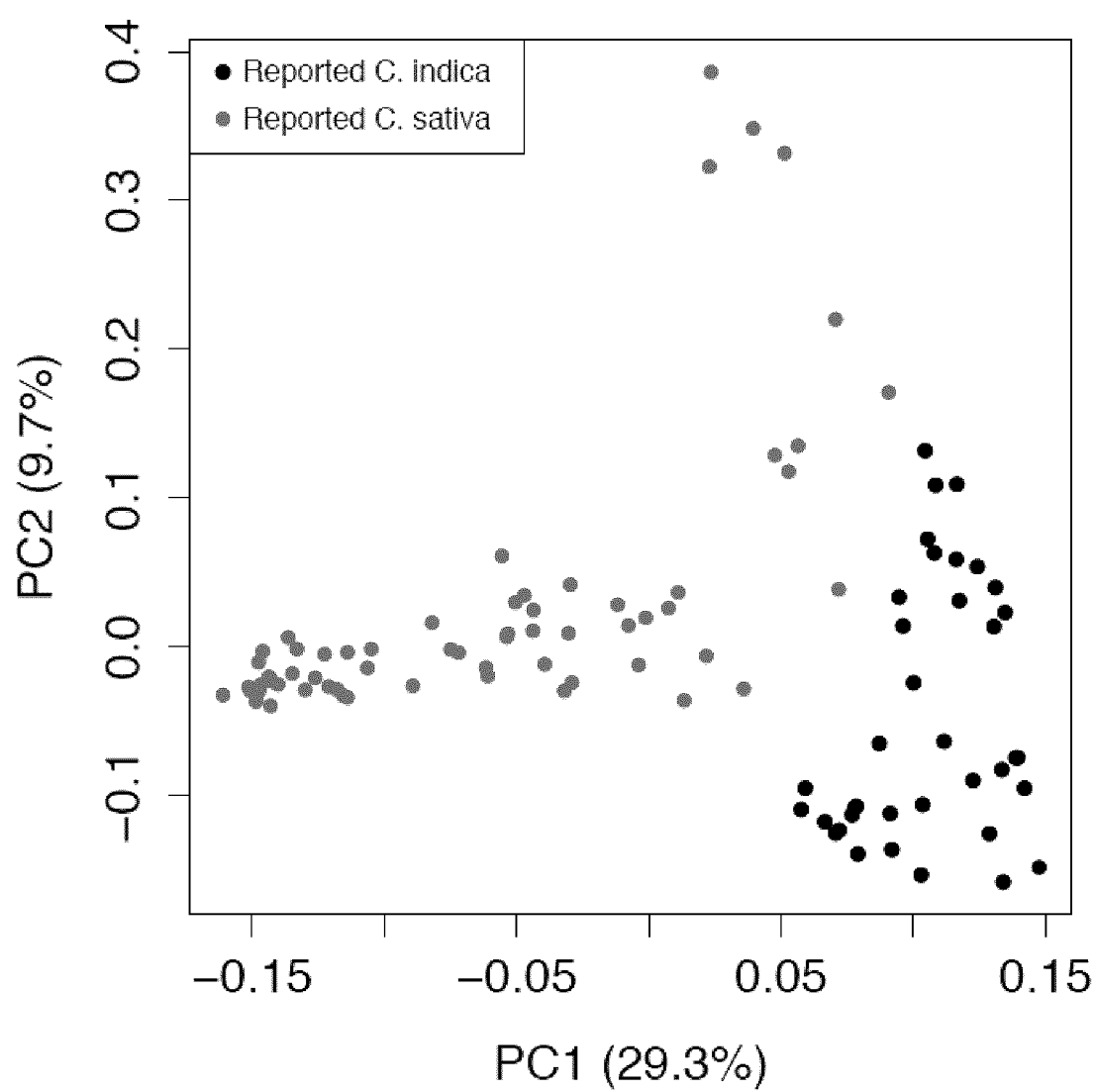
FIG. 8. Example PCA of 100 marijuana strains using 9123 SNPs.

Table 8 identifies the major and minor alleles identified in *Cannabis sativa* and *Cannabis indica* and Table 9 provides upstream and downstream sequence for each SNP. Table 10 provides reference information on the reported ancestry. FIG. 8 shows a PCA analysis based on whether the strain is reported as *C indica* or *C sativa*.

TABLE 1

Positions and allele frequencies of the top 50 SNPs by FST between marijuana and hemp calculated according to equation 10 in Weir and Cockerham (1984) [19].

| Scaffold | SNP Position on Scaffold | FST Between Hemp and Marijuana | Reference Allele | Non-Reference Allele | Non-Reference Allele Frequency in Marijuana | Non-Reference Allele Frequency in Hemp |
|---|---|---|---|---|---|---|
| scaffold13038 | 51303 | 0.865332249 | C | A | 0 | 0.8158 |
| scaffold25092 | 11841 | 0.85295301 | A | G | 0.08333 | 0.9583 |
| scaffold23837 | 26190 | 0.81783437 | C | T | 0.04938 | 0.8605 |
| scaffold152474 | 1505 | 0.813648101 | C | A | 0.01282 | 0.7857 |
| scaffold152474 | 1465 | 0.810651442 | G | A | 0.03205 | 0.8214 |
| scaffold13038 | 51162 | 0.805163299 | C | T | 0 | 0.7436 |
| scaffold5841 | 136325 | 0.782037623 | A | T | 0.006329 | 0.7059 |
| scaffold5876 | 22669 | 0.779767209 | A | T | 0.175 | 1 |
| scaffold764 | 75880 | 0.770853139 | C | A | 0 | 0.7024 |
| scaffold32076 | 9119 | 0.767411438 | C | A | 0.01316 | 0.7143 |
| scaffold7992 | 917 | 0.763602811 | T | A | 0.006329 | 0.7073 |
| scaffold118405 | 2916 | 0.761994625 | C | T | 0.03125 | 0.7564 |

TABLE 1-continued

Positions and allele frequencies of the top 50 SNPs by FST between marijuana and
hemp calculated according to equation 10 in Weir and Cockerham (1984) [19].

| Scaffold | SNP Position on Scaffold | FST Between Hemp and Marijuana | Reference Allele | Non-Reference Allele | Non-Reference Allele Frequency in Marijuana | Non-Reference Allele Frequency in Hemp |
|---|---|---|---|---|---|---|
| scaffold2418 | 77480 | 0.758065142 | G | T | 0 | 0.6618 |
| scaffold34829 | 1873 | 0.746880355 | T | C | 0.1645 | 0.9535 |
| scaffold38125 | 4641 | 0.743833337 | G | T | 0.03704 | 0.7558 |
| scaffold37469 | 74270 | 0.740257391 | G | A | 0.1013 | 0.8611 |
| C32100775 | 1618 | 0.736074476 | T | C | 0.01316 | 0.6613 |
| scaffold5190 | 41424 | 0.734073333 | C | G | 0.109 | 0.869 |
| scaffold5190 | 41454 | 0.734073333 | G | A | 0.109 | 0.869 |
| scaffold49917 | 1105 | 0.726261988 | A | G | 0.08642 | 0.8256 |
| scaffold4775 | 75747 | 0.719005761 | T | A | 0 | 0.625 |
| scaffold26152 | 15432 | 0.712320041 | G | A | 0.05921 | 0.7571 |
| scaffold5841 | 135056 | 0.712144097 | G | A | 0 | 0.6429 |
| scaffold5876 | 106401 | 0.711616024 | A | G | 0 | 0.6395 |
| scaffold5113 | 138895 | 0.711038199 | A | G | 0 | 0.6111 |
| scaffold5113 | 239777 | 0.710611128 | G | A | 0 | 0.631 |
| scaffold5841 | 135067 | 0.70853417 | G | A | 0 | 0.6429 |
| scaffold25099 | 7321 | 0.702374753 | A | G | 0.05556 | 0.7439 |
| scaffold14172 | 40875 | 0.702287484 | A | C | 0.01282 | 0.5682 |
| scaffold158332 | 502 | 0.702084439 | A | G | 0.006173 | 0.6395 |
| scaffold16869 | 149709 | 0.700892589 | T | G | 0.1562 | 0.9024 |
| scaffold114539 | 1119 | 0.695979272 | C | T | 0 | 0.6111 |
| scaffold3842 | 272682 | 0.69126068 | T | G | 0.01266 | 0.6 |
| scaffold60331 | 8510 | 0.690556532 | G | C | 0.03425 | 0.6892 |
| scaffold2360 | 22109 | 0.689941474 | G | A | 0.07143 | 0.7639 |
| scaffold72613 | 1728 | 0.689632536 | G | A | 0.04321 | 0.7093 |
| C32052717 | 309 | 0.688864374 | A | T | 0.142 | 0.8721 |
| scaffold71943 | 13435 | 0.685008651 | C | T | 0.01852 | 0.6512 |
| scaffold71943 | 13471 | 0.685008651 | T | C | 0.01852 | 0.6512 |
| scaffold128544 | 170 | 0.679301025 | G | T | 0.01875 | 0.6316 |
| scaffold98263 | 1069 | 0.677597364 | T | C | 0.07407 | 0.7558 |
| C32058675 | 292 | 0.673619414 | A | G | 0.01852 | 0.6395 |
| scaffold823 | 11824 | 0.673537258 | C | T | 0.01299 | 0.6111 |
| scaffold75287 | 5899 | 0.673496392 | G | T | 0.04321 | 0.6905 |
| scaffold16869 | 149730 | 0.671387324 | C | T | 0.1562 | 0.875 |
| scaffold3842 | 543149 | 0.670719701 | C | T | 0.02469 | 0.6212 |
| C32058613 | 508 | 0.67046277 | T | C | 0 | 0.5588 |
| C32058613 | 563 | 0.67046277 | C | T | 0 | 0.5588 |
| scaffold7146 | 70340 | 0.669199626 | C | T | 0.1667 | 0.8889 |
| scaffold23125 | 41276 | 0.669066022 | G | A | 0.03846 | 0.675 |

TABLE 2

Sample names and reported *C. sativa* and *C. indica* ancestry of genotyped marijuana strains.

| Sample ID | Sample Name | Reported Proportion C. Sativa | Reported Proportion C. indica | Reference for Reported Ancestry |
|---|---|---|---|---|
| P2_A01_M_0001 | *C. indica* (Afghanistan) | 0 | 100 | Author D H |
| P2_A02_M_0002 | Ata Tundra | 0 | 100 | http://www.gorilla-cannabis-seeds.co.uk/seedsman/regular/ata-tundra.html |
| P2_A03_M_0003 | Big Bang | 20 | 80 | http://www.kindgreenbuds.com/marijuana-strains/big-bang/ |
| P2_A04_M_0004 | Big Bang (Autoflowering) | 10 | 80 | http://azarius.net/seedshop/greenhouseseeds/big_bang_autoflowering_greenhouse/ |
| P2_A05_M_0005 | Dr. Grinspoon | 100 | 0 | http://www.leafly.com/sativa/dr-grinspoon |
| P2_A06_M_0006 | Hash Passion | 0 | 100 | http://www.seedsman.com/en/hash-passion-seeds |
| P2_A07_M_0007 | Indian Haze (Haze Mist) | 100 | 0 | http://en.seedfinder.eu/strain-info/Indian_Haze/Seedsman/ |
| P2_A09_M_0009 | King Kush | 30 | 70 | http://grow-marijuana.com/strain-reviews/king-kush |
| P2_A10_M_0010 | Master Kush | 5 | 95 | http://sensiseeds.com/en/cannabis-seeds/whitelabel/master-kush |
| P2_A11_M_0011 | Master Kush | 5 | 95 | http://sensiseeds.com/en/cannabis-seeds/whitelabel/master-kush |
| P2_A12_M_0012 | Master Kush | 5 | 95 | http://sensiseeds.com/en/cannabis-seeds/whitelabel/master-kush |
| P2_B01_M_0013 | Master Kush | 5 | 95 | http://sensiseeds.com/en/cannabis-seeds/whitelabel/master-kush |
| P2_B03_M_0015 | Neville's Haze | 75 | 25 | http://www.leafly.com/hybrid/nevilles-haze |
| P2_B04_M_0016 | *C. indica* (Pakistan) | 0 | 100 | Author D H |
| P2_B05_M_0017 | *C. sativa* (South Africa) | 100 | 0 | Author D H |
| P2_B07_M_0019 | White Rhino | 10 | 90 | http://www.kindgreenbuds.com/marijuana-strains/white-rhino/ |
| P2_B08_M_0020 | White Widow | 50 | 50 | http://www.royalqueenseeds.com/122-white-widow.html |
| P2_B09_M_0021 | Chemdawg | 50 | 50 | http://www.tweed.com/collections/all-strains/products/donegal-chem-dawg |

TABLE 2-continued

Sample names and reported *C. sativa* and *C. indica* ancestry of genotyped marijuana strains.

| Sample ID | Sample Name | Reported Proportion *C. Sativa* | Reported Proportion *C. indica* | Reference for Reported Ancestry |
|---|---|---|---|---|
| P2_B10_M_0022 | Vanilla Haze | 20 | 80 | https://www.barneysfarmshop.com/seeds/vanilla-kush.html |
| P2_B12_M_0024 | Sunshine | 90 | 10 | Author D H |
| P2_C01_M_0025 | NL5 Haze Mist | 50 | 50 | http://www.popularseeds.com/green-house-seeds/nl5-haze-mist |
| P2_C03_M_0027 | El Nino | 40 | 60 | http://www.kindgreenbuds.com/marijuana-strains/el-nino/ |
| P2_C04_M_0028 | Shark | 25 | 75 | http://www.weedyard.com/Strains/SharkShock.html |
| P2_C05_M_0029 | King Kush | 30 | 70 | http://www.wikileaf.com/strain/kings-kush/ |
| P2_C06_M_0030 | Dr. Grinspoon | 100 | 0 | http://www.leafly.com/sativa/dr-grinspoon |
| P2_C07_M_0031 | Exodus Cheese | 40 | 60 | http://www.gorilla-cannabis-seeds.co.uk/greenhouseseeds/feminized/exodus-cheese-feminized.html |
| P2_C08_M_0032 | Jenni | 75 | 25 | Author D H |
| P2_C09_M_0033 | Hawaiian Snow | 90 | 10 | http://www.kindgreenbuds.com/marijuana-strains/hawaiian-snow/ |
| P2_C10_M_0034 | GH Cheese | 40 | 60 | http://azarius.net/seedshop/greenhouseseeds/cheese_greenhouse_feminised/ |
| P2_C11_M_0035 | Kalishnikova | 20 | 80 | http://azarius.net/seedshop/greenhouseseeds/kalashnikova_greenhouse_feminized/ |
| P2_D01_M_0037 | Great White Shark | 25 | 75 | http://www.kindgreenbuds.com/marijuana-strains/white-shark/ |
| P2_D02_M_0038 | Strawberry Haze | 70 | 30 | http://www.kindgreenbuds.com/marijuana-strains/arjans-strawberry-haze/ |
| P2_D03_M_0039 | Himalayan Gold | 0 | 100 | http://www.kindgreenbuds.com/marijuana-strains/himalaya-gold/ |
| P2_D04_M_0040 | Ortega BC | 0 | 100 | http://www.leafly.com/indica/ortega |
| P2_D05_M_0041 | Atomic Haze | 80 | 20 | http://www.cannaseur.com/index.php/online-store/female-seeds/atomic-haze-female-detail |
| P2_D06_M_0042 | Domina Haze | 85 | 15 | Author D H |
| P2_D07_M_0043 | Rio | 25 | 75 | Author D H |
| P2_D08_M_0044 | Damn Sour | 60 | 40 | http://www.cannabissearch.com/strains/damn-sour/ |
| P2_D09_M_0045 | Nina | 75 | 25 | http://www.kindgreenbuds.com/marijuana-strains/la-nina/ |
| P2_D10_M_0046 | White Widow | 50 | 50 | http://www.royalqueenseeds.com/122-white-widow.html |
| P2_E01_M_0049 | Purple Sativa | 70 | 30 | Author D H |
| P2_E02_M_0050 | Bubba Kush | 10 | 90 | http://www.tweed.com/collections/all-strains/products/norfolk-bubba-kush |
| P2_E03_M_0051 | Delahaze | 70 | 30 | https://www.paradise-seeds.com/en/delahaze.html |
| P2_E05_M_0053 | Super Silver Haze | 75 | 25 | http://www.tweed.com/collections/all-strains/products/leonidas-super-silver-haze |
| P2_E06_M_0054 | Jack Herer | 70 | 30 | http://www.tweed.com/collections/all-strains/products/birds-eye-jack-herer |
| P2_E07_M_0055 | Pennywise | 40 | 60 | http://www.tweed.com/collections/all-strains/products/nova-pennywise |
| P2_E08_M_0056 | White Berry | 25 | 75 | http://www.harborsidehealthcenter.com/learn/white-berry-medical-cannabis.html |
| P2_E09_M_0057 | Skunk Haze | 55 | 45 | http://www.kindgreenbuds.com/marijuana-strains/skunk-haze/ |
| P2_E10_M_0058 | Durban Poison | 100 | 0 | http://www.leafly.com/sativa/durban-poison |
| P2_E12_M_0060 | Happy Face | 25 | 75 | Author D H |
| P2_F01_M_0061 | White Rhino | 10 | 90 | http://www.kindgreenbuds.com/marijuana-strains/white-rhino/ |
| P2_F03_M_0063 | Ice Cream | 40 | 60 | http://www.kindgreenbuds.com/marijuana-strains/ice-cream/ |
| P2_F04_M_0064 | *C. sativa* (Thailand/Laos) | 100 | 0 | Author D H |
| P2_F05_M_0065 | Diamond Girl (Silver Pearl) | 40 | 60 | Author D H |
| P2_F06_M_0066 | AMS | 30 | 70 | http://www.kindgreenbuds.com/marijuana-strains/ams/ |
| P2_F07_M_0067 | Lemon Skunk | 60 | 40 | http://www.kindgreenbuds.com/marijuana-strains/lemon-skunk/ |
| P2_F08_M_0068 | Arjans Haze #2 | 90 | 10 | http://www.kindgreenbuds.com/marijuana-strains/arjans-haze-2/ |
| P2_F10_M_0070 | White Domina | 0 | 100 | http://www.headsite.com/white-domina-feminised-seeds-kannabia-446-p.asp |
| P2_F11_M_0071 | Blue Hell | 20 | 80 | http://www.cannabis-seeds.co.uk/medicalseeds/bluehell.html |
| P2_F12_M_0072 | Neville's White Widow | 80 | 20 | Author D H |
| P2_G01_M_0073 | Alaskan Ice | 70 | 30 | http://www.kindgreenbuds.com/marijuana-strains/alaskan-ice/ |
| P2_G03_M_0075 | Arjans Ultra Haze #1 | 80 | 20 | http://www.cannabissearch.com/strains/arjans-ultra-haze/ |
| P2_G04_M_0076 | Ken's Sweet Tooth | 20 | 80 | https://www.barneysfarmshop.com/seeds/barneys-farm-sweet-tooth.html |
| P2_G05_M_0077 | Neville's Haze | 75 | 25 | http://www.kindgreenbuds.com/marijuana-strains/nevilles-haze/ |
| P2_G06_M_0078 | Arjans Haze #3 | 80 | 20 | http://www.kindgreenbuds.com/marijuana-strains/arjans-haze-3/ |
| P2_G07_M_0079 | Cupid | 50 | 50 | Author D H |
| P2_G08_M_0080 | Super Critical | 25 | 75 | http://www.wikileaf.com/strain/super-critical/ |
| P2_G09_M_0081 | Super Bud | 35 | 65 | http://www.kindgreenbuds.com/marijuana-strains/ed-rosenthal-super-bud/ |
| P2_G10_M_0082 | LadyBurn 1974 | 50 | 50 | http://www.cannabissearch.com/strains/ladyburn-1974/ |
| P2_G11_M_0083 | Trainwreck | 90 | 10 | http://www.wikileaf.com/strain/trainwreck/ |
| P2_G12_M_0084 | *C. indica* (Afghanistan) | 0 | 100 | Author D H |
| P2_H01_M_0085 | Almighty Whitey | 50 | 50 | Author D H |
| P2_H02_M_0086 | *C. sativa* (Guatemala) | 100 | 0 | http://www.seedsman.com/en/guatemala-regular-seeds |
| P2_H03_M_0087 | *C. sativa* (Laos) | 100 | 0 | Author D H |
| P2_H04_M_0088 | La Riena de Africa | 100 | 0 | http://www.seedsman.com/en/la-reina-de-africa-feminised-seeds |

TABLE 2-continued

Sample names and reported *C. sativa* and *C. indica* ancestry of genotyped marijuana strains.

| Sample ID | Sample Name | Reported Proportion C. Sativa | Reported Proportion C. indica | Reference for Reported Ancestry |
|---|---|---|---|---|
| P2__H05__M__0089 | Raspberry Cough | 70 | 30 | http://www.kindgreenbuds.com/marijuana-strains/raspberry-cough/ |
| P2__H06__M__0090 | Super Lemon Haze | 80 | 20 | http://www.wikileaf.com/strain/super-lemon-haze/ |
| P2__H08__M__0092 | Jocelyn | 60 | 40 | Author D H |
| P2__H09__M__0093 | Big Bang | 20 | 80 | http://www.kindgreenbuds.com/marijuana-strains/big-bang/ |
| P2__H10__M__0094 | C. indica (Afghanistan) | 0 | 100 | Author D H |
| P2__H11__M__0095 | Jamaican Lambs Bread | 100 | 0 | http://www.leafly.com/sativa/lamb-s-bread |

TABLE 3

Sample names of genotyped hemp varieties.

| Sample ID | Sample Name |
|---|---|
| P1__A02__H__0001__2 | Felina |
| P1__A04__H__0002__2 | Ferimon |
| P1__A06__H__0003__2 | Kompolti |
| P1__A08__H__0004__2 | Uniko B |
| P1__A10__H__0005__2 | Fedora 19 |
| P1__A11__H__0006__1 | Futura 77 |
| P1__B01__H__0007__1 | Fedrina |
| P1__B04__H__0008__2 | Suditalien or Sudi |
| P1__B05__H__0009__1 | LKSD or LKCSD |
| P1__B09__H__0011__1 | Bialobrzeskie |
| P1__B12__H__0012__2 | VIR 541 |
| P1__C01__H__0013__1 | VIR 569 |
| P1__C04__H__0014__2 | VIR 575 |
| P1__C05__H__0015__1 | Silesia |
| P1__C08__H__0016__2 | VIR 577 |
| P1__C10__H__0017__2 | Carmagnola |
| P1__D02__H__0019__2 | Zolotonsha 15 |
| P1__D03__H__0020__1 | Fedora 17 |
| P1__D05__H__0021__1 | K110 |
| P1__D07__H__0022__1 | Novosadska |
| P1__D09__H__0023__1 | Jus 8 |
| P1__E01__H__0025__1 | Delores |
| P1__E03__H__0026__1 | Petera |
| P1__E05__H__0027__1 | CAN 29/94 |
| P1__E07__H__0028__1 | CAN 37/97 |
| P1__E10__H__0029__2 | CAN 40/99 |
| P1__F03__H__0032__1 | CAN 39/98 |
| P1__F06__H__0033__2 | CAN 100/01 |
| P1__F07__H__0034__1 | CAN 18/95 |
| P1__F09__H__0035__1 | CAN 20/02 |
| P1__F11__H__0036__1 | CAN 24/89 |
| P1__G01__H__0037__1 | CAN 23/99 |
| P1__G04__H__0038__2 | CAN 17/95 |
| P1__G05__H__0039__1 | CAN 19/87 |
| P1__G07__H__0040__1 | CAN 22/88 |
| P1__G10__H__0041__2 | CAN 26/93 |
| P1__G11__H__0042__1 | CAN 16/94 |
| P1__H02__H__0044__1 | CAN 28/01 |
| P1__H04__H__0045__1 | Chameleon |
| P1__H07__H__0046__2 | Tygra |
| P1__H09__H__0047__2 | Carmen |
| P1__H10__H__0048__1 | Alyssa |
| P2__H12__H__0096 | Finola |

TABLE 4

Positions and allele frequencies of the top 100 SNPs by FST between *Cannabis Sativa* and *Cannabis Indica* calculated according to equation 10 in Weir and Cockerham (1984) [19]

| SNP Name | SEQ ID | SEQ ID | Minor Allele | Major Allele | FST | Minor Allele Frequency (*Indica*) | Minor Allele Frequency (*Sativa*) |
|---|---|---|---|---|---|---|---|
| scaffold14566:24841 | 1 | 2 | C | T | 1 | 0 | 1 |
| scaffold2257:59436 | 3 | 4 | A | C | 0.941 | 0 | 0.9444 |
| scaffold123303:7086 | 5 | 6 | A | C | 0.938 | 0 | 0.9444 |
| scaffold21832:18317 | 7 | 8 | C | T | 0.937 | 0 | 0.9375 |
| scaffold10653:22776 | 9 | 10 | C | T | 0.937 | 0 | 0.9375 |
| scaffold34968:5203 | 11 | 12 | C | A | 0.933 | 0 | 0.9375 |
| scaffold41828:12391 | 13 | 14 | T | C | 0.883 | 0 | 0.8889 |
| C32084869:1171 | 15 | 16 | A | T | 0.876 | 0.9444 | 0.05556 |
| scaffold1342:67015 | 17 | 18 | C | T | 0.876 | 0.05556 | 0.9444 |
| scaffold5876:136612 | 19 | 20 | C | T | 0.876 | 0.05556 | 0.9444 |
| scaffold10653:22755 | 21 | 22 | G | A | 0.868 | 0.05556 | 0.9375 |
| scaffold65043:4386 | 23 | 24 | C | A | 0.866 | 0 | 0.875 |
| scaffold39548:5676 | 25 | 26 | T | C | 0.866 | 0 | 0.875 |
| scaffold39548:5703 | 27 | 28 | A | G | 0.866 | 0 | 0.875 |
| scaffold17605:9224 | 29 | 30 | G | A | 0.866 | 0 | 0.875 |
| scaffold94301:10558 | 31 | 32 | C | T | 0.858 | 0.0625 | 0.9375 |
| scaffold52608:15151 | 33 | 34 | G | A | 0.857 | 0 | 0.8571 |
| scaffold9110:12755 | 35 | 36 | G | A | 0.845 | 0.8571 | 0 |
| C32099389:1875 | 37 | 38 | G | A | 0.835 | 0.0625 | 0.9167 |
| C32076905:769 | 39 | 40 | G | T | 0.825 | 0 | 0.8333 |

TABLE 4-continued

Positions and allele frequencies of the top 100 SNPs by FST between *Cannabis Sativa* and *Cannabis Indica* calculated according to equation 10 in Weir and Cockerham (1984) [19]

| SNP Name | SEQ ID | SEQ ID | Minor Allele | Major Allele | FST | Minor Allele Frequency (*Indica*) | Minor Allele Frequency (*Sativa*) |
|---|---|---|---|---|---|---|---|
| scaffold50412:1217 | 41 | 42 | T | C | 0.825 | 0.8333 | 0 |
| scaffold73281:3231 | 43 | 44 | T | C | 0.825 | 0 | 0.8333 |
| scaffold60591:9229 | 45 | 46 | T | C | 0.825 | 0 | 0.8333 |
| scaffold60591:9364 | 47 | 48 | G | T | 0.825 | 0 | 0.8333 |
| scaffold27976:11462 | 49 | 50 | T | A | 0.825 | 0.8333 | 0 |
| scaffold4591:18700 | 51 | 52 | A | G | 0.825 | 0.8333 | 0 |
| scaffold96873:16326 | 53 | 54 | A | G | 0.817 | 0 | 0.8333 |
| scaffold6777:12771 | 55 | 56 | C | T | 0.816 | 0 | 0.8333 |
| C31894837:130 | 57 | 58 | A | G | 0.812 | 0 | 0.8125 |
| scaffold1342:66883 | 59 | 60 | C | T | 0.812 | 0.8125 | 0 |
| C32035477:264 | 61 | 62 | G | A | 0.811 | 0.8889 | 0.05556 |
| scaffold6360:1717 | 63 | 64 | T | C | 0.811 | 0.05556 | 0.8889 |
| scaffold132623:4144 | 65 | 66 | T | C | 0.811 | 0.8889 | 0.05556 |
| scaffold72006:11851 | 67 | 68 | T | A | 0.809 | 0 | 0.8 |
| scaffold6742:34122 | 69 | 70 | C | T | 0.807 | 0 | 0.8333 |
| scaffold3108:8782 | 71 | 72 | G | A | 0.806 | 0 | 0.8333 |
| scaffold11225:9528 | 73 | 74 | A | G | 0.806 | 0 | 0.75 |
| scaffold11225:9539 | 75 | 76 | T | A | 0.806 | 0 | 0.75 |
| scaffold2579:59858 | 77 | 78 | A | G | 0.803 | 0.8889 | 0.05556 |
| scaffold5876:136559 | 79 | 80 | T | C | 0.803 | 0.8889 | 0.05556 |
| scaffold5876:136606 | 81 | 82 | T | C | 0.803 | 0.8889 | 0.05556 |
| scaffold23386:12397 | 83 | 84 | A | G | 0.803 | 0 | 0.8125 |
| scaffold93032:4944 | 85 | 86 | A | G | 0.791 | 0 | 0.8125 |
| scaffold94004:13663 | 87 | 88 | A | G | 0.791 | 0.8125 | 0 |
| scaffold26621:73038 | 89 | 90 | C | A | 0.791 | 0 | 0.8125 |
| scaffold26621:73058 | 91 | 92 | G | A | 0.791 | 0 | 0.8125 |
| scaffold62259:15201 | 93 | 94 | C | A | 0.781 | 0 | 0.75 |
| scaffold38801:13810 | 95 | 96 | A | G | 0.768 | 0 | 0.7778 |
| scaffold6550:117010 | 97 | 98 | C | T | 0.768 | 0 | 0.7778 |
| scaffold94863:28465 | 99 | 100 | T | C | 0.767 | 0.1667 | 1 |
| scaffold130551:553 | 101 | 102 | T | A | 0.759 | 0 | 0.7778 |
| scaffold21832:579 | 103 | 104 | C | A | 0.759 | 0 | 0.7778 |
| C32090201:1470 | 105 | 106 | C | T | 0.759 | 0 | 0.7778 |
| scaffold117639:1939 | 107 | 108 | C | A | 0.759 | 0 | 0.7778 |
| scaffold73281:2531 | 109 | 110 | A | G | 0.759 | 0 | 0.7778 |
| scaffold95390:2586 | 111 | 112 | T | C | 0.759 | 0 | 0.7778 |
| scaffold109105:3417 | 113 | 114 | C | T | 0.759 | 0.7778 | 0 |
| scaffold9670:13701 | 115 | 116 | T | C | 0.759 | 0 | 0.7778 |
| scaffold45478:20587 | 117 | 118 | C | T | 0.759 | 0 | 0.7778 |
| scaffold23700:29096 | 119 | 120 | C | A | 0.759 | 0.7778 | 0 |
| scaffold10732:30120 | 121 | 122 | A | G | 0.759 | 0 | 0.7778 |
| scaffold16969:31933 | 123 | 124 | T | C | 0.759 | 0.7778 | 0 |
| scaffold3884:40695 | 125 | 126 | A | G | 0.759 | 0 | 0.7778 |
| scaffold829:52127 | 127 | 128 | A | G | 0.759 | 0 | 0.7778 |
| scaffold6550:117004 | 129 | 130 | G | A | 0.759 | 0.7778 | 0 |
| scaffold27604:1398 | 131 | 132 | A | G | 0.757 | 0 | 0.6667 |
| scaffold125644:4761 | 133 | 134 | G | A | 0.757 | 0.7778 | 0 |
| scaffold16027:10666 | 135 | 136 | C | T | 0.757 | 0 | 0.7778 |
| scaffold2502:17437 | 137 | 138 | G | A | 0.757 | 0 | 0.7778 |
| scaffold2502:17515 | 139 | 140 | C | G | 0.757 | 0 | 0.7778 |
| scaffold70502:1951 | 141 | 142 | C | T | 0.754 | 0.8571 | 0.0625 |
| scaffold40620:28184 | 143 | 144 | T | C | 0.751 | 0 | 0.75 |
| scaffold40620:28194 | 145 | 146 | G | A | 0.751 | 0 | 0.75 |
| scaffold40620:28201 | 147 | 148 | A | T | 0.751 | 0 | 0.75 |
| scaffold118158:666 | 149 | 150 | C | G | 0.74 | 0.1111 | 0.8889 |
| scaffold41951:881 | 151 | 152 | T | A | 0.74 | 0.1111 | 0.8889 |
| scaffold95666:9974 | 153 | 154 | T | C | 0.74 | 0.8889 | 0.1111 |
| scaffold12645:86648 | 155 | 156 | C | T | 0.74 | 0.1111 | 0.8889 |
| scaffold6627:26364 | 157 | 158 | T | C | 0.738 | 0.05556 | 0.8333 |
| C32050599:443 | 159 | 160 | T | C | 0.738 | 0.75 | 0 |
| scaffold20861:14886 | 161 | 162 | A | G | 0.737 | 0.7778 | 0 |
| scaffold30119:28969 | 163 | 164 | T | A | 0.732 | 0.8333 | 0.0625 |
| scaffold2257:75397 | 165 | 166 | T | C | 0.731 | 0 | 0.7778 |
| scaffold46867:905 | 167 | 168 | T | C | 0.73 | 0.7143 | 0 |
| scaffold65132:21260 | 169 | 170 | A | T | 0.729 | 0 | 0.75 |
| scaffold94863:28441 | 171 | 172 | C | T | 0.729 | 0.1667 | 1 |
| scaffold94004:13590 | 173 | 174 | T | C | 0.726 | 0.75 | 0 |
| scaffold94004:13632 | 175 | 176 | T | A | 0.726 | 0.75 | 0 |
| scaffold39420:9067 | 177 | 178 | T | C | 0.723 | 0.1111 | 0.875 |
| scaffold42291:6484 | 179 | 180 | C | T | 0.717 | 0.7143 | 0 |
| scaffold23828:34435 | 181 | 182 | G | T | 0.714 | 0.9286 | 0.1667 |
| scaffold15017:4539 | 183 | 184 | C | T | 0.714 | 0.07143 | 0.8333 |

TABLE 4-continued

Positions and allele frequencies of the top 100 SNPs by FST between *Cannabis Sativa* and *Cannabis Indica* calculated according to equation 10 in Weir and Cockerham (1984) [19]

| SNP Name | SEQ ID | SEQ ID | Minor Allele | Major Allele | FST | Minor Allele Frequency (*Indica*) | Minor Allele Frequency (*Sativa*) |
|---|---|---|---|---|---|---|---|
| scaffold16607:2589 | 185 | 186 | T | C | 0.713 | 0.875 | 0.1111 |
| scaffold27758:4907 | 187 | 188 | G | A | 0.713 | 0.875 | 0.1111 |
| scaffold20809:7695 | 189 | 190 | G | C | 0.713 | 0.875 | 0.1111 |
| scaffold36583:13571 | 191 | 192 | T | C | 0.713 | 0.875 | 0.1111 |
| scaffold36500:1728 | 193 | 194 | T | C | 0.712 | 0 | 0.7222 |
| scaffold36500:1740 | 195 | 196 | C | T | 0.712 | 0 | 0.7222 |
| scaffold36500:1749 | 197 | 198 | T | C | 0.712 | 0 | 0.7222 |
| scaffold153198:2269 | 199 | 200 | A | T | 0.712 | 0 | 0.7222 |

TABLE 5

Positions and allele frequencies of the top 100 SNPs by FST between marijuana and hemp calculated according to equation 10 in Weir and Cockerham (1984) [19]

| SNP Name | SEQ ID | SEQ ID | Minor Allele | Major Allele | FST | Minor Allele Frequency (Marijuana) | Minor Allele Frequency (Hemp) |
|---|---|---|---|---|---|---|---|
| scaffold13038:51303 | 201 | 202 | C | A | 0.865332249 | 0 | 0.8378 |
| scaffold25092:11841 | 203 | 204 | A | G | 0.85295301 | 0.08333 | 0.9571 |
| scaffold23837:26190 | 205 | 206 | C | T | 0.81783437 | 0.0375 | 0.881 |
| scaffold152474:1505 | 207 | 208 | C | A | 0.813648101 | 0 | 0.8049 |
| scaffold152474:1465 | 209 | 210 | G | A | 0.810651442 | 0.01948 | 0.8415 |
| scaffold13038:51162 | 211 | 212 | C | T | 0.805163299 | 0 | 0.7632 |
| scaffold5841:136325 | 213 | 214 | A | T | 0.782037623 | 0.00641 | 0.7273 |
| scaffold5876:22669 | 215 | 216 | A | T | 0.779767209 | 0.1646 | 1 |
| scaffold764:75880 | 217 | 218 | C | A | 0.770853139 | 0 | 0.7195 |
| scaffold32076:9119 | 219 | 220 | C | A | 0.767411438 | 0.01316 | 0.7353 |
| scaffold7992:917 | 221 | 222 | T | A | 0.763602811 | 0.00641 | 0.725 |
| scaffold118405:2916 | 223 | 224 | C | T | 0.761994625 | 0.03165 | 0.75 |
| scaffold2418:77480 | 225 | 226 | G | T | 0.758065142 | 0 | 0.6818 |
| scaffold34829:1873 | 227 | 228 | T | C | 0.746880355 | 0.1533 | 0.9524 |
| scaffold38125:4641 | 229 | 230 | G | T | 0.743833337 | 0.0375 | 0.7738 |
| scaffold37469:74270 | 231 | 232 | G | A | 0.740257391 | 0.1026 | 0.8611 |
| C32100775:1618 | 233 | 234 | T | C | 0.736074476 | 0.006667 | 0.6613 |
| scaffold5190:41424 | 235 | 236 | C | G | 0.734073333 | 0.1104 | 0.878 |
| scaffold5190:41454 | 237 | 238 | G | A | 0.734073333 | 0.1104 | 0.878 |
| scaffold49917:1105 | 239 | 240 | A | G | 0.726261988 | 0.075 | 0.8452 |
| scaffold4775:75747 | 241 | 242 | T | A | 0.719005761 | 0 | 0.6429 |
| scaffold26152:15432 | 243 | 244 | G | A | 0.712320041 | 0.04667 | 0.7794 |
| scaffold5841:135056 | 245 | 246 | G | A | 0.712144097 | 0 | 0.6585 |
| scaffold5876:106401 | 247 | 248 | A | G | 0.711616024 | 0 | 0.6548 |
| scaffold5113:138895 | 249 | 250 | A | G | 0.711038199 | 0 | 0.6111 |
| scaffold5113:239777 | 251 | 252 | G | A | 0.710611128 | 0 | 0.6463 |
| scaffold5841:135067 | 253 | 254 | G | A | 0.70853417 | 0 | 0.6585 |
| scaffold25099:7321 | 255 | 256 | A | G | 0.702374753 | 0.04375 | 0.7439 |
| scaffold14172:40875 | 257 | 258 | A | C | 0.702287484 | 0 | 0.5952 |
| scaffold158332:502 | 259 | 260 | A | G | 0.702084439 | 0 | 0.6548 |
| scaffold16869:149709 | 261 | 262 | T | G | 0.700892589 | 0.1456 | 0.9 |
| scaffold114539:1119 | 263 | 264 | C | T | 0.695979272 | 0 | 0.6111 |
| scaffold3842:272682 | 265 | 266 | T | G | 0.69126068 | 0 | 0.6207 |
| scaffold60331:8510 | 267 | 268 | G | C | 0.690556532 | 0.02083 | 0.7083 |
| scaffold2360:22109 | 269 | 270 | G | A | 0.689941474 | 0.05797 | 0.7857 |
| scaffold72613:1728 | 271 | 272 | G | A | 0.689632536 | 0.04375 | 0.7262 |
| C32052717:309 | 273 | 274 | A | T | 0.688864374 | 0.1437 | 0.8929 |
| scaffold71943:13435 | 275 | 276 | C | T | 0.685008651 | 0.01875 | 0.6667 |
| scaffold71943:13471 | 277 | 278 | T | C | 0.685008651 | 0.01875 | 0.6667 |
| scaffold128544:170 | 279 | 280 | G | T | 0.679301025 | 0.01266 | 0.6316 |
| scaffold98263:1069 | 281 | 282 | T | C | 0.677597364 | 0.06875 | 0.7738 |
| C32058675:292 | 283 | 284 | A | G | 0.673619414 | 0.00625 | 0.6548 |
| scaffold823:11824 | 285 | 286 | C | T | 0.673537258 | 0 | 0.6286 |
| scaffold75287:5899 | 287 | 288 | G | T | 0.673496392 | 0.04375 | 0.7073 |
| scaffold16869:149730 | 289 | 290 | C | T | 0.671387324 | 0.1456 | 0.8718 |
| scaffold3842:543149 | 291 | 292 | C | T | 0.670719701 | 0.025 | 0.6406 |
| C32058613:508 | 293 | 294 | T | C | 0.67046277 | 0 | 0.5758 |
| C32058613:563 | 295 | 296 | C | T | 0.67046277 | 0 | 0.5758 |
| scaffold7146:70340 | 297 | 298 | C | T | 0.669199626 | 0.1688 | 0.8857 |
| scaffold23125:41276 | 299 | 300 | G | A | 0.669066022 | 0.02597 | 0.675 |
| scaffold2418:77508 | 301 | 302 | A | C | 0.66841944 | 0 | 0.5758 |

TABLE 5-continued

Positions and allele frequencies of the top 100 SNPs by FST between marijuana and hemp calculated according to equation 10 in Weir and Cockerham (1984) [19]

| SNP Name | SEQ ID | SEQ ID | Minor Allele | Major Allele | FST | Minor Allele Frequency (Marijuana) | Minor Allele Frequency (Hemp) |
|---|---|---|---|---|---|---|---|
| scaffold12000:86305 | 303 | 304 | T | G | 0.668293303 | 0.06494 | 0.75 |
| scaffold24181:60784 | 305 | 306 | T | G | 0.665305819 | 0.02985 | 0.7083 |
| scaffold26621:72993 | 307 | 308 | G | C | 0.66089327 | 0.01493 | 0.6389 |
| scaffold6391:16360 | 309 | 310 | T | C | 0.658649381 | 0 | 0.5952 |
| scaffold88759:12655 | 311 | 312 | A | T | 0.656740474 | 0.1824 | 0.9091 |
| scaffold37469:74336 | 313 | 314 | C | T | 0.65627789 | 0.2062 | 0.9405 |
| scaffold12000:86310 | 315 | 316 | T | C | 0.655527354 | 0.06494 | 0.7375 |
| scaffold6143:103796 | 317 | 318 | G | A | 0.651968566 | 0.00625 | 0.5976 |
| scaffold33135:78155 | 319 | 320 | A | G | 0.648604326 | 0.1 | 0.7976 |
| C32058675:317 | 321 | 322 | G | A | 0.644770212 | 0.025 | 0.6667 |
| scaffold1976:5193 | 323 | 324 | G | A | 0.644158158 | 0.01333 | 0.569 |
| C32098343:2061 | 325 | 326 | T | G | 0.643381806 | 0.225 | 0.9405 |
| scaffold158089:295 | 327 | 328 | A | G | 0.642783505 | 0.01316 | 0.6053 |
| scaffold17267:6243 | 329 | 330 | T | C | 0.641890359 | 0.7372 | 0 |
| scaffold491:22100 | 331 | 332 | A | G | 0.640380595 | 0 | 0.575 |
| scaffold121522:9070 | 333 | 334 | C | A | 0.634641583 | 0.1899 | 0.9167 |
| scaffold24615:2202 | 335 | 336 | G | C | 0.63300106 | 0.0125 | 0.5952 |
| C32052323:699 | 337 | 338 | A | G | 0.62920484 | 0.00625 | 0.5789 |
| C32052323:711 | 339 | 340 | C | T | 0.62920484 | 0.00625 | 0.5789 |
| scaffold14925:8868 | 341 | 342 | G | T | 0.626191251 | 0 | 0.5714 |
| scaffold133681:2742 | 343 | 344 | A | T | 0.624116063 | 0.03125 | 0.631 |
| scaffold9639:84033 | 345 | 346 | G | C | 0.623460076 | 0 | 0.5488 |
| scaffold61482:2893 | 347 | 348 | T | C | 0.623250917 | 0 | 0.5714 |
| scaffold30395:12115 | 349 | 350 | C | T | 0.622098398 | 0.2562 | 0.95 |
| C32064647:1071 | 351 | 352 | T | C | 0.621516382 | 0.06757 | 0.6935 |
| scaffold2452:1249 | 353 | 354 | C | T | 0.62106722 | 0.1709 | 0.869 |
| scaffold11436:6161 | 355 | 356 | G | A | 0.619484202 | 0.02597 | 0.5833 |
| scaffold4156:16965 | 357 | 358 | G | A | 0.61693912 | 0 | 0.5476 |
| scaffold43435:8325 | 359 | 360 | T | C | 0.616228929 | 0 | 0.4783 |
| scaffold11297:60144 | 361 | 362 | T | A | 0.615278463 | 0.7063 | 0.0125 |
| scaffold51841:4904 | 363 | 364 | A | C | 0.612402044 | 0.02083 | 0.5811 |
| scaffold38015:40961 | 365 | 366 | A | G | 0.611084671 | 0.01899 | 0.5789 |
| scaffold16206:63417 | 367 | 368 | A | G | 0.607275173 | 0 | 0.5366 |
| scaffold13781:319 | 369 | 370 | T | C | 0.603383314 | 0.02564 | 0.6143 |
| scaffold27023:20610 | 371 | 372 | T | C | 0.603215502 | 0.025 | 0.5952 |
| scaffold4618:83522 | 373 | 374 | T | C | 0.600515019 | 0.03289 | 0.6094 |
| scaffold111383:2928 | 375 | 376 | G | A | 0.598738059 | 0.0443 | 0.6341 |
| scaffold29335:25795 | 377 | 378 | C | T | 0.598716088 | 0.1447 | 0.8 |
| scaffold122455:2010 | 379 | 380 | C | G | 0.597062664 | 0 | 0.5238 |
| scaffold13362:101120 | 381 | 382 | A | C | 0.595795194 | 0 | 0.5238 |
| scaffold38557:23764 | 383 | 384 | A | T | 0.595178777 | 0.01923 | 0.5 |
| scaffold38557:23794 | 385 | 386 | G | A | 0.595178777 | 0.01923 | 0.5 |
| scaffold50091:2544 | 387 | 388 | G | A | 0.595100084 | 0.006494 | 0.5 |
| scaffold16614:72706 | 389 | 390 | A | T | 0.594825378 | 0 | 0.4483 |
| scaffold4877:4542 | 391 | 392 | A | G | 0.593079588 | 0 | 0.5 |
| scaffold65894:5390 | 393 | 394 | A | T | 0.590807732 | 0 | 0.4857 |
| scaffold90107:10791 | 395 | 396 | T | C | 0.590194744 | 0 | 0.5122 |
| scaffold68873:1704 | 397 | 398 | A | T | 0.586079433 | 0 | 0.4875 |
| scaffold3842:188176 | 399 | 400 | C | T | 0.584333199 | 0 | 0.5161 |

TABLE 6

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 14566:24841 | 1 | CAGATCCTAAATATGCTGATATATTCTTTTA GAGAATTATGCAGCATTTCAGAATAGGTACAT ATTTCATTCTTTTATTTTTCTCCTGTATCTT TCAT | C | T | 2 | ATAAGGAGTTATTATTATTGTTTGGGTGCATTGTG AGTAGAAGCAGTTTCATGCAGCTTGTATGACCTAGCCA ATGTTGCCTACCCTAGCCAAGT |
| scaffold 2257:59436 | 3 | CAATAAGACTTTCGATCGCTCTTGGTGCTGCA CGAGGCAAGATTCTATATTTGATATTGGCTT GTCCCATTTGACAATTTTCCATTAAAATGGCT GATG | A | C | 4 | AATGGGTATTGAGGTTTGAAGAATTCTTTCATATGAA TCTGCAGGATTAACTTATCTTCACACATATGCCGGCTG CGTTATACATAGGGATGTGAAATC |
| scaffold 123303:7086 | 5 | TCCTCGATTGTTGAAGGAATTGTGGGGAGGCC TGCTTTGCGCTGCTGCTGGGCCCATGATAGTT TTTGCTGTAGTTTCACATTTTCTGGTTCAACT GTGA | A | C | 6 | AGCAAACTGCAAGTTCTTGACAGTGTACTGAGGCAACA CAAAGTGCAATTGTCAATTATGATCTGGAAGAGAAAGG TTCGCAGCAAAAGACCGAACTAGA |
| scaffold 21832:18317 | 7 | CTGAAGCCAGGACAATGCAGCCAGCCAGTAGT GAGTATCATCAGTATGTTGTTGCTGTCAA TGGCATGATGGACCCGAGTCCACGGAAGAGTT CAAG | C | T | 8 | GGGCAAAGTTTGCAGCCAGTCAGCCCAATTCGGAAA TAACTCAGATTATAGTCCAAGTTTTTGTAGAGGCTCTC CTACAGCAGCATATGCAATGAGA |
| scaffold 10653:22776 | 9 | CCATCATGAAATTCCCTTACCCTGGTGCCTTA ACTGCTCTGCAGTATTCACTAGTGCTTTTGG GGTCTTCATTTGTGGATGGCTTAAGTTCATTG AGCA | C | T | 10 | GACCGACTTGAGCTCCTCACAATGTGGCGTTCTACC TGCTCGTGTTATATTCTATCTTCCCTTTTCACCAATA GTGAGTTGCTCCTTCATGCCAATG |
| scaffold 34968:5203 | 11 | CCCATGAAACAAAAGTTCCCTGATATCAAAC AGTGAAAAACTTTAGCACACACAGCAGCATA GATATCGATAAGGAAACAGATTAATTGAAAAG AAAA | C | A | 12 | ACAAGTACTGACCTCAGGAGTTCCAAGAACCCAGTCAC GGATTGTGATCACAAGCAGAGCTGGCAGCAGATAAAGCA CTTGATAGCTTACGAGCTTTGATA |
| scaffold 41828:12391 | 13 | AACCATTCATCTTCTTATCACTGCTCCATTT CTTGTTTGAATGTCATAAATTTTGAATTGGCA GGATTCTTGAATAGCATGAACGATCTCATCAC ACGA | T | C | 14 | GTATAGGCCACACAACAACAAAGATTAGCCTTGTTGTT TTTGGCAGTAGCTTTCATGACTTTCTCAGCAGCAACTC TCACAGGCTCATTCAACAGTTTCA |
| C32084869: 1171 | 15 | AATGGTTCCTCAAATCTTCAAATCATCAGAAGC TCCTTGTTAGCTCGACTTCTTCCTCACGAAG CAGCTCCATCAAATGCCTTCTCATTCAGATAA TAGC | A | T | 16 | CCCAAGGCCAAGTTCCACCTGTTTCATCAGGCCATGCA TTATCAACTTCCCAACAAGTTCCAGTTGGCAGTTATGGG TCCCAATCACCAGCAGCTGCGTC |
| scaffold 1342:67015 | 17 | CGTACCGTTCATTGTCTTAGCTAACGACGCC AATGAAGCAGCAGCCATCCGATCCGTTCTTCCAA TGACCCCGTGTAAAGAATTGCTATCTGTTCCC ATAT | C | T | 18 | AGGCATAGGATTGGCTCATTGGCAGCAATTGGGGGTAA GCCGAGGTACTCGTCGTCCTCGATCGCAGGCAGAGGCAG AAACCCGAAGGAGCCAAGAGACAT |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 5876:136612 | 19 | GCTCCGCTGCTGAAGATGTTTCCAAACCTGCA CACCAAGGAGTCTCTCGTATCCCCTGATGAGC TTGGTCCTTTTCAGGTAAAACTATCTTGCTCA TCAT | C | T | 20 | TGCTGCTGAGTTCTTTTCATTAGTTGAATTAATGTA TCTACAAACTATTTGTTACTGCTAAAAGCTTATTGTCT TTAACTTATTATCACATCTATACT |
| scaffold 10653:22755 | 21 | TCTCTATAATCAACAAATGGGCCATCATGAAA TTCCCTTACCCTGGTGCCTTAACTGCTCTGCA GTATTTCACTAGTGCTTTTGGGGTTCATTT GTGG | G | A | 22 | TGGCTTAAGTTCATTGAGCATGACCGACTTGAGCTCCT CACAATGTGGCGCTTTCTACCTGCTGTGTTATATTCT ATCTTTCCCTTTTCACCAATAGTG |
| scaffold 65043:4386 | 23 | CGCGAAATAACATTCTCACCTTCTCTCTCTC GCCACCGCTGCTGCCCGCTGTCGCATACGTTTT TCTCTCCTCCGATGATCGTGATCATAAGG CCGC | C | A | 24 | ATCGAACACGGAATTCGCAAATACGGTGATTCGATCAA TAACGTTTTCGTTCACATTAAGCAAACCGGTTGCTG CTTCGGTTCTCTGGCAATCGCTTA |
| scaffold 39548:5676 | 25 | AATAAAAACATGAGCTTCTTGATATTCCACTA AGTTTGGGTAGTGCATAGTCTTTGGAGAAGC AGCTCGAGAAAGTGAGGAAATAGTACTTTTGG AGTC | T | C | 26 | GATCGCTCCAGGTAAAGCCTCCTCCTCTGTATGCAGCCAA GTGAGCATAATAAACTGGGGGAACCAAAGAAACTGTT TAGTACACCTTACGTATGTATAAC |
| scaffold 39548:5703 | 27 | CACTAAGTTTGGGTAGTGCATAGTCTTTTGGA GAAGCAGCTCGAGAAAGTGAGAAATAGTACT TTTGGAGTCCGATCGCTCCAGGTAAAGCCTGC CTCT | A | G | 28 | TATGCAGCCAAGTGAGCATAATAAACTGGGGAACCAA AGAAACTGGTTAGTACACCTTACGTATGTATAACAA GATTGTACACCAGTTTCTGTAGTT |
| scaffold 17605:9224 | 29 | TACCATTTTCTTGCCCACAGGTTATTTGCTG CTATCCTTGCCTGGTTGTGGCCCACTCTGGCC AAATCCGTTATCCTCATCAACAGTGCTGGAAA TGTC | G | A | 30 | TTCCAGGATATTCCTTGTGCCATTAGTAAAGTGAGT CTAAAAGCAATGCTTATCTTTAAATATGGTATCTGGTG CAGCTGCTGACAACTGAAAGCTGT |
| scaffold 94301:10558 | 31 | TCAAGAGTTGGTTAGAAATTTATAACATACCA GAAGCAGCAGAAAATGCTGTACCGCTTCTTTT CTCAGCATCATGATGGTCTTTTGTAGTTTTTC CAGG | C | T | 32 | GTTGATGAAGTTTTCGGCTCACATCTTTACCTGCTG AGAGCCAGTTGCAGCATCTGTTCCTCCTTCACGTTTTT GTCGAGCTTGTTCAGCCATAAGCT |
| scaffold 52608:15151 | 33 | CTAGCAGCTTCAAAATGGGTTTCTTTCTTTGG AACAGCTGGGATATGTCCTCCGAGGCCAATCT GTCAAACAGAACTTGAAGTGAAGCAGAGAGCA AAGC | G | A | 34 | CCACCAACCAATTCAGCAGCCATATTGATCAATGACAA AAGTAACAAGTTCTTTGTTGAATCTGTGTAGGGGTTAC GGATGAGAATGAAGAAGAAGAA |
| scaffold 9110:12755 | 35 | CCCAAAGAGTTGGTTATTTCCTAGTGTTACG ACTGTTGGAAAGGCCCCTTCTTATTGTGGTGGC TGCCAGTTATGAGCCATGGTGCAGTGTTTG AAAT | G | A | 36 | GTTTGTGAAGTGGGACCACTATTCCTGCAGATGAAAC AACCGTGATCCCCTTTGATGCTCATGGAAGGACCCAA TTGCAATTGTGTCACGCAGATCAA |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| C32099389: 1875 | 37 | TTGATCTACTGTTGCAGAAACATGTATGCTCAG TTGCTGCCTCTTGCTTTGCCTGCCCCACCTAT GCCGGGAATGGGAGGACCAGGAATGGGAGGCT ATGC | G | A | 38 | CCACCTCCTATGGGGGAATGGGAATGCCTCCAATGCC ACCCTATGGCATGCCACCCATGGGAGCAGCTATTGAG ATGTATCAGGACTACGAGTTGTGA |
| C32076905: 769 | 39 | CTGACAATATAGCAATGCTTCATTAAATCTCA TTATTACAAATACACTCATAAGCTCATCAATA TAGATAATAGATATAGTAAGATACAAGCTGCA ATAC | G | T | 40 | CAAAATTCAAACACCAGAGATCACTCTAACAAGTCACAA CAAACACATAAAAGCATCACTCTAGCAGCACCACCAC CACCAAACCAAGGCATCATCCCGA |
| scaffold 50412:1217 | 41 | GACTAAGCCTCAACTGGGTTTGGAAGAATTTT GACCATGAATCTGAACCGTCCGCTGCTCTCAA AAAGTAATGTAACTGAGAACGATGGAACCGGC ACCG | T | C | 42 | TTAGGGAACCCAGTGACCTGAAATTCTTCAGACTCTGT TTTCCGGTGAGGGAGTTCGTTCCAGATAGAAATGAAGG CTGCAGAGCCGTAAGCGCCAGAAG |
| scaffold 73281:3231 | 43 | ACAAGAAGAATAGAAAAGGCTGCTCTTACTATT TTCTATGCCTTGGCCTTGGCTGAAGCTCTGTT GTTTCTAATGGGAGAAAAGCTTATTGGGAATGGA AGGT | T | C | 44 | ACTTACTGCAAGCTGCTTGATGAGTGAACAAAGAGAG TGAATTGGGAGGAGCTTCGTGTATGTTTCAATCAGAA GGTTCTTCTATGATGCCTATTCGA |
| scaffold 60591:9229 | 45 | CCAATTCCGCCACTGCTCCACTGCTCCTGCT AGATTCTTCAGATGAGCGCTCAATCTCTTT TGACAAAGATCCACCAAGCTCAGGCTTATCAT CACC | T | C | 46 | GTTTCAGCAGCATCATTACCATTAATTTATCCTCGTAC TGGGCTGCTGTCTGGACCCCATTCTGATGAGTCTTAA CATCTGCTTCAACTTCATGCGAGG |
| scaffold 60591:9364 | 47 | GTACTGGGCTGCTGTCTGGACCCATTCTGAT GAGTCTTTAACATCTGCTTCAACTTCATGCGA GGTAGATGTAGATACCACAGATTCTGACATAG TTTC | G | T | 48 | GTTTCTAAACTAGCTGCAGTAGCATCCATTGATCCAC AGTTTCCAAGGAAGATCCAGATCTATTATAATTCCAC CAGTGAGGGGTGCATCCACATCAT |
| scaffold 27976:11462 | 49 | TCCATTGCAAAACTACCACCATGGCTCTGAT CAGCAGCAAAAGAGCTAGCTTCACTTCC TCCACAAGATCAAACTCTTTCTCTCTGCTT GGTT | T | A | 50 | GATCAGAAGATTTATGAGTTGCTTCTTCAGAAGTTGG TAACTTGTTCCGAGTGTTGACTTGAGGTATTTGCTGC AAATGGAGACTTCTCTCGCTGGCT |
| scaffold 4591:18700 | 51 | AAGCAGCATGGCGGCGATAACAGTAAGAAAAG CTTGAAGAGTCTCTTAGGGAAGGAGAATAG GTTGCAGGATGCGTTGGCCAAGGCCGGGGCGA GCTC | A | G | 52 | CCTAGTTTAGGTGCCACCATTTATGCTCACGCTTTGC TGCAAACGCACTGCGTGCCATAAGGCGTAATAGTACAC GTAAAACAAGGATGCCGAAAGAA |
| scaffold 96873:16326 | 53 | AGGAGGCAAGCGACTCTTCAACTTAGCCAGCAG CGGAAGGCGAGGTTTAGGAATCGGAGGCAAG GAGTTTGATCGGCATAGGGCGGAGCATTCTC CTTG | A | G | 54 | AAGATTTCTGCTTCCGGATGTCGGATCTTGGCGGTG GTGCTGCTAGGGTTTGGAGATGGCGGAGGTTCCGTCTC TCTCAAGATGTTATTCTTGGCTG |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 6777:12771 | 55 | ACCATTATGCCGTGTGCAAATTCGAATTGC TCTCCCATCTGAGTAGTTCGATATCAAGTGA TCTGATGGACTTCTTGTGCTGCTATCTGAACC CACC | C | T | 56 | CTTCTTCATCTTCAGAACTCTCATCATCATCCTTGAAA ATTGACCCTGGTGTTAATCTTTGTTTTGTTTTGAGCT GTTCAAGATTTCTCCATTGTACTT |
| C31894837: 130 | 57 | ACTTCGGCTCTTAGGCAGCCCTGCCTTCGCAT TCCTAGCCTCAAACACCGAAGCCGAGTATGAA GCCCTAATTGCAGGACTAAAGTTATCAAAGGC CGTA | A | G | 58 | GGGCTGCAAGAGTAGAAGTCTTCAGCGATTCACAGTTA GTGGTCAATCAAGTGTCGGGGGAATACCAAACGCGTGG AGAAAAAATAGCCGCTTACGTAGC |
| scaffold 1342:66883 | 59 | TGTGTTCAACGCTTTCCGGGTTCACGCCCCAGA CGCCCAATTGCCGTGCAGCATTCCTGACC TTCCATTCGGCCTTCTTTTGCCAATTTCAGAA GTGG | C | T | 60 | GCCACCCCACCTTCTCAATAATAAGCTTACCGTACCG TTCATTGTCTTTAGCTAACGACGCCAATGAAGCAGCAG CATCCGATCGTTCTTCCAATGACC |
| C32035477: 264 | 61 | GAGAAGAGAAATTATCATATGCCACCATGAGC AAAACCGCAGCCTCCTTTGCGAGGATAGAATT TTCTACCGAGAGAGTTTTGTCGGTCGCTTCT CCAT | G | A | 62 | GCAAACAGTGCTGTTCTTGTTTCTCCATTCGTTTCGAACATT TAGCATGTATTATCACTAGCAGCTTTTTTGGAAAAAC TAAGGAAATACTTCAAGATGCGA |
| scaffold 6360:1717 | 63 | ACTTGCAATGTTAGCAGCCTGGTCCAGAGAA CTAGAGAGCAAGGGATGGAAGCATATATGGTC CACAATACCAAGCCGGGGATGACTGCCACTGT GCAA | T | C | 64 | TCAAGTCAATGGACTCCAGAGCAGCCTTAACCATGGC TAGGACTGAGGTTCTCAAGGGCATGGATCCGAAGATG GTTGTGGATCCAACTTGGAAACAA |
| scaffold 132623:4144 | 65 | GTAAAATGCAGTCCTTGTGATTGTTGTTGTGT AAATGCCCGTCCGTCTGTTTCAGTTGCTCGTTACC AAAATGCGTTGCCCTCGTTGTTTCATGTTCGT GTCC | T | C | 66 | CGACCAAATTGCTGTAAAAGAAGTCATGCAACAGAAG TTGTTGCTGCCTATTCCCTACTTCTTGTTGTTCATGCC CTGATTGCCCCTCTTGCAGATGCA |
| scaffold 72006:11851 | 67 | ATTGCTCTAGGGGCAGCCGAGGCTTAGCTTA TCTACATGAAGACTCCAATCCACGAGTGATTC ATCGAGATTTCAAGTCCAGCAACATCCCGTTA GAGC | T | A | 68 | TGACTTTACACCTAAGGTCTCAGACTTTGGATTGGCCA GAGCAGCATTAGACGGTAACAGACATATCTCAACACAT GTTATGGGCACTTTTGGGTAAGGA |
| scaffold 6742:34122 | 69 | AAAAAGTTGCAGCGGCAACAAAAGGTCTGTGT TGGGATTGAGAGGCTTTGAGAAGAAGACCCT CGAGGGAGAAACCCACGAAGACTGAGGAGCTA GGTT | C | T | 70 | GGTGGGTTGTTGGAGCCAATTGAGTATATTTCAACGGA GGAAGTGTCGGAATCGGAGTCGAAAAAGGCCATGGCTG CGAACCGGTCCAAGGCCGTGACTG |
| scaffold 3108:8782 | 71 | AGATAAAAGTCGCTCATTCTGAACCTCTTCCT CTAACGAGCTGTCTTTTAAGAGCAAGGTGTTG ACCTCATTTTCAACTACTCTCAATCGAGACTC TGCC | G | A | 72 | ATTCTCTTAGCTTGTGATGCTTTTACTTCTTCCTCT GCAGCTTCTTGATTCAGTAGCAAGAACCATCTTTAT TTGCAGCTCCTGCAAATCCATTGC |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 11225:9528 | 73 | AAGCAATTAACAACCTGCTTATCAACCAAAC CCGATGAGTAGTGACTACATAAGGGTTATTA TCATGGGCAGCCACCGGGTTCATTTAGAATGCT AACC | A | G | 74 | AGGCTCCACTAGCAATTGATCTTCTGCACCCTTCTC ACTAAGTCTTGAGCAGCCCATATACTCCGCCAATAAA ACTAGGATTATTTCCTAACTCAGC |
| scaffold 11225:9539 | 75 | CAACCTGCTTATCAACCAAACCCGATGAGTA GTGACTACATAAGGGTTATTATCATGGGCAG CCACGGGTCATTTAGAATGCTAACCGAGGCTC CACT | T | A | 76 | GCAATTGATCTTCTGCACCCTTCCTCACTAAGTCTTG AGCAGCCCATATACTCCGCCAATAAAACTAGGATTAT TTCCTAACTCAGCATCAAGAAGG |
| scaffold 2579:59858 | 77 | TGCCGGATTTAGTGTGTAATAAAGACGAATCG AGCAGCTTTGGGTTCAAGAATTTGATGGAGAC TTTCTCGGGTTGACGTTCAAGAAGCTGAAGAGA GACC | A | G | 78 | TTGAGGCTTAAACTCATCACTGAGCCTGCTGAGACTGC TTCGTCGTCTCAGCTTCAAATATGGCCATTAGAGTTG AATTGAGGAATGGCTGCGTCGGAT |
| scaffold 5876:136559 | 79 | GCACTTCCATTTACTTGGCCTCAGGCAAAATA TACCAGAAGAGAAAACATCTAGCTCCGCTGCT GAAGATGTTTCCAAACCTGCACACCAAGGAGT CTCT | T | C | 80 | GTATCCCCTGATGAGCTTGGTCCTTTTCAGGTAAAACT ATCTTGCTCATCATCTGCTGCTGAGTTTCTTTTCATT AGTTGAATTAATGTATCTACAAAC |
| scaffold 5876:136606 | 81 | CATCTAGCTCCGCTGCTGAAGATGTTTCCAAA CCTGCACACCAAGGAGTCTCTTGTATCCCCTG ATGAGCTTGGTCCTTTTCAGGTAAAACTATCT TGCT | T | C | 82 | ATCATCTGCTGCTGAGTTTCTTTTTCATTAGTTGAATT AATGTATCTACAAACTATTTGTTACTGCTAAAAGCTTA TTGTCTTTAACTTATTATCACATC |
| scaffold 23386:12397 | 83 | CTAGTTTTAAGGATGCACAGTGGCTCCTCATC CAGAAAGTCGAAGAGAAAAGCTTCTTCAAGT GACTATTAAGCTGCCAGAGGAGAAACTAAATA AGTT | A | G | 84 | ATAAATGACTTCAATGAGTACTATCTTAGTGATGGTGT TAGTAAGTCTGCTCAACTGTGGAATGAGCAGCGAAAGT TGATATTGCAGGATGCTCTTTTA |
| scaffold 93032:4944 | 85 | TGCAGCCCATTGTTGAGATGAATGAGATGTTTA CATGCTTGAAGTTATGTTGATGTCTCATTTCT CTTTCCTTAGCTATCATAGTCAAAGCATCACC AATG | A | G | 86 | AAGCAGCAACTTCTGTGATATCCAGTGGGTTTACTAAA ATAGGCCAGCACCGAGTGAATTTACTGCCACCTGCACA CTAAATTTAAATGGAATAAACAAG |
| scaffold 94004:13663 | 87 | TGTTAACAGCATCAGCAGCAGCAGTATTA TCCCTATTTCGTAAGGAACAAGGACGCCACAT ATATGTTACAGGAGCGATCGGCTTAGAAACTG GTGC | A | G | 88 | CCAAATATGGTGAGCTGCAACATGGGGATTAGTCAGAC ATAGCCAATTCCTTAATCCACCTCAATGAAAAGAAAA GGACAGTAACTAACCATTGCATTA |
| scaffold 26621:73038 | 89 | ACGACCCTACTACCAATAACCCAAATAGGGC AGCAAGGATGATGATGAACCACACAATCCT GCTCCCCAACACTCTCCAGACACCCAACACA TCCA | C | A | 90 | TACTACTACTACTACTACTACTACTGCTGCCTTCT TCAGGGGTAGCACCATGGTGCATAAGCTAATCAAGGCC AGAAGATCATCATCAACAACACCT |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 26621:73058 | 91 | CCCAAATAGGGCAGCAAGGATGATGATGA CCACACAATCCTGCTCCCCACACTCCAGA CCACCCAACACAATCCAATACTACTACTAC TACT | G | A | 92 | CTACTACTGCTGCCTTCTTCAGGGGTAGCACCATGTG GATAAGCTAATCAAGGCCAGAAGATCATCATCAACAAC ACCTACCTACATATTATAACAA |
| scaffold 62259:15201 | 93 | ATGATGATTTAAAATGCATTAACTTCACATCC CAATATTTCTCACCCAACCCATAGACTCATAAC TTTAGCCTTTCCCTCTAAATATTGGATTGCAA ATTT | C | A | 94 | CTCGGAAAAGGCTGCAAAAATGATAATCATAACTAGCA TAAAATATTGATCTTAATTCATAACTAAACCATATATT TATAGAATCAAAACTTTTCAAACA |
| scaffold 38801:13810 | 95 | CAAAACCATCCGCGAGAGAGAGGTTGTTT TCAGCATCTCGCTCAGCCTTGTTGAAGGCATT GGAGGCGATGAGGATGGAGGCGTCGCAGCTT CGAC | A | G | 96 | AGGCAATCATGGAAGAGGAGGCGGAGAGTGGCGGCAGC TGTGGTTGGGACCACCGATTGCTTTTCCTGTACAATCT GCCGTACGATGTCGGGGAATTTCG |
| scaffold 6550:117010 | 97 | TCGCCTTACAGGCTTTACTTGCACAGTCAAAG ACCGGTCTCAGCTCTTTGCATCGTGGGCAGAT TTCGATGTCTATCGTTGGCTGGTCTTTTGTAGT AATG | C | T | 98 | CTGATTGTTGAGAAGTTTTTGTACTCGTGAAATAGAAG GAGAGGCCGTGTGGCTTTTGCTGTCTGCTCTTTCGGGTTAT GTTGAAGACACGAAGAGAGTGTTT |
| scaffold 94863:28465 | 99 | TTGGGTGGTGGCTATGGCTGCAGGCACTAAGA GCAAGCCCACAACCAAGCTGTTGAAAGAAGC ATGCAGCCCGTATAATGCCACAGACTTTGCTG ATTT | T | C | 100 | TTCTCCAATCTGAACCCACTCTCTCCGATCTCGGGGC TCAGATTCGAGAGGGAGATAAGTGGTTTGCAACGGCGC AGCAGGCACGGGGATCAGACCCTG |
| scaffold 130551:553 | 101 | GAAAACGAATGCTGCAAATCGATCGGTGAGCC TGTTATGCAACTCCTCTTGTTTATTTGATGA TCTTTTTAGTCTCTTTTCATACATTATTGTAA TTGT | T | A | 102 | ATAACAAATCTTGGAGCTGCATTGTGATGATGATGATG ATGATGATGATTGATTGATAGTCATGGTGTTATGTTTT CACAATAATAAAAAAAGAAGTC |
| scaffold 21832:579 | 103 | AAAGCCTGCTGCGCTTCCCGGGCTCTTGAGGA GATTCTTCACTTACAATTTGCTTAGCTAATTC TTGTAAGAGATCATGCATCCATATTTTGTCAC CAAC | C | A | 104 | ATAGTTACCATAGATTTTCTGTCAATACTTTTAAATC GATACCCGATAGCATTCGCAGCATTCTAAAATCTTTT TCACCCGAATTTCGCTCTCCCT |
| C320902:01 1470 | 105 | GATTATACCCAGAAAACCAAAGCAGCCTTAGGA CATTCCAGATTTCGTTTACACAATCCATAGC CGAAGTACCCAAAAGCTCATCTTCCCTTCTCT CAAA | C | T | 106 | CTTAACCAAGCAGCCAGAACAATTTTGGTGTGAACATC AACAGCATGCTGCCTTGCTGACCGGAGACTCCGCCCGA AAAATTTGGGATCCGGAGAGTCCT |
| scaffold 117639:1939 | 107 | GATTCGAGTCATAACTTGGCACACATAAACTA CAGTCCTGACAGTCGGATCCACAACTGTGAA AAAAGCAGCAATATCTCGCCCAGATATAAAAA ACCG | C | A | 108 | GAGTAAACACTTTTCCTCGTTCATCAGACTGACTCTC CTGCAGTCATTAAATTACTCAATTCTGATGATGCAAAA TCAACTTGAAACAGACTAAGTTAT |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 73281:2531 | 109 | AGTCCAGTTACAACAATGTTTGAGCCTCAAAATAGTATAGAGAAAAGGACAATAGTAGCAATGCAAATTCTGGCTCTGCAGCCTTAACAAAAACAGTAA | A | G | 110 | AGCACCAGAAAGAAGCTTACCCTCTTTGCTCTTAGGCTTGCTGTTCTTGAAAAGCAGCAACTGGCCTTGGAACACTTGGTTTATCTGGGCAACAGTT |
| scaffold 95390:2586 | 111 | GTTTTAGATACCAAAAATAAAAGATGTAGATGACCGGAGGAAACAAGCAGCTGGGTCTGCCAATTCAAAACAGTCTCAGTTGCATAATTACTTGTCTTAA | T | C | 112 | ATCTCTTTTTTGGCTAATGCAGCTATAAAGCATGGGTTCTCTTCTGGGACACAGTTATCAGAAAGAGACATTATTGTGGCGTGCATAGATTACAGGTT |
| scaffold 109105:3417 | 113 | CTAACTCAATATGTTTCATTCTTGCATGATAAACAGAACTTGCAGCTGGTGCACTAGCACTCATGTTGTCACACCATGTTACTGATGTGCATAATTGTGT | C | T | 114 | TGTTGTAGAAAGAGCAGCAGCGAACATAAGTTTTAAGTTCAAGTAATTTGTTAGTCAAATTTCAAAGTGACACTTCCTTTATTGGAAAGGAAAAGGTACA |
| scaffold 9670:13701 | 115 | CCCATGGCTTGGACGAGCTCCGACCTGTGATCAGACATCCTGTTACAGACTGAGAATTTGCAGAATGGTTCTGGCTGGCATCCCTGCCCTTAAGGCCA | T | C | 116 | AGGTGCCATTTCCGTCACTCCCTCACTGAGCAGGAGAAGTTGATGCTGCCTCATTGATCACCATGGAAGTGAAATTATACCCTTTAGCAGGCAGATTAAG |
| scaffold 45478:20587 | 117 | GTTGTATTGCTGCCACGATAAAATTGCTTGGACATATCTAAAGTAGACTCTGACTTGCTCCCTGATTTTGTCTCCCGGCCAACTTTGCTTGCAGAAACA | C | T | 118 | GTGGCTCAACCTTGCTCTATATTCAGTATTTTGGTTACAGCTGCAGGAATGGTAGTCATATCTCCAACTGTTCTTCCATTGCTGGAGCAGTGAAACTT |
| scaffold 23700:29096 | 119 | TCTTTGTCTTTAATCATATCAAAGACTTCTTGAGCAGCTTCCAATTGCCCACACTTGGAATACATGTCAACAAGTGAATTTCCAACTAAAACATTATCTA | C | A | 120 | AAGACCAATCTTAATTGCAAAAGCATGGACTTCCAGCCCTTTGTTGAGTGATCTTAGAGATGCACAAGCTGAAGCTGCACTTGCTATAGTAACTGCATTC |
| scaffold 10732:30120 | 121 | GACATAATGAGTAGACAATGAAGGTATTAAGATGTGGGCCTATTCAATAACACGGAAGCAAAATGAGTACCTTAGCTTCCAGGTTCATCTAAGGTGTCTA | A | G | 122 | ACTCTCACATAGTGTTGCAATGATGGATTCGTAGCTGCAAGGGAATAGAGATAAAACAAAATTTTAAGGAGATTTAATAATAATAATAATAATAA |
| scaffold 16969:31933 | 123 | AATTACAGGAACAAGGGCTAAAGCCAGAATCACATCACCTTTTTGGGTGTTTAGCTGCCTGTACTCATGGAGGTCTTGTTGATGAAGGAGAAATATT | T | C | 124 | GAAATTATGAGAAAGGAATTCAATGTAATGCCAGGGCTGCAGCACTATGCTTGCTCGGTAAGTCTGTTAGGTCCGCAGGCTTGCTTGAAGGGCATTGA |
| scaffold 3884:40695 | 125 | TACCCCATCATTATATTGATTTTGATTGAGGTAGTGGAACAGGGAAGGAGTATGCAGCGGCTGCGGCAGCCCTTGGTGGTGGGCTTGGCATCGCCATTG | A | G | 126 | TATCGAAAGCTTGGCTTTAAGTGCTCCTAGTAAGCCCTCTGAGGCTGCAGAGCTAGTAGGAGCACACACTTGCTCGAAACAAAGGGCCTCCAAGTTATT |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 829:52127 | 127 | GGTGGCCTTAATGCCTGGTTCGGAACAGGCTGCAGCAATGACAGCCATAGCCACTTGCTCAACGCTTTTAGGCCGATTATTAATGAGTCTCCGTGACT | A | G | 128 | CTGCATCCCACCAACATCCCGTGGTTGTGAGATGATACTAGCAGTACTACTAGTCATCGGTGACTGCAGCTACTATATATATATATATATATATATAT |
| scaffold 6550:117004 | 129 | CCATTTTCGCCTTACAGGCTTTACTTGCACAGTCAAAGACCGGTCTCAGCTCTTTGCATCGTGGGCAGATTTCGATGTCTATCGTTGGCTGGTCTTTGTA | G | A | 130 | TAATGTCTGATTGTTGAGAAGTTTTTGTACTCGTGAAATAGAAGGAGGCCGCTGTGCTTTTGCTGCTCTTTCGGGTTATGTTGAAGACACGAAGAGA |
| scaffold 27604:1398 | 131 | TGTAGGCTGGAGTTTCTGAACATGCAAAAGCATTAGGGCCAAAAGGGTCAGATGCCCCACAAAGCAGCTGTAATAGGTGACACAATTGGGGATCCCCTTAA | A | G | 132 | GACACTTCTGTCCTTCACTTAATATTCTCATCAAACTTATGGCAGTTGAGTCTTTGGTCTTTGCTCCATTCTTTGCTGCTCATGGGGGCTTAATCTTCA |
| scaffold 125644:4761 | 133 | TCCTCCGTTACTTGGATCAATTCGGTAAGACAAAAGTCCACACTAAATCTCTGTCCCTTTTTCGGGCACCCCGAATCCCCAGTCCCATGCCCCCTCGCCGCT | G | A | 134 | AGGGCAGGCATGGGGCAGCCTAGAGCCCTGATAGGGCGTCTTAGGGCAGCTTTTGAGGAGCATGGGGAAAACCCGAGGCGAACCCTTTCGGGGCTCGGG |
| scaffold 16027:10666 | 135 | GGGTTCAAGCTCCATCAAGACTTGGCTGCTCGTCTTCCCAGCTTTCGTTCTTCTTATGTACCCTGCAACTTCTCAAAAACGAGCTCCACATCATCGTGTCT | C | T | 136 | CGTTTCCCTTTGCCTTAATTAGCAGCTTCTCGGCTTCATCTAGTAAGCCTGCACGGCCTAAGAGATCAACCATACATGAATAATGTTGTCGATCAGGGCA |
| scaffold 2502:17437 | 137 | GAGAAATTCTATAGCTCACAGGCTTTAGGGGGTCACCAAAATGCTCACAAGAGAAGAGAGCAGCCAAGAGTACCACTCTCATAGAATGATGATG | G | A | 138 | ACACAATGGCTTGGGCTTTAACCCTTTCACCAACTCACTACCACCTCGATCTCTTGGAGTCCAGGCCCACTCTCTCGTTCACAAGCCCAATAGCAGAGA |
| scaffold 2502:17515 | 139 | CCACTCTCATAGAATGATGATGAACACAATGGGCTTATGGGCTTTAACCCTTTCACCAACTCACTACACCTCGATCTCTTGGAGTCCAGGCCCACTCTCTC | C | G | 140 | TTCACAGCCCAATAGCAGAGAAGTAGCGTCCTCGCTGCTATGGTTGCAAGATTAGTGATGCTGAAACTGGATTTGGGTCTGGGTCGGGCCTGGGCC |
| scaffold 70502:1951 | 141 | AGCTTGTCTCCCCACGGCAGCCAGCCACTAGCCAGCTGCCCACTTGTCCGCCTCTCGTTCAATCCGAGCTCCAGCAGCCTCCCATGTGCCCAAGTGTCGTCTC | C | T | 142 | TCCTTCCATCCGCCATTTTCAAATATTTGATGCTGCCAAGTCCCAATGCATGAAAAAGTACTCAAAATGTCAATTTCAAAAATACATTACAATTTT |
| scaffold 40620:28184 | 143 | CTCACTTTTCGAGGAGATGCTTACCTATCGAAATGATCATGCGATGCAAAGTAATGGCTTCTACACTTACGACGCCTTCATAACTGCTGCTAGAATTTTT | T | C | 144 | CGGGCTTTGATACTTGGCTCTCTTTGAACTTCGTACAAGAGAACTAGCTGCGTTCTTTGGCCAAACTTCTCAGGAAACCACGGAATACATACTGTTC |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 40620:28194 | 145 | GAGGAGATGCTTACCTATCGAAATGATCATCG ATGCAAAAGTAATGGCTTCTACACTTACGACG CCTTCATAACTGCTGCTAGAATTTTTCCGGGC TTTG | G | A | 146 | TACTACTGGCTCTCTTGAAACTCGTACAAGAGAACTAG CTGCGTTCTTTTGGCCAAACTTCTCAGGAAACCACAGGA ATACATACTGTTCATTTTATACAT |
| scaffold 40620:28201 | 147 | TGCTTACCTATCGAAATGATCATCGATGCAAA AGTAATGGCTTCTACACTTACGACGGCCTTCAT AACTGCTGCTAGAATTTTTCCGGGCTTTGATA CTAC | A | T | 148 | GGCTCTCTTGAAACTCGTACAAGAGAACTAGCTGCGTT CTTTGCCAAACTTCTCAGGAAACCACAGGAATACATA CTGGTTCATTTTATACATGAAATGT |
| scaffold 118158:666 | 149 | CGAGCTCAAGCATTTCATTCTCTGATTCTCG ACGACCCGATTGTCAGTCGAGTTTTTGGGGAA GCCGGATTTAGGAGCTGCGATATCAAGCTAGC GATT | C | G | 150 | TTCATCCACCGACACCGGCGAGGCAAGCCTCCTCATTC ATTAGGGGCCCGTGCCCACCCATGTTCCTCTGTAATCT TACTGATTCGGATCCGGGTCTTCG |
| scaffold 41951:881 | 151 | CAACGCTCTTCTTGGCCATGGAAGACAACTCCC CTGACCGGAGTCCCACCACCATTGGCGGAGCC GAAAGAGCGGAGCGTGGAGGCGCACGGCGTGGG AGAA | T | A | 152 | AGAGGGTCGCTCGTGCTGTGAACGCCGGAGGCGAGGAGTGT GGTGGGCGGACGGAGGGAAGAGAGGTGAGAGTTGAA GGAGAGAAGAACGAGTGCGGGAAG |
| scaffold 95666:9974 | 153 | CCTTTGGGAAGCGGCCGAACCATGCTCCGT TTCCCTGTCCATTTCTTTTTCGGGTGGGGA AACAGTGTCAGCAGCATGTTTGTTGTTTCGT TGCT | T | C | 154 | GGTGCCTGTTGAGGAGGGGTTGATGAGTTACCAGAGCC CGATGGAGGGAGGAAAACTCCAGTGCCAAGGAACAGGCA AGCGAGGTGAGGATGCCTCCGTG |
| scaffold12 645:86648 | 155 | CATTGACCGCCATGGATCCCCATCAGCTGCTT TTGGCAGTATCCCCTTTCGGCTCCCGGAACCA AATCCTCTCCTCCTCCTCCGTCATCTGACGATG GAAG | C | T | 156 | GGCGGTTTCGATGATTACGGAGCGTGGTATGGGAATAT CCAGTACTTGATTAACATTTCGGCGATTGGGCATTCT TCTGCGTCTTCATATTCGTCTTCT |
| scaffold 6627:26364 | 157 | AAGAAGGAAGAGGTTGCCATCCGGGCATGGCG AGAAGGCCATTAGCCGGGTTGATTGAAGCCGG ATCAATACTCGTCGCTACTAGCAGCGTCACCA TCTC | T | C | 158 | CTATCTCTCTTTAGTTCACTGTCGAGTGGAATTTAGTA GAAGAAAAAGTTGGCCGACGTACAAGAGAAAAGAAGA GAAGAGAGTGGAGTCTTATTACAT |
| C32050599:443 | 159 | GAAGAGCTATCTTTAGAAAGTAATGACAAAAT CTCTTCAGCAAGTGAATTTAGGTTCACAGCAG CAGAAAGCCCAAAAAGAACCTGATAATTAAAT GATT | T | C | 160 | AAAAGCATAAAAAATCAACACATTCCAATACATTTTGC AACAATTCAATCAAAACAAACACCAAAAGAAAATTTGT TGTTCAGCAGAAGACACAATGAA |
| scaffold 20861:14886 | 161 | GTCTTACATTTTATATTCTTTTTCAGATATGG TATGCAGCTTCAAAAGCTAGAGCTGAGAAAGC TGGTTGGGAATTTGCAAAAGAGAATGGGATTG AATT | A | G | 162 | ATCACCACCATTCATCCAGGAGTAACACTTGGCCCTCTT GCAGCCCATTATGAATGACAGTGTCAGTCTCATTATGA ATCTAACAAAATGGTACACATCATG |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 30119:28969 | 163 | AATGGATCCTTTGCGCCTCTGCAAGTGAAA TAACTTTCCCAGCTTTCTTCTTTTTGTTGTTA TTATTATTACTTTGGTTCCCGTTTTGCATAG TTTC | T | A | 164 | TGTCACTGGACTCAGTGAAGCTGATTACCCTGGA GAGGAAGCTGCATTCTTTTTAGCTTCTGTCTGATTACT GGGGCTGTAACAACTTTTGTGT |
| scaffold 2257:75397 | 165 | TGCTGCTTCTTAAGAGTTTTTTAACCCCAATC GCCCCGCCCTGCTCGACAATTAGAAAACCAC ACAAACAACCCTGCCAACTCCATTTCACAGCTC CATG | T | C | 166 | AACAGCTGATCATCAACATTGCAAATCAAGCAAAGGCT GCAACGTCTAAAAGGCCATTGTGCCTAAGCAGTGCCTC AGGTGAAGGTTCGCGCGCCTCGAA |
| scaffold 46867:905 | 167 | TTAAATTTGAATTAGTTATGATTTTTGAAGTT TCGGAAAAATCAGAATCGTGCAACAGGGCCAC GCGCGGAGGACAGCACGCATTCAGAAAAGCTGC TCGA | T | C | 168 | GAGCGCCCTGTCTGAACCGCTCATCCGCGCGTGGAAATG CTGCAAACTCCTCCCCTGCCGCCGAGGTTTCTCGGCCAAG CACTCCCCTTGCGCACGCGGAAAT |
| scaffold 65132:21260 | 169 | GGCTCATGCCACTGTTGCTGCCACTTAAACTA TCATCATCGCTAGAATCTTCAAGTTCGCTTGG TGGATAACCATGGTCATCTGAAGTATTCCATG AATA | A | T | 170 | CGACTAGTGAAATAACTGGTATCTAGTGCACTCTCCGA CGAGGAACAAATGCAGCCTGCACAAATAATGAGTCGA GTTAATGTATAGGAAGCGCAACCA |
| scaffold 94863:28441 | 171 | CTTCAAAACTAGTAATAATAATTAGTGGGTGG TGGCTATGCGTCAGGCACTAAGAGCAAGCCC ACAAACCAAGCTGTTGAAAGAAGCATGCCAGCC CGTA | C | T | 172 | AATGCCACAGACTTTGCTGATTTCTTCCAATCTGAA CGCCACTCTCCGATCTCGGGGCTCAGATTCGAGAGG GAGATAAGTGGTTTGCAACGGCGC |
| scaffold 94004:13590 | 173 | GCATGTATCCAGACCCAAAGCTGGCGAAAACA AGACCCTAAATCTGTAGTCTCTGGTTTCACAG ATCCTAGACTGTTAACAGCATCAGCAGCAGCA GCAG | T | C | 174 | ATTATCCCTATTTCGTAAGGAACAAGGACGCCACATAT ATGTTACAGGAGCGATCGGCTTAGAAAACTGGTGCACCA ATATGTGGAGCTGCAACATGGGG |
| scaffold 94004:13632 | 175 | TCTGTAGTCTCTGGTTTCACAGATCCTAGACT GTTAACAGCATCAGCAGCAGCAGTATTAT CCCTATTTCGTAAGGAACAAGGACGCCACATA TATG | T | A | 176 | TACAGGAGCGATCGGCTTAGAAACTGGTGCACCAATAT GGTGGAGCTGCAACATGGGGATTAGTCAGACATAGCCA ATTCCTTAATCCACCTCAATGAAA |
| scaffold 39420:9067 | 177 | TTTTTGATGTTAAGAATTGTACGTTGAGACAT GAGAACTAGCAGCCAGTGTTTCTCACCTGCAT CATAGTTTTTGAGAAAGTCAGGAGACAAATTA TGGT | T | C | 178 | TGCTTCTTGCTGCCAGTTTCTCAAAGAGGCTCATAATG TTATGATAAGCTTTTGCAAACATAGAGAAAAATAGGAT GAAACAGAAGTTGTATTAATAAT |
| scaffold 42291:6484 | 179 | TGAGTTTTGCAGCGGCAGCTCGGCCTGATGCA CCAGAGAACATAAGGTCCATTCTCATCAATCA GTGCACCTCAGTAGATGATCAAGACTGTCAAT TTCT | C | T | 180 | GACTGCAATTCAGGTGGCTGCCAGCCACCCGAGTCTGT TATCGAGCTTTTCATGGAGTCTGAATTCTGTTTGCAGC CACCAGGAGATAGCCCAACTAGAA |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 23828:34435 | 181 | GAACTTGATCAATCCCATAACTCAGTCCTCCA TTGTCATGGAGCCAGCGGCTCTTCTCCCTACC CTGCAATCAAAAGAGTCTTGGCTGCCATAAA ACCC | G | T | 182 | GACATGTTCTTCCGCTGAATGAGGCACCCATAACTCTT GCAAGTATAAGGATCCCAAATGATGCTGTCTCCGGCG GGATTGACCAGAGGCTGTCTGGAA |
| scaffold 15017:4539 | 183 | TGCCTAATTGTTGTTTATTTGTCATTGGTGG CAGCATGATGCTGCATGCCGTGTGATTGCAAG ACTAAAGAAGAAAGAGATGAAGCAAGATCAC TACT | C | T | 184 | GCTCAGGCTGAGAGACACATCCCGCATCAACACCCAT TACAGTAAATCGTCTGCAGTTAGCAATGGAAGAACAG GTCCTTTTTGTTTATATATGCTG |
| scaffold 16607:2589 | 185 | GGCCGTTCTTGGGACGACCTCTCCGTCCGAT TCGCCAAACTCAGAGCCTCCTTGTCTTCAGTCG CCTGCTGCTTCCATTTCCGGCACTGGTGGCGT TCGT | T | C | 186 | CCAATACAAAATTGGAGAGCCTTGGTGATGAAGATGAA GAGGAGGATGAAGATGATGAGGTTGAGAAGTTGATTAG GTGGGCCAAGGACGCGCTGCTCGCCT |
| scaffold 27758:4907 | 187 | TACATACATACATACACAAATAAAATAATTATA AATAGTAATACCTCCACTAGAGCAGCCTCTTT CCTGGGAAGTGACCCCAATTATGCGGGAGACA CACC | G | A | 188 | GCGTCTCTGGCACCTGCAACCATTGCAGCTTCGGTCCA CCCCAACTTAAGCTGCACCAACTCATCCCAAACGCTAC AATTAAAAATTCACCCCCAATTTT |
| scaffold 20809:7695 | 189 | TTTTAGGTGTTTTGAAACAGTCTCAGAATCAG CATACGAATTTGTCTTGCTGAACACTGATGC TGCTTGGGCAAGAATGTAGAGAAAAGATCCG TTTG | G | C | 190 | AGTAATGGAAAGTTGTTTCTCTATCGATGTCTTCGAGTT TGTTTCTGCTGCTAAGAATTACTGGTCTTCAGAAGTTC TCTCTGTGTTTTATGGTTCTAC |
| scaffold 36583:13571 | 191 | TATTCCCTTCTTGGGTGCAAATGACATTAG AATCTTTACCAATTGTGTTAGCATGCTGCCCT TTCTCTATGGGTTACGAATCGCTTCTGAGATA TCTT | T | C | 192 | TACCACCTGCTGTGTCAAATTCTTAAACCTGTCATTC CTCTTTCTATTGATGACTGTAGTCATTAAAAAAATTA TTAACTTAAACTAAAGTTAGTTG |
| scaffold 36500:1728 | 193 | TCACTCTCTTCCTAATGGGATTGACCATTAGT TGGAATGGTTCTGCTGCAAATGGTCCATGTT TGCTGAGGTTGTCCCAGCCACCACCGACCA TGAT | T | C | 194 | TATGCCTTTGATCGAGCTTTCGAGGGCTCCGTCTCTTC CTTCCAGCTCCCTTGGTTGGAATTCTGTCGGAGAAAA TGTTCGGGTATGATTCGAAAGGGG |

TABLE 6-continued

Upstream, Allele and Downstream sequences for SNPs from Table 4

| SNP Name | SEQ ID | Upstream Sequence | Minor | Major | SEQ ID | Downstream Sequence |
|---|---|---|---|---|---|---|
| scaffold 36500:1740 | 195 | TAATGGGATTGACCATTAGTTGGAATGGTTCTGCTGCAAATGTCCCATGTTTGCTGAGGTTGTCCCAGCCAAGCACCCGACCATGATCTATGCCTTTGA | C | T | 196 | CGAGCTTTCGAGGGCTCGGTCTCTTCCTTCGCAGCTCCCTTGGTTGGAATTCTGTCGGAGAAATGTTCGGGTATGATTCGAAAGGGGTGGATCCATTGT |
| scaffold 36500:1749 | 197 | TGACCATTAGTTGGAATGGTTCTGCTGCAAATGGTCCCATGTTTGCTGAGGTTGTCCCAGCCAAGCACCCGACCATGATCTATGCCTTTGATCGAGCTTT | T | C | 198 | GAGGGCTCGGTCTCTTCCTTCGCAGCTCCCTTGGTTGGAATTCTGTCGGAGAAATGTTCGGGTATGATTCGAAAGGGGTGGATCCATTGTTGGGGTCTA |
| scaffold 153198:2269 | 199 | CAGAGAAAGAAGAGAAAGGTACTAAAATTGGCACAGACTAACCGGGCCTCCATGGTGTTGAGTGGGCCCCCACCCACGAACTGTAACGGGGCCCATTCAT | A | T | 200 | GGGACACGTGTCAAGCATCACTCGGTTGAGAGTGGGGCCCATCACAGGGTGGACTCGAGGTGGGCCTTTTGCCTGTTTCATGCTGCGTCAGGTAAAACCA |

TABLE 7

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 13038:51303 | 201 | TCCAGTAGCCAAGGTCATCGGCGGTGCCCTAAACAAG CTCTCCAAGATTAAGGTTGTGAGGCTTTTAAGTTTGG ATTGCTCGTGTTGACGGTGATATC | C | A | 202 | CGAATGCATAAGGCTGCTGTAAAGAATGTTTACGAG AACAAGAGGTTCATTCCACTCGATCTCCATAGGAAG AAGATCAGGGAGATTTGCAGAAGGCTTA |
| scaffold 25092:11841 | 203 | TCTTATTCAACCAAATGCCATAACCGGCCATAGCTGC ATAAAAAATATCAGCTATAAACCTCTCGGGCTTTCTG CTATTCATCCAATGTATCCAGTCCTC | A | G | 204 | TGAACACTCGGCCAAAGCTTGCTGCCTAGCCCTTC CCAATGAGATGCATAACTGGCCAAGAGTAAGGACAA GAGAAAATAAATCAGAATGGCTCCAAA |
| scaffold 23837:26190 | 205 | ATGACCGCTGTTCCAATGCTGCCAACTTGGTGACTGA AACAAAGTTTACTTCATGTTACTAGTTGTTCCTCTGCC ATTGGGCAGCTCGCAAAAGGTCGGAA | C | T | 206 | AAGGAAGACAAAGAGAGCGAGCTACAATCTCTGGCA GCAGCAGCCTTGGAGAAGGACTACAAACGAAGAGCA CCTGCAACACTGTCCTTGATTACGACCG |
| scaffold 152474:1505 | 207 | TAGTAGTGGTAGTGCCACTCTCGGTGCTTTAGCCAAA ATCGCCCTCCAAGCAGCGGCTTCAAGTGCCAAAAACA CCCAAGCCCAGATCACTCAGCCTACTC | C | A | 208 | AAACCCTACCGATAAGAGTGTCATAGCGGCCTTGA AGGATTGCAGTGATAATTATGATAGCGCCAATGAGG AACTCGGTGACTCGCTCAAAGCTATTGA |
| scaffold 152474:1465 | 209 | TGTACAAAGATCTTTGTGAGAAGACACTGCCAGCAGA CCCTAGTAGTGTAGTGCCACTCTCGGTGGTTTAGCC AAAATCGCCCTCCAAGCAGCCGGCTTC | G | A | 210 | AGTGCCAAAAACACCCAAGCCCAGATCACTAGCCTA CTCAAAACCGCTACCGATAAGAGTGTCATAGCGGCC TTGAAGGATTGCAGTGATAATTATGATA |
| scaffold 13038:51162 | 211 | TCCAATTTCAGTGAGAGAGAGCTGCTGTATGGAAG CTAAAAAAAGCAGCAATGACAAGAATCAAGGTTGAC CAGCTGAGGCAGAGAACAAGACCTTT | C | T | 212 | TGAACAAGCTTAGGGATCTCAAGGCTGAGCTCCTTT TCCTTCCAGTAGCCAAGGTCATCGGCGGTGCCTAA ACAAGCTCTCCAAGATTAAGGTTGTGAG |
| scaffold 5841:136325 | 213 | ACTGCTGGAAATGGTAGTGTTCTTTTCACTATTTCTT AAGTTGCCTCCCAGAGAGGTAGTTTCATCAATGTGCA AGCTGCTGTCTTCATCCATGGTGGTC | A | T | 214 | TCCCTAAATCTAACAACAACCAACTTTTGCACAGTTT CTGCTGACAAGTAGCATCTTTTGACACATATTAT CATGCAATGCAGCGACCTCAATACTACA |
| scaffold 5876:22669 | 215 | CTGTAATAAGCTGCTCGCTGCTGCTGAAGCTGTTACTCT TGCAAAAGCAGCTGGGGTTGCAAGGATGCTGCT CTGCTAGTGAAAACTTCTGAAAAACA | A | T | 216 | CAAAGTACTTCTGTAGTTACTTTAGAAGCTAGTTAT TCGGATTTAAGGGTGTTCATAATATGAAAAACTACA CAAGCTGCTGTATTAGGAGATTCTGTGG |
| scaffold 764:75880 | 217 | TTCTTGGTTGGTGTATATTGCAGCACTTTCACCCTTG AAGATTAGGCTAGGGGCACTTTACAAGACAAAGTCA TATACCAGAACCAGAGTGAAAAAACT | C | A | 218 | AAGCAGCCCAATCTTGTACTTGTACTTTGATTTTGTTA AAAATGCTCTGAATTATTTAGCTTCTCCTCATGGTT GCTTATCCTATGTCTCCGTGGGATCAACT |
| scaffold 32076:9119 | 219 | CATATACAATGCTGACTGGGCACATGTGTAGGACACA AGAAGGTCCAAAACAGGTTTTGTGTTTCCTTGGGA GATCTTTAGTGTCCTGAAAAGTAAG | C | A | 220 | AACAACCGCAATACCGAGGTCCTCAGCTGAAGCTG ATTGTAGGGCTATGTGAAACACTAGTGAATTGGTAT GGCTGCTATCATTACTTAAAGGAACTGAA |
| scaffold 7992:917 | 221 | GAGGTAGACTTTGTATTTTGAAGCTTTTGGATATTAG AGCTTACAGGGTTTTAATGGCTTCCCAGGTGAATAAC GATGGCCTTGAGAAATTGTTAGCTGC | T | A | 222 | AGCAAGTCATTGAGGTTAGCTTAGAGAAATCAAAG TCCCTAGGGTTAGCTCTACAGAAGACAGGACCTAGA TTGGAAGAGATTAACCAACGATTACCTG |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 118405:2916 | 223 | ACACTTTCATTAAATATGTCGGTATGTACAGAAC GCAACATTCATGGCATAATTAACACGTCAGCCAAATA ACATTCAATCATAATCAATTGCAGCA | C | T | 224 | TGCATCTTTAGACACAAATTACACATTGAAGTTGATAC TTCTAGCTGAGCTAGGCTAGGCTGGCCGACTCGCAGCTAA TATTTAATCAATAAAAAGTACCTAAAA |
| scaffold 2418:77480 | 225 | AGGTGAGATATGAGAGAGGGTCGAATGTAAAATATAC AATGTGCAATTTATTGCTAAGAGAGAATAGTAAAAAG AGCACATGTATTTGCTGCTGAAACTC | G | T | 226 | GATTGAAGGAGGAGCGGACAAGTGTCGCTCATGTGA TGGCTGGAGAGGAGAGCTGCTGGAGAGAGGGGA CAGGCGGGTCCCACGCAGCTGGCGCTGG |
| scaffold 34829:1873 | 227 | GTTGATACTTGACTAATTTCATATGGTCGTGTGGAAA TGTAACAGGTGGATGTTGTGGATACAGTTGGTTGCGG GGATAGTTTTGTAGCTGCTATTGCAT | T | C | 228 | TGGTTTTATAAACAGTTTGCCGATGGCTAGTACGCT GTCAATTGCAAACGCAGTTGGTGCTCCAACTGCTAT GGGTTGTGGTGCTGTTAGGAATGTGGCA |
| scaffold 38125:4641 | 229 | TATAGGTGTGTTCGGCTATGGAGATAAGTGGATTCTT CTTGTGCTTAGTTGGGGCCAGCCAGAATAACCACAGA GCTCAAAGGATAGTGTCGATAGCAAC | G | T | 230 | AGATGGCACGTGCTTGTCACATGCGCATCAGCAGCT GGTGGGCCGGACCCATCCAAAGCCCATTTTCTAGAA GCCAATTGCAAGGATGATCAGCAGAGGT |
| scaffold 37469:74270 | 231 | TTCTTACTCCGATGCTGTGCAGATCACTGCTCAGT CAGCATTATCATTCAAGGAAGCCCCTACTGGATGGC ACCTGAGGTAAAATCTTATGAAGTT | G | A | 232 | TTTTGCTGTGCTTGCTTGATATTCTTCATTGTGTA TGATCTTGATTCTATTTCATCCTTCCTCCTCCCTTT CTCCCAGTGATAATAAAGAATTCAACTGGC |
| C32100775: 1618 | 233 | ATTTGAGATCCTTAGCCGATAGAGAATTTGTTGGTTAAG TCTCTGAATCTCCTCATCAGCTTGTTTTAGTTCCTTA TCCCAATTAAGAGAATCTTGCTCCCT | T | C | 234 | GCCATGACGCCTCCAATTCTTGTTCCTCTGCTTCC AAATGTGCAGCATGTGCAGACTCCAACGACTCCTTC GTTGCAATCAGCTCGATAGTGAGTTCCT |
| scaffold 5190:41424 | 235 | TTGGTTCCTTCTATTGGGTTTACTATACTTTCGGAACAT GAATAGGCGAGGGTGGATTGAGTATTCTGTGCGCC TTGATTTGGTCCCGTCGGGGAATTTGGG | C | G | 236 | ATGACACTGCTTCCAAAGCACAGAGAGTTCAAAGGTT TGGGGAGTTCCCATGGTTCCATGGCTGCCATCTCTG TCTATTGTGTTAATCTTTTCTTATTG |
| scaffold 5190:41454 | 237 | GGAACATGAATAGGCGAGGGTGGATTGAGTATTCTGT GGCTGCCTTGATTTGGTCCCGTGGGAATTTGGGATG ACACTGCTTCCAAAGCAGAGAGTTCC | G | A | 238 | AAGGTTTGGGAGTTCCCATGGTTCCATGGCTGCCA TCTCTGCTTATTGTGGTTAATCTTTTTCTTATTGGG TCTTTTGGGAATGGTGGCCTTCTTCAGGT |
| scaffold 49917:1105 | 239 | GTATTGGACCTCGATCTCCAACTTTCGACCGGCTTC TGGAGGTGAACGCCCGAGGAGTTGCGGCGTCGTGAA GCATGCGGGCCGCCGGCATGGTGGAGC | A | G | 240 | GCGCGTGAGGAGGAAGCGTTGTTTGCAGCGGCAGCGT GGCTGCCTCGTCGGTTGAGGACACGACGACAGATTA CTGCACATGTCGAAACACGCGGTTGGGG |
| scaffold 4775:75747 | 241 | GTCACCAAATAAATATGTTTTTAAATATTTCAGAGG AGGTTTGCAGGGAGTTGCTGCGCATCGATCTTTT CGACTCTGAGTATGTTTGTCCTTTCT | T | A | 242 | CTGCATATCATTTACATTTCATGTTTCTTTCTGC TGCTACTTGCCAAACTCCGATGATGTAAATGACT GTTTTGCAGGTATATTTACCATCTTACA |
| scaffold 26152:15432 | 243 | AAACTTTGGCTGCACCTCCTGCTGAAGAGAGTGCA TTGCGCTGTGCTGCTGTAGAAGCCAGTTTAGTTGGCAAG AGACTGCTGAGAACTCGTGTTACTTC | G | A | 244 | TGCATTGTTGCCGATCAGTTGGTGTTTCTTGCTG CAAAGCAATGCAAGTTGAAATACCTTCCTAACCGCC CCGAGATCCTTACATGTAGCTGTGATTT |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 5841:135056 | 245 | CACAAACGTTTTATCAGCTCTCCATCTTCGCTACAA GTTTCATTAGATATTTGACAGCCAGACATGGCATCTA ATATGCATGCATTGGATGCAGTAATC | G | A | 246 | GGGAGTGCTGAGAATCAATGTTTCTTAGAGCATCAG GCACCAACTCCATAGCTTCATCACTGGAGTAGCAG CGGAACTCCATTTTGATCAACAGGCAA |
| scaffold 5876:106401 | 247 | CCTTAGCATCTCCTGATTTTTATGATGTGAGTCTTGT TGACGGTTTCAACTTGCCCATAGTCGTCACCACTC CACGGGCAAGGAAATTGCAGCGTGGC | A | G | 248 | GGATGTGATGGCGACCTCCGACCAGTTGCCTAAC GAGCTGGCGGTCAAGAGCAATGGGAAAACGATTGCC TGCCGAGCGCGTGACGTTCGATA |
| scaffold 5113:138895 | 249 | CAAGAACTTGCCTTGCTGCTGCATCTGCTGAACTGCA GACAACATTCATTGCTCCAATCCTTTCTGAATAAAGA CCCAAATTTTTACTGTAAGACTGAGC | A | G | 250 | ATCAAAACTTCCATGCCACGTGCAGCAAACAGTCTC ACCGATGATGCATCAGCATCAAGGCTTCCACTAGCA AATCCCTTTAAAGAAAATAAAATATA |
| scaffold 5113:239777 | 251 | TATACACAGAGACTTCACTGCCAAACTTAATCTCTC TGTTTAAGCAGCACCACCAGTCCACCACCAAACACAT TTGAGCAAACACTACTAGTTCTCATC | G | A | 252 | TCATCATCATACAACCAGAGAAAAAAAAAACA GTGATGCATTTTACAGAGAAAGAAAAAAGCTGCAAT GATTTCTAAGCAGCCTTTTTTTAAACAA |
| scaffold 5841:135067 | 253 | TTATCAGCTCTCCATCTTCGCTACAAGTTTCATTAGA TATTTGACAGCCAGACATGGCATCTAATATGCATGCA TTGGATGCAGTAATCAGGGAGTGCTG | G | A | 254 | GAATCAATGTTTCTTAGAGCATCAGGCACCAACTCC ATAGCTTCATCACTGGAGTAGCAGCGGACACTCCA TTTTGATCAACAGGCAAAGAGAGATCAT |
| scaffold 25099:7321 | 255 | ATACTTCATATTCCATTTCTCTATCTCCACTCTGCCT CTGGCATGAAGTAGTCCTTCAGTGGTTTTTGCAGCA GAAAGATCTACGGCCTGAAAACTCGC | A | G | 256 | GTTAAATCTTCCACCTTCCGCTGCAAAAGAGGAACA TTTATAAATCAATGTACAATATCAGAACTGACTTATTGAG TGCATAAATCGATTAAATCCATTAACAA |
| scaffold 14172:40875 | 257 | GCTAATTGGCTCTTATTGCTCAGTCGTTGAAGTGGCAG CAACACCAAGGTATATATACAATCTTATTGTGCATTG ACAAGAGAACCATATTATCTTGCAAT | A | C | 258 | TCTTTAAAGTAACAATTTGTTCTCCATTCCAGGGT TACTTCCTCCAGGCACAATTCTTCTCCTCCTCCGTT ATCTCAACTGTTGGGTACAAGATCCTTC |
| scaffold 158332:502 | 259 | AAAGGGCATTCAATCCTTACGGTTCCAGCTGCTTACGA CTTCATCACCATGGAACTTACAGAGGAGGACTTAAC ACCTTCCGCCATTGTTGCAATAGCTTC | A | G | 260 | AAACCCCTTCACGTTTACGGAAGCCCAACTTACGAG TGTCAATGGCTCAGAATTCTTCTCCTCCTCCCGTT ATCTCAACTGTTGGGTACAAGATCCTTC |
| scaffold 16869:149709 | 261 | CTACAAAGGTTGCGTTTGGACCCGAGCTCCTTAGCCGT GGCTAGGCCAGCATTGTTGATGTGCTATGACT ACTTTTGCCACCATTGTTGATGAATTT | T | G | 262 | GTGGCTGGTTGCGTTTGCCTATTCCGCTTGCTGCTCCT GTTATTAGTGCCACCTTCCCATCAAGCCTGTTATTT TCAATGAGTGAAGAAATTGTCTGAGTAG |
| scaffold 114539:1119 | 263 | AATTGGCTAGCGAGGAGAGTTCATATGCCAAAGGTTAGC TTCAGCTGCTGCTGTTGAACTGAAGGCATTATCTGAA GAAGTTGCCAAACTGATGAACAATAA | C | T | 264 | GAGAGACTAGCAGCTGCTGATCTAGCCGCATCCAAGAAC TCCCCACTCCAGCCAAAGTGGCAGTATGGTCAAG AATGGGCGAAGAGAGCATGAACAAGC |
| scaffold 3842:272682 | 265 | TTCACCCAAGAAGAAAAAATGTGATTGTCACATATGT TTGCTGCATGTGCATGGACCATTGGGTTTAATCTTGC ATCATGCTGTTTCTATTATTATGATCT | T | G | 266 | TTATTGTTATGAAATCTATGGTTGTTCAGTCTAGTG CATTTCACCCACAAAAAAAATGTGATTGTCGTATATG CGTGCTGCATGCATGGGCCATTGGGTTT |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 60331:8510 | 267 | CACCAGCGCCGCTCATGTCATGAAAGTTTGAATAGC AGCAAAGCCATCATTGTTATGAGAGCAACAAGTGATC ATGGCATTGTGAGAAACAGTATCT | G | C | 268 | ATGCTCAATGGAGTTCAAAGAATATATCCCTTGCT AACTTAAGACTCCCAGCAGCAGAGAGTAGGCAGCAATC ATTGTCGTTCTCGAAACAATATCTGTT |
| scaffold 2360:22109 | 269 | TTCACGGAATTTAAATATTTTACGATTTTTTTGAT TTAAAATGAAATACCTTCAAATCCTCCGACTGGTGTA AATAGCTGCAATGGTTGGACAGAGAG | G | A | 270 | GGAGAGAGTTAGAGCAAAGACGATGGTATGGAAGAA GTGGCTAAGTGCTCTGCTGCAGTAGTACAAGTAGTA TATATATGGAAGGGTATAAATGGGAAATC |
| scaffold 72613:1728 | 271 | GCAATTTAAACAACCTCTCCTTCACTGAACTCACAGA AGACGATGACAAAGATCTCCATCTGCCTCATGA TACAGTCTCCCTCTATAGGCAGCAAG | G | A | 272 | TCGGCATAGTACACTGGCGGTACCAAGGAGACAGT TTGGTCAGCCAGCCATGGTAAAACACATGCTATAT ATGAGCTTCTGCAATTGGTCAGAAGTAA |
| C32052717: 309 | 273 | TGGTCATGACGTTGTACTCAACTGAATGTGCGCTGCA GTCTTTGGCCCCAGCAGGCATTTCCCAGGCCCCAAT GATATGTTAGAGGTGCCGAAGTCAGT | A | T | 274 | CGGTCAAACATGATGACACGGTCGTTGTTGAGAAGC TGCATGTGCATGGCCCGAAATGCCAATGCTTGGTGTC AAGAATTTCCACCGGCCACCGGCTGCAT |
| scaffold 71943:13435 | 275 | TTTCGCCCAAAAATTTGATGCTACCGAAACCGTGTCG TCCAACACAAAGTCCTTGACACGGCAGCAGAATCCT GGTTCGGCCCTTTCCTTGGCAGCAAG | C | T | 276 | TCTTGATTCGTCGGTCGGTGTAGTAATCAGAGCGC CTGAGCTTTGGCATTTGAGCCTCAATATCTGCACCG TGCTCGTACACAATAGCAGCCTCACCAG |
| scaffold 71943:13471 | 277 | GTCCAACAACAAAGTCCTTGACACGGCAGCAGAATCC TGGTTCGCGCCCTTTCCTTGGCAGCAAGTTCTTGGATT CGTGGCTCGGTGTAGTAATCAGAGCG | T | C | 278 | CTGAGCTTTGCATTTGAGCCTCAATATCTGCACCG TGCTCGTACACAATAGCAGCCTCACCAGTCTGTGC CCGCTAAGGGTCTTATAAGAATCCCCT |
| scaffold 128544:170 | 279 | CCTGTTGTTCCCGAACCTTGGAAGCCACTACATACAC TGCCGCCTCTCTTTCCAGGTCTTGAAATGAATGTTGA TGCAGCAATCAGTATTTCTACTCGAT | G | T | 280 | GTAAGGATGTTCATGGGCATGTGACTACTGCTTAC TCGAAGGCACATTCAAATCACATGAGAATGAAGTTAT GACACTTTTCATAGCCTTCTTTGGGCA |
| scaffold 98263:1069 | 281 | TAAGAGTGAGAATTTTATTATGAAGATTGAGGCGATT ACCAGTAGTACAGAACGTGTTCTGGAGTTTAGGG GCATTGGGGTTTTGGGTTTTTTGTGG | T | C | 282 | TGAGTTTGCTGCTGGTGCTGCTGTTGTTGTTGGAGCGT CGAAGAGAGGAGAGGTGGTTCGATACGGAGGCGG CGCTTCCTGCCACGGCCGCCTCAGCTGCAG |
| C32058675: 292 | 283 | TTTTTTGTATGATTAATTTATTATAATATACAGATAAT AACGAATGGAGATTCAAGACGCTGGACATAGAGTG TTGGCAGCTGGGGGAGGTGGGCCTGA | A | G | 284 | AATGGCTCTAGGACTGGGCCTAGAATATCAGCAGCT TGCTTTTTTATCCAAGCATTCCCAATATTGCGAAA CCTTACGGCCCAATTAAAGAGCTTCTCT |
| scaffold 823:11824 | 285 | ACCTGAAGATGCCTAATTAAAGGCATTCCATTCTCT TCCTTTTCAGCTGCCAATGCTCGTAAATGACTTTAAT TACATCCATGGCCCAACTCCAGCAG | C | T | 286 | GAGCTCTTCTTCTATTTCATCGATGTCAACAGTCCG CTGTTGAGAATATGCAGCCTTCTCAAACATGTCCAT AATTTTCTCAAACATCTTCAGATATC |
| scaffold 75287:5899 | 287 | GGTTGGGGCTACAAGTCTATGGTCAGGCACCAATG AGAAATCTACCTATGCTTGGTTCCATCACCAGTTGA TTGGTATGGCAAAATTATATCGTTCA | G | T | 288 | TAGCTTTATCCTTAACACTGCTTTTTCGTTTTCTAT GTTCATGGAGCTCCCTTGCCAGGTGCGTTGGCGAGG TGCGAAAACTGGCAGCTGGTGGTGGCCA |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 16869:149730 | 289 | CGAGCTCCTTAGCCGTGGCTAGGCCCGAGATTGTGTTG GATGTCTGCTATGACTACTTTGGCACCATTGTTGATG AATTTGTGGCTGTTGCTTTGCCTAT | C | T | 290 | CCGCTTGCTGCTCCTCTGTTATTAGTGCCACCTTCCA TCAAGCCTGTTATTTTCAATGAGTGAAGAAATTGTC TGAGTAGAAAGAAGGTAAAGAAAGCAAT |
| scaffold 3842:543149 | 291 | TTATTCATGTGAAGTAGCTCTATAAAACTGTCTCTA ACATGGTATTTAAAGTGTTTGCATTGGAAAAATGTTC TTACCAAATGCAGCTTGAGCCAGTTC | C | T | 292 | ACATATCGTTGTACCTCTTTCCTGGAACAGCTTCA TGTAGCTGAACTAAAACCCACAGAGTATAAAGCTGC CAACAGTAGGCTATGCTCAAGAGAAGTA |
| C32058613: 508 | 293 | TTGACATTACTAACAATTACTGAAGCCCCATTACAC TAATTTGGGCCAATAAGCTTGACTCCTCGCTTTCCA AACGTGTTATATTGTTGCTGCCATAA | T | C | 294 | AGAAGCAAGCACCTATTTTTGCTCTTCGAACTCTT CCTCTTCCTTATCCATTTTATAAGCTGCTAAATCAT GAACACTTAAGTCTTCTAGTTCAGCCAA |
| C32058613: 563 | 295 | CTTGACTCCTCGCTTTCCAAACGTGTTATATTGTTGC TGCCATAACAGAAGCAAGCACCTATTTTTGCTCTTC GAACTCTTCCTCTTCCTTATCCATTT | C | T | 296 | ATAAGCTGCTAAATCATGAACACTTAAGTCTTCTAG TTCAGCCAAATTTTGAGCACTTCTATACGTATTCTG TTGCTAGGACAGAAAAAGAAAAGGTGTT |
| scaffold 7146:70340 | 297 | CGGTGTGGGCTGTGGTTGGGTATGCACGTTGTCGTT TAAGAAATAGTGGGAACATACTTGGTGGGAGTAGTG GGCCTTGCCGGGTGTTTTGCCCAGA | C | T | 298 | TGGGCTTATTTCGACCGTGACTTCTCTGCTGGATC CACCCAGTTACCGCTGATGAAAGGGCCTCTCATGCT GCTTCTCACAGATCTGGACTACCAAGGC |
| scaffold 23125:41276 | 299 | TGCAATCCTGTGTGCACTAGAACCGCCGCCGCCATC AGCATCTGTCTCCTTCCCACTGAAAAGCTCCAGTTGC AAACTAGACAAAGCCCTTGCCGTAAG | G | A | 300 | CCGTGTGGCTTCTCGTTCTGTTCTCCAAGATTTGC AGCCTTACAGTTGGGAGCTCAGATTAGTAGATGGG GAACGTCAGTTGATAAACTTGTAGAGT |
| scaffold 2418:77508 | 301 | AAAATATACAATGCTGCAATTTATTGCTACTGAAGAAAT AGTAAAAGAGCACATGTATTTGCTGCTGAAACTCTG ATTGAAGGAGGAGGCGGACAAGTGTCG | A | C | 302 | TCATGATGGCTGGAGGAGGAGGAGCTGCTGGAGAG AGAGGGACAGGGCGGGTCCCACGCAGCTGGCGCTGG CAGGCTGGGCAGGAGGAGGACAGGCGCTT |
| scaffold 12000:86305 | 303 | CCAGCTCCTGCCGGATTCCAATCCGTACCGACCTCGCC TTGGCCGGAGCCTCTCCGTACCGAACCCTCCGCT GCCGGAAACCTTTCGTCATCCCGATGC | T | G | 304 | CCGGCCAGTCATCTTCAACGGCCAGCAGATTCTGATT TCGATGCGAAAGTGTTCCGTAAGAACTTGGTCCGAA GCAAGAACTACAATCCGAAAGGTTTTGG |
| scaffold 24181:60784 | 305 | GTTGCTTTATTTGAATTTTGTGAAGCTTCATGATCTGGC AATGAGTTAATACTACAGCTCTACTAATAAACGAC AAAAGTTTGTGTCGTTTTTTGTTTC | T | G | 306 | GGGGTCGTTCTGCACAATAAAAAGAACATTTTTA GGTATATACCAAGATAGGCTGCTCTGACATCATTT AGCAAGGGTCACCATCTTCTAGCAAAAC |
| scaffold 26621:72993 | 307 | ACAGTACCAGTACATCAGGAAAGAGCAAGAGCAAGAG CAAGAGCAACGACGCCTACTACCAATAACCCAAATAG GGCAGCAAGGATGATGATGACCA | G | C | 308 | ACAATCCTGCTCCCCAACACTCCCAGACACCCAA CACATCCAATACTACTACTACTACTACTACTAC TGCTGCCTTCTTCAGGGGTAGCACCATG |
| scaffold 6391:16360 | 309 | ACGCCACTGTGTTGACGTAATTTCTACATGTAGCAGC GTAATGACAGTATTCATTGCTGGAACGCTATTGCT GAAATGTTATTTCTTCATTTTGTGT | T | C | 310 | GCCGAGCTACTGTGTTGACGTTGACTTCTACATGTA GCATTGTAATGCCAGTATTCTATTGCTGCAATGTTA TTTCTTCATTTTATGTCGCCAATGCTA |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 88759:12655 | 311 | GAAACCTCTGTGCCTTGGAATTCTTGCTCTTAATTAGCCATATTCGATACACCTAGGCCCAAAAGAACCAAATGAGAAGTAGAAATGACTAAAGACTC | A | T | 312 | ATTGCACAAGGTGTGTAAGAACCAAAAGCACTCTCTACTATCTTTCCCAAACCCATAAGCTGCAGGCTTACAATACCAACTTAGTAGCTCAAACCTCA |
| scaffold 37469:74336 | 313 | TGGATGCGACCTGAGGTAAAAATCTTATGAAGTTATTTTTGCTGCTGTCTTGATAATTCTTTCATTGTGTATGATCTTGATTCTATTTCATCCTTCTTCC | C | T | 314 | GCCTTTCTCCCAGGTAATAAAGAATTCAACTGGCTGCAACCTTGCTGTGATATTTGGAGCCTTGGATGCACTGTTTTGGAAATGGCTACTACAAAACCA |
| scaffold 12000:86310 | 315 | TCTGCCGGATTCCAATCCGTACCGACCTCGCCTTGCGGAGCCTCTCCGTAACCGGAACCCTCCGCTGCCGGAAACCTTTCGTCATCCGATGCGCCGG | T | C | 316 | GAGTCATCTTCAACGGCAGCAGATTCTGATTCGATGCGAAAGTGTTCCGTAAGAACTTGGTCCGAAGCAAGAACTACAATCGGAAAGGTTTTGGCCATA |
| scaffold 6143:103796 | 317 | GCTTGACACAATCATAAATCCAATCAGAGGTAATTGTATGTATCCCCATTTACAAGCAGCCTCATACTTTGGTCCACTTGCAAACTTGCAAATGAGATG | G | A | 318 | GTGACCTTATTTGTCAATCTCTCTACTAATTTGGTTCCAAGAACAAAGCATAAATTTCTCAAAAGCAGCCGATCTTTCTTCTTCATATTGTGAAACACAAA |
| scaffold 33135:78155 | 319 | GGACTCCAATCACCAATGCTGACCCCAAAGCTGCATTCATTAACTCAAAGTAAGAGAAATCTAGTCCTCTTCCAATGCTTAATTTGGCCAACCCGAGCTCTGC | A | G | 320 | ATGCCATAATTGTTTTCGCTACAAAATGTGGCATTGCGAGCTAGCTGCTGGGAAATTAGAATTGGATCACAAACACAGCAAATTTATTTGAAATCCCTAC |
| C32058675:317 | 321 | TATACAGATAATAACGAATGGAGAATTCAAGAGCGTGGAGCATAGAGTTGTGGCAGCTGGGGAGGTGGGCCTGAGAATGGGCCTAGGACTGGGCCTAGA | G | A | 322 | TATCCAGCAGCTGCTTTTTTATCCAAGCATTCCCAATATTGCGAAACTTACGGCCCAATTAAAGAGCTTCTCTCTCACCACCACCACTCTACAA |
| scaffold 1976:5193 | 323 | TTTCCAACCATCCTTGGATGCTTCCCTTTCATAAGTGAATCCATCAGCAGCCACCTGAGGGTCATGCATATTTCCTGAAAGTAAACCAGAACATTAGG | G | A | 324 | TGTGAGCCAAGTTAAAGAACAAGTTTGAACCTTACACCCAAATTTCGGAAAGCTTGAGCTTGTTTTAGAGTTGGGGTTTGATTGAAAGACATGAGAAGCA |
| C32098343:2061 | 325 | AAAGCTTCAGACAGTTTAGAGGCAAGCTGTTCCAGAGGCCTCAAGCTACAGCTATCACTCTTTTGTACGTTTCACCACTTTCCTCGAAAAAGGCAGCC | T | G | 326 | CCGCCATACATCAACATTATTCTCACAACCATGCAGAGATCAAGGTATGCAAGATACTGAAGAAGAACCTCGGGCTGCTCTTCTTCTAGTGCTGCAAGG |
| scaffold 158089:295 | 327 | AAATTCTTAAACATGATAAAAGAAAAAAGGTTAGAGGAAAATCAATCATGAAAATCTTTAATAACTTCTGCAGCATTACTGCTATTTGTAGCAAAGTA | A | G | 328 | GGCAATTATTACCAGCTTGCAGTTTGTTAAGGGAACTCTTCTGAGCGGGCAAGGCTGGGCAAGAAGAGAACCCACTGCAGCCGCCATTTTGAATCGCAGG |
| scaffold 17267:6243 | 329 | TTGACCCTTTTAATGTGGCAGCCCTTCGTTGCGCGGCTGAGTTTCTCAAATGCAAATGATGCTGAAGAATACTGTCATGGAAACCTCTGAGACGCTTTGATCTCTA | T | C | 330 | ATGAACCAAGTTGTACTGCCAGAGTTGGGATGGACACACTAATAGTCCTCCAAAAGTGCCAAACTCTGCTTCCCTGGTCTGAGGAGCTTCTGATTGTGAGCC |
| scaffold 491:22100 | 331 | CCTAAGCTAAATTCTAGCTAATTGTAAGCCGAATAAAAAAAACCCTACAAACTGCTGCCCCTTAAGTTTAGATCGATGAGGCAGATGAATCATGAAC | A | G | 332 | AACAGTCCATAATCCTTTTGGTTTCGTCGCAGAATGCAAGCAGCCAAAAAGGAATAACTAGAAATGCTAATCAAATTTACATGGAATTCCTTCACCC |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 121522:9070 | 333 | CCAGTGAATGGGACTATTGCAGCGTACGGTGGACAT TATTATTATGTCCTCTTCCCCACCTTGGAAGCCGTCG ACTGTCTTCACCTTTACTTGGAAGCC | C | A | 334 | TCATTCCACTGTACTTGTTCCCAAGTTGGTCTTGA ATTGCAACCACTTGAGCAGCATATGGAGACACAATA CCAATACTGAGCTCACATTCGACTTAA |
| scaffold 24615:2202 | 335 | GGGCCAAAGCAAGCAGCAAGATGGTCAGGCCCTGATAAAGT GTGCAAGCAACCAGCAAAGAAACCAGTCCATGCACTA CTTAGCAGTTCAGTCCGAATCAGTGT | G | C | 336 | CCCCCAACTGCTGCAGCAGCAGGGCACCTGTC TTAGCTGCAGTTTGAAAAGTTGCAAAAGCTGCAGGT GCGAAAATTGGTTGAATTAAGATCATAA |
| scaffold C32052323: 699 | 337 | ATCATGTTCTTGAGAAGGTTGGTACTTTGCTTAGTG TTTGAGTTGCAAAAGTTGATGGGAATTTGGAAAGGAA GGGAGTGTGGGTCTTGCTCTTTTCTA | A | G | 338 | AGCGATTTTCATTTGCTGCTGTCATAATATAAT AAATAAGCATAAATAGGAGAATAATAAAAGGTTAG AAATGGGATTTTTGAGCTGCTTATGGTG |
| scaffold C32052323: 711 | 339 | GAGAAGGTTGGTACTTTGCTTAGTGTTTGAGTTGCAA AAGTTGATGGGAATTTGGAAAGGAAGGGAGTGTGGGT CTTGCTCTTTTCTAGAGCGATTTTCA | C | T | 340 | TTGCTGCTGTGTCATAATATAAATAAATAAGCATAA ATAGGAGAATAATAAAAGGTTAGAAATGGGATTTT TGAGCTGCTTATGGTGGTCTAGTAGTAA |
| scaffold 14925:8868 | 341 | AATGACTTCTGCACTTCAGCTCCTTTTGATCTAGGGT AGTGTGCAGCAATAGAGCCAGTTTCAAGGAAAATCG ATCCCTTGGATCCGAATAGGAAATT | G | T | 342 | TACTGTAATGACATTCAACTGTGTAAGACCTCT AATTGCAGCCTCGTATATCTAGAATAAGTTTTCAAG TTAGCCCACTAAAATAATTAGATGGAAA |
| scaffold 133681:2742 | 343 | GCTTCGTAGCAAGATGCAATTAGCATAAGCAGCCAGA ATAATTTTCTGTAGAGTATTGCTGCCTTCAGTAATG CAGTGAGGTTGTTTTCTGGTGGACTT | A | T | 344 | GTAGAGGTCTAAAGACAGACGAAAAGACATTGGTGA GTATTATAAACATAGCTAAAACGGGGTCGCTTGT TGTGTGGCTGCAAGGCCACATGGATCTC |
| scaffold 9639:84033 | 345 | TTCATCACCATCACCACCACCAAGTATTTCAACCA CGGCCGCCCCTCAGATTATTCAGCCGATGAATTGCT TTCGGTGGTGGCGGAGCAGCAGGTAC | G | C | 346 | GAATTCGAGCGCGAAGATCTTAATCTTACGGATCC ACCGCCGAGGCTGCTGCTGCAGCGGCGCACCG CCTCCTTTCGGGTCAAAGAAGCGGTTCA |
| scaffold 61482:2893 | 347 | CAGCAGTCAACCCAGCAGGACGACCAGCTCCTATGACAAT AATTTCTTTCAACGTTGTATGACACCGTGGATAA AGATTCCTCCTTGGCATCATCATTAAA | T | C | 348 | GCAGCTTGAATAGGGATGGACTCTTTTTCTACATCC AGAGTCACAATGGGACTTTACCACTTCCAATGTT TCACATGATATTTCTGTACTTCCAACAT |
| scaffold 30395:12115 | 349 | AGAGTCTCAACCCTGCCATTCTTCCGCGGGAGTATGCA CGGCTATGTTCGGCCAATCTGCTGCAGCAGTTGATTGT AATAAAGACCCCGACATGAAAATTTT | C | T | 350 | GGTAAGTTACCTAGGAAGAGGCAACAAAGTATAT GTCAACTACATGAAGACAGCAAGTATTGCATTTGT GCAAAAGGGTATGAAGTCAATAGTCCTA |
| scaffold C32064647: 1071 | 351 | GAGCTAATTCTGAAGAAAACCCTGTTGATTATAGTC GACAACAAGGAGGAGGTTAGTCTTGATTATGATTTGTT AAACCTGTAGTTTGCTTTCCTGCTGC | T | C | 352 | AATTATAGGCTGAAAGTGAATGAATCTATATTGCAGTG AATATGGTTGAATGGTTAAAAACTTTGGTTGGAAT CGGAAATCTGAGCAAGTAATTGATCCA |
| scaffold 2452:1249 | 353 | GTGAACAACCTGTGAAAGCAGTGAGGTGCTTGGCTTCT CTTGGCTGCTTGCATTTGAATGTAATACTCTTTAAAC TCAACCGGGCAATTCCTAACTAGTTC | C | T | 354 | GTCATGTCTTCTTCATCGCGCTGCAAATGAAGAGAA TTATTAGACAAACTCTAGTATTTGAACTTGGTTGA GAATTGTACTAAAACTATAACTATTCCT |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 11436:6161 | 355 | AAGCAGTCACACAACAAGAACCTCCACGAAAATCTTG TTTAAGAAAGTCTGAATCTGTTCAGGTAACCATGC TTAACTGCCTCCTCCAATGTGGTCATC | G | A | 356 | CCATCCTTGCTCACTAATTCAGCCAATACGTTCTTT TCCAAGTTATCAGCTGCAAATGCTGCAGCTTTTGAG CCTCCATGTCCATCAATACAACCAAAGA |
| scaffold 4156:16965 | 357 | CCTTCTCCTGCAACTGCAATCAATGAGTCTCCAAAAG AAACACCATCTAAACCATCGTAAAACCTCCAACACC ATCTGGTGCAGCCACTAAGTCACCTA | G | A | 358 | AGAAACACCATCAATCCAACTCTCAAACCCCAAAC ATCTTCTACTCCAAGTCCCAAATTTAAAACACCATC TCGTGCAGCCACTGAATCTCCAAAGTA |
| scaffold 43435:8325 | 359 | CCTTCTGCCATCCCATTGTCAAGTCTGGCTGAGGCAG GAAATCTTATTGGATGGTGGAGACTGATCGCTGGTAGC ATTATTGCTGTCTTCTTGTGTAACTA | T | C | 360 | TGCTGTGAATCATTGTTGTTCTTGATGTAACTG TGAAGATGAATGCTTATTCCTACGGCGTCCAGCACC CACAGGTACACATTTCTAATTGTTCCCCG |
| scaffold 11297:60144 | 361 | ATTTGCAGGGAAATGAGCCGCTGGACTGCAACTTCT GCTGCTTCTGGAATACCCTGAAGAGAAAACATCAATA GTTAAAACAAGATAAAACAGGTGTCA | T | A | 362 | CAGATTCAGTGAATTAAACATACAGAGTACAAATA GTCGACTGCGCGTTCGGATTGTTATATGCTGCTCG AAGTGCACGAGTAACAGTTTCTCTGTCC |
| scaffold 51841:4904 | 363 | GCAGAGTGTCCAACTGTTCGTGCCGTAACGATAGATGG CAGCAACTCAAGCATGGTCAGTTTTGTTGGTTGAGCAG CCCACTTCATCTACCACTTCTTCAA | A | C | 364 | ACTCTCGTATCTCTTCCTAACATGAGTAAGGAACAA TGGCAAACCATTGCTGCCATGTTTGATAACGTTCAA TATTCTAGCAATGCTTTGCACAATGAGT |
| scaffold 38015:40961 | 365 | TTGAAGTGTGCTCGATAGAAGTAGATGGGCCCGAGC TTCGTTGATTCTTTCAGTGGGAATTTCAACAAGGTAT GTGTATGCAACTTACAAGAAAAACCC | A | G | 366 | GTGACCACGAATGAAGCTGAAGCTTGGGAAGCAGCC AAGAAAGCTTCAGGAGGTTTCATTTCCTTGCCATT CAAGAAGACTTGGATTCAGATGACTGTG |
| scaffold 16206:63417 | 367 | CATATATTATTATTATTATTATTATTATTATTCTATTT AACTGCTGCCCTTATTATTTCTCCATTTCGATAGCC CGAAAAGCGAAAAGACTTGTTGCCC | A | G | 368 | GCTTGTTGATGATCTTCCTCCTCCTCCTCCTCCTC CTCCTCGCTTCGTTGGTAATGGCGGTTGCAGAGA CATCTTTGCTCTGTTTTTGATGCTCCAT |
| scaffold 13781:319 | 369 | CCTTCCACCTCTACGCTCCTAAGTCTCCTTCTACTCG CTTCCCCAACCCTTCCACCGCTTCACGCCGCTCCACT GCAACTCCACTATCTGCAATTACTAC | T | C | 370 | TCCTCCGCCACAACCGCCGAGGCTCCGCAGCCTAAA TCCTCCTCTTCTTCTTACTTCCAGCAAGCCATTCAACGT CTCCAGGTTGTTCTCCAATGTCTAATTG |
| scaffold 27023:20610 | 371 | TCAGAGACTAAGAAACATGCCACTACTATAAAATACGCC ATCTTGTAATACTAAGAAATCTCACCTCACCGCAGC AGGCACACATCTTCTTCCAGGAAGTTAT | T | C | 372 | GAAATCCAGTCATATTTAAAGATTAACTCAAACTG TTGCTGCAAAATCTTCAAGTGTAGCAGAAATGTTCTC CTGCAGGTCCATAAACTGTTCAGGGAAT |
| scaffold 4618:83522 | 373 | TATATTTATATAAGAAAAAGATGAGAAGAAGAGGAA GATTTAGAAGGCAGCAAGGACCATATCCTCCTCCA TTAAGGCAACTAAACCCAACTAACTA | T | C | 374 | TCTCTATACATGTGAACCGTAGCCATTAGCCCATT TCCATTAGCACCATAAGGACCTTGTCTCTGTTTT CTTCTTCTTCAGTACGTAAAACCATGTA |
| scaffold 111383:2928 | 375 | GCAGCCTAGCAGCACTGCTTGCCTCCACGGCCACGGCC ACCAGATGGTGATTTTGAACCGAACTTCGTATATCTG GAAGAACTCTTCCTAGTTAATCTTAC | G | A | 376 | GGAAGAATTTGCAGCCTTGGATTCTGCTCCGTGCCT GAGTTTTCAGCTGCCAACTGATAGCTTTTGACCAGC TCAAGCTGTCGCGCAATTATTTCCGAGC |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 35:25795 293 | 377 | GGTCATTCATTAATGTATGGTTAGTTATTGGCTGCTG GCACTTGTCTGTTATGCATGAAATACTTATTGTTATA TGGTGAGTTTTCAAAAACATTTGCA | C | T | 378 | GATTTTTATTCAAGAACTGAATTCTTTATGCAGGC TGCTTACAGCTACAGTTGCTGGCCTTTCCCAGCCA TTATTTACATTGGAATTATTCTTTCGAC |
| scaffold 122455:2010 | 379 | TGATATAGTACAGTGCGTCCATGGCGTCATCGTAGGC TGCAGGCAGACCGGTGCTCCGGAGCCAGACGATACTCC ACAGAACTACAATGGCAAAGATTTC | C | G | 380 | GCGGCTAAGTTGAATGTGAAATTATGAGTCACAGTT GAGGCTGCACTGAATAGGATGGAATCCACCGCCATGG AAGTAGACTATAAGAGGCAATCGTAGCT |
| scaffold 13362:101120 | 381 | TAAATTGGTCGTTTATTATTAATGTTATAAAGAACGCC CTAGCTTTAGCTAGAGCAGCTAGAGCCGTGAACCCGGA CTAGTTTTTTTTTACTTCTTGCTCGT | A | C | 382 | TCTTCTATCTTCTAGGGTTTGGTAGTTCCCTTGGAC GAAATCGTGGCTGCTTTACTGTTTTTTGGGTTTCAT GGAAGATTTTTATGAGAATCGAAGCAAT |
| scaffold 38557:23764 | 383 | CCAGAGACCATATCTATGCGTAATACATGTAAAGGCT ATTTGAAGCAGCACACAGGCAAGTGAGTTTTCCGTTGGA TGCCAAGCAAGATGGAGCAACTTTGT | A | T | 384 | GTGAAATCGAAACCATTTCCGTTTGCATCAGTTCCA GAGGTATCCGCACCTTTGTGGATAAACAAGTCAGTT AAGAGACAAAATGGGATGAAAATTAAAA |
| scaffold 38557:23794 | 385 | AAAGGCTATTTGAAGCAGCACAGGCAAGTGAGTTTTC GGTTGGATGCCAAGCAAGATGGAGCAACTTTGTTGTG AAATCGAAACCATTTCCGTTTGCATC | G | A | 386 | GTTCCAGAGGTATCCGCACCTTTGTGGATAAACAAG TCAGTTAAGAGACAAAATGGGATGAAAATTAAAAGT TAGCTAAAAGTGGCAAGACATACCTC |
| scaffold 50091:2544 | 387 | GAAGGCGAATGACTTGGCGTTGGAGGACTGAGATAGC GCCTACGCAGCCGTAGACAGGATCTTTCATCCTGGCC TCGGCTTCGTGAGGCCAGAGAATTAAC | G | A | 388 | GCGTCCTCTCTTGGTGAGGGAGGACCTCGTTCAGG AGCTTGCTCACATTGCTCGCCCCAATATTTTGTG ACGTTTGCGAATTCTGTGCTCTTCAG |
| scaffold 16614:72706 | 389 | GTGATCTTCCAACATCTGTTGATTGGAGGAGAAAGG AGCAGTCACTGGAGTCAAAACCAAGCAACTGTGT AGCTGTTGGGCATTCTCAGCTGTAGC | A | T | 390 | GCAGTTGAAGGTGTCAACCAAATCGAAACAAAGGAG CTGGTATCTTTGTCTGAACAAGAATTGGTTGATTGC AGCTCGAAAAACCATGGTTGTGAAGGGG |
| scaffold 4877:4542 | 391 | AGCCATCAAAGAATGCGAAATCAACAGGGAAATTGGG ATCGTTGGAGGCTGATAAAAGGATAGATGTTTACA GTAAAGGAACCTCCATTGTCGCTTAA | A | G | 392 | AACTTAACGATGGCCACCATGAGATCTTTATGTCT GTTCTGAAGTACCGTGGAAGGTTTCTCACTCGAG CTGCCATATACATCAGCGTTTAAAGGGA |

TABLE 7-continued

Upstream, Allele and Downstream sequences for SNPs from Table 5

| SNP Name | SEQ ID | Upstream Sequence | Minor | Major | SEQ ID | Downstream Sequence |
|---|---|---|---|---|---|---|
| scaffold 65894:5390 | 393 | TAGCAAAGATCGAAGCCTCACATCAACACTCACAGAT CGAAGCTGCCTCACATCAAAACTCACAGATCAAAACT GCACAACACTCGCAGATCGAAGC | A | T | 394 | GCACAACACTCGCAGATCGAAGATCGAAGAAAGGATGCCCACG TCTCACAATTTCGGTTCCAACTTTGCCAGCTTTTCCT CCCAGCTTCACCTCATTGCTGACAAGTT |
| scaffold 90107:10791 | 395 | CATCCGAAGTAGGATCATGTGCGGTTGCGCGATG GGCCCCACTTCACTGTCCTTTTCTCACAACACTCAGG ACCCACATAACACATACACATAACCCCT | T | C | 396 | CTCCCTCTTCTTTATACTTCTACACAGCAGCAACT ACTTAACTTAGCCTCATCAAAATTCAGCCAGGAAGG ACCAGATGAGATGACCTTGCTTCTTCCT |
| scaffold 68873:1704 | 397 | CAATGAAGATTCAAGACCAACATGTCAATGCCCAAGA AAGTACTCTTTTATTGATCCCAATGACGAATATGGAA GCTGCAAACCCGATTTCATACAAGGC | A | T | 398 | GCGCTGAAGACGAGCTTACTCCCGACATAGAAGATC TCTATGATGTTGAGGAGCTGCGCAATGTAGATTGGC CCTTATCAGATTATGTTGCACTGAAGCC |
| scaffold 3842:188176 | 399 | AGGTTGAGACTGCAAGATTTACAATGTTGATGATCT GAAAGAGGTTGAGCTGCTAATAAAGAAGAGATCGTCTC CGCAAAGCAATGGAGGCTCAGGCAAT | C | T | 400 | ATTGCTGATGAATCAAAACAATTGAAGCATGGAGG GACTCACTGGAGACTGTTCCGACCATCAAGAAACTG AGAGCTTATGCTGAAAGAATAAGGGCTG |

TABLE 8

| SNP Name | SEQ ID | SEQ ID | Minor Allele | Major Allele | FST | Minor Allele Frequency (Indica) | Minor Allele Frequency (Sativa) |
|---|---|---|---|---|---|---|---|
| scaffold6803:13242 | 401 | 402 | A | G | 0.733989 | 0 | 0.7745 |
| scaffold543:54226 | 403 | 404 | A | G | 0.722743 | 0 | 0.7647 |
| scaffold281:231978 | 405 | 406 | A | T | 0.720457 | 0.9722 | 0.2049 |
| scaffold729:175391 | 407 | 408 | G | A | 0.708923 | 0.01389 | 0.76 |
| scaffold281:232029 | 409 | 410 | G | A | 0.70327 | 0.8333 | 0.1048 |
| scaffold2409:27009 | 411 | 412 | A | T | 0.6646 | 0.8243 | 0.1228 |
| scaffold25:303031 | 413 | 414 | A | T | 0.650114 | 0.9306 | 0.2241 |
| scaffold63:301758 | 415 | 416 | A | G | 0.631811 | 0.01515 | 0.7037 |
| scaffold92:214563 | 417 | 418 | A | G | 0.628155 | 0.8714 | 0.1875 |
| scaffold3286:29761 | 419 | 420 | C | T | 0.6277 | 0.04167 | 0.7188 |
| scaffold823:18400 | 421 | 422 | A | G | 0.61526 | 0.02703 | 0.6923 |
| scaffold1697:24776 | 423 | 424 | C | T | 0.592909 | 0.8333 | 0.1786 |
| scaffold414:37377 | 425 | 426 | A | G | 0.592212 | 0.9028 | 0.2414 |
| scaffold5405:41764 | 427 | 428 | C | T | 0.591134 | 0.8611 | 0.2054 |
| scaffold6803:13272 | 429 | 430 | A | T | 0.591045 | 0.7414 | 0.1132 |
| scaffold2317:118844 | 431 | 432 | T | C | 0.587962 | 0.8514 | 0.1983 |
| scaffold370:274852 | 433 | 434 | A | G | 0.586146 | 0 | 0.6364 |
| scaffold1014:55374 | 435 | 436 | C | T | 0.585084 | 0.7581 | 0.1273 |
| scaffold3831:62396 | 437 | 438 | A | T | 0.583082 | 0 | 0.6275 |
| scaffold2449:58347 | 439 | 440 | A | T | 0.581874 | 0.6087 | 0.05833 |
| scaffold1006:18102 | 441 | 442 | C | T | 0.581751 | 0.03704 | 0.7 |
| scaffold143:176913 | 443 | 444 | G | A | 0.581249 | 0.08333 | 0.7315 |
| scaffold2317:118609 | 445 | 446 | G | C | 0.580874 | 0.8514 | 0.2034 |
| scaffold3:20935 | 447 | 448 | T | A | 0.576848 | 0.6212 | 0.05556 |
| scaffold543:54256 | 449 | 450 | A | T | 0.576198 | 0.7308 | 0.1182 |
| scaffold360:162466 | 451 | 452 | T | C | 0.575327 | 0.5882 | 0.03448 |
| scaffold423:66668 | 453 | 454 | A | T | 0.573557 | 0.01667 | 0.6604 |
| scaffold1317:10314 | 455 | 456 | G | A | 0.572596 | 0.8676 | 0.2255 |
| scaffold1517:10238 | 457 | 458 | C | G | 0.571584 | 0.01515 | 0.6471 |
| scaffold1880:146873 | 459 | 460 | C | A | 0.571491 | 0.7571 | 0.1339 |
| scaffold1297:57086 | 461 | 462 | A | G | 0.571186 | 0.7833 | 0.1552 |
| scaffold682:73395 | 463 | 464 | C | T | 0.570734 | 0.7344 | 0.123 |
| scaffold92:214750 | 465 | 466 | A | T | 0.569779 | 0.08333 | 0.7212 |
| scaffold143:176964 | 467 | 468 | T | A | 0.567528 | 0.7778 | 0.1509 |
| scaffold942:90233 | 469 | 470 | T | A | 0.566759 | 0 | 0.6293 |
| scaffold942:89745 | 471 | 472 | G | A | 0.566759 | 0 | 0.6293 |
| scaffold24:306989 | 473 | 474 | T | A | 0.565856 | 0.8143 | 0.1827 |
| scaffold1281:68808 | 475 | 476 | C | G | 0.564701 | 0.803 | 0.1735 |
| scaffold1880:146829 | 477 | 478 | A | G | 0.56444 | 0.7273 | 0.1182 |
| scaffold3:20953 | 479 | 480 | A | G | 0.561743 | 0.5938 | 0.04918 |
| scaffold580:4170 | 481 | 482 | C | T | 0.559158 | 0.7429 | 0.13 |
| scaffold604:135874 | 483 | 484 | T | C | 0.559151 | 0.8571 | 0.2241 |
| scaffold1692:85945 | 485 | 486 | C | G | 0.55769 | 0.06667 | 0.7037 |
| scaffold1041:93642 | 487 | 488 | A | G | 0.555826 | 0.1111 | 0.7407 |
| scaffold1926:69537 | 489 | 490 | C | G | 0.554742 | 0.9348 | 0.2845 |
| scaffold4210:100547 | 491 | 492 | G | A | 0.554584 | 0.9 | 0.2627 |
| scaffold759:86606 | 493 | 494 | A | C | 0.553393 | 0.7069 | 0.1132 |
| scaffold25:425571 | 495 | 496 | C | T | 0.553335 | 0.8571 | 0.2308 |
| scaffold692:20843 | 497 | 498 | G | A | 0.552253 | 0.8281 | 0.2018 |
| scaffold2515:21370 | 499 | 500 | T | C | 0.551959 | 0.8065 | 0.1842 |
| scaffold48:65442 | 501 | 502 | C | G | 0.551514 | 0.8784 | 0.25 |
| scaffold48:65391 | 503 | 504 | T | C | 0.551514 | 0.8784 | 0.25 |
| scaffold3177:95787 | 505 | 506 | C | T | 0.550219 | 0.7727 | 0.161 |
| scaffold3681:699 | 507 | 508 | T | C | 0.550046 | 0.01389 | 0.6311 |
| scaffold3570:26136 | 509 | 510 | C | T | 0.548187 | 0.7241 | 0.1311 |
| scaffold388:236449 | 511 | 512 | C | A | 0.546671 | 0.8194 | 0.2 |
| scaffold763:27574 | 513 | 514 | C | A | 0.546635 | 0.05556 | 0.6698 |
| scaffold794:150222 | 515 | 516 | A | G | 0.54559 | 0.06452 | 0.6909 |
| scaffold152:25430 | 517 | 518 | G | T | 0.545375 | 0.8243 | 0.2059 |
| scaffold108:362803 | 519 | 520 | G | A | 0.545191 | 0.7222 | 0.1271 |
| scaffold388:350925 | 521 | 522 | A | C | 0.544283 | 0.04054 | 0.6518 |
| scaffold2218:32474 | 523 | 524 | T | C | 0.542777 | 0.7188 | 0.1271 |
| scaffold604:135639 | 525 | 526 | G | C | 0.542612 | 0.8472 | 0.2281 |
| scaffold2741:33031 | 527 | 528 | G | A | 0.542595 | 0.8194 | 0.2034 |
| scaffold4991:44264 | 529 | 530 | A | C | 0.542051 | 0.01351 | 0.614 |
| scaffold2483:94844 | 531 | 532 | G | A | 0.541013 | 0.8125 | 0.1961 |
| scaffold3871:24039 | 533 | 534 | T | G | 0.540111 | 0.07143 | 0.6897 |
| scaffold616:154319 | 535 | 536 | T | C | 0.540002 | 0.06061 | 0.681 |
| scaffold1005:75114 | 537 | 538 | T | A | 0.539944 | 0.01562 | 0.6293 |
| scaffold4991:44417 | 539 | 540 | T | C | 0.538537 | 0.01351 | 0.6121 |
| scaffold38:121620 | 541 | 542 | G | A | 0.537429 | 0.8611 | 0.2455 |
| scaffold1005:75091 | 543 | 544 | A | G | 0.536369 | 0.01562 | 0.6271 |
| scaffold298:209613 | 545 | 546 | A | G | 0.534826 | 0.07143 | 0.6864 |
| scaffold152:25429 | 547 | 548 | T | C | 0.534254 | 0.8243 | 0.2143 |
| scaffold1003:70848 | 549 | 550 | T | C | 0.534107 | 0.02778 | 0.6333 |
| scaffold839:64955 | 551 | 552 | A | G | 0.533035 | 0.7419 | 0.15 |

TABLE 8-continued

| SNP Name | SEQ ID | SEQ ID | Minor Allele | Major Allele | FST | Minor Allele Frequency (*Indica*) | Minor Allele Frequency (*Sativa*) |
|---|---|---|---|---|---|---|---|
| scaffold4070:22473 | 553 | 554 | C | G | 0.532019 | 0.06944 | 0.6731 |
| scaffold1419:187408 | 555 | 556 | T | G | 0.53116 | 0.8636 | 0.25 |
| scaffold3871:24091 | 557 | 558 | G | A | 0.531082 | 0.07353 | 0.6864 |
| scaffold3871:23604 | 559 | 560 | C | A | 0.531082 | 0.07353 | 0.6864 |
| scaffold3871:23603 | 561 | 562 | G | A | 0.531082 | 0.07353 | 0.6864 |
| scaffold3:388526 | 563 | 564 | C | T | 0.530397 | 0.5625 | 0.04839 |
| scaffold4:729494 | 565 | 566 | A | G | 0.530117 | 0.5735 | 0.05 |
| scaffold2283:29120 | 567 | 568 | C | G | 0.528671 | 0.7286 | 0.1404 |
| scaffold4350:64549 | 569 | 570 | T | C | 0.528523 | 0 | 0.5784 |
| scaffold2283:29096 | 571 | 572 | T | A | 0.527957 | 0.8235 | 0.2155 |
| scaffold3469:17543 | 573 | 574 | A | C | 0.526758 | 0.6774 | 0.1091 |
| scaffold1022:170497 | 575 | 576 | A | T | 0.526672 | 0.6111 | 0.07143 |
| scaffold964:106240 | 577 | 578 | C | T | 0.526638 | 0.8824 | 0.2705 |
| scaffold1419:187788 | 579 | 580 | T | A | 0.525371 | 0.8429 | 0.2368 |
| scaffold3386:35408 | 581 | 582 | T | A | 0.524758 | 0.4848 | 0.01613 |
| scaffold575:241067 | 583 | 584 | G | C | 0.524744 | 0 | 0.5877 |
| scaffold1863:93953 | 585 | 586 | C | G | 0.524401 | 0.8571 | 0.25 |
| scaffold575:459449 | 587 | 588 | G | C | 0.524202 | 0.8333 | 0.2288 |
| scaffold773:155167 | 589 | 590 | T | C | 0.523913 | 0.4483 | 0.008197 |
| scaffold773:155164 | 591 | 592 | G | A | 0.523913 | 0.4483 | 0.008197 |
| scaffold107:154377 | 593 | 594 | C | T | 0.522808 | 0.5862 | 0.06557 |
| scaffold371:34271 | 595 | 596 | C | T | 0.522699 | 0.02857 | 0.625 |
| scaffold78:341641 | 597 | 598 | A | G | 0.522194 | 0.7571 | 0.1667 |
| scaffold156:85625 | 599 | 600 | T | A | 0.521494 | 0.01429 | 0.5918 |

TABLE 9

| SNP Name | SEQ ID | Upstream Sequence | Minor | Major | SEQ ID | Downstream Sequence |
|---|---|---|---|---|---|---|
| scaffold 6803:13242 | 401 | AAGGAAGAAGTTGGCAGCAAGCTCACCGTG GTATCCACTGAGGAGATCATCCTCGAGCGA CCTAGGGCTCTCCGTACTTTATTATCATTC CACAATGATT | A | G | 402 | TTCAACTGATTCTATTCAATTCATAAATTTTGTT TTTGAAAGTTGGATTATAATTATTATAGGTAGCAA GGGGGAAGAAGCTAAGAATTCCGGGGAT |
| scaffold 543:54226 | 403 | AAGGAAGAAGTTGGCAGCAAGCTCACCGTG GTATCCACTGAGGAGATCATCCTCGAGCGA CCTAGGGCTCTCCGTACTTTATTATCATTC CACAATGATT | A | G | 404 | TTCAACTGATTCTATTCAATTCATAAATTTTGTT TTTGAAAGTTGGATTATAATTATTATAGGTAGCAA GGGGGAAGAAGCTAAGAATTCCGGGGAT |
| scaffold 281:231978 | 405 | TCATGTTACTGCTGATTATCGTCACCGATA ATTGCTTCTAACCTTTCTACATTGTGGTTT TTTTGACCTGGCTGCGAAGTTGAAAACA GAGTAAGAAT | A | T | 406 | CTGAGTGATTTAAGAGAACTTGCTTCAGCAGAGAGG CCTGGATACTTCACGCTCATTTACACAAATATTCTC GAACATCAACCTGACTGCCCGGTAACTT |
| scaffold 729:175391 | 407 | CCAGCAAAAGTGGCTCGTGCTGATGAGAGT CGGGATTGCTTTTCCTGAAACCAGAGATAA CTCTCACCCGGGCCAAAGAGGGGTGTTCTG AAACATGCAG | G | A | 408 | TCAGATACCACCAGTACCATCCACAATAACCCTGTG CAGACAAGTTCTCAAGCTAGTAGGAATGAATGTCCT CCGCAAATTGAAACCACTGTTCGGATCT |
| scaffold 281:232029 | 409 | TTTGTGGTTTTTTGACCTGGCTGCAGAAAG TTGAAAACAGAGTAAGAATACTGAGTGATT TAAGAGAACTTGCTTCAGCAGAGAGGCCTG GATACTTCAC | G | A | 410 | CTCATTTACCACAAATATTCTCGAACATCAACCTGAC TGCCCGTAACTTATCTGATACTACAGAAATTGCAT TTTGTTCTAAGCATTGCTTCGGTTTTT |
| scaffold 2409:27009 | 411 | CGATGTGTGGGTTTTCAGATCTCTTTTAAG GCCTAAGAAATTTAATAAAGGAATTGAC TATATAGGCAGGCAGCAAGAAGATGGTGG CTTCACTTTC | A | T | 412 | TAAGATTAAAAACATAAACAATATGATAACACTCA TGCAGATTACAAGGAAAATGCACATGGCCACTGCAG GTAACATGTTTGACTTTTTGTTAATTA |
| scaffold 25:303031 | 413 | ATGAAGCAGGCCCGAGAAAAAGACGTTTTC CTGTTTTAAACAATCACTAAAGTTAGGAGT TAGGAGAACTGAAAAACAAGTATGAGATGT AATCAAATTA | A | T | 414 | GAAGAGTTGCGAAGAGAACTGCTTTTTTGCACCTTA ATAATTTAAACACTCAGCATTATTCTTATTCGCAGA GAAAGAGAGGCCTCTTCGGATGA |
| scaffold 63:301758 | 415 | TGCGACCCATAGCCTGTGAATCAGAAGATA TAATGCTCGATTGCCCCATATCATGCAAAA TATCTTCTGCAGCAATTGTTTCTGCCCTTA TTCTTGATTC | A | G | 416 | GCAAAAGCTACATCTTCCGGATGTTCTTGTCAAGG TGATGCAGACCATCTGTATCGTAGCAAGACGAAAGT GAGAATATTGAACAGCCATAGTGCACCT |

TABLE 9-continued

| SNP Name | SEQ ID | Upstream Sequence | Minor | Major | SEQ ID | Downstream Sequence |
|---|---|---|---|---|---|---|
| scaffold 92:214563 | 417 | ATTGTTGGTGCATATGAGGAAGGCCACCTG CAGGTCCATAATATCCTTGCCAGTACATTG GCATAGCAAGCCCCACCATTTGCACTCG GTGCAGGAGG | A | G | 418 | GAAGTCCCCATGACCCTAAATTCCCCCAGGTTGA TACAAGGCAATGAACCTTGAAAAGTGGACCCAGGA AGTCCCAGTTGTGCTGTATGGGAACCAA |
| scaffold 3286:29761 | 419 | GCCACAACTCCCACCATCTTCCTCAGCCAC CCTGCAGCTTCATTCTTCTAGAAGCTGAG GAAAAACATAAAAGACACAATTAGGAAACT AAATTAAATA | C | T | 420 | ATATGTGAAAAAAAAGAACAGAAAATTTTCAAAAT TGGAAGATTACAAGTACTGGCCATAAACACCAAACA CCAAAATTCTCAAGAGTCAGATCCTAAT |
| scaffold 823:18400 | 421 | TAGAATGGTTTTGCTATTTGTATATGAATC ATGTTCACTTGAGTAGAAGTCTATACTCAG CAAAGAATCTGAAGCAATCACTTATCTGC TCCCAGTTTT | A | G | 422 | TACGCTGATTCATGCAAACAAATCTTCTCAAGCTTC GTAGGCCAATCTTCTCCGAGAAGCAAAGGGTTCATT TCCATTACAACCCGCGAAATCTATCATGG |
| scaffold 1697:24776 | 423 | CCAAAAACTTTCATTTAACTGTTCTCATG TTAAAACTGTGGAACAAGGAACGAGTAGCT GCAGCTGCGAAAGTTTGCAGGTAAATTTG AGTTTGATAA | C | T | 424 | AGCTGGTGCCTGGAAGTCAGTACTAACTGATAAGCT AATTCTTTCTTTCCTTCCAGAGTGTCTCTTCTAAAG TGATGGAACCTTGGAGAATCGGCCCGTC |
| scaffold 414:37377 | 425 | CGCCTGAGCACCCTTAATGGGAGTGGTTG GAGCAGACCTCTTCTGCTGCAGCGAATGGA GTTCGTCGATGGTTGGGCCTTCACCGTTG GCGCACTGTC | A | G | 426 | TCATGGCATATTTCGCTATGTTTCTTCTGCGTCTGA ATTTTCGACAGTCCGTTCCGTCGTCCCTTTCCCG GTCCGAAGCTGAACTCGCCGTTAGCGTT |
| scaffold 5405:41764 | 427 | CCAATCAATCTCGAGTGACGAACCTCAGCT GAGACATGAGAAAACCAAACACAAATGACAG TATGTTTTCATGTAAGCTCTCCCCAAATC CAGCCCCATT | C | T | 428 | GCTTTTGCTTATCACCAACATCAACCACTGTCGTCG CAACCATCGTTTATTCAATGCGCACTGACGAAACAA GGCCACCGCTTCCTCTCCACTCTCTCAG |
| scaffold 6803:13272 | 429 | GTATCCACTGAGGAGATCATCCTCGAGCGA CCTAGGCCTCTCCGTACTTTATTATCATTC CACAATGATTGTTCAACTGATTCTATTTCA AATTCATAAAT | A | T | 430 | TTTGTTTTGAAAGTTGGATTATATAATATTATATAGG TAGCAAGGGGGAAGAAGCTAAGAATTCCGGGATCC ATTGAGTGCGAAAGGCGGTGCTGTCTC |
| scaffold 2317:118844 | 431 | ACCAATGAGAAAACAAAATTAGTTACACT TTTCGGTTTTAAACATCTCTAAACTTTAAA CCAATAAACACGTTCCAGCATTATAAGGGT GTTCGTTCAG | T | C | 432 | TACCTGAAGTTTATAGGATCAGGATTTGATCCATC AATAATGTCAATAGCTCCATTGATCCGGAATTGCTC CCAAGAGTCAGTGAAGTACCAACAAATC |
| scaffold 370:274852 | 433 | AATATCATTTGCTATCTTTGTAAAGCTCTAA AGCTGCAGGTAGATTTTGTGCCTCCTTTCC CATTCCAACTGCTTGAGCACCCTGAAATAA GAAACAGACA | A | G | 434 | GACACAAAATAGCTCAATAATAACTATACCGAATC AACATACAAACAACAATCCAACGCACACTACAAA AGGATTCAAGAATTATGTCTCCGACTAA |
| scaffold 1014:55374 | 435 | CTATTAGACTGTAGAGCATTGCATGAAAGG CTTACTTTATTGTTTAAAAGTATAGTTC GGGTAGATGGATTCTGCAGATAAAGTTTCA TCTTTCCCAT | C | T | 436 | ACATTAGGCAACTCCTGCTGAATGCCAGTGCTTACC TGTTCCGGAAATGTATGTTCACACAAAATCAGGC TCAGTATGACCTTTATAATGTCAATTAG |

TABLE 9-continued

| SNP Name | SEQ ID | Upstream Sequence | Minor | Major | SEQ ID | Downstream Sequence |
|---|---|---|---|---|---|---|
| scaffold 3831:62396 | 437 | GAAAAAACACCCCTCCAGCCTGCAACATCA ATTCAGTTGACAGCTTGCAGGACTCGAGCA AGTTCGTACCAGTAACTCTGCAGATCACA GAAAGGTATC | A | T | 438 | GTTGAGAAACAAACGAAACATTTAAATCCAAGGAAC ACGCAAGTCACAAATGCCTTGAACCGACCACCATTCT TCCCAAGATAAAAATAACACGATGACAT |
| scaffold 2449:58347 | 439 | CGATCATTCGTACCTGCAGTTGAAAGTTGA ACCTTTCAAGTTCAAATGTTGATGAATTA ACAATACAAGGAGACATTTGATCTTCATCC ATGTTTGTTG | A | T | 440 | ACATGATGTTACTTTTCAGTAACACTACCCCAACT ACTTCCATTTAAGGTTGGTAACCCAATACTTCTACC TTCATCACATGTTGATATTTTTCGATTC |
| scaffold 1006:18102 | 441 | TGTAAGACCAACGTGAACAGAGCTAAGGAC CATAAGAAGTTGAAGGCCCTTGAGGAACCA GGCGAACACTTGTCTCGTAATGAGTGAACGT CGTCGTTTGG | C | T | 442 | TCCACTAGGATTTCCATAGCAATGCTTGGCTGCAG AGTGACATGCTTATTCGGAAGTAACCAGCGTGAAAC CTGGTTAAAATAGATGATATATGGGTT |
| scaffold 143:176913 | 443 | CGTAATGCTGTTCTTGCTGTTATGTCTGTT TATCGACTTCCTGGTGGTGATCAATTGCTT GTCGATGCACCGGAGATTATAGAGAAGTTT TATCTTCGA | G | A | 444 | CAGGATAATTCTAGTAAGCATAATGCTTTTCTTATG CTTTTTACTTGTGATGAAGATCGTGCTGTTAATTAC CTTTTTACACATGTTGATAGAATTACTG |
| scaffold 2317:118609 | 445 | CGCTAGAATTGTCGAGAAAGTTTCTTTAG TCGGATCTTCATCTATACTTGGAAGACCTG GATTAGGCCCAAATACTGCAGCCTAGATT TAAGAGAACT | G | C | 446 | GAAAACCATGATTCTCTCTTGCTGCATCATTCAG AAAAGAAAAGACAAAATATGTGGAAAATTAGATAGT TCAAAGGGAAGTTAAAAGCTGAACTAGC |
| scaffold 3:20935 | 447 | GACTCCTCAACCTTTGATGGAGACGAAGAA GATGAATTGTACCAACACTTAGTTTAAAAC AAAGCTTTTTACTAGATTTTCTAATCATTA TTATTTGTG | T | A | 448 | ATCCGGGCATCATTCAGTGCCTTATTTATTCTTG GTGTAAAGATTAAAGATTAAAAATCAAAAATCAAAA ATCAAAATTCTTTCAGAAGATTTCAAGC |
| scaffold 543:54256 | 449 | GTATCCACTGAGGAGATCATCCTCGAGCGA CCTAGGGCTCTCGGTACTTATTATCATTC CACAATGATTGTTCAACTGATTCTATTTCA ATTCATAAAT | A | T | 450 | TTTGTTTTGAAAGTTGGATTATATATTATATAGG TAGCAAGGGGGAAGAAGCTAAGAATTCCGGGATCC ATTGAGTGCGAAGGCGGTGCTGTTCTC |
| scaffold 360:162466 | 451 | TGGAAACAGGAATAGATGCCCCACCGGAAC TTTCTTCTGTATTTTCACCTAAATCTCTGG GCAAATCCTTCACAGCTTCTGCCATTTTCT TCATAATTTT | T | C | 452 | CGCCGCTTCTTCTTCCTTCAATTGTTCTTCATA AGAAGCTTTTCCCTATATTCTAACTCATCATAATAG GCCTTCTTTTGAGCTTTGGAAAGCTTTG |
| scaffold 423:66668 | 453 | GAAAAAACACCCCTCCAGCCTGCAACATCA ATTCAGTTGACAGCTTGCAGGACTCGAGCA AGTTTCGTACCAGTAACTCTGCAGATCACA GAAAGGTATC | A | T | 454 | GTTGAGAAACAAACGAAACATTTAAATCCAAGGAAC ACGCAAGTCACAAATGCCTTGAACCGCCACCATTCTT CCCAAGATAAAAATAACACGATGACATC |

TABLE 9-continued

| SNP Name | SEQ ID | Upstream Sequence | Minor | Major | SEQ ID | Downstream Sequence |
|---|---|---|---|---|---|---|
| scaffold 1317:10314 | 455 | GGAAGTAAAGCCAAACTAGGCCAAGAGAAA AGGCGAAGGAGATGGAGCAATGTAGCATCC ATAAAAGATGGAACAACTAGCATTAAAGAG CTCTGTGACA | G | A | 456 | CAGTGTGCCAAGGTGTGTTCCTGCAGGTATTGAGCT TAAGAAGTTGAAAATGTCCAATACACCAGATAGGAC AATGGACGATCCAAAGCTTCCAAGCTTCCACGTA |
| scaffold 1517:10238 | 457 | CACATCATAAAGAGTATCACCAATCTTTAG CTTGATGGCACCACTTCTGTATACAAGCAT TTTACCCACCAAGCCTGCAGGTATCTCGTT CAATGCACAA | C | G | 458 | ACTTCTTGACAGTGTTCGCAGCCAAGGTGCCCGTG TGCTTTCGTTTACTGCTGGCCATCATTGGTAACTA ATTGTTTCATCAGAGGCATAGTGTGTGG |
| scaffold 1880:146873 | 459 | TACTAAAAATCTGGCCCGACAATGACGAAT TCAAATGAGTAATTCATCCCGAAAAAAGA GCAATAAAATAATTTCTTTAACAAAAAAT CCTGATCACA | C | A | 460 | GCAGGGTAGGTAGGAGCAGCAGCTGTACTATGTT TACCCAAATTTGAAGCCACCAGGGTAGGGTGGGTT GGCTTGCTCCAAAAGGAAAACCCTTGTTG |
| scaffold 1297:57086 | 461 | GGTGCCATGAACTACCGGGATAGTTCCATA TCTCATCGCATACAATTGATTCAAGCCACA GGGCTCAAATCTCGAAGGCATCAGCAGTAT ATCACAGCTG | A | G | 462 | GCAACCAGATCAAGAACTCAGTCCATGAACAT ATTTCATTATGTTAAATAGTGAAATAAAGAGTCAC ATCCCAAAGTTTTGCGTATCTATAAAATA |
| scaffold 682:73395 | 463 | TTTCTACTTTTCCCCTTCACACCTCCCACAC CCCACCGAGACTTCACTTTCATCATCAAG GTTCTCGCCTACAACCGCCTCGACTCGCTG GCCGCTGCCT | C | T | 464 | CGCTCCTCCGCCGCTGCCAGATTATCTCCCGATCGGG TACACCTCCACGTCTATATCGACCACTTCGCATTCG TCAATGCTCCACTGATGTGGATCGTAT |
| scaffold 92:214750 | 465 | TGTATGGGAACCAATATCAGTCAAAGGCCC AGTAACAGCTGATGGCAAGCTTGAAGATGA GGTAACTGGGCGAGTATAGTGAGACTGCAA CATAGATTCA | A | T | 466 | TTTTTTAAAGCAAGTCAACATTTATTTCACCATTT GGAAGATGTATTATCAATAAGTTAAAAAAACATTC CCAATCTCCCATACCTGAATAGATAGCCG |
| scaffold 143:176964 | 467 | CAATTGCTTGTCCATGCACCGGAGATTATA GAGAAGTTTATCTTCGGAACAGGATAATT CTAGTAAGCATAAATGCTTTTCTTATGCTTT TTACTTGTGA | T | A | 468 | GAAGATCGTGCTGTTAATTACCTTTTTACACATGTT GATAGAATTACTGATTGGGTGAACAGCTTCAGATGG TTGTGTTAGAATTGATTAAGAAAGTTTG |
| scaffold 942:90233 | 469 | GGAAACGAAAGGCACCACGCCAAACGTGAG CGCTCCAGCTGCTTGAACTGACACAGAGAA TCCACACAAGACAACAATGGAGCCCCCATAG CGAGTTACCT | T | A | 470 | GGCCAGTAACACGCAGAGACAACCCGGCCACTGTCT GCACTGCCCAGGAACCCCAAAGTCTCCCTCTCCAATT TTTCTTTCTATAACTTCTTTGCATTTTT |
| scaffold 942:89745 | 471 | CTTCGATTTCTGAGCTTACTAAGTGAGCCA TGCTGTTTGACGTGGCTTATCTGCAGTAAA CGGTCCACTCCACTTTACAAGGTATTTTCT TAAAGTTTAC | G | A | 472 | AACCATTTGAAACAAATAGGTTCCTGATAGAAAGAA GCCATCCACATATCTTCTGTTGCCTTGGCAGATTT TCAGAGCAATGTACTTCATCGTTCAATG |

TABLE 9-continued

| SNP Name | SEQ ID | Upstream Sequence | Minor | Major | SEQ ID | Downstream Sequence |
|---|---|---|---|---|---|---|
| scaffold 24:306989 | 473 | TAACGTTTCCATTCTTTATGTCTTTGATTTT TTGCACAGGTTGGATTAAAGCAAGGACTGG AAATGTTGAATATATTCAAGAGTTACACAC CGAAGACTTC | T | A | 474 | TTGTTAGACGATTTTAGCTTCTACGAAAGCCGAGAA AAGGTCCTCCTAGCCAAAGAGGCCATTAACATCAAG CCTGCAGCAACATTGAAGATGAAACCA |
| scaffold 1281:68808 | 475 | ACAGTACTAATGAATCAACGAGGAGATG ACGTGTTTGATTCTTCATCAATCGGTGAC GAGGGGCTTTGGAGCAAATATTTCAGTAC ATGGAAAGA | C | G | 476 | TGGTACTACTTGCAAGGAAGAAGAGGCAGTACAGA AAACGACCACCAATGATGACACAAACGACAACTCGAA AAACTGCAGATTTCTTCCAATCAACAAC |
| scaffold 1880:146829 | 477 | AAATACTTCAATATAACAAATTCCATAGAC GAGCCTATGTGCCATACTAAAAATCTGGCC CGACAATGACGAATTCAAATGAGTAATTCA TCCCGGAAAA | A | G | 478 | AGAGCAATAAAATAATTTCTTAACAAAAAATCCT GATCACACGCAGGGTAGGGTAGAGAGCAGCAGCTGT ACTATGTTTACCCAAATTTGAAGCCACC |
| scaffold 3:20953 | 479 | GGAGACGAAGAAGATGAATTGTACCACAC TTAGTTAAAACAAAGCTTTTTACTAGATT TTCTAATCATTATTATTTTGTGAATCCGGG CATCATTTCA | A | G | 480 | TGCCTTATTTTATTCTTGGTGTAAAGATTAAAGATT AAAATCAAAAATCAAAATCAAAATTCTTTCAGAA GATTTCAAGCATTGTAGTAAATCTTTAT |
| scaffold 580:4170 | 481 | GATCATAATGAGTACTTCGATCTAGCTTGAG CACTGTTCATCCACAAGTTGACAGAAGCTA AAACCTTTTCCTTCAAAAATCAGGCTGCAG AAGTAGACAA | C | T | 482 | TGGTAGTTAGATTCAGAGTGGAGAACAAAGGACTCTT TGTTAGATGGCCATAGAGTAGTAAACACAGACTGGT CCAAGAGATTTACAAACCGTTATTAAT |
| scaffold 604:135874 | 483 | ACCAATGAGAAAAACAAAATTAGTTACACT TTTTCGGTTTAACATCTCTAAACTTTAAA CCAATAAACACGTTCCAGCATTATAAGGGT GTTCGTTCAG | T | C | 484 | TACCTGAAGTTTTATAGGATCAGGATTTGATCCATC AATAATGTCAATAGCTCCATTGATCCGGAATTGCTC CCAAGAGTCAGTGAAGTACCAACAAATC |
| scaffold 1692:85945 | 485 | AAAAATAGTTTTGTTTATATTATAATCTCTC ATGGAAAATAGCTAATAGTATTCATTTGAA TTGAAATGTTGAACAGACCATTCTGGGCAG GAGCTGCAGG | C | G | 486 | AATGCAGTGATGATCATTGAGGCAGATGCTTTCAAAGAA TCAGATGTTATCTACAAAGCCCTTAGCTCTAGAGGC |
| scaffold 1041:93642 | 487 | TATATAATATATATAATAAGATAATTAGA TAACATAACATGTAATTAAGGATTAAGCAT GAAATTATTAATTTAATTTTAACATACCG GCAGCCAATA | A | G | 488 | CACAAAATAGTTACACCCAAGCAAATGTTGATATG ACCAAGCAAGGTAAAAAATATGGAAATCTGTTATT CATAATTATAAGGTTAATATGTCATTAA |
| scaffold 1926:69537 | 489 | ACAATTGAAAAAGTTGTAATTCATTTATTG AGGGATGGAGATCCAACATAGAGTGAGCT CCTTACCATCTGACCCACCCCCTTTGCAGCT GCAGAACATG | C | G | 490 | GCCATCTTTTTCACTTTTTGTTATTGTATTATAG TATAGGTACCTCGTAGAAGAAAATGAGAAGAAGAG AATTAAGGAATAGGTGATATTATTATAT |

TABLE 9-continued

| SNP Name | SEQ ID | Upstream Sequence | Minor | Major | SEQ ID | Downstream Sequence |
|---|---|---|---|---|---|---|
| scaffold 4210:100547 | 491 | GCTTGAGGAGAGAAGAGAGAGTAAGAAGGG GAATGAGCAACGATCACGTTCTGACATCA CACCCTTGATGGTACGGTTGTAAGCAACTC CGGAGTAACC | G | A | 492 | AGCTTCCATGCCATAGTAGCTAGCTTGATCCGAGTA GCCTTATCAGACGGCAAGGCTCCAAATATGGTATA TTGAGATCAAAGAAACCCATTCCTACTC |
| scaffold 759:86606 | 493 | GGGGAGATAATTGTACGACATTCGATGTTA TGTCGTTGTTGTGCAGTTGGAGATGGTGG CAGACGCACTGCAGCCTTTAAAGAGGCAT GGAAAGCTGC | A | C | 494 | TGTGTGTTGAATCCGGTGTCGTTTTGGCCCTGCT GATTATTGTTTTAAAATTACTTCTACTATCTTTTG GACCCTGCAGCCCCGGATTAATGTTCCA |
| scaffold 25:425571 | 495 | CCAATCAATCTGCAGTGACGAACCTCAGCT GAGACTGAGAAAACCAAACACAAATGACAG TATGTTTTCATGTAAGCTCTCCCCAAATCC CAGCCCCATT | C | T | 496 | GCTTTTGCTTATCACCAACATCAACCACTGTCGTCG CAACCATCGTTTATTCAATGCGCACTGACGAAACAA GGCCACCGCTTCCTCCTCCACTCTCTCAG |
| scaffold 692:20843 | 497 | ATATTTAGCCCAAATGAAAAATTAGGAATT TTTCCTTTCACTTTGATTTTGATTTTAAA ATGTTATAACATTATGGCCGGCTAACTTAG CTATCGATTT | G | A | 498 | CTTTTTGGGTGTTATTAGCAAATAATTTTAAGCTGA ATTTTCTGCAGCTCTTGGCTGAGGACCCATCTTTAA AGCGATTCAAGTCACATAAGCCTAATGT |
| scaffold 2515:21370 | 499 | AAACGATCTGACGCCCTTCATCTTGATCAA TCTCAATTAAACAAGATTTAGCTGAGTCCC CTTTACAGTGTATTTGAGCCTTAGATCAATTG AGATGTCGTA | T | C | 500 | CCTCGCCCTATTGAGCCAATTGCAATCTCTGCAGCT TTTGGAGCTGGAACTTTCAGCGCCATAACTCACCAA CGCCTGTTCCTTCCTTCACCAATCCCAGATCT |
| scaffold 48:65442 | 501 | TTTCTTCACCGTACATGTATAAGGAACAAC CGGTCATAGTTTGAAGCCACCACCACAG ATGACGCATCATCACAGAATTCAACTGCCA CAGGATGACC | C | G | 502 | CCAGCGGGCAAGTTTATTCTGAGGAATCTGCAGAGA TAAATTCATAAATTTGAGGATAAGTACCCAAAAC GAAGAAAATCCATAAATGATCATTGGAA |
| scaffold 48:65391 | 503 | CAGGAAGAGGAGGCTTGGTTTGCTGGTTAG CTCCATCAGAAGATTTGGTCTTTTCTTCAC CGTACATGTATAAGGAACAACCCGGTCATAG TTTGAGAAGC | T | C | 504 | ACAACCACAGATGACCCATCATCACAGAATTCAACT GCCACAGGATGACCGCAGCCGGCCAAGTTTATTCTG AGGAATCTGCAGAGATAAATTTCATAAA |
| scaffold 3177:95787 | 505 | TACCCCTCCCGGACTTCCTATGATGCGTCT GCAGCGTGTTTTCAGGCTCGGAATCGTCG ACCTGGAAAACGAGGACGAAGACGAAGAAG AAGTAATGGC | C | T | 506 | TTCCCCCTTCCGGCGTATATATGGACCAGCTCTCC ATCAGCATCTCTCACGCACGCTACGTGTAGATTG TACTTCTTGACTTAGACCCGTAGCTCC |
| scaffold 3681:699 | 507 | AGCCTCATTTGGCTCGATTTGAACAGCAAT CAACTCTCGGCACTGTCCCCGCCGACTTG CTAACCAGGCTGGCCTAGTGGTTCCCGGTA TTGTTTCTGG | T | C | 508 | AAGCAATTTGCATTGTGAGAAATGAGGGTGGAACA GCCTGCAGGGAGCCGGAGACTAGTTGAATTCGAG GGTGTTCGGCCTGAGAGACTAGAAAACT |

TABLE 9-continued

| SNP Name | SEQ ID | Upstream Sequence | Minor | Major | SEQ ID | Downstream Sequence |
|---|---|---|---|---|---|---|
| scaffold 3570:26136 | 509 | TCTACTTTTCCCCTTCACCTCCCACACC CCCACCGAGACTTCACTTTCATCATCAAGG TTCTCGCCTACAACCGCCTCGACTCGTGG CCCGCTGCCT | C | T | 510 | CGCTCCTCCGCCGCTGCAGATTATCTCCGATGGG TACACCTCCACGTCTATATGACCACTTCGCATTCG TCAATGGCTCCTGATGTGGATCGTATGT |
| scaffold 388:236449 | 511 | TAGAGAAGAGAAACTGTAATGCTACTTAG TTTCACTCAAGTAAGAAGAGTCTGATTTTA CAGTTGAAGACGCTGCTGAACCCTTGGCAC TAGCTTCCTT | C | A | 512 | TTCAACCAAACAAAGAACCGGAACTTCCTTATCC TCATCATCTTCATCAATATCACTGTCTTCTTCACTA AGCAAAGCCCCAATGCCCAACCTTTTTC |
| scaffold 763:27574 | 513 | TCGCGAGCAAGTATGTGTAGGTGGATGAT TCCTTCTCAAAGAGCTGACGGAAGAGGAGC TTGCCAAAGAGATGAGACGACGTCGTATAA GAGCAAGTCG | C | A | 514 | TGTTTTTAAACACCCTAACTTGGTCGACTTTACCGG ACTCGATAAAATCCTCGAAGAACAATTCAACAAAGC TGGATTAGATCCAGTAATGGTGAAGACT |
| scaffold 794:150222 | 515 | GCCACCAAATGGGGGCATTGAGGCCAGGCT TTGGGCATACGCGCGGGTCAAGGCTGCAG TGGAGTCTTATGACGCAGATACTTGCAAAGG AGTTGAAGGG | A | G | 516 | ACGGGATCACAGCCAACTGCCTAGCCCCGGGCCGA TCGCAACAGATATGTTCTATATGGAAAGACTGAGG AACAAATTCAGAAAGCGGCGGAGGAAAA |
| scaffold 152:25430 | 517 | ATATAAAAATTCAATGCCAAGTGATTCAAAA CCGGTTTAATCTTCAATAAATCTTTATTAG TAATGGCTTGCATTCTTCAAAAAGAATCAA CCTTTACAAT | G | T | 518 | TGTACGGTCATATTTCTTAAAACAAATAAATAAATA AATCACACAGCCAATTGGAAAGAGGCTATTCAAC TTTATCAATTAGACCTATAATGTACT |
| scaffold 108:362803 | 519 | CAAAGTACCACAGAGCCATTTCCAACATGC CCAGCGTAATCACTAGAGTAATACAGTTCT GCAGAGGCAGAACTTCTCTCCAAAATCTTG CATACTGTGA | G | A | 520 | AACCAAAAGAGCCCAAGTAATACAAAAGCAAATGAC ATGAGCCCATAAAATTTCATAAGTGGTGCCATTCTG CCGGTAGATATCCATTTGGGTTTTTCCA |
| scaffold 388:350925 | 521 | ATCAGTAACCAGATTCACCCAAAAAGCTGC ACTGGTATCATACATTCGGTATTCCCAATG CTGCAGTCAAGAATATGGATATAACCCTCTC CAACATTTGA | A | C | 522 | GATATCATGTACCTGAAAATTGACAATATGAACAGA ACTATATAAGTTGCTCAACAATGAGATATTTCATAT AAGAAAGGGTATATATGCAGAACTAAGA |
| scaffold 2218:32474 | 523 | CTCCTGTGTACAGGCAGTACTTGAAGATGA TGGAACCTCATCTTAATTAATTGTTCCAAT CCCACAAAAACTTTATGGAAAAGTTTGATT ACCCTTCCCA | T | C | 524 | ACCTTTCTACCAGGTAATCAAATTGGATACAACAAA GTAACCAAAACTCACAGGGTTCTCACTTCATGGAAG AATTCCAAAGACCCCTTTACCCGGCCTTT |
| scaffold 604:135639 | 525 | CCGCTAGAATTGTCGAGAAAAGTTCTTTA GTCGGATCTTCATCTATTATTGAAGACGCT GGATTGGCCCCAAATACTGCCAGCCTAGATT TAAGAGAACT | G | C | 526 | GAAAACCATGATTTCTCTTTGCTGCATCATTCAG AAAGAAAAGACAAATAATGTGGAAAATTTAGATAGT TCAAAGGGAAGTTAAAAGCTGAACTAGC |

TABLE 9-continued

| SNP Name | SEQ ID | Upstream Sequence | Minor | Major | SEQ ID | Downstream Sequence |
|---|---|---|---|---|---|---|
| scaffold 2741:33031 | 527 | AATTTCGATCAGGTTGCAGCCAACTTAAA CAAAATGTCTTTGAGTTCTTACATCAAT TGTATGAATAGGTTCACCTGGTCAGCAGAA GAAGAAATCT | G | A | 528 | ATTCCAGTAAAAAACTTGATATTATTTTCAGGG CCGGGTCACCATTTCTCTGCATGGACTACAAGTT CTAGATTCTTCATGGAACAACCTTTCAA |
| scaffold 4991:44264 | 529 | GCAACATACATATAATTAATGTCAGCCGGT GATAAAACATTTCTATCAATAAATTCTA ATTAAGAACATCAAACACTTTGACCATTAC AAATAATAAA | A | C | 530 | TCATTTCTAGTTGGAGCAACAAAGATAATAATTAGAT ATCATCCAAGGAGATAGACACATGACATTGATAT GTGTTATTACGTTTGAAGACCCGAGCAT |
| scaffold 2483:94844 | 531 | CTTAGGGCTAATCCCTCCAACCTGCATCAA CAAAACAATGCTAGATTTTAAGAAATCACA AACCATTAATAAATTCTTTGTTAGCATCA ATTGCAGTTT | G | A | 532 | CTCACTTTAAGTCCGGTCTCCTTTCAAACACAATTG AGAAAGCCTGTCGAATAGACAAGTCTTCGGTGATTT CTTGTCTTACTTTATCTGTCTGCATTAT |
| scaffold 3871:24039 | 533 | ATAAATAAAGGCTAAAATGAGTTGAACTCA ACACCAAGAGTTTGTGGACACTACAT CAAATGGGCCACAACATCTTTTACATTAGG AAAATTTACA | T | G | 534 | TTGATTTATGATGTTCTTTGACATTCTATAAAGATA AATCTATTTGTCTCATATCTATCAAATATCTTCCA CCTTACCGGAGATATTAATATGTGAGTA |
| scaffold 616:154319 | 535 | TAGATCCACCTCCAATGAGGGAAGAAAGC TATACTTCTTAGCAAATTCTGCCCACCGGT TTAAAAGTCTATCCTCTGCCAACCATG CAGCAGATTT | T | C | 536 | AGAATTGTAGCCTGTTACAAAAATTAGGAAAGATAT ATTGACCAAAAATCACAAATTGAATACATACGTA TCGATCATGAAAAAACAAGTTTATCATG |
| scaffold 1005:75114 | 537 | ATATTATTTCCATCCAGATGTTTCCAGATC CGGGTATTATAAAAATGCAAGTTAAAATCT TGCTAATATTAGATTGAGAAAAGATGGCA TTGAAAAGGA | T | A | 538 | AACTGGGCATATAGTAATAACCAACTTTTATCAGTG GAGCACTGGTCATCATCATCCATTCCTGCAGCAGGAAT TCTGGTTAATATCACATACAATATCT |
| scaffold 4991:44417 | 539 | GACACATATGACATTGATATGTGTTATTAC GTTTGAAGACCCGAGCATAGTTTATTGAAA TTAGCCAGCTGATCAGAAAAGTTAGATATG AGAAAACACA | T | C | 540 | CAGAAGTATTTGAGTCACACTTCATCAGTTTAGTGT AAAAACAAGATCCTTACAGATACTGCAGCAACAGGA TAATAAATCCAACACTAACATGCTCCTC |
| scaffold 38:121620 | 541 | ACTATGTCTTCTAAGGCGATTTTGTTTCGG TTGTTTAGGCGACCGACCATGAATCTTCT CGTATGTAGTACTATTAGAATGTTTAATCT GTTTTACTTG | G | A | 542 | ATGAATCTTTTGTAGGCCTTGGACACCTTTAACACA GCAGTTATATCTCCGGTCTACTATGTTATGTGTTAC GTCGTTCACCATCTCGGAGCTGATCATG |
| scaffold 1005:75091 | 543 | ATGTAAGGAAATAAACCTATGTAATATTAT TTCCATCCAGATGTTTCCAGATCCGGGTAT TATAAAAATGCAAGTTAAAATCTTGCTAAT ATTAGATTGA | A | G | 544 | AAAAAGATGGCATTGAAAAGGAAAACTGGGCATATA GTAATAACCAACTTTTATCAGTGGAGCACTGGTCAT CATCCTCATTCCTGCAGCAGGAATTCTGG |

TABLE 9-continued

| SNP Name | SEQ ID | Upstream Sequence | Minor | Major | SEQ ID | Downstream Sequence |
|---|---|---|---|---|---|---|
| scaffold 298:209613 | 545 | CATGATAAACTGTTTTTCATGATCGATA CGTATGTATTCAAATTTGTGATTTTTGTC AATATATCTTTCCTAATTTTTGTAACAGG CTACAATTCT | A | G | 546 | AAATCTGCTGCATTGTTGGCACAGAGGATAGACTT TTAAACCGGTGGGCAGAATTGCTAAGAAGTATAGC TTTCTTCCCTCATTGAGGTGGATCTAC |
| scaffold 152:25429 | 547 | AATATAAAATTCAATGCCAAGTGATTCAA ACCGGTTTAATCTTCAATAACTTTATTA GTAATGGCTTGCATTCTTCAAAAGAATCA ACCTTTACAA | T | C | 548 | GTGTACGGTCATATTCTTAAAACAAATAATAAAT AAATCACACAAGCCAATTGAAAGAGGCTATTCAA CTTTATACAATATAGACCTATAAGTAC |
| scaffold 1003:70848 | 549 | AGCCTCATTTGCTCGATTTGAACAGCAATC AACTTCTCGGCACTGTCCCCGCCGAGCTTG CTAACCAGGCTGGCCTAGTGGTTCCCGGTA TTGTTTCTGG | T | C | 550 | AAGCAATTTGCATTGTGAGAAATGAGGGTGGAACA GCCTGCAGGGGCCGGAGGACTAGTTGAATTCGAGG TGTTCGGCCTGAGAGACTAGAAAACTCT |
| scaffold 839:64955 | 551 | CCAGAAGTATTCCATGTTCATTTGCACTAT CGACCTACATCATTGAAATGAACCAGGAAC AAAAATATCTTGACTTAATTAAAACAATAT AGATATATAT | A | G | 552 | TATATTATATTATAAATCTCAAGAGCTGCAGAGATT GAAAAAAAAAAGTCATACCCTAATTACCGTAGCAT TCTTGCAAGATCATTATCAATTACAAC |
| scaffold 4070:22473 | 553 | TGTGAAAACCTTTCCGTGGTATCAATCCAA TACTTTGGTTTTGCTTGCAGTCACCCAAT TGCAGTTGAGTTACCGGGCTAATCAAGTC ATCGCAACTT | C | G | 554 | TTCTCTCACACAAGCATTCTTGGGATTGCATAAAA ATAATCTTCCTCCCTTTGGCCTGTCTGCAATTACTCT GCGTCGACTTGGTTGTCCCATCCTTTTC |
| scaffold 1419:187408 | 555 | GTTACACCATGATGATGGTGAACTCTCCGGAAC TTGGCCATTGGACATATTGCACACCTACAA ATCAAACTTTGGAATAAGACAACTATCAAC AATTACATAT | T | G | 556 | TAACATTTAATATTGTACTAATTCTAATTACCACAGA TACCTTCAATTTCTGTAAACTGGCTTTGCATACAA ATGATCAATACCAAGAAAGTAACGATCG |
| scaffold 3871:24091 | 557 | CACTACATCAAATGGGCCACAACATCTTTT ACATTAGGAAAATTACAGTTGATTTATGA TGTTCTTTGACATTCTATAAAGATAAATCT ATTTGTGCTC | G | A | 558 | TATCTATCAAATATCTTCCACCTTACCGGAGATATT AATATGAGTATGCTCAAATAATATGACCAGAAAA TATAACAAAATCAATATTCATCGACTAC |
| scaffold 3871:23604 | 559 | CCAATTGTTCTTCACAATACCACACACCT TCTCCACTGTTCTTTCTTTGGCCTGCAGAA GGATGCCATACATAATTAGCTCCAAAATAA AAGTAAAAA | C | A | 560 | CAAAATCATTACCTTTACACAAGGGTTGATAGCAGAA ACATCAATGATGCTGTCATAAGGCTAAACACAA AGTAACGGATGTCAATGGAACAACTACA |
| scaffold 3871:23603 | 561 | GCCAATTGTTCTTCACAATACCACACACC TTCTCCACTGTTCTTTCTTTGGCCTGCAGA AGGATGCCATACATAATTAGCTCCAAAATA AAGTAAAAA | G | A | 562 | ACAAATCATTACCTTTACACAAGGGTTGATAGCAGA AACATCAATGATGCTGTCATAAGGCTAAACACA AAGTAACGGATGTCAATGGAACAACTAC |

TABLE 9-continued

| SNP Name | SEQ ID | Upstream Sequence | Minor | Major | SEQ ID | Downstream Sequence |
|---|---|---|---|---|---|---|
| scaffold 3:388526 | 563 | CGAGACGAGACGCGACCTGGTTTGAAAC CACAACAACAACTAGGGTTCATCCTA CCAAAAACCCCTCTTTACAATTCCTGCAGA TTTACCGCTT | C | T | 564 | TTCTTTTCGCGGAACCCAAACAGGAAATACAATTGA CCATGTCGAAGAGGAAATTCGGATTCGAAGGCTTTG GCATAAACCGCCAAACGACTTACAACTT |
| scaffold 4:729494 | 565 | GATTACCTTACAAACCGCATTCAAAATGA GGAACTGAGGTCGTCGAGGTAAATTCTTT ATTTCTTTTAGTTGATGAATGCCTGCAG TTCATTTGGA | A | G | 566 | GTTAGTTAGTCTGTTCAAATTTCCGAATCTGAAG TAGTATGACTTTGGTATCTCACTGAAGTTCATT TTGGTATCTCAGTAAACCAAGTAATTGC |
| scaffold 2283:29120 | 567 | CTGAGCTCCATTATCTATATAAACTCATGA GCACTTCCGGACGACTTCTCAACGATATCC ACGGCTTCAAGGTAACAATAGTTTATCCTT TCCACTGGTC | C | G | 568 | ATAAGATACCTGTTTAAAACCAGAAAGATAAAATA TAAGTTTCGTTGTGATGAGTTTTGGCATTTTCTA ATCACTCTATTGGTTATGCTGCAGAGAG |
| scaffold 4350:64549 | 569 | CTGGAACCACTAGCGAAGAGCAGCGAAAG TGACATCATTGCATTCTAATTGTTTGCCCC GGATATAGAATTGGGGCCCGATCACCCAAT TGTATGTAAC | T | C | 570 | ACACAACTCCTGGAGACAAAAATGTTCTGATCAGGT TAGAGATGCTCATGTGTCAACATATTTATTTCGGGTA GCTGGGTAGCCACTCCTTTTTTTCACAGA |
| scaffold 2283:29096 | 571 | TTTCTGAGGATGTTACAAGACACTCCTGAGC TCCATTATCTATATAAACTCATGAGCACTT CCGGACGACTTCTCAACGATATCCACGGCT TCAAGGTAAC | T | A | 572 | ATAGTTTATCCTTCCACTGGTCGATAAGATACCTT GTTTAAAACCAGAAAGATAAAATATAAGTTTTCGTT GTGATGAGTTTTTGGCATTTTCTAATCA |
| scaffold 3469:17543 | 573 | AGGGGGATAAATTGTACGACATTCGATGTTA TGTCGTTTGGTGCAGTTGGAGATGGTGTGG CAGACGACACTGCAGCCTTTAAAGAGGCAT GGAAAGCTGC | A | C | 574 | TGTGGTGTTGAATCCGGTGTCGTTTGGCCCCTGCT GATTATTGTTTAAATTACTTCTACTATCTTTCT GGACCCTGCAGCCCCGATTAATGTTCC |
| scaffold 1022:170497 | 575 | ACCCGTGATTCTCTGAAATCATTTTATTTT CCGTGCCTTATTACATAAGGAAGGAAGAAA AGAACTCGTATTTTGGGTTCTTTCCATCTT CGTATGTGTT | A | T | 576 | GTATTTGTATGTTTGTGTAAGATAAATCATAAATTT CTAACGAACTCTTTAAACCACAGTTCCATGACCGCC ACCACCTTCATCGACCGCCCCGGTTATAT |
| scaffold 964:106240 | 577 | GAGTAGGAATGGTTTCTTTGATCTCAATA TACCATATTTGGAGGCCTTGCCGTCTGATA AGGCTACTCGGATCAAGCTAGCTACTATGG CCATGGAGCT | C | T | 578 | GGTTACTCCGGAGTTGCTTACAACCGTACCATCAAG GGTGTGATGTCAGAACGTGATCGTTGCTCCATTCCC CTTCTTACTCTCTCTCTCTCCTCCAAGC |
| scaffold 1419:187788 | 579 | ATCATAAACTTATTTGGCTTAAATCTGAAAA TAGCCAACATAAATGATGAAATAACAGAAG AAAAGCAAGTAAATTTAAGAATTCAGCGAT GAAATTATCT | T | A | 580 | ACCATGTAAACAGAGGTATCATTGATGGAAGTGAA GAGGCTGCAGTAACACTTTGAATTTCCAATCAGGA ACGTATAGACCATATAATAACCCCGTGT |

TABLE 9-continued

| SNP Name | SEQ ID | Upstream Sequence | Minor | Major | SEQ ID | Downstream Sequence |
|---|---|---|---|---|---|---|
| scaffold 3386:35408 | 581 | TTTCTAGCATTGGAGATGACATTGATATGG TAATGATGTCGACACCATCAGCAATAGCGT CGTCAAAAGCTGCCAACATAGCTTCTGAAT AGCACCCTGT | T | A | 582 | GGGCTGCAGACTTTATAAGCAGCAATTCTGCAGAG GGAACTCCTCCTCTTGCAATGCCTTCTTTTAGTCCA TAGAAACTGACATTTTTACATTGTTCC |
| scaffold 575:241067 | 583 | TATAATCTGCTCTTCTTGTTAGTATGTTTG CCTTTATATTCCGGGTAGATTTGTCTTAT TTAAAAACCCTTTCTGTGAGAAGACTTTTA TATGTATAGT | G | C | 584 | AGGATTGTGTTTGACATTTTCTTATCTTGGTGGAAA CATTTTTAAGCAAACACGTGTGCAGGCTTGACTAA TCTGATTTTCACGTGGAAGATTGAACTT |
| scaffold 1863:93953 | 585 | AGAATTTATACAGTAGAACCTCACTAATAT ATACGAAGAATAACCTCAAAAATTAAATCT TGGGCAGTTATAATAAAAATAATTTTTAA ATTGTAAAAC | C | G | 586 | TTGTTTATAAAATTTTAATCATTAAGAAACACAGCA AATAAACCTAACAAGTATTGAAAAATGTCCATTAAA AGAAACCATCGTTCTTTCCGGTCTTGAA |
| scaffold 575:459449 | 587 | GACCATAAGACACTGCAGAGCTATGGCTCG AATCACCACCATTTCCATTTTCTGTTGAGT TCAAATGCAAATTAGCATTCCCCCTGTACT GATAACTATG | G | C | 588 | CCCCCCGGATCAGCACCGTGACCATGTTCTCCCGAG TTCGAATGTGAACTATTATTCCCTCGTATCGATTA GACTATACGAAGCTGAAACACTGTCATT |
| scaffold 773:155167 | 589 | TCTGTTTAAGGATTTCTGCAGCAATCGGGA CGGTTGAGTTGACTGGATTACTGATTATGT GGATAAAGGCATCAGGGCAGTTGTCAGCAA CAGCCTCAAT | T | C | 590 | AGTGTCTTTACTATACCGGCATTGATGTTGAATAGG TCATCACGAGTCATTCCAGGCTTTCTCGGAACTCCA GCAGGAATGACAACAACATTTACGCTT |
| scaffold 773:155164 | 591 | CCTTCTGTTTAAGGATTTCTGCAGCAATCG GGACGGTTGAGTTGACTGGATTACTGATTA TGTGGATAAAGGCATCAGGGCAGTTGTCAG CAACAGCCTC | G | A | 592 | ATCAGTGTCTTTACTATACCGGCATTGATGTTGAAT AGGTCATCACGAGTCATTCCAGGCTTTCTCGGAACT CCAGCAGGAATGACAACAACATTTACGC |

TABLE 9-continued

| SNP Name | SEQ ID | Upstream Sequence | Minor | Major | SEQ ID | Downstream Sequence |
|---|---|---|---|---|---|---|
| scaffold 107:154377 | 593 | TATTTGAATCCACTCAAGTCCACTTCACAA TAAGTGGTTACAAGCTCACGCGGCCGGTGG TGTGAAGCTCACAATGCAACATTTGAGCCT TTGTAGGGAT | C | T | 594 | CAACTCAAGTCCATGTAGTTGGTTGTTGATACTTGT GATTTACTTATATAAGAGTAACGATATGCCACTCA AATTATGCATCAAAATATTAGATACAAT |
| scaffold 371:34271 | 595 | GAACACACATCTTTCTCCGGCAACTTTAGT ACATTGCCGTTCAGTGCTTGCAGAAGCTTC CTTCCAATAGCAGCAAGTACACATATTCGT GTGATGGATA | C | T | 596 | ACCTTCAACTTCCTAATTGACAATGCATTTGGTAAT GATTTTTTTTCTTCAGGTTACCTTGAAATTGTTC ACATTTATAGCAGCATGAATGGTTGAAA |
| scaffold 78:341641 | 597 | TAATAGTTCTTCTATTGCTGGTAATCGTCT GTGCTGAAGTGTCGGTGGTCCTCACCTACA TGCATCTCTGCCTAGAGGATTGGCGGTGGT GGTGGAAGGC | A | G | 598 | TTCTTCGCATCAGGTTCAGTTGCCCTTTATGTATTC TTGTACTCTATCAATTACTTGGTGTTTGACCTGCAG AGTTTGAGTGGACCCGTCTCCGCTGTAC |
| scaffold 156:85625 | 599 | CCTATGTGATCGTCCGAATGTGTTATCAA GTGCAGGAAGGTGGGAAGAAGTTTCTGAAG TTGAGGAAGATGATGAAAAACCAGAGGGTGA AGAAGGAAGT | T | A | 600 | GGGCGTAGTTGGATTGAAGTCGCGGTAAGGTCCAC GAGTTCTTAGCCGGCGATCACATACACGAAATGAGG GACGATATTTATAAGAAACTAACCGAGT |

TABLE 10

| Sample ID | Sample Name | Sample Type | Reference for Reported Ancestry |
|---|---|---|---|
| 1 | Afghani Regular | indica | http://medicannseeds.com/seed/afghani-regular/ |
| 2 | Afghani Regular | indica | http://medicannseeds.com/seed/afghani-regular/ |
| 3 | Afghani Regular | indica | http://medicannseeds.com/seed/afghani-regular/ |
| 4 | Afghani Regular | indica | http://medicannseeds.com/seed/afghani-regular/ |
| 5 | Hindu Kush | indica | https://www.kiwiseeds.com/kiwiseeds/kiwiseeds-hindu-kush-34671.html |
| 6 | Pakistan Chitral Kush | indica | https://www.cannabiogen.com/Producto/PAKISTAN%20CHITRAL%20KUSH%20-6.html |
| 7 | Pakistan Chitral Kush | indica | https://www.cannabiogen.com/Producto/PAKISTAN%20CHITRAL%20KUSH%20-6.html |
| 8 | Ketama | indica | http://www.worldofseeds.eu/wos_en/ketama.html |
| 9 | Pure Afghan | indica | http://dnagenetics.com/seeds/pure-afghan |
| 10 | Enemy Of The State | indica | http://superstrains.biz/shop/enemy-of-the-state/ |
| 11 | Enemy Of The State | indica | http://superstrains.biz/shop/enemy-of-the-state/ |
| 12 | Enemy Of The State | indica | http://superstrains.biz/shop/enemy-of-the-state/ |
| 13 | Master Kush | indica | http://homegrown-fantaseeds.com/product/masterkush |
| 14 | Master Kush | indica | http://homegrown-fantaseeds.com/product/masterkush |
| 15 | Master Kush | indica | http://whitelabelseeds.com/seeds/wlsc/master-kush |
| 16 | Master Kush | indica | http://whitelabelseeds.com/seeds/wlsc/master-kush |
| 17 | Master Kush | indica | http://whitelabelseeds.com/seeds/wlsc/master-kush |
| 18 | Master Kush | indica | http://whitelabelseeds.com/seeds/wlsc/master-kush |
| 19 | Master Kush | indica | http://whitelabelseeds.com/seeds/wlsc/master-kush |
| 20 | Pakistan Valley | indica | http://www.worldofseeds.eu/wos_es/pakistan-valley.html |
| 21 | Pakistan Valley | indica | http://www.worldofseeds.eu/wos_es/pakistan-valley.html |
| 22 | Afghani | indica | http://homegrown-fantaseeds.com/product/afghani |
| 23 | Afghani | indica | http://homegrown-fantaseeds.com/product/afghani |
| 24 | Northern Lights | indica | http://www.ministryofcannabis.com/feminized-cannabis-seeds/northern-lights-moc-feminized |
| 25 | Northern Lights | indica | http://www.ministryofcannabis.com/feminized-cannabis-seeds/northern-lights-moc-feminized |
| 26 | Northern Lights | indica | http://www.ministryofcannabis.com/feminized-cannabis-seeds/northern-lights-moc-feminized |
| 27 | Hash Passion | indica | http://www.seedsman.com/en/hash-passion-seeds |
| 28 | Narkush | indica | http://www.seedsman.com/en/narkush-seeds |
| 29 | Narkush | indica | http://www.seedsman.com/en/narkush-seeds |
| 30 | Narkush | indica | http://www.seedsman.com/en/narkush-seeds |
| 31 | Narkush | indica | http://www.seedsman.com/en/narkush-seeds |
| 32 | Kush | indica | http://www.ceresseeds.com/online/en/regular-seeds/182-ceres-kush.html |
| 33 | Kush | indica | http://www.ceresseeds.com/online/en/regular-seeds/182-ceres-kush.html |
| 34 | Kush | indica | http://www.ceresseeds.com/online/en/regular-seeds/182-ceres-kush.html |
| 35 | Hindu Kush | indica | https://sensiseeds.com/en/cannabis-seeds/sensi-seeds/hindu-kush |
| 36 | Hindu Kush | indica | https://sensiseeds.com/en/cannabis-seeds/sensi-seeds/hindu-kush |
| 37 | Hindu Kush | indica | https://sensiseeds.com/en/cannabis-seeds/sensi-seeds/hindu-kush |
| 38 | Malawi | sativa | http://www.aceseeds.org/en/malawifem.html |
| 39 | Malawi | sativa | http://www.aceseeds.org/en/malawifem.html |
| 40 | Guatemala | sativa | http://www.aceseeds.org/en/guatemalastd.html |
| 41 | Guatemala | sativa | http://www.aceseeds.org/en/guatemalastd.html |
| 42 | Guatemala | sativa | http://www.aceseeds.org/en/guatemalastd.html |
| 43 | Malawi Gold | sativa | http://www.seeds-of-africa.com/malawi-gold/ |

TABLE 10-continued

| Sample ID | Sample Name | Sample Type | Reference for Reported Ancestry |
|---|---|---|---|
| 44 | Malawi Gold | *sativa* | http://www.seeds-of-africa.com/malawi-gold/ |
| 45 | Malawi Gold | *sativa* | http://www.seeds-of-africa.com/malawi-gold/ |
| 46 | Malawi Gold | *sativa* | http://www.seeds-of-africa.com/malawi-gold/ |
| 47 | Pondo Mystic | *sativa* | http://www.seeds-of-africa.com/pondo-mystic/ |
| 48 | Swazi Gold | *sativa* | http://www.seeds-of-africa.com/swazi-gold/ |
| 49 | Swazi Gold | *sativa* | http://www.seeds-of-africa.com/swazi-gold/ |
| 50 | Swazi Gold | *sativa* | http://www.seeds-of-africa.com/swazi-gold/ |
| 51 | Swazi Gold | *sativa* | http://www.seeds-of-africa.com/swazi-gold/ |
| 52 | Swazi Gold | *sativa* | http://www.seeds-of-africa.com/swazi-gold/ |
| 53 | Swazi Gold | *sativa* | http://www.seeds-of-africa.com/swazi-gold/ |
| 54 | Durban Magic | *sativa* | http://www.seeds-of-africa.com/durban-magic/ |
| 55 | Mozambica | *sativa* | http://www.seeds-of-africa.com/mozambica/ |
| 56 | Mozambica | *sativa* | http://www.seeds-of-africa.com/mozambica/ |
| 57 | Mozambica | *sativa* | http://www.seeds-of-africa.com/mozambica/ |
| 58 | Mozambica | *sativa* | http://www.seeds-of-africa.com/mozambica/ |
| 59 | Transkei | *sativa* | http://www.seeds-of-africa.com/transkei/ |
| 60 | Transkei | *sativa* | http://www.seeds-of-africa.com/transkei/ |
| 61 | Transkei | *sativa* | http://www.seeds-of-africa.com/transkei/ |
| 62 | Transkei | *sativa* | http://www.seeds-of-africa.com/transkei/ |
| 63 | Zimbabwe | *sativa* | http://www.seeds-of-africa.com/zimbabwe/ |
| 64 | Zimbabwe | *sativa* | http://www.seeds-of-africa.com/zimbabwe/ |
| 65 | Zimbabwe | *sativa* | http://www.seeds-of-africa.com/zimbabwe/ |
| 66 | Lao Sativa | *sativa* | http://original-ssc.com/laos-luang-prabang-lao-sativa-seeds-ace-seeds.html |
| 67 | Lao Sativa | *sativa* | http://original-ssc.com/laos-luang-prabang-lao-sativa-seeds-ace-seeds.html |
| 68 | Purple Haze | *sativa* | http://en.seedfinder.eu/strain-info/Purple_Haze/ACE_Seeds/ |
| 69 | Purple Haze | *sativa* | http://en.seedfinder.eu/strain-info/Purple_Haze/ACE_Seeds/ |
| 70 | Zimbabwe | *sativa* | http://www.seeds-of-africa.com/zimbabwe/ |
| 71 | Malawi Gold | *sativa* | http://www.seeds-of-africa.com/malawi-gold/ |
| 72 | Malawi Gold | *sativa* | http://www.seeds-of-africa.com/malawi-gold/ |
| 73 | Durban Magic | *sativa* | http://www.seeds-of-africa.com/durban-magic/ |
| 74 | Durban Magic | *sativa* | http://www.seeds-of-africa.com/durban-magic/ |
| 75 | Durban Magic | *sativa* | http://www.seeds-of-africa.com/durban-magic/ |
| 76 | Durban Magic | *sativa* | http://www.seeds-of-africa.com/durban-magic/ |
| 77 | Durban Magic | *sativa* | http://www.seeds-of-africa.com/durban-magic/ |
| 78 | Pondo Mystic | *sativa* | http://www.seeds-of-africa.com/pondo-mystic/ |
| 79 | Pondo Mystic | *sativa* | http://www.seeds-of-africa.com/pondo-mystic/ |
| 80 | Pondo Mystic | *sativa* | http://www.seeds-of-africa.com/pondo-mystic/ |
| 81 | Pondo Mystic | *sativa* | http://www.seeds-of-africa.com/pondo-mystic/ |
| 82 | Pondo Mystic | *sativa* | http://www.seeds-of-africa.com/pondo-mystic/ |
| 83 | Coffee Gold | *sativa* | http://www.seeds-of-africa.com/coffee-gold/ |
| 84 | Coffee Gold | *sativa* | http://www.seeds-of-africa.com/coffee-gold/ |
| 85 | Coffee Gold | *sativa* | http://www.seeds-of-africa.com/coffee-gold/ |
| 86 | Coffee Gold | *sativa* | http://www.seeds-of-africa.com/coffee-gold/ |
| 87 | Mozambica | *sativa* | http://www.seeds-of-africa.com/mozambica/ |
| 88 | Mozambica | *sativa* | http://www.seeds-of-africa.com/mozambica/ |
| 89 | Mozambica | *sativa* | http://www.seeds-of-africa.com/mozambica/ |

TABLE 10-continued

| Sample ID | Sample Name | Sample Type | Reference for Reported Ancestry |
|---|---|---|---|
| 90 | Mozambica | sativa | http://www.seeds-of-africa.com/mozambica/ |
| 91 | Mozambica | sativa | http://www.seeds-of-africa.com/mozambica/ |
| 92 | Mozambica | sativa | http://www.seeds-of-africa.com/mozambica/ |
| 93 | Transkei | sativa | http://www.seeds-of-africa.com/transkei/ |
| 94 | Transkei | sativa | http://www.seeds-of-africa.com/transkei/ |
| 95 | Transkei | sativa | http://www.seeds-of-africa.com/transkei/ |
| 96 | Swazi Gold | sativa | http://www.seeds-of-africa.com/swazi-gold/ |
| 97 | Swazi Gold | sativa | http://www.seeds-of-africa.com/swazi-gold/ |
| 98 | Swazi Gold | sativa | http://www.seeds-of-africa.com/swazi-gold/ |
| 99 | Swazi Gold | sativa | http://www.seeds-of-africa.com/swazi-gold/ |
| 100 | Swazi Gold | sativa | http://www.seeds-of-africa.com/swazi-gold/ |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Hillig K. Genetic evidence for speciation in Cannabis (Cannabaceae). Genet. Resour. Crop Evol. 2005; 52(2):161-80.
2. de Meijer E P M. The Chemical Phenotypes (Chemotypes) of Cannabis. In: Pertwee R G, editor. Handbook of Cannabis. Handbooks in Psychopharmacology: Oxford University Press; 2014. p. 89-110.
3. van Bakel H, Stout J, Cote A, Tallon C, Sharpe A, Hughes T, et al. The draft genome and transcriptome of Cannabis sativa. Genome Biol. 2011; 12(10):R102.
4. Bostwick J M. Blurred Boundaries: The Therapeutics and Politics of Medical Marijuana. Mayo Clin. Proc. 2012; 87(2):172-86.
5. Elshire R J, Glaubitz J C, Sun Q, Poland J A, Kawamoto K, Buckler E S, et al. A Robust, Simple Genotyping-by-Sequencing (GBS) Approach for High Diversity Species. PLoS ONE. 2011; 6(5):e19379.
6. Raj A, Stephens M, Pritchard J K. fastSTRUCTURE: Variational Inference of Population Structure in Large SNP Datasets. Genetics. 2014.
7. de Meijer E P M, Bagatta M, Carboni A, Crucitti P, Moliterni V M C, Ranalli P, et al. The Inheritance of Chemical Phenotype in Cannabis sativa L. Genetics. 2003; 163(1):335-46.
8. Piluzza G, Delogu G, Cabras A, Marceddu S, Bullitta S. Differentiation between fiber and drug types of hemp (Cannabis sativa L.) from a collection of wild and domesticated accessions. Genet. Resour. Crop Evol. 2013; 60(8):2331-42.
9. Hinds D A, Stuve L L, Nilsen G B, Halperin E, Eskin E, Ballinger D G, et al. Whole-Genome Patterns of Common DNA Variation in Three Human Populations. Science. 2005; 307(5712):1072-9.
10. Hazekamp A, Fischedick J T. Cannabis—from cultivar to chemovar. Drug Test Anal. 2012; 4(7-8):660-7.
11. Small E, Cronquist A. A Practical and Natural Taxonomy for Cannabis. Taxon. 1976; 25(4):405-35.
12. Salentijn E M J, Zhang Q, Amaducci S, Yang M, Trindade L M. New developments in fiber hemp (Cannabis sativa L.) breeding. Ind Crops Prod. 2014.
13. Franz-Warkentin P. Hemp production sees steady growth in Canada 2013 [cited 2014]. Available from: http://www.agcanada.com/daily/hemp-production-sees-steady-growth-in-canada.
14. Agricultural Act of 2014, Pub. L. No. 113-17 Stat. 128 (Feb. 7, 2014, 2014).
15. Sonah H, Bastien M, Iquira E, Tardivel A, Légeré G, Boyle B, et al. An Improved Genotyping by Sequencing (GBS) Approach Offering Increased Versatility and Efficiency of SNP Discovery and Genotyping. PLoS ONE. 2013; 8(1):e54603.
16. Gardner K M, Brown P, Cooke T F, Cann S, Costa F, Bustamante C, et al. Fast and Cost-Effective Genetic Mapping in Apple Using Next-Generation Sequencing. G3 (Bethesda). 2014; 4(9):1681-7.
17. Purcell S, Neale B, Todd-Brown K, Thomas L, Ferreira M A R, Bender D, et al. PLINK: A Tool Set for Whole-Genome Association and Population-Based Linkage Analyses. Am J Hum Genet. 2007; 81(3):559-75.
18. Jombart T, Ahmed I. adegenet 1.3-1: new tools for the analysis of genome-wide SNP data. Bioinformatics. 2011; 27(21):3070-1.
19. Weir B S, Cockerham C C. Estimating F-Statistics for the Analysis of Population Structure. Evolution. 1984; 38(6):1358-70.
20. Hilling K W, Mahlberg P G. A Chemotaxonomic Analysis of Cannabinoid Variation in Cannabis (Cannabaceae). American Journal of Botany. 2004, 91(6):966-975
21. Willing E-M, Dreyer C, van Oosterhout C. Estimates of Genetic Differentiation Measured by $F_{ST}$ Do Not Necessarily Require Large Sample Sized When Using Many SNP Markers. PLOS ONE. 2012, 7(8):e42649.

22. McClure K A, Sawler J, Gardner K M, Money D, Myles S. Genomics: A Potential Panacea for the Perrenial Problem. Am J Botany 2014 101:1780-90.
23. Paetkau D, Calvert W, Stirling I, Strobeck C (1995) Microsatellite analysis of population structure in Canadian polar bears. Molecular Ecology, 4, 347-354
24. Hansen M M, Kenchington E, Nielsen E E (2001) Assigning individual fish to populations using microsatellite DNA markers: Methods and applications. Fish and Fisheries, 2, 93-112.
25. Campton D E and Utter F M, 1985. Natural hybridization between steelhead trout (*Salmo gairdneri*) and coastal cutthroat trout (*Salmo clarki clarki*) in two Puget Sound streams. Can J Fish Aquat Sci 42:110-119.
26. Poland J A, Brown P J, Sorrells M E, Jannink J L. Development of High-Density Genetic Maps for Barley and Wheat Using a Novel Two-Enzyme Genotyping-by-Sequencing Approach. PLoS ONE. 2012; 7(2):e32253.
27. Melo A T, Bartaula R, Hale I. GBS-SNP-CROP: a reference-optional pipeline for SNP discovery and plant germplasm characterization using variable length, paired-end genotyping-by-sequencing data. BMC Bioinformatics. 2016; 17:29

The invention claimed is:

1. A method for testing a sample comprising *cannabis* to determine if the *cannabis* is hemp or marijuana, the method comprising:

I) obtaining a test sample comprising genomic DNA,

II) genotyping the test sample for a set of SNPs, the set comprising at least 10, 20, 30, 40, 48, 50, 60, 70, 80, 90, 96 or 100 of the SNPs in Table 5, each SNP comprising a major allele and a minor allele as provided in Table 5;

III) detecting for each SNP of the set the presence or absence of the major allele and/or the minor allele in the test sample;

IV) determining the sample is hemp or marijuana according to the set of SNPs, wherein at least 10, 20, 30, or 40 of the genotyped SNPs of the set have an FST of greater than 0.679 as provided in Table 5, and at least 2 of the genotyped SNPs of the set have a major allele or minor allele with an allele frequency of 0 as provided in Table 5, wherein the test sample is determined to be hemp if the major alleles and/or minor alleles in combination when compared to the reference profiles provided in Table 5 are most similar to major alleles and/or minor alleles more commonly found in hemp, or the test sample is identified as marijuana if the major alleles and/or minor alleles in combination when compared to the reference profiles provided in Table 5 are most similar to major alleles and/or minor alleles more commonly found in marijuana; and V) displaying and/or providing a document displaying one or more features of the major and/or minor allele for each SNP in the set and/or the identity of the test sample as hemp or marijuana, wherein one or more features and/or identity of the test sample is used to select a sample with desired combination of major alleles and/or minor alleles, wherein the test sample is selected from a genomic DNA sample, a plant sample, a seed sample, leaf sample, a flower sample, a trichome sample, a pollen sample, and a sample of dried plant material including flower, pollen and trichomes, and the obtaining the sample comprises isolating genomic DNA, wherein the method further comprises using the presence or absence of the major allele and/or the minor allele for each SNP of the set in marker assisted selection (MAS) to select a cultivated *cannabis* plant, crossing the cultivated *cannabis* plant with a wild type *cannabis* plant, and selecting an offspring *cannabis* plant with a desired combination of major alleles and/or minor alleles.

2. The method of claim 1, wherein the set of SNPs comprises the SNPs in Table 5 with an Fst of greater than 0.679.

3. The method of claim 1, wherein the genotyping method comprises a PCR based method.

4. A method of *cannabis* ancestry selection breeding, the method comprising:
   a) obtaining one or more *cannabis* plant offspring having a desired trait;
   b) determining the hemp or marijuana ancestry contribution of the *cannabis* plant offspring;
   c) selecting one or more *cannabis* plant offspring having a desired hemp or marijuana ancestry contribution; and
   d) crossing the selected *cannabis* plant offspring with cultivated hemp or marijuana;
   wherein determining the hemp or marijuana ancestry contribution of the *cannabis* plant offspring in step b) comprises:
   I) obtaining a sample comprising genomic DNA from the *cannabis* plant offspring,
   II) genotyping the sample for a set of SNPs, the set comprising at least 10, 20, 30, 40, 48, 50, 60, 70, 80, 90, 96 or 100 of the SNPs in Table 5, each SNP comprising a major allele and a minor allele as provided in Table 5;
   III) detecting for each SNP of the set the presence or absence of the major allele and/or the minor allele in the sample; and
   IV) determining the hemp or marijuana ancestry contribution of the *cannabis* plant offspring according to the set of SNPs based on the reference profiles for marijuana and/or hemp provided in Table 5;
   wherein at least 10, 20, 30, or 40 of the genotyped SNPs of the set have an FST of greater than 0.679 as provided in Table 5, and wherein at least 2 of the genotyped SNPs of the set have a major allele or minor allele with an allele frequency of 0.

5. The method of claim 4, wherein the *cannabis* plant offspring is F2 offspring obtained by: crossing an initial cultivated hemp or marijuana strain with a wild *cannabis* strain having a desired trait to obtain F1 offspring having the desired trait; and backcrossing the F1 offspring having the desired trait to the initial cultivated hemp or marijuana strain to obtain F2 offspring having the desired trait.

6. The method of claim 4, wherein the set of SNPs comprises the SNPs in Table 5 with an Fst of greater than 0.679, and wherein the method further comprises displaying and/or providing a document displaying one or more features of the major and/or minor alleles.

7. The method of claim 4, wherein the test sample is selected from a genomic DNA sample, a plant sample, a seed sample, leaf sample, a flower sample, a trichome sample, a pollen sample, and a sample of dried plant material including flower, pollen and trichomes, and the obtaining the sample comprises isolating genomic DNA.

8. The method of claim 4, wherein the genotyping method comprises a PCR based method.

9. The method of claim 8, wherein the genotyping method comprises DNA amplification using forward and reverse primers and/or primer extension.

10. A method for testing a sample comprising *cannabis* to determine if the *cannabis* is hemp or marijuana, the method comprising:
   I) obtaining a test sample comprising genomic DNA;
   II) genotyping the test sample for a set of SNPs, the set comprising at least 10, 20, 30, 40, 48, 50, 60, 70, 80, 90, 96 or 100 of the SNPs in Table 5, each SNP comprising a major allele and a minor allele as provided in Table 5;
   III) detecting for each SNP of the set the presence or absence of the major allele and/or the minor allele in the test sample;
   IV) determining the sample is hemp or marijuana according to the set of SNPs, wherein at least 10, 20, 30, or 40 of the genotyped SNPs of the set have an FST of greater than 0.679 as provided in Table 5, and at least 2 of the genotyped SNPs of the set have a major allele or minor allele with an allele frequency of 0 as provided in Table 5, wherein the test sample is determined to be hemp if the major alleles and/or minor alleles in combination when compared to the reference profiles provided in Table 5 are most similar to major alleles and/or minor alleles more commonly found in hemp, or the test sample is identified as marijuana if the major alleles and/or minor alleles in combination when compared to the reference profiles provided in Table 5 are most similar to major alleles and/or minor alleles more commonly found in marijuana; and
   V) using the presence or absence of the major allele and/or the minor allele for each SNP of the set in marker assisted selection (MAS) to select a cultivated *cannabis* plant, crossing the cultivated *cannabis* plant with a wild type *cannabis* plant, and selecting an offspring *cannabis* plant with a desired combination of major alleles and/or minor alleles.

11. The method of claim 10, wherein the test sample is selected from a genomic DNA sample, a plant sample, a seed sample, leaf sample, a flower sample, a trichome sample, a pollen sample, and a sample of dried plant material including flower, pollen and trichomes, and the obtaining the sample comprises isolating genomic DNA.

12. The method of claim 10, wherein the genotyping method comprises a PCR based method.

13. The method of claim 12, wherein the genotyping method comprises DNA amplification using forward and reverse primers and/or primer extension.

14. The method of claim 3, wherein the genotyping method comprises DNA amplification using forward and reverse primers and/or primer extension.

* * * * *